US012570730B2

(12) United States Patent
Gottschalk et al.

(10) Patent No.: US 12,570,730 B2
(45) Date of Patent: Mar. 10, 2026

(54) CHIMERIC ANTIGEN RECEPTORS FOR DIRECT AND INDIRECT TARGETING OF FIBRONECTIN-POSITIVE TUMORS

(71) Applicant: St. Jude Children's Research Hospital, Inc., Memphis, TN (US)

(72) Inventors: Stephen Gottschalk, Germantown, TN (US); Jessica Wagner, Memphis, TN (US); Timothy Isham Shaw, Memphis, TN (US); Jinghui Zhang, Memphis, TN (US)

(73) Assignee: ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 999 days.

(21) Appl. No.: 17/628,483

(22) PCT Filed: Jul. 17, 2020

(86) PCT No.: PCT/US2020/042565
§ 371 (c)(1),
(2) Date: Jan. 19, 2022

(87) PCT Pub. No.: WO2021/016091
PCT Pub. Date: Jan. 28, 2021

(65) Prior Publication Data
US 2022/0267425 A1        Aug. 25, 2022

Related U.S. Application Data

(60) Provisional application No. 62/876,158, filed on Jul. 19, 2019.

(51) Int. Cl.
| | |
|---|---|
| *C07K 16/18* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |

(52) U.S. Cl.
CPC .............. *C07K 16/18* (2013.01); *A61K 40/11* (2025.01); *A61K 40/31* (2025.01); *A61K 40/4202* (2025.01); *A61P 35/00* (2018.01); *C07K 14/70517* (2013.01); *C07K 14/70521* (2013.01); *A61K 2239/31* (2023.05); *A61K 2239/38* (2023.05); *A61K 2239/55* (2023.05); *C07K 2317/622* (2013.01); *C07K 2319/03* (2013.01); *C07K 2319/33* (2013.01)

(58) Field of Classification Search
CPC .............. C07K 16/18; C07K 2317/622; C07K 2319/03; C07K 2319/33; C07K 16/30; A61K 40/11; A61K 40/31; A61K 40/4202; A61P 35/00
See application file for complete search history.

(56) References Cited

U.S. PATENT DOCUMENTS

| | | | |
|---|---|---|---|
| 8,097,254 B2 | 1/2012 | Neri et al. | |
| 9,670,281 B2 * | 6/2017 | Lim ....................... | C07K 16/28 |
| 2016/0361360 A1 | 12/2016 | Chang et al. | |
| 2017/0281766 A1 * | 10/2017 | Wiltzius ................. | A61P 35/00 |
| 2019/0125840 A1 | 5/2019 | Berdel et al. | |

FOREIGN PATENT DOCUMENTS

| | | |
|---|---|---|
| WO | 2017193059 A1 | 11/2017 |
| WO | 2018133877 A1 | 7/2018 |

OTHER PUBLICATIONS

Dotti, et al., Design and Development of Therapies using Chimeric Antigen Receptor-Expressing T cells, Immunol Rev. Jan. 2014 ; 257(1): .doi:10.1111/imr.12131.
Eshhar, et al., Specific activation and targeting of cytotoxic lymphocytes through chimeric single chains consisting of antibody-binding domains and the gamma or zeta subunits of the immunoglobulin and T-cell receptors, Proc. Natl. Acad. Sci. USA, vol. 90, pp. 720-724 (Jan. 1993).
Kaspar, et al., Fibronectin as target for tumor therapy, Int. J. Cancer: 118, 1331-1339 (2006).
Jailkhani, et al., Noninvasive imaging of tumor progression, metastasis, and fibrosis using a nanobody targeting the extracellular matrix, www.pnas.org/lookup/suppl/doi:10.1073/pnas.1817442116/-/DCSupplemental, (Oct. 2018).
Morsut, et al., Engineering Customized Cell Sensing and Response Behaviors Using Synthetic Notch Receptors, Cell, Feb. 11, 2016; 164(4): 780-791. doi:10.1016/j.cell.2016.01.012.
Santimaria, et al., Immunoscintigraphic Detection of the ED-B Domain of Fibronectin, a Marker of Angiogenesis, in Patients with Cancer, Clinical Cancer Research, vol. 9, 571-579, Feb. 2003.
Sauer, et al., Expression of the oncofetal ED-B-containing fibronectin isoform in hematologic tumors enables ED-B-targeted 131 I-L19SIP radioimmunotherapy in Hodgkin lymphoma patients, Blood, Mar. 5, 2009, vol. 113, No. 10.
Ventura, et al., Alternative Splicing of the Angiogenesis Associated Extra-Domain B of Fibronectin Regulates the Accessibility of the B-C Loop of the Type III Repeat 8, PLoS One 5(2): e9145. doi:10.1371/journal.pone.0009145 (2010).
(Continued)

*Primary Examiner* — Fereydoun G Sajjadi
*Assistant Examiner* — Masudur Rahman
(74) *Attorney, Agent, or Firm* — Troutman Pepper Locke LLP

(57) ABSTRACT

The application relates to a chimeric antigen receptor that directly and/or indirectly targets cells and their uses in tumor immunotherapy. The application also relates to polynucleotides that encode the chimeric antigen receptor and optionally accessory genes, vectors, and host cells comprising the chimeric antigen receptor and optionally a second antigen targeting moiety (e.g., a second chimeric antigen receptor or a bispecific molecule). The application also relates to methods for preparing host cells comprising the chimeric antigen receptor and optionally the second antigen targeting moiety.

48 Claims, 50 Drawing Sheets

Specification includes a Sequence Listing.

(56)  References Cited

OTHER PUBLICATIONS

Xie, et al., Nanobody-based Car T cells that target the tumor microenvironment inhibit the growth of solid tumors in immunocompetent mice, www.pnas.org/lookup/suppl/doi:10.1073/pnas.1817147116/-/DCSupplemental, (Apr. 1, 2019).

International Search Report mailed Nov. 9, 2020 for International Patent Application No. PCT/US2020/042565, which was filed Jul. 17, 2020 and published as WO 2021/016091 on Jan. 28, 2021 (Applicant: St. Jude Children's Research Hospital, Inc. // Inventor: Gottschalk, et al.) (5 pages).

Written Opinion mailed Nov. 9, 2020 for International Patent Application No. PCT/US2020/042565, which was filed Jul. 17, 2020 and published as WO 2021/016091 on Jan. 28, 2021 (Applicant: St. Jude Children's Research Hospital, Inc. // Inventor: Gottschalk, et al.) (6 pages).

* cited by examiner

Direct targeting of
EDB+ tumor cells

FN-EDB
TAA
Stroma

Indirect targeting of
EDB+ tumor cells

Recognition of EDB in ECM by T cells
induces expression of TAA-specific
CAR or BiTE (for additional detail see
FIG. 8A,B)

FIG. 3A
| LP | L19 scFv | SH | CD28 TM | CD28 | $\zeta$ | 2A | tCD19 |
LP: leader peptide
scFv: single chain variable fragment
SH: short hinge
TM: transmembrane domain
t: truncated
FIG. 3B
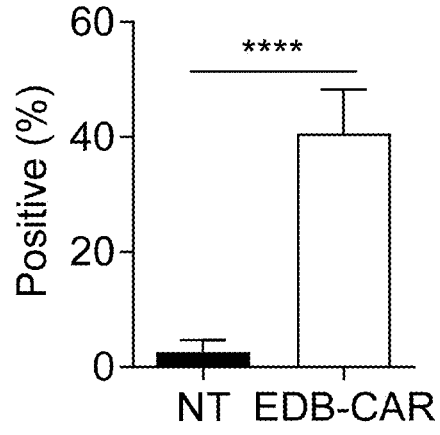
FIG. 3C
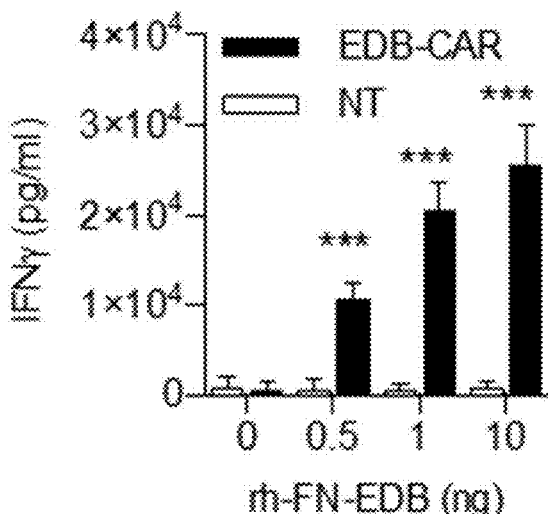

FIG. 4A
FIG. 4B
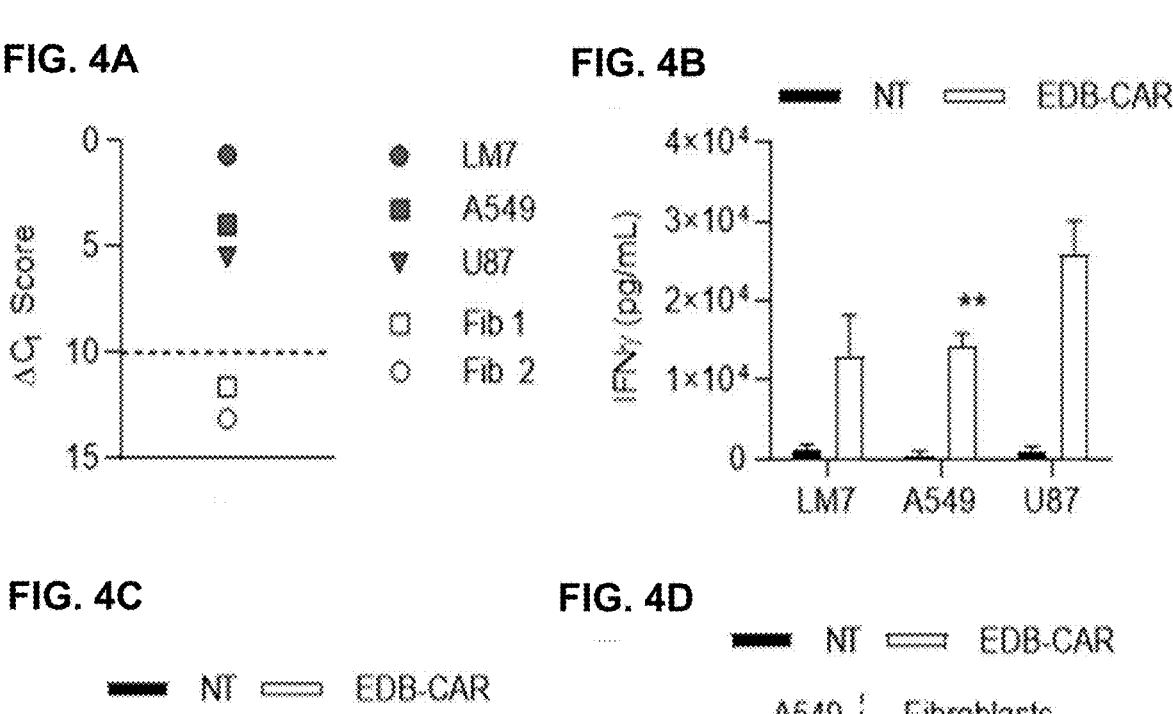
FIG. 4C
FIG. 4D
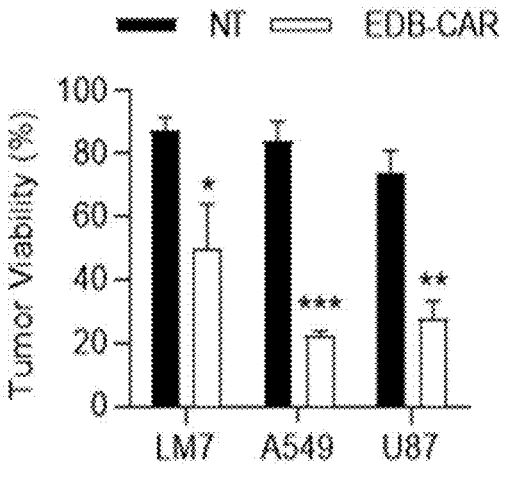
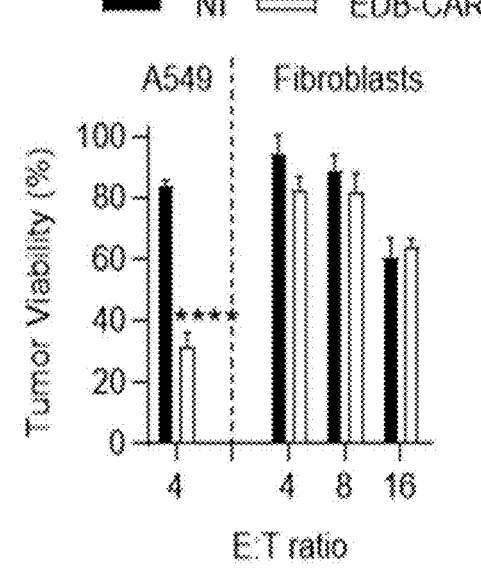

Day 0

Tumor cells
(A549,
$2 \times 10^6$ sc)

Day 20

CAR T cells
($3 \times 10^6$ iv)

Day 0       Day 20

Tumor cells     CAR T cells
(U87,       ($1 \times 10^6$ iv)
$2 \times 10^6$ sc)

Day 0

Tumor cells
(A549.ffLuc,
$2\times10^6$ iv)

Day 7

CAR T cells
($1\times10^6$ iv)

Radiance
(p/sec/cm²/sr)

Color Scale
Min = 1.00e4
Max = 1.00e5

TAA-specific
CAR or BiTE

EA2-EBD-notch

Gal4
DBD

1. At baseline only EDB-notch
TM.Gal4VP64 is expressed

2. Once EDB-notch TM.Gal4VP64
binds to EDB, Gal4VP64 is cleaved

3. Gal4VP64 translocates to the nucleus
and binds to GAL4 binding sites

4. Gal4VP64 induces expression of
TAA-specifc CAR or BiTE

FIG. 8C

EA2-EBD-notch-CAR

TAA-specific
CAR or BiTE

Gal4
DBD

MND

EDB-CAR

2A

EDB-notch TM.Gal4VP64

FIG. 9A

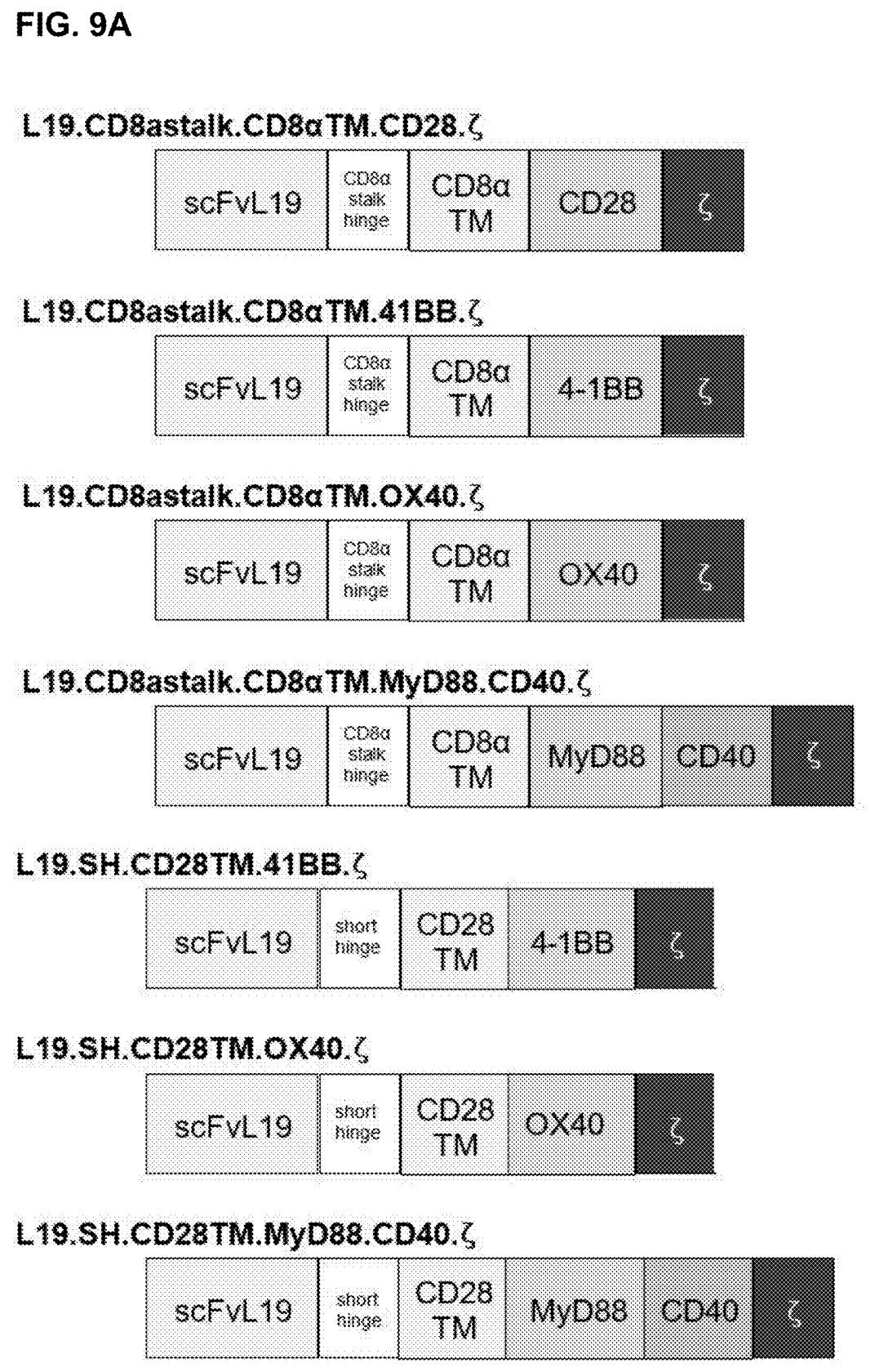

L19.CD8astalk.CD8αTM.CD28.ζ

| scFvL19 | CD8α stalk hinge | CD8α TM | CD28 | ζ |
|---|---|---|---|---|

L19.CD8astalk.CD8αTM.41BB.ζ

| scFvL19 | CD8α stalk hinge | CD8α TM | 4-1BB | ζ |
|---|---|---|---|---|

L19.CD8astalk.CD8αTM.OX40.ζ

| scFvL19 | CD8α stalk hinge | CD8α TM | OX40 | ζ |
|---|---|---|---|---|

L19.CD8astalk.CD8αTM.MyD88.CD40.ζ

| scFvL19 | CD8α stalk hinge | CD8α TM | MyD88 | CD40 | ζ |
|---|---|---|---|---|---|

L19.SH.CD28TM.41BB.ζ

| scFvL19 | short hinge | CD28 TM | 4-1BB | ζ |
|---|---|---|---|---|

L19.SH.CD28TM.OX40.ζ

| scFvL19 | short hinge | CD28 TM | OX40 | ζ |
|---|---|---|---|---|

L19.SH.CD28TM.MyD88.CD40.ζ

| scFvL19 | short hinge | CD28 TM | MyD88 | CD40 | ζ |
|---|---|---|---|---|---|

Figure 9B:
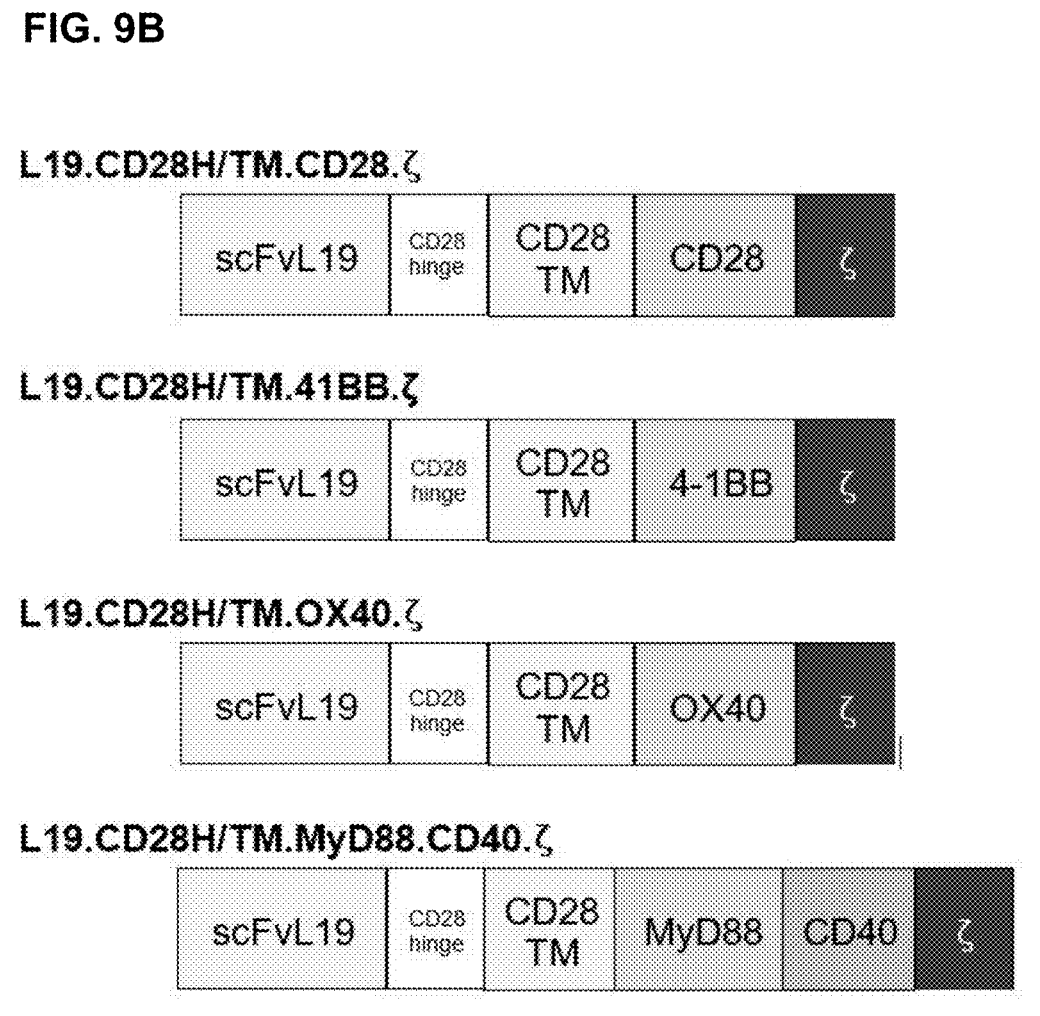

| scFvL19 | CD28 hinge | CD28 TM | CD28 | ζ |

L19.CD28H/TM.41BB.ζ

| scFvL19 | CD28 hinge | CD28 TM | 4-1BB | ζ |

L19.CD28H/TM.OX40.ζ

| scFvL19 | CD28 hinge | CD28 TM | OX40 | ζ |

L19.CD28H/TM.MyD88.CD40.ζ

| scFvL19 | CD28 hinge | CD28 TM | MyD88 | CD40 | ζ |

Fig. 10A

LIST OF SEQUENCES

SEQ ID NO: 1 Leader.L19.SH.CD28TM.CD28.ζ.2A.tCD19 amino acid sequence
Italic: *Leader Sequence*
Bold: scFV L19
Dotted underline: IgG1 Short Hinge
Regular: additional amino acids before and after Hinge
Dashed underline: CD28 Transmembrane Domain
Bold & italic: *CD28.zeta (CD28 underlined)*
Double underline: 2A
Wave underline: tCD19

*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIKDLEPKSCDKTHTCPPCPDPKFWVLV
VVGGVLACYSLLVTVAFIIFWV*RSKRSRLLHSDYMNMTPRRPGPTRKHYQPYAPPRDFAAYRSRVKFSRS*
*ADAPAYQQGQNQLYNELNLGRREEYDVLDKRRGRDPEMGGKPRRKNPQEGLYNELQKDKMAEAYSEIGMK*
*GERRRGKGHDGLYQGLSTATKDTYDALHMQALPPR*AEGRGSLLTCGDVEENPGPMPPPRLLFFLLFLTPM
EVRPEEPLVVKVEEGDNAVLQCLKGTSDGPTQQLTWSRESPLKPFLKLSLGLPGLGIHMRPLAIWLFIFN
VSQQMGGFYLCQPGPPSEKAWQPGWTVNVEGSGELFRWNVSDLGGLGCGLKNRSSEGPSSPSGKLMSPKL
YVWAKDRPEIWEGEPPCLPPRDSLNQSLSQDLTMAPGSTLWLSCGVPPDSVSRGPLSWTHVHPKGPKSLL
SLELKDDRPARDMWVMETGLLLPRATAQDAGKYYCHRGNLTMSFHLEITARPVLWHWLLRTGGWKVSAVT
LAYLIFCLCSLVGILHLQRALVLRRKRKRMTDPTRRF

Fig. 10B

<u>SEQ ID NO: 2</u> Leader.L19.SH.CD28TM.CD28.ζ.2A.tCD19 CAR DNA sequence

*ATGGACTGGATCTGGCGCATCCTCTTCCTCGTCGGCGCTGCTACCGGCGCTCATTCT*<b>GAGGTTCAGCTTC</b>
<b>TTGAGTCTGGGGGCGGCCTGGTGCAACCTGGTGGCAGTCTTAGGCTGAGTTGCGCCGCGTCAGGGTTTAC</b>
<b>TTTTTCTTCCTTCAGCATGTCATGGGTCCGCCAGGCTCCAGGTAAGGGCCTGGAATGGGTTAGTAGCATC</b>
<b>AGTGGCAGTAGTGGTACAACATACTACGCTGATAGTGTTAAAGGGAGATTCACTATAAGTAGGGATAATT</b>
<b>CTAAAAATACCCTTTATCTGCAAATGAATTCTTTGAGGGCCGAAGATACTGCGGTCTATTACTGTGCCAA</b>
<b>ACCTTTTCCATACTTTGATTACTGGGGCCAGGGGACGCTTGTCACTGTCTCCTCTGGCGACGGCTCCTCC</b>
<b>GGCGGAAGTGGAGGCGCGTCAGAAATTGTACTGACTCAGTCCCCGGGCACGCTCTCACTCAGTCCAGGCG</b>
<b>AAAGAGCTACGTTGTCTTGTCGCGCAAGCCAGTCCGTAAGCTCTAGCTTCCTCGCATGGTATCAACAAAA</b>
<b>GCCCGGGCAGGCTCCGCGGCTGCTCATTTACTATGCTAGTTCAAGGGCTACGGGAATTCCAGACCGATTT</b>
<b>AGTGGATCTGGGAGTGGAACTGACTTCACACTTACGATCAGCAGGCTTGAGCCGGAAGATTTTGCCGTGT</b>
<b>ACTACTGCCAGCAAACTGGAAGAATCCCCCCAACATTCGGACAAGGCACGAAGGTGGAAATCAAG</b>GATCT
<u>CGAGCCCAAATCTTGTGACAAAACTCACACATGCCCACCGTGCCCGGATCCCAAGTTCTGGGTGCTGGTG</u>
<u>GTCGTGGGCGGAGTGCTGGCCTGTTACAGCCTGCTCGTGACCGTGGCCTTCATCATCTTTTGGGTG</u>*CGCA*
*GCAAGCGGAGCCGGCTGCTGCACAGCGACTACATGAACATGACCCCCAGACGGCCTGGCCCCACCAGAAA*
*GCACTACCAGCCTTACGCCCCTCCCAGAGACTTCGCCGCCTACCGGTCCAGAGTGAAGTTCAGCAGAAGC*
*GCCGACGCCCCTGCCTATCAGCAGGGCCAGAACCAGCTGTACAACGAGCTGAACCTGGGCAGACGGGAAG*
*AGTACGACGTGCTGGACAAGCGGAGAGGCAGGGACCCTGAGATGGGCGGCAAGCCCAGAAGAAAGAACCC*
*CCAGGAAGGCCTGTATAACGAACTGCAGAAAGACAAGATGGCCGAGGCCTACAGCGAGATCGGCATGAAG*
*GGCGAGCGGAGAAGAGGCAAGGGCCACGATGGCCTGTACCAGGGACTGAGCACCGCCACCAAGGACACCT*
*ACGACGCCCTGCACATGCAGGCCCTGCCTCCAAGA*<u>GCCGAGGGCAGAGGCAGCCTGCTGACATGTGGCGA</u>
<u>CGTGGAAGAGAACCCAGGCCCCATGCCTCCCCCAGACTGCTGTTCTTCCTGCTGTTCCTGACCCCTATG</u>
<u>GAAGTGCGGCCCGAGGAACCCCTGGTCGTGAAAGTGGAAGAGGGCGACAACGCCGTGCTGCAGTGTCTGA</u>
<u>AGGGCACCTCCGATGGCCCTACCCAGCAGCTGACCTGGTCCAGAGAGAGCCCCCTGAAGCCCTTCCTGAA</u>
<u>GCTGTCTCTGGGCCTGCCTGGCCTGGGCATCCATATGAGGCCACTGGCCATCTGGCTGTTCATCTTCAAC</u>
<u>GTGTCCCAGCAGATGGGAGGCTTCTACCTGTGCCAGCCTGGCCCACCTTCTGAGAAGGCTTGGCAGCCTG</u>
<u>GCTGGACCGTGAACGTGGAAGGATCTGGCGAGCTGTTCCGGTGGAACGTGTCCGATCTGGGCGGCCTGGG</u>
<u>ATGCGGCCTGAAGAACAGATCTAGCGAGGGCCCCAGCAGCCCCAGCGGCAAACTGATGAGCCCCAAGCTG</u>
<u>TACGTGTGGGCCAAGGACAGACCCGAGATTTGGGAGGGCGAGCCCCCTTGCCTGCCCCCTAGAGATAGCC</u>
<u>TGAACCAGAGCCTGAGCCAGGACCTGACAATGGCCCCTGGCAGCACACTGTGGCTGAGCTGTGGCGTGCC</u>
<u>ACCCGACTCTGTGTCTAGAGGCCCTCTGAGCTGGACCCACGTGCACCCTAAGGGCCCTAAGAGCCTGCTG</u>
<u>TCCCTGGAACTGAAGGACGACAGGCCCGCCAGAGATATGTGGGTCATGGAAACCGGCCTGCTGCTGCCTA</u>
<u>GAGCCACAGCCCAGGATGCCGGCAAGTACTACTGCCACAGAGGCAACCTGACCATGAGCTTCCACCTGGA</u>
<u>AATCACCGCCAGACCCGTGCTGTGGCACTGGCTGCTGAGAACCGGCGGATGGAAAGTGTCCGCCGTGACT</u>
<u>CTGGCCTACCTGATCTTCTGCCTGTGCTCCCTCGTGGGCATCCTGCATCTGCAGAGGGCTCTGGTGCTGC</u>
<u>GGCGGAAGCGGAAGAGAATGACCGACCCTACCCGGCGGTTC</u>

<u>SEQ ID NO: 3</u> Leader.L19.CD8αstalk.CD8αTM.CD28.ζ amino acid sequence
Italic: *Leader Sequence*
Bold: scFV L19
Dotted underline: <u>CD8astalk.CD8aTM</u>
Bold & italic: *CD28.zeta (CD28* <u>*underlined*</u>*)*

*MDWIWRILFLVGAATGAHS*<b>EVQLLESGGGLVQPGGSLRLSCAASGFTFSSFSMSWVRQAPGKGLEWVSSI</b>
<b>SGSSGTTYYADSVKGRFTISRDNSKNTLYLQMNSLRAEDTAVYYCAKPFPYFDYWGQGTLVTVSSGDGSS</b>
<b>GGSGGASEIVLTQSPGTLSLSPGERATLSCRASQSVSSSFLAWYQQKPGQAPRLLIYYASSRATGIPDRF</b>
<b>SGSGSGTDFTLTISRLEPEDFAVYYCQQTGRIPPTFGQGTKVEIK</b><u>PAKPTTTPAPRPPTPAPTIASQPLS</u>
<u>LRPEACRPAAGGAVHTRGLDFACDIYIWAPLAGTCGVLLLSLVITLYCNHRN</u>*RSKRSRLLHSDYMNMTPR*
*RPGPTRKHYQPYAPPRDFAAYRSRVKFSRSADAPAYQQGQNQLYNELNLGRREEYDVLDKRRGRDPEMGG*
*KPRRKNPQEGLYNELQKDKMAEAYSEIGMKGERRRGKGHDGLYQGLSTATKDTYDALHMQALPPR*

Fig. 10C

<u>ID NO: 4</u>  Leader.L19.CD8αstalk.CD8αTM.CD28.ζ DNA sequence

*ATGGACTGGATCTGGCGCATCCTCTTCCTCGTCGGCGCTGCTACCGGCGCTCATTCT*GAGGTTCAGCTTC
TTGAGTCTGGGGGGCGGCCTGGTGCAACCTGGTGGCAGTCTTAGGCTGAGTTGCGCCGC
GTCAGGGTTTACTTTTTCTTCCTTCAGCATGTCATGGGTCCGCCAGGCTCCAGGTAAGGGCCTGGAATGG
GTTAGTAGCATCAGTGGCAGTAGTGGTACAACATACTACGCTGATAGTGTTAAAGGGAGATTCACTATAA
GTAGGGATAATTCTAAAAATACCCTTTATCTGCAAATGAATTCTTTGAGGGCCGAAGATACTGCGGTCTA
TTACTGTGCCAAACCTTTTCCATACTTTGATTACTGGGGCCAGGGGACGCTTGTCACTGTCTCCTCTGGC
GACGGCTCCTCCGGCGGAAGTGGAGGCGCGTCAGAAATTGTACTGACTCAGTCCCCGGGCACGCTCTCAC
TCAGTCCAGGCGAAAGAGCTACGTTGTCTTGTCGCGCAAGCCAGTCCGTAAGCTCTAGCTTCCTCGCATG
GTATCAACAAAAGCCCGGGCAGGCTCCGCGGCTGCTCATTTACTATGCTAGTTCAAGGGCTACGGGAATT
CCAGACCGATTTAGTGGATCTGGGAGTGGAACTGACTTCACACTTACGATCAGCAGGCTTGAGCCGGAAG
ATTTTGCCGTGTACTACTGCCAGCAAACTGGAAGAATCCCCCCAACATTCGGACAAGGCACGAAGGTGGA
AATCAAG<u>CCAGCCAAGCCCACCACAACCCCTGCTCCTAGACCTCCTACCCCAGCCCCTACCATTGCCTCC</u>
<u>CAGCCACTGTCTCTGAGGCCCGAGGCTTGTAGACCTGCTGCAGGCGGAGCCGTGCACACCAGAGGACTGG</u>
<u>ATTTCGCCTGCGACATCTATATCTGGGCCCCTCTGGCCGGCACCTGTGGCGTGCTGCTGCTGTCACTCGT</u>
<u>GATCACCCTGTACTGCAACCACCGGAAC</u>*CGCAGCAAGCGGAGCCGGCTGCTGCACAGCGACTACATGAAC*
*ATGACCCCCAGACGGCCTGGCCCCACCAGAAAGCACTACCAGCCTTACGCCCCTCCCAGAGACTTCGCCG*
*CCTACCGGTCCAGAGTGAAGTTCAGCAGAAGCGCCGACGCCCCTGCCTATCAGCAGGGCCAGAACCAGCT*
*GTACAACGAGCTGAACCTGGGCAGACGGGAAGAGTACGACGTGCTGGACAAGCGGAGAGGCAGGGACCCT*
*GAGATGGGCGGCAAGCCCAGAAGAAAGAACCCCCAGGAAGGCCTGTATAACGAACTGCAGAAAGACAAGA*
*TGGCCGAGGCCTACAGCGAGATCGGCATGAAGGGCGAGCGGAGAAGAGGCAAGGGCCACGATGGCCTGTA*
*CCAGGGACTGAGCACCGCCACCAAGGACACCTACGACGCCCTGCACATGCAGGCCCTGCCTCCAAGA*

<u>SEQ ID NO: 5</u>  Leader.L19.CD8αstalk.CD8αTM.41BB.ζ amino acid sequence
Italic: *Leader Sequence*
Bold: scFV L19
Dotted underline: <u>CD8astalk.CD8aTM</u>
Bold & italic: *41BB.zeta (41BB underlined)*
*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIK<u>PAKPTTTPAPRPPTPAPTIASQPLS</u>
<u>LRPEACRPAAGGAVHTRGLDFACDIYIWAPLAGTCGVLLLSLVITLYCNHRN</u>*KRGRKKLLYIFKQPFMRP*
*VQTTQEEDGCSCRFPEEEEGGCELRVKFSRSADAPAYQQGQNQLYNELNLGRREEYDVLDKRRGRDPEMG*
*GKPRRKNPQEGLYNELQKDKMAEAYSEIGMKGERRRGKGHDGLYQGLSTATKDTYDALHMQALPPR*

Fig. 10D

SEQ ID NO: 6  Leader.L19.CD8αstalk.CD8αTM.41BB.ζ DNA sequence

*ATGGACTGGATCTGGCGCATCCTCTTCCTCGTCGGCGCTGCTACCGGCGCTCATTCT*GAGGTTCAGCTTC
TTGAGTCTGGGGGGCGGCCTGGTGCAACCTGGTGGCAGTCTTAGGCTGAGTTGCGCCGCGTCAGGGTTTAC
TTTTTCTTCCTTCAGCATGTCATGGGTCCGCCAGGCTCCAGGTAAGGGCCTGGAATGGGTTAGTAGCATC
AGTGGCAGTAGTGGTACAACATACTACGCTGATAGTGTTAAAGGGAGATTCACTATAAGTAGGGATAATT
CTAAAAATACCCTTTATCTGCAAATGAATTCTTTGAGGGCCGAAGATACTGCGGTCTATTACTGTGCCAA
ACCTTTTCCATACTTTGATTACTGGGGCCAGGGGACGCTTGTCACTGTCTCCTCTGGCGACGGCTCCTCC
GGCGGAAGTGGAGGCGCGTCAGAAATTGTACTGACTCAGTCCCCGGGCACGCTCTCACTCAGTCCAGGCG
AAAGAGCTACGTTGTCTTGTCGCGCAAGCCAGTCCGTAAGCTCTAGCTTCCTCGCATGGTATCAACAAAA
GCCCGGGCAGGCTCCGCGGCTGCTCATTTACTATGCTAGTTCAAGGGCTACGGGAATTCCAGACCGATTT
AGTGGATCTGGGAGTGGAACTGACTTCACACTTACGATCAGCAGGCTTGAGCCGGAAGATTTTGCCGTGT
ACTACTGCCAGCAAACTGGAAGAATCCCCCCAACATTCGGACAAGGCACGAAGGTGGAAATCAAG~~CCAGC~~
~~CAAGCCCACCACAACCCCTGCTCCTAGACCTCCTACCCCAGCCCCTACCATTGCCTCCCAGCCACTGTCT~~
~~CTGAGGCCCGAGGCTTGTAGACCTGCTGCAGGCGGAGCCGTGCACACCAGAGGACTGGATTTCGCCTGCG~~
~~ACATCTATATCTGGGCCCCTCTGGCCGGCACCTGTGGCGTGCTGCTGCTGTCACTCGTGATCACCCTGTA~~
~~CTGCAACCACCGGAAC~~*AAACGCGGCCGCAAAAAACTGCTGTATATTTTTAAACAGCCGTTTATGCGCCCG*
*GTGCAGACCACCCAGGAAGAAGATGGCTGCAGCTGCCGCTTTCCGGAAGAAGAAGAAGGCGGCTGCGAAC*
*TGCGCGTGAAATTTAGCCGCAGCGCGGATGCGCCGGCGTATCAGCAGGGCCAGAACCAGCTGTATAACGA*
*ACTGAACCTGGGCCGCCGCGAAGAATATGATGTGCTGGATAAACGCCGCGGCCGCGATCCGGAAATGGGC*
*GGCAAACCGCGCCGCAAAAACCCGCAGGAAGGCCTGTATAACGAACTGCAGAAAGATAAAATGGCGGAAG*
*CGTATAGCGAAATTGGCATGAAAGGCGAACGCCGCCGCGGCAAAGGCCATGATGGCCTGTATCAGGGCCT*
*GAGCACCGCGACCAAAGATACCTATGATGCGCTGCATATGCAGGCGCTGCCGCCGCGC*

SEQ ID NO: 7  Leader.L19.CD8αstalk.CD8αTM.OX40.ζ amino acid sequence
Italic:  *Leader Sequence*
Bold:  scFV L19
Dotted underline:  CD8astalk.CD8aTM
Bold & Italic:  *OX40.zeta (OX40 underlined)*
*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIK~~PAKPTTTPAPRPPTPAPTIASQPLS~~
~~LRPEACRPAAGGAVHTRGLDFACDIYIWAPLAGTCGVLLLSLVITLYCNHRN~~*RDQRLPPDAHKPPGGGSF*
*RTPIQEEQADAHSTLAKIRVKFSRSADAPAYQQGQNQLYNELNLGRREEYDVLDKRRGRDPEMGGKPRRK*
*NPQEGLYNELQKDKMAEAYSEIGMKGERRRGKGHDGLYQGLSTATKDTYDALHMQAL*PPR

Fig. 10E

SEQ ID NO: 8 Leader.L19.CD8αstalk.CD8αTM.OX40.ζ DNA sequence

*ATGGACTGGATCTGGCGCATCCTCTTCCTCGTCGGCGCTGCTACCGGCGCTCATTCT*GAGGTTCAGCTTC
TTGAGTCTGGGGGCGGCCTGGTGCAACCTGGTGGCAGTCTTAGGCTGAGTTGCGCCGCGTCAGGGTTTAC
TTTTTCTTCCTTCAGCATGTCATGGGTCCGCCAGGCTCCAGGTAAGGGCCTGGAATGGGTTAGTAGCATC
AGTGGCAGTAGTGGTACAACATACTACGCTGATAGTGTTAAAGGGAGATTCACTATAAGTAGGGATAATT
CTAAAAATACCCTTTATCTGCAAATGAATTCTTTGAGGGCCGAAGATACTGCGGTCTATTACTGTGCCAA
ACCTTTTCCATACTTTGATTACTGGGGCCAGGGGACGCTTGTCACTGTCTCCTCTGGCGACGGCTCCTCC
GGCGGAAGTGGAGGCGCGTCAGAAATTGTACTGACTCAGTCCCCGGGCACGCTCTCACTCAGTCCAGGCG
AAAGAGCTACGTTGTCTTGTCGCGCAAGCCAGTCCGTAAGCTCTAGCTTCCTCGCATGGTATCAACAAAA
GCCCGGGCAGGCTCCGCGGCTGCTCATTTACTATGCTAGTTCAAGGGCTACGGGAATTCCAGACCGATTT
AGTGGATCTGGGAGTGGAACTGACTTCACACTTACGATCAGCAGGCTTGAGCCGGAAGATTTTGCCGTGT
ACTACTGCCAGCAAACTGGAAGAATCCCCCCAACATTCGGACAAGGCACGAAGGTGGAAATCAAG̲C̲C̲A̲G̲C̲
C̲A̲A̲G̲C̲C̲C̲A̲C̲C̲A̲C̲A̲A̲C̲C̲C̲C̲T̲G̲C̲T̲C̲C̲T̲A̲G̲A̲C̲C̲T̲C̲C̲T̲A̲C̲C̲C̲C̲A̲G̲C̲C̲C̲C̲T̲A̲C̲C̲A̲T̲T̲G̲C̲C̲T̲C̲C̲C̲A̲G̲C̲C̲A̲C̲T̲G̲T̲C̲T̲
C̲T̲G̲A̲G̲G̲C̲C̲C̲G̲A̲G̲G̲C̲T̲T̲G̲T̲A̲G̲A̲C̲C̲T̲G̲C̲T̲G̲C̲A̲G̲G̲C̲G̲G̲A̲G̲C̲C̲G̲T̲G̲C̲A̲C̲A̲C̲C̲A̲G̲A̲G̲G̲A̲C̲T̲G̲G̲A̲T̲T̲C̲G̲C̲C̲T̲G̲C̲G̲
A̲C̲A̲T̲C̲T̲A̲T̲A̲T̲C̲T̲G̲G̲G̲C̲C̲C̲C̲T̲C̲T̲G̲G̲C̲C̲G̲G̲C̲A̲C̲C̲T̲G̲T̲G̲G̲C̲G̲T̲G̲C̲T̲G̲C̲T̲G̲C̲T̲G̲T̲C̲A̲C̲T̲C̲G̲T̲G̲A̲T̲C̲A̲C̲C̲C̲T̲G̲T̲A̲
C̲T̲G̲C̲A̲A̲C̲C̲A̲C̲C̲G̲G̲A̲A̲C̲*CGCGATCAGCGCCTGCCGCCGGATGCGCATAAACCGCCGGGCGGCGGCAGCTTT*
*CGCACCCCGATTCAGGAAGAACAGGCGGATGCGCATAGCACCCTGGCGAAAATTCGCGTGAAATTTAGCC*
*GCAGCGCGGATGCGCCGGCGTATCAGCAGGGCCAGAACCAGCTGTATAACGAACTGAACCTGGGCCGCCG*
*CGAAGAATATGATGTGCTGGATAAACGCCGCGGCCGCGATCCGGAAATGGGCGGCAAACCGCGCCGCAAA*
*AACCCGCAGGAAGGCCTGTATAACGAACTGCAGAAAGATAAAATGGCGGAAGCGTATAGCGAAATTGGCA*
*TGAAAGGCGAACGCCGCCGCGGCAAAGGCCATGATGGCCTGTATCAGGGCCTGAGCACCGCGACCAAAGA*
*TACCTATGATGCGCTGCATATGCAGGCGCTG*CCGCCGCGC

SEQ ID NO: 9 Leader.L19.CD8αstalk.CD8αTM.MyD88.CD40.ζ amino acid sequence
Italic: *Leader Sequence*
Bold: scFV L19
Dotted underline: C̲D̲8̲a̲s̲t̲a̲l̲k̲.̲C̲D̲8̲a̲T̲M̲
Bold & italic: *MyD88.CD40.zeta (MyD88.CD40 underlined)*
*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIKP̲A̲K̲P̲T̲T̲T̲P̲A̲P̲R̲P̲P̲T̲P̲A̲P̲T̲I̲A̲S̲Q̲P̲L̲S̲
L̲R̲P̲E̲A̲C̲R̲P̲A̲A̲G̲G̲A̲V̲H̲T̲R̲G̲L̲D̲F̲A̲C̲D̲I̲Y̲I̲W̲A̲P̲L̲A̲G̲T̲C̲G̲V̲L̲L̲L̲S̲L̲V̲I̲T̲L̲Y̲C̲N̲H̲R̲N̲V̲*AAGGPGAGSAAPVSSTS*
*SLPLAALNMRVRRRLSLFLNVRTQVAADWTALAEEMDFEYLEIRQLETQADPTGRLLDAWQGRPGASVGR*
*LLELLTKLGRDDVLLELGPSIEEDCQKYILKQQQEEAEKPLQVAAVDSSVPRTAELAGITTLDDPLGHMP*
*ERFDAFICYCPSDIV*EKKVAKKPTNKAPHPKQEPQEINFPDDLPGSNTAAPVQETLHGCQPVTQEDGKES
RISVQERQRVKFSRSADAPAYQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR

Fig. 10F

<u>SEQ ID NO: 10</u>  Leader.L19.CD8αstalk.CD8αTM.MyD88.CD40.ζ DNA sequence

*ATGGACTGGATCTGGCGCATCCTCTTCCTCGTCGGCGCTGCTACCGGCGCTCATTCT*__GAGGTTCAGCTTC__
__TTGAGTCTGGGGGCGGCCTGGTGCAACCTGGTGGCAGTCTTAGGCTGAGTTGCGCCGCGTCAGGGTTTAC__
__TTTTTCTTCCTTCAGCATGTCATGGGTCCGCCAGGCTCCAGGTAAGGGCCTGGAATGGGTTAGTAGCATC__
__AGTGGCAGTAGTGGTACAACATACTACGCTGATAGTGTTAAAGGGAGATTCACTATAAGTAGGGATAATT__
__CTAAAAATACCCTTTATCTGCAAATGAATTCTTTGAGGGCCGAAGATACTGCGGTCTATTACTGTGCCAA__
__ACCTTTTCCATACTTTGATTACTGGGGCCAGGGGACGCTTGTCACTGTCTCCTCTGGCGACGGCTCCTCC__
__GGCGGAAGTGGAGGCGCGTCAGAAATTGTACTGACTCAGTCCCCGGGCACGCTCTCACTCAGTCCAGGCG__
__AAAGAGCTACGTTGTCTTGTCGCGCAAGCCAGTCCGTAAGCTCTAGCTTCCTCGCATGGTATCAACAAAA__
__GCCCGGGCAGGCTCCGCGGCTGCTCATTTACTATGCTAGTTCAAGGGCTACGGGAATTCCAGACCGATTT__
__AGTGGATCTGGGAGTGGAACTGACTTCACACTTACGATCAGCAGGCTTGAGCCGGAAGATTTTGCCGTGT__
__ACTACTGCCAGCAAACTGGAAGAATCCCCCCAACATTCGGACAAGGCACGAAGGTGGAAATCAAG__CCAGC
CAAGCCCACCACAACCCCTGCTCCTAGACCTCCTACCCCAGCCCCTACCATTGCCTCCCAGCCACTGTCT
CTGAGGCCCGAGGCTTGTAGACCTGCTGCAGGCGGAGCCGTGCACACCAGAGGACTGGATTTCGCCTGCG
ACATCTATATCTGGGCCCCTCTGGCCGGCACCTGTGGCGTGCTGCTGCTGTCACTCGTGATCACCCTGTA
CTGCAACCACCGGAAC*GCTGCTGGCGGACCTGGCGCCGGATCTGCTGCTCCTGTGTCTAGCACAAGCAGC*
*CTGCCTCTGGCCGCCCTGAACATGAGAGTGCGGAGAAGGCTGAGCCTGTTCCTGAACGTGCGGACACAGG*
*TGGCCGCCGATTGGACAGCCCTGGCCGAGGAAATGGACTTCGAGTACCTGGAAATCCGGCAGCTGGAAAC*
*CCAGGCCGACCCTACAGGCAGACTGCTGGATGCTTGGCAGGGCAGACCAGGCGCTTCTGTGGGAAGGCTG*
*CTGGAACTGCTGACCAAGCTGGGCAGGGACGACGTGCTGCTGGAACTGGGCCCTAGCATCGAAGAGGACT*
*GCCAGAAGTACATCCTGAAGCAGCAGCAGGAAGAGGCCGAGAAGCCTCTGCAGGTGGCAGCCGTGGATAG*
*CAGCGTGCCAAGAACAGCCGAGCTGGCCGGCATCACCACCCTGGATGATCCTCTGGGCCACATGCCCGAG*
*AGATTCGACGCCTTCATCTGCTACTGCCCCAGCGACATC*GTGGAA__AAGAAGGTGGCCAAGAAGCCCACCA__
__ACAAGGCCCCCCACCCCAAGCAGGAACCCCAGGAAATCAACTTCCCCGACGACCTGCCCGGCAGCAATAC__
__TGCTGCACCCGTGCAGGAAACCCTGCACGGCTGTCAGCCTGTGACCCAGGAAGATGGCAAAGAAAGCCGG__
__ATCTCTGTGCAGGAACGCCAGAGAGTGAAGTTCAGCAGGAGCGCAGACGCCCCCGCGTACCAGCAGGGCC__
__AGAACCAGCTCTATAACGAGCTCAATCTAGGACGAAGAGAGGAGTACGATGTTTTGGACAAGAGACGTGG__
__CCGGGACCCTGAGATGGGCGGCAAGCCCAGAAGAAAGAACCCCCAGGAAGGCCTGTATAACGAACTGCAG__
__AAAGACAAGATGGCCGAGGCCTACAGCGAGATCGGCATGAAGGGCGAGCGGAGAAGAGGCAAGGGCCACG__
__ATGGCCTGTACCAGGGACTGAGCACCGCCACCAAGGACACCTACGACGCCCTGCACATGCAGGCCCTGCC__
__TCCAAGA__

<u>SEQ ID NO: 11</u>  Leader.L19.SH.CD28TM.41BB.ζ amino acid sequence

Italic: *Leader Sequence*
Bold: scFV L19
Dotted underline: IgG1 Short Hinge
Regular: additional amino acids before and after Hinge
Dashed underline: CD28 Transmembrane Domain
Bold & italic: *41BB.zeta (41BB underlined)*

*MDWIWRILFLVGAATGAHS*__EVQLLESGGGLVQPGGSLRLSCAASGFTFSSFSMSWVRQAPGKGLEWVSSI__
__SGSSGTTYYADSVKGRFTISRDNSKNTLYLQMNSLRAEDTAVYYCAKPFPYFDYWGQGTLVTVSSGDGSS__
__GGSGGASEIVLTQSPGTLSLSPGERATLSCRASQSVSSSFLAWYQQKPGQAPRLLIYYASSRATGIPDRF__
__SGSGSGTDFTLTISRLEPEDFAVYYCQQTGRIPPTFGQGTKVEIK__DLEPKSCDKTHTCPPCPDPKFWVLV
VVGGVLACYSLLVTVAFIIFWV*KRGRKKLLYIFKQPFMRPVQTTQEEDGCSCRFPEEEEGGCELRVKFSR*
*SADAPAYQQGQNQLYNELNLGRREEYDVLDKRRGRDPEMGGKPRRKNPQEGLYNELQKDKMAEAYSEIGM*
*KGERRRGKGHDGLYQGLSTATKDTYDALHMQALPPR*

Fig. 10G

<u>SEQ ID NO: 12</u> Leader.L19.SH.CD28TM.41BB.ζ DNA sequence

*ATGGACTGGATCTGGCGCATCCTCTTCCTCGTCGGCGCTGCTACCGGCGCTCATTCT*GAGGTTCAGCTTC
TTGAGTCTGGGGGCGGCCTGGTGCAACCTGGTGGCAGTCTTAGGCTGAGTTGCGCCGCGTCAGGGTTTAC
TTTTTCTTCCTTCAGCATGTCATGGGTCCGCCAGGCTCCAGGTAAGGGCCTGGAATGGGTTAGTAGCATC
AGTGGCAGTAGTGGTACAACATACTACGCTGATAGTGTTAAAGGGAGATTCACTATAAGTAGGGATAATT
CTAAAAATACCCTTTATCTGCAAATGAATTCTTTGAGGGCCGAAGATACTGCGGTCTATTACTGTGCCAA
ACCTTTTCCATACTTTGATTACTGGGGCCAGGGGACGCTTGTCACTGTCTCCTCTGGCGACGGCTCCTCC
GGCGGAAGTGGAGGCGCGTCAGAAATTGTACTGACTCAGTCCCCGGGCACGCTCTCACTCAGTCCAGGCG
AAAGAGCTACGTTGTCTTGTCGCGCAAGCCAGTCCGTAAGCTCTAGCTTCCTCGCATGGTATCAACAAAA
GCCCGGGCAGGCTCCGCGGCTGCTCATTTACTATGCTAGTTCAAGGGCTACGGGAATTCCAGACCGATTT
AGTGGATCTGGGAGTGGAACTGACTTCACACTTACGATCAGCAGGCTTGAGCCGGAAGATTTTGCCGTGT
ACTACTGCCAGCAAACTGGAAGAATCCCCCCAACATTCGGACAAGGCACGAAGGTGGAAATCAAGGATCT
CGAGCCCAAATCTTGTGACAAAACTCACACATGCCCACCGTGCCCGGATCCCAAGTTCTGGGTGCTGGTG
GTCGTGGGCGGAGTGCTGGCCTGTTACAGCCTGCTCGTGACCGTGGCCTTCATCATCTTTTGGGTG*AAAC*
*GCGGCCGCAAAAAACTGCTGTATATTTTTAAACAGCCGTTTATGCGCCCGGTGCAGACCACCCAGGAAGA*
*AGATGGCTGCAGCTGCCGCTTTCCGGAAGAAGAAGAAGGCGGCTGCGAACTGCGCGTGAAATTTAGCCGC*
*AGCGCGGATGCGCCGGCGTATCAGCAGGGCCAGAACCAGCTGTATAACGAACTGAACCTGGGCCGCCGCG*
*AAGAATATGATGTGCTGGATAAACGCCGCGGCCGCGATCCGGAAATGGGCGGCAAACCGCGCCGCAAAAA*
*CCCGCAGGAAGGCCTGTATAACGAACTGCAGAAAGATAAAATGGCGGAAGCGTATAGCGAAATTGGCATG*
*AAAGGCGAACGCCGCCGCGGCAAAGGCCATGATGGCCTGTATCAGGGCCTGAGCACCGCGACCAAAGATA*
*CCTATGATGCGCTGCATATGCAGGCGCTGCCGCCGCGC*

<u>SEQ ID NO: 13</u> Leader.L19.SH.CD28TM.OX40.ζ amino acid sequence
Italic: *Leader Sequence*
Bold: scFV L19
Dotted underline: <u>IgG1 Short Hinge</u>
Regular: additional amino acids before and after Hinge
Dashed underline: <u>CD28 Transmembrane Domain</u>
Bold & italic: *OX40.zeta (OX40 underlined)*
*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIK<u>DLEPKSCDKTHTCPPCPDPKFWVLV</u>
<u>VVGGVLACYSLLVTVAFIIFWV</u>*RDQRLPPDAHKPPGGGSFRTPIQEEQADAHSTLAKIRVKFSRSADAPA*
*YQQGQNQLYNELNLGRREEYDVLDKRRGRDPEMGGKPRRKNPQEGLYNELQKDKMAEAYSEIGMKGERRR*
*GKGHDGLYQGLSTATKDTYDALHMQALPPR*

Fig. 10H

<u>SEQ ID NO: 14</u>  Leader.L19.SH.CD28TM.OX40.ζ DNA sequence

*ATGGACTGGATCTGGCGCATCCTCTTCCTCGTCGGCGCTGCTACCGGCGCTCATTCT*GAGGTTCAGCTTC
TTGAGTCTGGGGGCGGCCTGGTGCAACCTGGTGGCAGTCTTAGGCTGAGTTGCGCCGCGTCAGGGTTTAC
TTTTTCTTCCTTCAGCATGTCATGGGTCCGCCAGGCTCCAGGTAAGGGCCTGGAATGGGTTAGTAGCATC
AGTGGCAGTAGTGGTACAACATACTACGCTGATAGTGTTAAAGGGAGATTCACTATAAGTAGGGATAATT
CTAAAAATACCCTTTATCTGCAAATGAATTCTTTGAGGGCCGAAGATACTGCGGTCTATTACTGTGCCAA
ACCTTTTCCATACTTTGATTACTGGGGCCAGGGGACGCTTGTCACTGTCTCCTCTGGCGACGGCTCCTCC
GGCGGAAGTGGAGGCGCGTCAGAAATTGTACTGACTCAGTCCCCGGGCACGCTCTCACTCAGTCCAGGCG
AAAGAGCTACGTTGTCTTGTCGCGCAAGCCAGTCCGTAAGCTCTAGCTTCCTCGCATGGTATCAACAAAA
GCCCGGGCAGGCTCCGCGGCTGCTCATTTACTATGCTAGTTCAAGGGCTACGGGAATTCCAGACCGATTT
AGTGGATCTGGGAGTGGAACTGACTTCACACTTACGATCAGCAGGCTTGAGCCGGAAGATTTTGCCGTGT
ACTACTGCCAGCAAACTGGAAGAATCCCCCCAACATTCGGACAAGGCACGAAGGTGGAAATCAAGGATCT
<u>CGAGCCCAAATCTTGTGACAAAACTCACACATGCCCACCGTGCCCGGATCCCAAGTTCTGGGTGCTGGTG</u>
<u>GTCGTGGGCGGAGTGCTGGCCTGTTACAGCCTGCTCGTGACCGTGGCCTTCATCATCTTTTGGGTG</u>*CGCG*
*ATCAGCGCCTGCCGCCGGATGCGCATAAACCGCCGGGCGGCGGCAGCTTTCGCACCCCGATTCAGGAAGA*
*ACAGGCGGATGCGCATAGCACCCTGGCGAAAATTCGCGTGAAATTTAGCCGCAGCGCGGATGCGCCGGCG*
*TATCAGCAGGGCCAGAACCAGCTGTATAACGAACTGAACCTGGGCCGCCGCGAAGAATATGATGTGCTGG*
*ATAAACGCCGCGGCCGCGATCCGGAAATGGGCGGCAAACCGCGCCGCAAAAACCCGCAGGAAGGCCTGTA*
*TAACGAACTGCAGAAAGATAAAATGGCGGAAGCGTATAGCGAAATTGGCATGAAAGGCGAACGCCGCCGC*
*GGCAAAGGCCATGATGGCCTGTATCAGGGCCTGAGCACCGCGACCAAAGATACCTATGATGCGCTGCATA*
*TGCAGGCGCTG*CCGCCGCGC

<u>SEQ ID NO: 15</u>  Leader.L19.SH.CD28TM.MyD88.CD40.ζ amino acid sequence
Italic: *Leader Sequence*
Bold: scFV L19
Dotted underline: IgG1 Short Hinge
Regular: additional amino acids
Dashed underline: CD28 Transmembrane Domain
Bold & italic: *MyD88.CD40.zeta (MyD88.CD40 underlined)*
*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIKDLEPKSCDKTHTCPPCPDPKFWVLV
VVGGVLACYSLLVTVAFIIFWV*AAGGPGAGSAAPVSSTSSLPLAALNMRVRRRLSLFLNVRTQVAADWTA*
*LAEEMDFEYLEIRQLETQADPTGRLLDAWQGRPGASVGRLLELLTKLGRDDVLLELGPSIEEDCQKYILK*
***QQQEEAEKPLQVAAVDSSVPRTAELAGITTLDDPLGHMPERFDAFICYCPSDIV*EKKVAKKPTNKAPHPK**
QEPQEINFPDDLPGSNTAAPVQETLHGCQPVTQEDGKESRISVQERQRVKFSRSADAPAYQQGQNQLYNE
LNLGRREEYDVLDKRRGRDPEMGGKPRRKNPQEGLYNELQKDKMAEAYSEIGMKGERRRGKGHDGLYQGL
STATKDTYDALHMQALPPR

Fig. 10I

<u>SEQ ID NO: 16</u> Leader.L19.SH.CD28TM.MyD88.CD40.ζ DNA sequence

*ATGGACTGGATCTGGCGCATCCTCTTCCTCGTCGGCGCTGCTACCGGCGCTCATTCT*GAGGTTCAGCTTC
TTGAGTCTGGGGGCGGCCTGGTGCAACCTGGTGGCAGTCTTAGGCTGAGTTGCGCCGCGTCAGGGTTTAC
TTTTTCTTCCTTCAGCATGTCATGGGTCCGCCAGGCTCCAGGTAAGGGCCTGGAATGGGTTAGTAGCATC
AGTGGCAGTAGTGGTACAACATACTACGCTGATAGTGTTAAAGGGAGATTCACTATAAGTAGGGATAATT
CTAAAAATACCCTTTATCTGCAAATGAATTCTTTGAGGGCCGAAGATACTGCGGTCTATTACTGTGCCAA
ACCTTTTCCATACTTTGATTACTGGGGCCAGGGGACGCTTGTCACTGTCTCCTCTGGCGACGGCTCCTCC
GGCGGAAGTGGAGGCGCGTCAGAAATTGTACTGACTCAGTCCCCGGGCACGCTCTCACTCAGTCCAGGCG
AAAGAGCTACGTTGTCTTGTCGCGCAAGCCAGTCCGTAAGCTCTAGCTTCCTCGCATGGTATCAACAAAA
GCCCGGGCAGGCTCCGCGGCTGCTCATTTACTATGCTAGTTCAAGGGCTACGGGAATTCCAGACCGATTT
AGTGGATCTGGGAGTGGAACTGACTTCACACTTACGATCAGCAGGCTTGAGCCGGAAGATTTTGCCGTGT
ACTACTGCCAGCAAACTGGAAGAATCCCCCCAACATTCGGACAAGGCACGAAGGTGGAAATCAAGGATCT

CGAGCCCAAATCTTGTGACAAAACTCACACATGCCCACCGTGCCCGGATCCCAAGTTCTGGGTGCTGGTG
GTCGTGGGCGGAGTGCTGGCCTGTTACAGCCTGCTCGTGACCGTGGCCTTCATCATCTTTTGGGTG*GCTG*
*CTGGCGGACCTGGCGCCGGATCTGCTGCTCCTGTGTCTAGCACAAGCAGCCTGCCTCTGGCCGCCCTGAA*
*CATGAGAGTGCGGAGAAGGCTGAGCCTGTTCCTGAACGTGCGGACACAGGTGGCCGCCGATTGGACAGCC*
*CTGGCCGAGGAAATGGACTTCGAGTACCTGGAAATCCGGCAGCTGGAAACCCAGGCCGACCCTACAGGCA*
*GACTGCTGGATGCTTGGCAGGGCAGACCAGGCGCTTCTGTGGGAAGGCTGCTGGAACTGCTGACCAAGCT*
*GGGCAGGGACGACGTGCTGCTGGAACTGGGCCCTAGCATCGAAGAGGACTGCCAGAAGTACATCCTGAAG*
*CAGCAGCAGGAAGAGGCCGAGAAGCCTCTGCAGGTGGCAGCCGTGGATAGCAGCGTGCCAAGAACAGCCG*
*AGCTGGCCGGCATCACCACCCTGGATGATCCTCTGGGCCACATGCCCGAGAGATTCGACGCCTTCATCTG*
*CTACTGCCCCAGCGACATCG*TGGAA*AAGAAGGTGGCCAAGAAGCCCACCAACAAGGCCCCCACCCCAAG*
*CAGGAACCCCAGGAAATCAACTTCCCCGACGACCTGCCCGGCAGCAATACTGCTGCACCCGTGCAGGAAA*
*CCCTGCACGGCTGTCAGCCTGTGACCCAGGAAGATGGCAAAGAAAGCCGGATCTCTGTGCAGGAACGCCA*
*GAGAGTGAAGTTCAGCAGGAGCGCAGACGCCCCCGCGTACCAGCAGGGCCAGAACCAGCTCTATAACGAG*
*CTCAATCTAGGACGAAGAGGAGTACGATGTTTTGGACAAGAGACGTGGCCGGGACCCTGAGATGGGCG*
*GCAAGCCCAGAAGAAAGAACCCCCAGGAAGGCCTGTATAACGAACTGCAGAAAGACAAGATGGCCGAGGC*
*CTACAGCGAGATCGGCATGAAGGGCGAGCGGAGAAGAGGCAAGGGCCACGATGGCCTGTACCAGGGACTG*
*AGCACCGCCACCAAGGACACCTACGACGCCCTGCACATGCAGGCCCTGCCTCCAAGA*

<u>SEQ ID NO: 17</u> Leader.L19.CD28H/TM.CD28.ζ amino acid sequence
Italic: *Leader Sequence*
Bold: scFV L19
Dotted underline: <u>CD28 Hinge</u>
Dashed underline: <u>CD28 Transmembrane Domain</u>
Bold&italic: *CD28.zeta (CD28 underlined)*
*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIK<u>IEVMYPPPYLDNEKSNGTIIHVKGK</u>
<u>HLCPSPLFPGPSKPFWVLVVVGGVLACYSLLVTVAFIIFWV</u>*RSKRSRLLHSDYMNMTPRRPGPTRKHYQP*
*YAPPRDFAAYRSRVKFSRSADAPAYQQGQNQLYNELNLGRREEYDVLDKRRGRDPEMGGKPRRKNPQEGL*
*YNELQKDKMAEAYSEIGMKGERRRGKGHDGLYQGLSTATKDTYDALHMQALPPR*

Fig. 10J

SEQ ID NO: 18 Leader.L19.CD28H/TM.CD28.ζ DNA sequence

*ATGGACTGGATCTGGCGCATCCTCTTCCTCGTCGGCGCTGCTACCGGCGCTCATTCT*GAGGTTCAGCTTC
TTGAGTCTGGGGGCGGCCTGGTGCAACCTGGTGGCAGTCTTAGGCTGAGTTGCGCCGCGTCAGGGTTTAC
TTTTTCTTCCTTCAGCATGTCATGGGTCCGCCAGGCTCCAGGTAAGGGCCTGGAATGGGTTAGTAGCATC
AGTGGCAGTAGTGGTACAACATACTACGCTGATAGTGTTAAAGGGAGATTCACTATAAGTAGGGATAATT
CTAAAAATACCCTTTATCTGCAAATGAATTCTTTGAGGGCCGAAGATACTGCGGTCTATTACTGTGCCAA
ACCTTTTCCATACTTTGATTACTGGGGCCAGGGGACGCTTGTCACTGTCTCCTCTGGCGACGGCTCCTCC
GGCGGAAGTGGAGGCGCGTCAGAAATTGTACTGACTCAGTCCCCGGGCACGCTCTCACTCAGTCCAGGCG
AAAGAGCTACGTTGTCTTGTCGCGCAAGCCAGTCCGTAAGCTCTAGCTTCCTCGCATGGTATCAACAAAA
GCCCGGGCAGGCTCCGCGGCTGCTCATTTACTATGCTAGTTCAAGGGCTACGGGAATTCCAGACCGATTT
AGTGGATCTGGGAGTGGAACTGACTTCACACTTACGATCAGCAGGCTTGAGCCGGAAGATTTTGCCGTGT
ACTACTGCCAGCAAACTGGAAGAATCCCCCCAACATTCGGACAAGGCACGAAGGTGGAAATCAAGATCGA
<u>AGTGATGTACCCGCCTCCTTACCTGGACAACGAGAAGTCCAACGGCACCATCATCCACGTGAAGGGAAAG
CACCTGTGTCCTTCTCCACTGTTCCCCGGACCTAGCAAGCCTTCTGGGTGCTGGTGGTCGTGGGCGGAGT
GCTGGCCTGTTACAGCCTGCTCGTGACCGTGGCCTTCATCATCTTTTGGGTG</u>*CGCAGCAAGCGGAGCCGG*
*CTGCTGCACAGCGACTACATGAACATGACCCCCAGACGGCCTGGCCCCACCAGAAAGCACTACCAGCCTT*
*ACGCCCCTCCCAGAGACTTCGCCGCCTACCGGTCCAGAGTGAAGTTCAGCAGAAGCGCCGACGCCCCTGC*
*CTATCAGCAGGGCCAGAACCAGCTGTACAACGAGCTGAACCTGGGCAGACGGGAAGAGTACGACGTGCTG*
*GACAAGCGGAGAGGCAGGGACCCTGAGATGGGCGGCAAGCCCAGAAGAAAGAACCCCCAGGAAGGCCTGT*
*ATAACGAACTGCAGAAAGACAAGATGGCCGAGGCCTACAGCGAGATCGGCATGAAGGGCGAGCGGAGAAG*
*AGGCAAGGGCCACGATGGCCTGTACCAGGGACTGAGCACCGCCACCAAGGACACCTACGACGCCCTGCAC*
*ATGCAGGCCCTGCCTCCAAGA*

SEQ ID NO: 19 Leader.L19.CD28H/TM.41BB.ζ amino acid sequence
Italic: *Leader Sequence*
Bold: scFV L19
Dotted underline: CD28 Hinge
Dashed underline: CD28 Transmembrane Domain
Bold & italic: *41BB.zeta (41BB underlined)*
*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIKIEVMYPPPYLDNEKSNGTIIHVKGK
HLCPSPLFPGPSKPFWVLVVVGGVLACYSLLVTVAFIIFWV*KRGRKKLLYIFKQPFMRPVQTTQEEDGCS*
*CRFPEEEEGGCELRVKFSRSADAPAYQQGQNQLYNELNLGRREEYDVLDKRRGRDPEMGGKPRRKNPQEG*
*LYNELQKDKMAEAYSEIGMKGERRRGKGHDGLYQGLSTATKDTYDALHMQALPPR*

Fig. 10K

SEQ ID NO: 20 Leader.L19.CD28H/TM.41BB.ζ DNA sequence

*ATGGACTGGATCTGGCGCATCCTCTTCCTCGTCGGCGCTGCTACCGGCGCTCATTCT*__GAGGTTCAGCTTC__
__TTGAGTCTGGGGGCGGCCTGGTGCAACCTGGTGGCAGTCTTAGGCTGAGTTGCGCCGCGTCAGGGTTTAC__
__TTTTTCTTCCTTCAGCATGTCATGGGTCCGCCAGGCTCCAGGTAAGGGCCTGGAATGGGTTAGTAGCATC__
__AGTGGCAGTAGTGGTACAACATACTACGCTGATAGTGTTAAAGGGAGATTCACTATAAGTAGGGATAATT__
__CTAAAAATACCCTTTATCTGCAAATGAATTCTTTGAGGGCCGAAGATACTGCGGTCTATTACTGTGCCAA__
__ACCTTTTCCATACTTTGATTACTGGGGCCAGGGGACGCTTGTCACTGTCTCCTCTGGCGACGGCTCCTCC__
__GGCGGAAGTGGAGGCGCGTCAGAAATTGTACTGACTCAGTCCCCGGGCACGCTCTCACTCAGTCCAGGCG__
__AAAGAGCTACGTTGTCTTGTCGCGCAAGCCAGTCCGTAAGCTCTAGCTTCCTCGCATGGTATCAACAAAA__
__GCCCGGGCAGGCTCCGCGGCTGCTCATTTACTATGCTAGTTCAAGGGCTACGGGAATTCCAGACCGATTT__
__AGTGGATCTGGGAGTGGAACTGACTTCACACTTACGATCAGCAGGCTTGAGCCGGAAGATTTTGCCGTGT__
__ACTACTGCCAGCAAACTGGAAGAATCCCCCCAACATTCGGACAAGGCACGAAGGTGGAAATCAAG__ATCGA
AGTGATGTACCCGCCTCCTTACCTGGACAACGAGAAGTCCAACGGCACCATCATCCACGTGAAGGGAAAG
CACCTGTGTCCTTCTCCACTGTTCCCCGGACCTAGCAAGCCTTCTGGGTGCTGGTGGTCGTGGGCGGAGT
GCTGGCCTGTTACAGCCTGCTCGTGACCGTGGCCTTCATCATCTTTTGGGTG*AAACGCGGCCGCAAAAAA*
*CTGCTGTATATTTTTAAACAGCCGTTTATGCGCCCGGTGCAGACCACCCAGGAAGAAGATGGCTGCAGCT*
*GCCGCTTTCCGGAAGAAGAAGAAGGCGGCTGCGAACTGCGCGTGAAATTTAGCCGCAGCGCGGATGCGCC*
*GGCGTATCAGCAGGGCCAGAACCAGCTGTATAACGAACTGAACCTGGGCCGCCGCGAAGAATATGATGTG*
*CTGGATAAACGCCGCGGCCGCGATCCGGAAATGGGCGGCAAACCGCGCCGCAAAAACCCGCAGGAAGGCC*
*TGTATAACGAACTGCAGAAAGATAAAATGGCGGAAGCGTATAGCGAAATTGGCATGAAAGGCGAACGCCG*
*CCGCGGCAAAGGCCATGATGGCCTGTATCAGGGCCTGAGCACCGCGACCAAAGATACCTATGATGCGCTG*
*CATATGCAGGCGCTGCCGCCGCGC*

SEQ ID NO: 21 Leader.L19.CD28H/TM.OX40.ζ amino acid sequence
Italic: *Leader Sequence*
Bold: scFV L19
Dotted underline: CD28 Hinge
Dashed underline: CD28 Transmembrane Domain
Bold & italic: *OX40.zeta (OX40 underlined)*
*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIKIEVMYPPPYLDNEKSNGTIIHVKGK
HLCPSPLFPGPSKPFWVLVVVGGVLACYSLLVTVAFIIFWV*RDQRLPPDAHKPPGGGSFRTPIQEEQADA*
*HSTLAKIRVKFSRSADAPAYQQGQNQLYNELNLGRREEYDVLDKRRGRDPEMGGKPRRKNPQEGLYNELQ*
*KDKMAEAYSEIGMKGERRRGKGHDGLYQGLSTATKDTYDALHMQALPPR*

Fig. 10L

<u>SEQ ID NO: 22</u> Leader.L19.CD28H/TM.OX40.ζ DNA sequence

*ATGGACTGGATCTGGCGCATCCTCTTCCTCGTCGGCGCTGCTACCGGCGCTCATTCT*GAGGTTCAGCTTC
TTGAGTCTGGGGGGCGGCCTGGTGCAACCTGGTGGCAGTCTTAGGCTGAGTTGCGCCGCGTCAGGGTTTAC
TTTTTCTTCCTTCAGCATGTCATGGGTCCGCCAGGCTCCAGGTAAGGGCCTGGAATGGGTTAGTAGCATC
AGTGGCAGTAGTGGTACAACATACTACGCTGATAGTGTTAAAGGGAGATTCACTATAAGTAGGGATAATT
CTAAAAATACCCTTTATCTGCAAATGAATTCTTTGAGGGCCGAAGATACTGCGGTCTATTACTGTGCCAA
ACCTTTTCCATACTTTGATTACTGGGGCCAGGGGACGCTTGTCACTGTCTCCTCTGGCGACGGCTCCTCC
GGCGGAAGTGGAGGCGCGTCAGAAATTGTACTGACTCAGTCCCCGGGCACGCTCTCACTCAGTCCAGGCG
AAAGAGCTACGTTGTCTTGTCGCGCAAGCCAGTCCGTAAGCTCTAGCTTCCTCGCATGGTATCAACAAAA
GCCCGGGCAGGCTCCGCGGCTGCTCATTTACTATGCTAGTTCAAGGGCTACGGGAATTCCAGACCGATTT
AGTGGATCTGGGAGTGGAACTGACTTCACACTTACGATCAGCAGGCTTGAGCCGGAAGATTTTGCCGTGT
ACTACTGCCAGCAAACTGGAAGAATCCCCCCAACATTCGGACAAGGCACGAAGGTGGAAATCAAG<u>ATCGA</u>
<u>AGTGATGTACCCGCCTCCTTACCTGGACAACGAGAAGTCCAACGGCACCATCATCCACGTGAAGGGAAAG</u>
<u>CACCTGTGTCCTTCTCCACTGTTCCCCGGACCTAGCAAGCCTTCTGGGTGCTGGTGGTCGTGGGCGGAGT</u>
<u>GCTGGCCTGTTACAGCCTGCTCGTGACCGTGGCCTTCATCATCTTTTGGGTG</u>*CGCGATCAGCGCCTGCCG*
*CCGGATGCGCATAAACCGCCGGGCGGCGGCAGCTTTCGCACCCCGATTCAGGAAGAACAGGCGGATGCGC*
*ATAGCACCCTGGCGAAAATTCGCGTGAAATTTAGCCGCAGCGCGGATGCGCCGGCGTATCAGCAGGGCCA*
*GAACCAGCTGTATAACGAACTGAACCTGGGCCGCCGCGAAGAATATGATGTGCTGGATAAACGCCGCGGC*
*CGCGATCCGGAAATGGGCGGCAAACCGCGCCGCAAAAACCCGCAGGAAGGCCTGTATAACGAACTGCAGA*
*AAGATAAAATGGCGGAAGCGTATAGCGAAATTGGCATGAAAGGCGAACGCCGCCGCGGCAAAGGCCATGA*
*TGGCCTGTATCAGGGCCTGAGCACCGCGACCAAAGATACCTATGATGCGCTGCATATGCAGGCGCTG*CCG
CCGCGC

<u>SEQ ID NO: 23</u> Leader.L19.CD28H/TM.MyD88.CD40.ζ amino acid sequence
Italic: *Leader Sequence*
Bold: scFV L19
Dotted underline: CD28 Hinge
Regular: additional amino acids
Dashed underline: CD28 Transmembrane Domain
Bold & italic: *MyD88.CD40.zeta (MyD88.CD40 underlined)*
*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIK<u>IEVMYPPPYLDNEKSNGTIIHVKGK</u>
<u>HLCPSPLFPGPSKPFWVLVVVGGVLACYSLLVTVAFIIFWV</u>*AAGGPGAGSAAPVSSTSSLPLAALNMRVR*
*RRLSLFLNVRTQVAADWTALAEEMDFEYLEIRQLETQADPTGRLLDAWQGRPGASVGRLLELLTKLGRDD*
*VLLELGPSIEEDCQKYILKQQQEEAEKPLQVAAVDSSVPRTAELAGITTLDDPLGHMPERFDAFICYCPS*
*DIVE*KKVAKKPTNKAPHPKQEPQEINFPDDLPGSNTAAPVQETLHGCQPVTQEDGKESRISVQERQRVKF
SRSADAPAYQQGQNQLYNELNLGRREEYDVLDKRRGRDPEMGGKPRRKNPQEGLYNELQKDKMAEAYSEI
GMKGERRRGKGHDGLYQGLSTATKDTYDALHMQALPPR

Fig. 10M

SEQ ID NO: 24 Leader.L19.CD28H/TM.MyD88.CD40.ζ DNA sequence

*ATGGACTGGATCTGGCGCATCCTCTTCCTCGTCGGCGCTGCTACCGGCGCTCATTCT***GAGGTTCAGCTTC
TTGAGTCTGGGGGCGGCCTGGTGCAACCTGGTGGCAGTCTTAGGCTGAGTTGCGCCGCGTCAGGGTTTAC
TTTTTCTTCCTTCAGCATGTCATGGGTCCGCCAGGCTCCAGGTAAGGGCCTGGAATGGGTTAGTAGCATC
AGTGGCAGTAGTGGTACAACATACTACGCTGATAGTGTTAAAGGGAGATTCACTATAAGTAGGGATAATT
CTAAAAATACCCTTTATCTGCAAATGAATTCTTTGAGGGCCGAAGATACTGCGGTCTATTACTGTGCCAA
ACCTTTTCCATACTTTGATTACTGGGGCCAGGGGACGCTTGTCACTGTCTCCTCTGGCGACGGCTCCTCC
GGCGGAAGTGGAGGCGCGTCAGAAATTGTACTGACTCAGTCCCCGGGCACGCTCTCACTCAGTCCAGGCG
AAAGAGCTACGTTGTCTTGTCGCGCAAGCCAGTCCGTAAGCTCTAGCTTCCTCGCATGGTATCAACAAAA
GCCCGGGCAGGCTCCGCGGCTGCTCATTTACTATGCTAGTTCAAGGGCTACGGGAATTCCAGACCGATTT
AGTGGATCTGGGAGTGGAACTGACTTCACACTTACGATCAGCAGGCTTGAGCCGGAAGATTTTGCCGTGT
ACTACTGCCAGCAAACTGGAAGAATCCCCCCAACATTCGGACAAGGCACGAAGGTGGAAATCAAG*ATCGA
AGTGATGTACCCGCCTCCTTACCTGGACAACGAGAAGTCCAACGGCACCATCATCCACGTGAAGGGAAAG
CACCTGTGTCCTTCTCCACTGTTCCCCGGACCTAGCAAGCCTTCTGGGTGCTGGTGGTCGTGGGCGGAGT
GCTGGCCTGTTACAGCCTGCTCGTGACCGTGGCCTTCATCATCTTTTGGGTG***GCTGCTGGCGGACCTGGC
GCCGGATCTGCTGCTCCTGTGTCTAGCACAAGCAGCCTGCCTCTGGCCGCCCTGAACATGAGAGTGCGGA
GAAGGCTGAGCCTGTTCCTGAACGTGCGGACACAGGTGGCCGCCGATTGGACAGCCCTGGCCGAGGAAAT
GGACTTCGAGTACCTGGAAATCCGGCAGCTGGAAACCCAGGCCGACCCTACAGGCAGACTGCTGGATGCT
TGGCAGGGCAGACCAGGCGCTTCTGTGGGAAGGCTGCTGGAACTGCTGACCAAGCTGGGCAGGGACGACG
TGCTGCTGGAACTGGGCCCTAGCATCGAAGAGGACTGCCAGAAGTACATCCTGAAGCAGCAGCAGGAAGA
GGCCGAGAAGCCTCTGCAGGTGGCAGCCGTGGATAGCAGCGTGCCAAGAACAGCCGAGCTGGCCGGCATC
ACCACCCTGGATGATCCTCTGGGCCACATGCCCGAGAGATTCGACGCCTTCATCTGCTACTGCCCCAGCG
ACATCGTGGAAAAGAAGGTGGCCAAGAAGCCCACCAACAAGGCCCCCACCCAAGCAGGAACCCCAGGA
AATCAACTTCCCCGACGACCTGCCCGGCAGCAATACTGCTGCACCCGTGCAGGAAACCCTGCACGGCTGT
CAGCCTGTGACCCAGGAAGATGGCAAAGAAAGCCGGATCTCTGTGCAGGAACGCCAGAGAGTGAAGTTCA
GCAGGAGCGCAGACGCCCCCGCGTACCAGCAGGGCCAGAACCAGCTCTATAACGAGCTCAATCTAGGACG
AAGAGAGGAGTACGATGTTTTGGACAAGAGACGTGGCCGGGACCCTGAGATGGGCGGCAAGCCCAGAAGA
AAGAACCCCCAGGAAGGCCTGTATAACGAACTGCAGAAAGACAAGATGGCCGAGGCCTACAGCGAGATCG
GCATGAAGGGCGAGCGGAGAAGAGGCAAGGGCCACGATGGCCTGTACCAGGGACTGAGCACCGCCACCAA
GGACACCTACGACGCCCTGCACATGCAGGCCCTGCCTCCAAGA*

SEQ ID NO: 25 L19 scFv amino acid sequence

EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIK

SEQ ID NO: 26 L19 scFv DNA sequence

GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAG

Fig. 10N

SEQ ID NO: 27 IgG1 short hinge domain amino acid sequence
EPKSCDKTHTCPPCP

SEQ ID NO: 28 IgG1 short hinge domain DNA sequence
GAGCCCAAATCTTGTGACAAAACTCACACATGCCCACCGTGCCCG

SEQ ID NO: 29 IgG2 short hinge domain amino acid sequence
ERKCCVECPPCP

SEQ ID NO: 30 IgG3 short hinge domain amino acid sequence
ELKTPLGDTTHTCPRCP(EPKSCDTPPPCPRCP)3

SEQ ID NO: 31 IgG4 short hinge domain amino acid sequence
ESKYGPPCPSCP

SEQ ID NO: 32 CD8α Stalk amino acid sequence
PAKPTTTPAPRPPTPAPTIASQPLSLRPEACRPAAGGAVHTRGLDFA

SEQ ID NO: 33 CD8α Stalk DNA sequence
CCAGCCAAGCCCACCACAACCCCTGCTCCTAGACCTCCTACCCCAGCCCCTACCATTGCCTCCCAGCCAC
TGTCTCTGAGGCCCGAGGCTTGTAGACCTGCTGCAGGCGGAGCCGTGCACACCAGAGGACTGGATTTCGC
CTGCGACATCTATATCTGGGCCCCTCTGGCCGGCACCTGTGGCGTGCTGCTGCTGTCACTCGTGATCACC
CTGTACTGCAACCACCGGAAC

SEQ ID NO: 34 CD28 hinge domain amino acid sequence
IEVMYPPPYLDNEKSNGTIIHVKGKHLCPSPLFPGPSKP

SEQ ID NO: 35 CD28 hinge domain DNA sequence
ATCGAAGTGATGTACCCGCCTCCTTACCTGGACAACGAGAAGTCCAACGGCACCATCATCCACGTGAAGG
GAAAGCACCTGTGTCCTTCTCCACTGTTCCCCGGACCTAGCAAGCC

SEQ ID NO: 36 CD28 transmembrane domain amino acid sequence
FWVLVVVGGVLACYSLLVTVAFIIFWV

SEQ ID NO: 37 CD28 transmembrane domain DNA sequence
TTCTGGGTGCTGGTGGTCGTGGGCGGAGTGCTGGCCTGTTACAGCCTGCTCGTGACCGTGGCCTTCATCA
TCTTTTGGGTG

SEQ ID NO: 38 CD8α transmembrane domain amino acid sequence
CDIYIWAPLAGTCGVLLLSLVITLYCNHRN

SEQ ID NO: 39 CD8α transmembrane domain DNA sequence
TGCGACATCTACATCTGGGCCCCTCTGGCCGGCACATGTGGCGTGCTGCTGCTGAGCCTCGT
GATCACCCTGTACTGCAACCACCGGAAC

Fig. 10O

SEQ ID NO: 40   CD28 costimulatory domain amino acid sequence
RSKRSRLLHSDYMNMTPRRPGPTRKHYQPYAPPRDFAAYRS

SEQ ID NO: 41   CD28 costimulatory domain DNA sequence 1
CGCAGCAAGCGGAGCCGGCTGCTGCACAGCGACTACATGAACATGACCCCCAGACGGCCTG
GCCCCACCAGAAAGCACTACCAGCCTTACGCCCCTCCCAGAGACTTCGCCGCCTACCGGTCC
AG

SEQ ID NO: 42   CD28 costimulatory domain DNA sequence 2
CGAAGCAAGCGGAGCCGGCTGCTGCACAGCGACTACATGAACATGACCCCTAGACGGCCCG
GACCAACCAGAAAGCACTACCAGCCTTACGCTCCTCCTAGAGATTTCGCCGCCTACCGGTCC

SEQ ID NO: 43   CD28 costimulatory domain DNA sequence 3
CGGTCCAAGAGAAGCAGACTGCTGCACAGCGACTACATGAACATGACCCCTAGACGGCCCG
GACCTACCAGAAAGCACTACCAGCCTTACGCTCCTCCTAGAGATTTCGCCGCCTACCGGTCC

SEQ ID NO: 44   CD28 costimulatory domain DNA sequence 4
AGGAGTAAGAGGAGCAGGCTCCTGCACAGTGACTACATGAACATGACTCCCCGCCGCCCCG
GGCCCACCCGCAAGCATTACCAGCCCTATGCCCCACCACGCGACTTCGCAGCCTATCGCTCC

SEQ ID NO: 45   4-1BB costimulatory domain amino acid sequence
KRGRKKLLYIFKQPFMRPVQTTQEEDGCSCRFPEEEEGGCEL

SEQ ID NO: 46   4-1BB costimulatory domain DNA sequence
AAACGGGGCAGAAAGAAACTCCTGTATATATTCAAACAACCATTTATGAGACCAGTACAAA
CTACTCAAGAGGAAGATGGCTGTAGCTGCCGATTTCCAGAAGAAGAAGAAGGAGGATGTGA
ACTG

SEQ ID NO: 47   OX40 costimulatory domain amino acid sequence
RDQRLPPDAHKPPGGGSFRTPIQEEQADAHSTLAKI

SEQ ID NO: 48 OX40 costimulatory domain DNA sequence
AGGGACCAGAGGCTGCCCCCCGATGCCCACAAGCCCCCTGGGGGAGGCAGTTTCCGGACCC
CCATCCAAGAGGAGCAGGCCGACGCCCACTCCACCCTGGCCAAGATC

SEQ ID NO: 49   MyD88 fragment 1 costimulatory domain amino acid sequence
AAGGPGAGSAAPVSSTSSLPLAALNMRVRRRLSLFLNVRTQVAADWTALAEEMDFEYLEIRQLE
TQADPTGRLLDAWQGRPGASVGRLLELLTKLGRDDVLLELGPSIEEDCQKYILKQQQEEAEKPL
QVAAVDSSVPRTAELAGITTLDDPLGHMPERFDAFICYCPSDI

Fig. 10P

SEQ ID NO: 50 MyD88 fragment 1 costimulatory domain DNA sequence
GCTGCTGGCGGACCTGGCGCCGGATCTGCTGCTCCTGTGTCTAGCACAAGCAGCCTGCCTCT
GGCCGCCCTGAACATGAGAGTGCGGAGAAGGCTGAGCCTGTTCCTGAACGTGCGGACACAG
GTGGCCGCCGATTGGACAGCCCTGGCCGAGGAAATGGACTTCGAGTACCTGGAAATCCGGC
AGCTGGAAACCCAGGCCGACCCTACAGGCAGACTGCTGGATGCTTGGCAGGGCAGACCAGG
CGCTTCTGTGGGAAGGCTGCTGGAACTGCTGACCAAGCTGGGCAGGGACGACGTGCTGCTG
GAACTGGGCCCTAGCATCGAAGAGGACTGCCAGAAGTACATCCTGAAGCAGCAGCAGGAAG
AGGCCGAGAAGCCTCTGCAGGTGGCAGCCGTGGATAGCAGCGTGCCAAGAACAGCCGAGCT
GGCCGGCATCACCACCCTGGATGATCCTCTGGGCCACATGCCCGAGAGATTCGACGCCTTCA
TCTGCTACTGCCCCAGCGACATC

SEQ ID NO: 51 MyD88 fragment 2 costimulatory domain amino acid sequence
MAAGGPGAGSAAPVSSTSSLPLAALNMRVRRRLSLFLNVRTQVAADWTALAEEMDFEYLEIRQ
LETQADPTGRLLDAWQGRPGASVGRLLDLLTKLGRDDVLLELGPSIEEDCQKYILKQQQEEAEK
PLQVAAVDSSVPRTAELAGITTLDDPLGHMPERFDAFICYCPSDI

SEQ ID NO: 52 MyD88 fragment 2 costimulatory domain DNA sequence
ATGGCCGCTGGGGGCCCAGGCGCCGGATCAGCTGCTCCCGTATCTTCTACTTCTTCTTTGCCG
CTGGCTGCTCTGAACATGCGCGTGAGAAGACGCCTCTCCCTGTTCCTTAACGTTCGCACACA
AGTCGCTGCCGATTGGACCGCCCTTGCCGAAGAAATGGACTTTGAATACCTGGAAATTAGAC
AACTTGAAACACAGGCCGACCCCACTGGCAGACTCCTGGACGCATGGCAGGGAAGACCTGG
TGCAAGCGTTGGACGGCTCCTGGATCTCCTGACAAAACTGGGACGCGACGACGTACTGCTTG
AACTCGGACCTAGCATTGAAGAAGACTGCCAAAAATATATCCTGAAACAACAACAAGAAGA
AGCCGAAAAACCTCTCCAAGTCGCAGCAGTGGACTCATCAGTACCCCGAACAGCTGAGCTT
GCTGGGATTACTACACTCGACGACCCACTCGGACATATGCCTGAAAGATTCGACGCTTTCAT
TTGCTATTGCCCCTCTGACATA

SEQ ID NO: 53 MyD88 fragment 3 costimulatory domain amino acid sequence
AAGGPGAGSAAPVSSTSSLPLAALNMRVRRRLSLFLNVRTQVAADWTALAEEMDFEYLEIRQLE
TQADPTGRLLDAWQGRPGASVGRLLDLLTKLGRDDVLLELGPSIEEDCQKYILKQQQEEAEKPL
QVAAVDSSVPRTAELAGITTLDDPLGHMPERFDAFICYCPSDI

SEQ ID NO: 54 MyD88 fragment 3 costimulatory domain DNA sequence
GCCGCTGGGGGCCCAGGCGCCGGATCAGCTGCTCCCGTATCTTCTACTTCTTCTTTGC
CGCTGGCTGCTCTGAACATGCGCGTGAGAAGACGCCTCTCCCTGTTCCTTAACGTTCGC
ACACAAGTCGCTGCCGATTGGACCGCCCTTGCCGAAGAAATGGACTTTGAATACCTGGAAAT
TAGACAACTTGAAACACAGGCCGACCCCACTGGCAGACTCCTGGACGCATGGCAGGGAAGA
CCTGGTGCAAGCGTTGGACGGCTCCTGGATCTCCTGACAAAACTGGGACGCGACGACGTACT
GCTTGAACTCGGACCTAGCATTGAAGAAGACTGCCAAAAATATATCCTGAAACAACAACAA
GAAGAAGCCGAAAAACCTCTCCAAGTCGCAGCAGTGGACTCATCAGTACCCCGAACAGCTG
AGCTTGCTGGGATTACTACACTCGACGACCCACTCGGACATATGCCTGAAAGATTCGACGCT
TTCATTTGCTATTGCCCCTCTGACATA

SEQ ID NO: 55 CD40 costimulatory domain amino acid sequence
KKVAKKPTNKAPHPKQEPQEINFPDDLPGSNTAAPVQETLHGCQPVTQEDGKESRISVQERQ

Fig. 10Q

SEQ ID NO: 56 CD40 costimulatory domain DNA sequence
AAGAAGGTGGCCAAGAAGCCCACCAACAAGGCCCCCCACCCCAAGCAGGAACCCCAGGAAATCAACT
TCCCCGACGACCTGCCCGGCAGCAATACTGCTGCACCCGTGCAGGAAACCCTGCACGGCTGTCAGCCT
GTGACCCAGGAAGATGGCAAAGAAAGCCGGATCTCTGTGCAGGAACGCCAG

SEQ ID NO: 57 CD3z signaling domain 1 amino acid sequence
RVKFSRSADAPAYQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR

SEQ ID NO: 58 CD3z signaling domain 1 DNA sequence
AGAGTGAAGTTCAGCAGAAGCGCCGACGCCCCTGCCTATCAGCAGGGCCAGAACCAGCTGT
ACAACGAGCTGAACCTGGGCAGACGGGAAGAGTACGACGTGCTGGACAAGCGGAGAGGCA
GGGACCCTGAGATGGGCGGCAAGCCCAGAAGAAAGAACCCCCAGGAAGGCCTGTATAACG
AACTGCAGAAAGACAAGATGGCCGAGGCCTACAGCGAGATCGGCATGAAGGGCGAGCGGA
GAAGAGGCAAGGGCCACGATGGCCTGTACCAGGGACTGAGCACCGCCACCAAGGACACCTA
CGACGCCCTGCACATGCAGGCCCTGCCTCCAAGA

SEQ ID NO: 59 CD3z signaling domain 2 amino acid sequence
RVKFSRSADAPAYQQGQNQLYNELNLGRREEYDVLDKRRGRDRRGRDPEMGGKPRRKNPQEG
LYNELQKDKMAEAYSEIGMKGERRRGKGHDGLYQGLSTATKDTYDALHMQALPPR

SEQ ID NO: 60 CD3z signaling domain 2 DNA sequence
AGAGTGAAGTTCAGCAGGAGCGCAGACGCCCCCGCGTACCAGCAGGGCCAGAACCAGCTCT
ATAACGAGCTCAATCTAGGACGAAGAGAGGAGTACGATGTTTTGGACAAGAGACGTGGCCG
GGACAGACGTGGCCGGGACCCTGAGATGGGGGGGAAAGCCGAGAAGGAAGAACCCTCAGGA
AGGCCTGTACAATGAACTGCAGAAAGATAAGATGGCGGAGGCCTACAGTGAGATTGGGATG
AAAGGCGAGCGCCGGAGGGGCAAGGGGCACGATGGCCTTTACCAGGGTCTCAGTACAGCCA
CCAAGGACACCTACGACGCCCTTCACATGCAGGCCCTGCCCCCTCGC

SEQ ID NO: 61 Leader sequence 1 amino acid sequence
MDWIWRILFLVGAATGAHS

SEQ ID NO: 62 Leader sequence 1 DNA sequence
ATGGACTGGATCTGGCGCATCCTCTTCCTCGTCGGCGCTGCTACCGGCGCTCATTCT

SEQ ID NO: 63 Leader sequence 2 amino acid sequence
MALPVTALLLPLALLLHAARP

SEQ ID NO: 64 Leader sequence 2 DNA sequence
ATGGCCTTACCAGTGACCGCCTTGCTCCTGCCGCTGGCCTTGCTGCTCCACGCCGCCAGGCC
G

Fig. 10R

SEQ ID NO: 65 tCD19 amino acid sequence
MPPPRLLFFLLFLTPMEVRPEEPLVVKVEEGDNAVLQCLKGTSDGPTQQLTWSRESPLKPFLKLS
LGLPGLGIHMRPLAIWLFIFNVSQQMGGFYLCQPGPPSEKAWQPGWTVNVEGSGELFRWNVSDL
GGLGCGLKNRSSEGPSSPSGKLMSPKLYVWAKDRPEIWEGEPPCLPPRDSLNQSLSQDLTMAPGS
TLWLSCGVPPDSVSRGPLSWTHVHPKGPKSLLSLELKDDRPARDMWVMETGLLLPRATAQDAG
KYYCHRGNLTMSFHLEITARPVLWHWLLRTGGWKVSAVTLAYLIFCLCSLVGILHLQRALVLRR
KRKRMTDPTRRF

SEQ ID NO: 66 tCD19 DNA sequence
ATGCCTCCCCCAGACTGCTGTTCTTCCTGCTGTTCCTGACCCCTATGGAAGTGCGGCCCGAG
GAACCCCTGGTCGTGAAAGTGGAAGAGGGCGACAACGCCGTGCTGCAGTGTCTGAAGGGCA
CCTCCGATGGCCCTACCCAGCAGCTGACCTGGTCCAGAGAGAGCCCCCTGAAGCCCTTCCTG
AAGCTGTCTCTGGGCCTGCCTGGCCTGGGCATCCATATGAGGCCACTGGCCATCTGGCTGTT
CATCTTCAACGTGTCCCAGCAGATGGGAGGCTTCTACCTGTGCCAGCCTGGCCCACCTTCTG
AGAAGGCTTGGCAGCCTGGCTGGACCGTGAACGTGGAAGGATCTGGCGAGCTGTTCCGGTG
GAACGTGTCCGATCTGGGCGGCCTGGGATGCGGCCTGAAGAACAGATCTAGCGAGGGCCCC
AGCAGCCCCAGCGGCAAACTGATGAGCCCCAAGCTGTACGTGTGGGCCAAGGACAGACCCG
AGATTTGGGAGGGCGAGCCCCCTTGCCTGCCCCCTAGAGATAGCCTGAACCAGAGCCTGAG
CCAGGACCTGACAATGGCCCCTGGCAGCACACTGTGGCTGAGCTGTGGCGTGCCACCCGACT
CTGTGTCTAGAGGCCCTCTGAGCTGGACCCACGTGCACCCTAAGGGCCCTAAGAGCCTGCTG
TCCCTGGAACTGAAGGACGACAGGCCCGCCAGAGATATGTGGGTCATGGAAACCGGCCTGC
TGCTGCCTAGAGCCACAGCCCAGGATGCCGGCAAGTACTACTGCCACAGAGGCAACCTGAC
CATGAGCTTCCACCTGGAAATCACCGCCAGACCCGTGCTGTGGCACTGGCTGCTGAGAACCG
GCGGATGGAAAGTGTCCGCCGTGACTCTGGCCTACCTGATCTTCTGCCTGTGCTCCCTCGTGG
GCATCCTGCATCTGCAGAGGGCTCTGGTGCTGCGGCGGAAGCGGAAGAGAATGACCGACCC
TACCCGGCGGTTC

SEQ ID NO: 67 synNotch receptor amino acid sequence
ILDYSFGGGAGRDIPPPLIEEACELPECQEDAGNKVCSLQCNNHACGWDGGDCSLNFNDPWKNCTQSLQC
WKYFSDGHCDSQCNSAGCLFDGFDCQRAEGQCNPLYDQYCKDHFSDGHCDQGCNSAECEWDGLDCAEH
VPERLAAGTLVVVVLMPPEQLRNSSFHFLRELSRVLHTNVVFKRDAHGQQMIFPYYGREEELRKHPIK
RAAEGWAAPDALLGQVKASLLPGGSEGGRRRRELDPMDVRGSIVYLEIDNRQCVQASSQCFQS
ATDVAAFLGALASLGSLNIPYKIEAVQSETVEPPPPAQLHFMYVAAAAFVLLFFVGCGVLLSRKR
RR

Fig. 10S

SEQ ID NO: 68 synNotch receptor DNA sequence
ATTCTGGATTATAGCTTTGGCGGCGGCGCGGGCCGCGATATTCCGCCGCCGCTGATTGAAGAAGCGTG
CGAACTGCCGGAATGCCAGGAAGATGCGGGCAACAAAGTGTGCAGCCTGCAGTGCAACAACCATGCG
TGCGGCTGGGATGGCGGCGATTGCAGCCTGAACTTTAACGATCCGTGGAAAAACTGCACCCAGAGCCT
GCAGTGCTGGAAATATTTTAGCGATGGCCATTGCGATAGCCAGTGCAACAGCGCGGGCTGCCTGTTTG
ATGGCTTTGATTGCCAGCGCGCGGAAGGCCAGTGCAACCCGCTGTATGATCAGTATTGCAAAGATCAT
TTTAGCGATGGCCATTGCGATCAGGGCTGCAACAGCGCGGAATGCGAATGGGATGGCCTGGATTGCGC
GGAACATGTGCCGGAACGCCTGGCGGCGGGCACCCTGGTGGTGGTGGTGCTGATGCCGCCGGAACAG
CTGCGCAACAGCAGCTTTCATTTTCTGCGCGAACTGAGCCGCGTGCTGCATACCAACGTGGTGTTTAAA
CGCGATGCGCATGGCCAGCAGATGATTTTTCCGTATTATGGCCGCGAAGAAGAACTGCGCAAACATCC
GATTAAACGCGCGGCGGAAGGCTGGGCGGCGCCGGATGCGCTGCTGGGCCAGGTGAAAGCGAGCCTG
CTGCCGGGCGGCAGCGAAGGCGGCCGCCGCCGCGAACTGGATCCGATGGATGTGCGCGGCAGCA
TTGTGTATCTGGAAATTGATAACCGCCAGTGCGTGCAGGCGAGCAGCCAGTGCTTTCAGAGCGCGACC
GATGTGGCGGCGTTTCTGGGCGCGCTGGCGAGCCTGGGCAGCCTGAACATTCCGTATAAAATTGAAGC
GGTGCAGAGCGAAACCGTGGAACCGCCGCCGCCGGCGCAGCTGCATTTTATGTATGTGGCGGCGGCG
GCGTTTGTGCTGCTGTTTTTTGTGGGCTGCGGCGTGCTGCTGAGCCGCAAACGCCGCCGC

SEQ ID NO: 69 T2A 1 amino acid sequence
AEGRGSLLTCGDVEENPGP

SEQ ID NO: 70 T2A 1 DNA sequence
GCCGAGGGCAGAGGCAGCCTGCTGACATGTGGCGACGTGGAAGAGAACCCAGGCCCC

SEQ ID NO: 71 T2A 2 amino acid sequence
EGRGSLLTCGDVEENPGP

SEQ ID NO: 72 T2A 2 DNA sequence
GAAGGCAGAGGATCACTGCTGACATGCGGCGACGTGGAAGAGAACCCTGGACCC

SEQ ID NO: 73 Thoseaasigna virus 2A amino acid sequence
GSGEGRGSLLTCGDVEENPGP

SEQ ID NO: 74 FMDV2A amino acid sequence
GSGSRVTELLYRMKRAETYCPRPLLAIHPTEARHKQKIVAPVKQLLNFDLLKLAGDVESNPGP

SEQ ID NO: 75 Sponge 2A amino acid sequence
LLCFLLLLLSGDVELNPGP

SEQ ID NO: 76 Sponge 2A amino acid sequence
HHFMFLLLLLAGDIELNPGP

SEQ ID NO: 77 Acorn Worm 2A amino acid sequence
WFLVLLSFILSGDIEVNPGP

SEQ ID NO: 78 Amphioxus 2A amino acid sequence
KNCAMYMLLLSGDVETNPGP

Fig. 10T

SEQ ID NO: 79 Amphioxus 2A amino acid sequence
MVISQLMLKLAGDVEENPGP

SEQ ID NO: 80 Porcine Teschovirus-1 2A amino acid sequence
GSGATNFSLLKQAGDVEENPGP

SEQ ID NO: 81 Equine Rhinitis A Virus 2A amino acid sequence
GSGQCTNYALLKLAGDVESNPGP

SEQ ID NO: 82  2A consensus sequence amino acid sequence
D-X-E-X-NPGP (X is any amino acid)

SEQ ID NO: 83 T2A sequence DNA sequence 2
GAGGGCAGAGGCAGCCTGCTGACATGTGGCGACGTGGAAGAGAACCCAGGCCCC

SEQ ID NO: 84 CD20 amino acid sequence
MTTPRNSVNGTFPAEPMKGPIAMQSGPKPLFRRMSSLVGPTQSFFMRESKTLGAVQIMNGLFHIA
LGGLLMIPAGIYAPICVTVWYPLWGGIMYIISGSLLAATEKNSRKCLVKGKMIMNSLSLFAAISG
MILSIMDILNIKISHFLKMESLNFIRAHTPYINIYNCEPANPSEKNSPSTQYCYSIQSLFLGILSVMLIF
AFFQELVIAGIVENEWKRTCSRPKSNIVLLSAEEKKEQTIEIKEEVVGLTETSSQPKNEEDIEIIPIQE
EEEEETETNFPEPPQDQESSPIENDSSP

SEQ ID NO: 85 CD20 DNA sequence 1
ATGACCACACCTCGGAACAGCGTGAACGGCACATTTCCCGCCGAGCCTATGAAGGGCCCTAT
CGCCATGCAGTCTGGCCCCAAGCCTCTGTTCAGACGGATGTCTAGCCTCGTGGGCCCCACAC
AGAGCTTTTTCATGAGAGAGAGCAAGACCCTGGGCGCCGTGCAGATCATGAACGGCCTGTTT
CACATTGCCCTCGGCGGCCTGCTGATGATCCCTGCCGGAATCTATGCCCCTATCTGCGTGACC
GTGTGGTATCCTCTGTGGGGCGGCATCATGTACATCATCTCTGGATCTCTGCTGGCCGCCACC
GAGAAGAACAGCAGAAAGTGTCTGGTCAAGGGCAAGATGATCATGAATAGCCTGAGCCTGT
TCGCCGCCATCAGCGGCATGATCCTGAGCATCATGGATATCCTGAATATCAAGATCAGCCAC
TTCCTGAAGATGGAAAGCCTGAACTTCATCAGGGCCCACACACCTTACATCAACATCTACAA
CTGCGAGCCCGCCAATCCTAGCGAGAAGAATAGCCCCAGCACACAGTACTGCTACTCTATCC
AGAGCCTGTTTCTGGGCATCCTGAGCGTGATGCTGATCTTCGCATTCTTCCAAGAGCTGGTTA
TCGCCGGCATCGTGGAAAACGAGTGGAAGCGGACCTGCAGCAGACCCAAGAGCAACATCGT
GCTGCTGAGCGCCGAGGAAAAGAAAGAGCAGACCATCGAGATCAAAGAGGAAGTCGTCGG
CCTGACCGAGACAAGCAGCCAGCCTAAGAACGAAGAGGACATTGAGATCATCCCCATCCAA
GAAGAGGAAGAAGAAGAGACTGAGACAAACTTCCCCGAGCCTCCTCAGGACCAAGAGAGC
AGCCCCATTGAGAACGATAGCAGCCCT

Fig. 10U

SEQ ID NO: 86 CD20 DNA sequence 2
ATGACCACCCCCAGAAACAGCGTGAACGGCACCTTCCCCGCCGAGCCTATGAAGGGCCCTA
TCGCCATGCAGAGCGGCCCCAAGCCCCTGTTCAGACGGATGTCTAGCCTCGTGGGCCCTACC
CAGAGCTTCTTCATGAGAGAGAGCAAGACCCTGGGCGCCGTGCAGATCATGAACGGCCTGT
TCCACATTGCCCTGGGCGGCCTGCTGATGATCCCTGCCGGAATCTACGCCCCCATCTGCGTG
ACCGTGTGGTATCCTCTGTGGGGCGGCATCATGTACATCATCAGCGGCAGCCTGCTGGCCGC
CACCGAGAAGAACAGCAGAAAGTGCCTCGTGAAGGGCAAGATGATCATGAATAGCCTGAGC
CTGTTCGCCGCCATCTCCGGCATGATCCTGAGCATCATGGATATCCTGAATATCAAGATCAG
CCACTTCCTGAAGATGGAAAGCCTGAACTTCATCCGGGCCCACACCCCCTACATCAACATCT
ACAACTGCGAGCCCGCCAACCCCAGCGAGAAGAATAGCCCCAGCACCCAGTACTGCTACTC
TATCCAGTCCCTGTTCCTGGGCATCCTGAGCGTGATGCTGATCTTCGCATTTTTTCAAGAGCT
CGTGATCGCCGGCATCGTGGAAAACGAGTGGAAGCGGACCTGCAGCCGGCCCAAGAGCAAC
ATCGTGCTGCTGAGCGCCGAGGAAAAGAAAGAGCAGACCATCGAGATCAAAGAGGAAGTC
GTGGGCCTGACCGAGACAAGCTCCCAGCCCAAGAACGAAGAGGACATTGAGATCATCCCAA
TCCAGGAAGAAGAGGAAGAGGAAACCGAGACTAACTTCCCCGAGCCCCCCCAGGACCAGG
AAAGCAGCCCCATCGAGAACGACAGCAGCCCCtga

SEQ ID NO: 87 Gal4 amino acid sequence
MKLLSSIEQACDICRLKKLKCSKEKPKCAKCLKNNWECRYSPKTKRSPLTRAHLTEVESRLERLE
QLFLLIFPREDLDMILKMDSLQDIKALLTGLFVQDNVNKDAVTDRLASVETDMPLTLRQHRISAT
SSSEESSNKGQRQLTVSAAAGGSGGSGGS

SEQ ID NO: 88 Gal4 DNA sequence
ATGAAACTGCTGAGCAGCATTGAACAGGCGTGCGATATTTGCCGCCTGAAAAAACTGAAAT
GCAGCAAAGAAAAACCGAAATGCGCGAAATGCCTGAAAAACAACTGGGAATGCCGCTATA
GCCCGAAAACCAAACGCAGCCCGCTGACCCGCGCGCATCTGACCGAAGTGGAAAGCCGCCT
GGAACGCCTGGAACAGCTGTTTCTGCTGATTTTTCCGCGCGAAGATCTGGATATGATTCTGA
AAATGGATAGCCTGCAGGATATTAAAGCGCTGCTGACCGGCCTGTTTGTGCAGGATAACGTG
AACAAAGATGCGGTGACCGATCGCCTGGCGAGCGTGGAAACCGATATGCCGCTGACCCTGC
GCCAGCATCGCATTAGCGCGACCAGCAGCAGCGAAGAAAGCAGCAACAAAGGCCAGCGCC
AGCTGACCGTGAGCGCGGCGGCGGGCGGCAGCGGCGGCAGCGGCGGCAGC

SEQ ID NO: 89 VP64 amino acid sequence
DALDDFDLDMLGSDALDDFDLDMLGSDALDDFDLDMLGSDALDDFDLDML

SEQ ID NO: 90 VP64 DNA sequence
GATGCGCTGGATGATTTTGATCTGGATATGCTGGGCAGCGATGCGCTGGATGATTTTGATCT
GGATATGCTGGGCAGCGATGCGCTGGATGATTTTGATCTGGATATGCTGGGCAGCGATGCGC
TGGATGATTTTGATCTGGATATGCTG

SEQ ID NO: 91 IgG1 short hinge domain amino acid sequence 2
DLEPKSCDKTHTCPPCPDPK

SEQ ID NO: 92 IgG1 short hinge domain DNA sequence 2
GATCTCGAGCCCAAATCTTGTGACAAAACTCACACATGCCCACCGTGCCCGGATCCCAAG

Fig. 10V

<u>SEQ ID NO: 93</u> Leader.EDB-synNotch amino acid sequence
Italic: *Leader Sequence*
Bold: scFV L19
Bold & italic: *minimal regulatory region of human Notch-1 including transmembrane domain (underlined)*
Double underline: <u><u>Gal4</u></u>
Wave underline: <u>VP64</u>

*MDWIWRILFLVGAATGAHS***EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIK** *ILDYSFGGGAGRDIPPPLIEEACEL
PECQEDAGNKVCSLQCNNHACGWDGGDCSLNFNDPWKNCTQSLQCWKYFSDGHCDSQCNSAGCLFDGFDC
QRAEGQCNPLYDQYCKDHFSDGHCDQGCNSAECEWDGLDCAEHVPERLAAGTLVVVVLMPPEQLRNSSFH
FLRELSRVLHTNVVFKRDAHGQQMIFPYYGREEELRKHPIKRAAEGWAAPDALLGQVKASLLPGGSEGGR
RRRELDPMDVRGSIVYLEIDNRQCVQASSQCFQSATDVAAFLGALASLGSLNIPYKIEAVQSETVEPPPP
AQLHFMYVAAAAFVLLFFVGCGVLLSRKRRR*<u>MKLLSSIEQACDICRLKKLKCSKEKPKCAKCLKNNWECR
YSPKTKRSPLTRAHLTEVESRLERLEQLFLLIFPREDLDMILKMDSLQDIKALLTGLFVQDNVNKDAVTD
RLASVETDMPLTLRQHRISATSSSEESSNKGQRQLTVSAAAGGSGGSGGS</u><u><u>DALDDFDLDMLGSDALDDFD
LDMLGSDALDDFDLDMLGSDALDDFDLDML</u></u>

Fig. 10W

SEQ ID NO: 94 Leader.EDB-synNotch DNA sequence

*ATGGACTGGATCTGGCGCATCCTCTTCCTCGTCGGCGCTGCTACCGGCGCTCATTCT*GAGGTTCAGCTTC
TTGAGTCTGGGGGCGGCCTGGTGCAACCTGGTGGCAGTCTTAGGCTGAGTTGCGCCGCGTCAGGGTTTAC
TTTTTCTTCCTTCAGCATGTCATGGGTCCGCCAGGCTCCAGGTAAGGGCCTGGAATGGGTTAGTAGCATC
AGTGGCAGTAGTGGTACAACATACTACGCTGATAGTGTTAAAGGGAGATTCACTATAAGTAGGGATAATT
CTAAAAATACCCTTTATCTGCAAATGAATTCTTTGAGGGCCGAAGATACTGCGGTCTATTACTGTGCCAA
ACCTTTTCCATACTTTGATTACTGGGGCCAGGGGACGCTTGTCACTGTCTCCTCTGGCGACGGCTCCTCC
GGCGGAAGTGGAGGCGCGTCAGAAATTGTACTGACTCAGTCCCCGGGCACGCTCTCACTCAGTCCAGGCG
AAAGAGCTACGTTGTCTTGTCGCGCAAGCCAGTCCGTAAGCTCTAGCTTCCTCGCATGGTATCAACAAAA
GCCCGGGCAGGCTCCGCGGCTGCTCATTTACTATGCTAGTTCAAGGGCTACGGGAATTCCAGACCGATTT
AGTGGATCTGGGAGTGGAACTGACTTCACACTTACGATCAGCAGGCTTGAGCCGGAAGATTTTGCCGTGT
ACTACTGCCAGCAAACTGGAAGAATCCCCCCAACATTCGGACAAGGCACGAAGGTGGAAATCAAGATTCT
GGATTATAGCTTTGGCGGCGGCGCGGGCCGCGATATTCCGCCGCCGCTGATTGAAGAAGCGTGCGAACTG
CCGGAATGCCAGGAAGATGCGGGCAACAAAGTGTGCAGCCTGCAGTGCAACAACCATGCGTGCGGCTGGG
ATGGCGGCGATTGCAGCCTGAACTTTAACGATCCGTGGAAAAACTGCACCCAGAGCCTGCAGTGCTGGAA
ATATTTTAGCGATGGCCATTGCGATAGCCAGTGCAACAGCGCGGGCTGCCTGTTTGATGGCTTTGATTGC
CAGCGCGCGGAAGGCCAGTGCAACCCGCTGTATGATCAGTATTGCAAAGATCATTTTAGCGATGGCCATT
GCGATCAGGGCTGCAACAGCGCGGAATGCGAATGGGATGGCCTGGATTGCGCGGAACATGTGCCGGAACG
CCTGGCGGCGGGCACCCTGGTGGTGGTGGTGCTGATGCCGCCGGAACAGCTGCGCAACAGCAGCTTTCAT
TTTCTGCGCGAACTGAGCCGCGTGCTGCATACCAACGTGGTGTTTAAACGCGATGCGCATGGCCAGCAGA
TGATTTTTCCGTATTATGGCCGCGAAGAAGAACTGCGCAAACATCCGATTAAACGCGCGGCGGAAGGCTG
GGCGGCGCCGGATGCGCTGCTGGGCCAGGTGAAAGCGAGCCTGCTGCCGGGCGGCAGCGAAGGCGGCCGC
CGCCGCCGCGAACTGGATCCGATGGATGTGCGCGGCAGCATTGTGTATCTGGAAATTGATAACCGCCAGT
GCGTGCAGGCGAGCAGCCAGTGCTTTCAGAGCGCGACCGATGTGGCGGCGTTTCTGGGCGCGCTGGCGAG
CCTGGGCAGCCTGAACATTCCGTATAAAATTGAAGCGGTGCAGAGCGAAACCGTGGAACCGCCGCCGCCG
GCGCAGCTGCATTTTATGTATGTGGCGGCGGCGGCGTTTGTGCTGCTGTTTTTTGTGGGCTGCGGCGTGC
TGCTGAGCCGCAAACGCCGCCGC*ATGAAACTGCTGAGCAGCATTGAACAGGCGTGCGATATTTGCCGCCT
GAAAAAACTGAAATGCAGCAAAGAAAAACCGAAATGCGCGAAATGCCTGAAAAACAACTGGGAATGCCGC
TATAGCCCGAAAACCAAACGCAGCCCGCTGACCCGCGCGCATCTGACCGAAGTGGAAAGCCGCCTGGAAC
GCCTGGAACAGCTGTTTCTGCTGATTTTTCCGCGCGAAGATCTGGATATGATTCTGAAAATGGATAGCCT
GCAGGATATTAAAGCGCTGCTGACCGGCCTGTTTGTGCAGGATAACGTGAACAAAGATGCGGTGAC
CGATCGCCTGGCGAGCGTGGAAACCGATATGCCGCTGACCCTGCGCCAGCATCGCATTAGCGCG
ACCAGCAGCAGCGAAGAAAGCAGCAACAAAGGCCAGCGCCAGCTGACCGTGAGCGCGGCGGCGG
GCGGCAGCGGCGGCAGCGGCGGCAGCGATGCGCTGGATGATTTTGATCTGGATATGCTGGGCAG
CGATGCGCTGGATGATTTTGATCTGGATATGCTGGGCAGCGATGCGCTGGATGATTTTGATCTG
GATATGCTGGGCAGCGATGCGCTGGATGATTTTGATCTGGATATGCTG*

Fig. 10X

SEQ ID NO: 95 L19.SH.CD28TM.CD28. ζ CAR amino acid sequence
Bold: scFV L19
Dotted underline: IgG1 Short Hinge
Regular: additional amino acids before and after Hinge
Dashed underline: CD28 Transmembrane Domain
Bold & italic: *CD28.zeta (CD28 underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKDLEPKSCDKTHTCPPCPDPKFWVLVVVGGVLACYSLLVTVAFII
FWV*RSKRSRLLHSDYMNMTPRRPGPTRKHYQPYAPPRDFAAYRSRVKFSRSADAPAYQQGQNQLYNELNL*
*GRREEYDVLDKRRGRDPEMGGKPRRKNPQEGLYNELQKDKMAEAYSEIGMKGERRRGKGHDGLYQGLSTA*
*TKDTYDALHMQALPPR*

SEQ ID NO: 96 L19.SH.CD28TM.CD28.ζ CAR DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGGATCTCGAGCCCAAATCTTGTGACAAAACTCACACATGCCCACCGTGCCCGGATCCCAAGTT
CTGGGTGCTGGTGGTCGTGGGCGGAGTGCTGGCCTGTTACAGCCTGCTCGTGACCGTGGCCTTCATCATC
TTTTGGGTG*CGCAGCAAGCGGAGCCGGCTGCTGCACAGCGACTACATGAACATGACCCCCAGACGGCCTG*
*GCCCCACCAGAAAGCACTACCAGCCTTACGCCCCTCCCAGAGACTTCGCCGCCTACCGGTCCAGAGTGAA*
*GTTCAGCAGAAGCGCCGACGCCCCTGCCTATCAGCAGGGCCAGAACCAGCTGTACAACGAGCTGAACCTG*
*GGCAGACGGGAAGAGTACGACGTGCTGGACAAGCGGAGAGGCAGGGACCCTGAGATGGGCGGCAAGCCCA*
*GAAGAAAGAACCCCCAGGAAGGCCTGTATAACGAACTGCAGAAAGACAAGATGGCCGAGGCCTACAGCGA*
*GATCGGCATGAAGGGCGAGCGGAGAAGAGGCAAGGGCACGATGGCCTGTACCAGGGACTGAGCACCGCC*
*ACCAAGGACACCTACGACGCCCTGCACATGCAGGCCCTGCCTCCAAGA*

SEQ ID NO: 97 L19.CD8astalk.CD8αTM.CD28.ζ amino acid sequence
Bold: scFV L19
Dotted underline: CD8astalk.CD8aTM
Bold & italic: *CD28.zeta (CD28 underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKPAKPTTTPAPRPPTPAPTIASQPLSLRPEACRPAAGGAVHTRGL
DFACDIYIWAPLAGTCGVLLLSLVITLYCNHRN*RSKRSRLLHSDYMNMTPRRPGPTRKHYQPYAPPRDFA*
*AYRSRVKFSRSADAPAYQQGQNQLYNELNLGRREEYDVLDKRRGRDPEMGGKPRRKNPQEGLYNELQKDK*
*MAEAYSEIGMKGERRRGKGHDGLYQGLSTATKDTYDALHMQALPPR*

Fig. 10Y

<u>SEQ ID NO: 98</u> L19.CD8αstalk.CD8αTM.CD28.ζ DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
<u>AAATCAAG</u>CCAGCCAAGCCCACCACAACCCCTGCTCCTAGACCTCCTACCCCAGCCCCTACCATTGCCTC
CCAGCCACTGTCTCTGAGGCCCGAGGCTTGTAGACCTGCTGCAGGCGGAGCCGTGCACACCAGAGGACTG
GATTTCGCCTGCGACATCTATATCTGGGCCCCTCTGGCCGGCACCTGTGGCGTGCTGCTGCTGTCACTCG
TGATCACCCTGTACTGCAACCACCGGAAC*CGCAGCAAGCGGAGCCGGCTGCTGCACAGCGACTACATGAA*
*CATGACCCCCAGACGGCCTGGCCCCACCAGAAAGCACTACCAGCCTTACGCCCCTCCCAGAGACTTCGCC*
*GCCTACCGGTCCAGAGTGAAGTTCAGCAGAAGCGCCGACGCCCCTGCCTATCAGCAGGGCCAGAACCAGC*
*TGTACAACGAGCTGAACCTGGGCAGACGGGAAGAGTACGACGTGCTGGACAAGCGGAGAGGCAGGGACCC*
*TGAGATGGGCGGCAAGCCCAGAAGAAAGAACCCCCAGGAAGGCCTGTATAACGAACTGCAGAAAGACAAG*
*ATGGCCGAGGCCTACAGCGAGATCGGCATGAAGGGCGAGCGGAGAAGAGGCAAGGGCCACGATGGCCTGT*
*ACCAGGGACTGAGCACCGCCACCAAGGACACCTACGACGCCCTGCACATGCAGGCCCTGCCTCCAAGA*

<u>SEQ ID NO: 99</u> L19.CD8αstalk.CD8αTM.41BB.ζ amino acid sequence
Bold: scFV L19
Dotted underline: CD8αstalk.CD8αTM
Bold & Italic: *41BB.zeta (41BB underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKPAKPTTTPAPRPPTPAPTIASQPLSLRPEACRPAAGGAVHTRGL
DFACDIYIWAPLAGTCGVLLLSLVITLYCNHRN*KRGRKKLLYIFKQPFMRPVQTTQEEDGCSCRFPEEEE*
*GGCELRVKFSRSADAPAYQQGQNQLYNELNLGRREEYDVLDKRRGRDPEMGGKPRRKNPQEGLYNELQKD*
*KMAEAYSEIGMKGERRRGKGHDGLYQGLSTATKDTYDALHMQALPPR*

Fig. 10Z

SEQ ID NO: 100  L19.CD8αstalk.CD8αTM.41BB.ζ DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGCCAGCCAAGCCCACCACAACCCCTGCTCCTAGACCTCCTACCCCAGCCCCTACCATTGCCTC
CCAGCCACTGTCTCTGAGGCCCGAGGCTTGTAGACCTGCTGCAGGCGGAGCCGTGCACACCAGAGGACTG
GATTTCGCCTGCGACATCTATATCTGGGCCCCTCTGGCCGGCACCTGTGGCGTGCTGCTGCTGTCACTCG
TGATCACCCTGTACTGCAACCACCGGAAC*AAACGCGGCCGCAAAAAACTGCTGTATATTTTTAAACAGCC*
*GTTTATGCGCCCGGTGCAGACCACCCAGGAAGAAGATGGCTGCAGCTGCCGCTTTCCGGAAGAAGAAGAA*
*GGCGGCTGCGAACTGCGCGTGAAATTTAGCCGCAGCGCGGATGCGCCGGCGTATCAGCAGGGCCAGAACC*
*AGCTGTATAACGAACTGAACCTGGGCCGCCGCGAAGAATATGATGTGCTGGATAAACGCCGCGGCCGCGA*
*TCCGGAAATGGGCGGCAAACCGCGCCGCAAAAACCCGCAGGAAGGCCTGTATAACGAACTGCAGAAAGAT*
*AAAATGGCGGAAGCGTATAGCGAAATTGGCATGAAAGGCGAACGCCGCCGCGGCAAAGGCCATGATGGCC*
*TGTATCAGGGCCTGAGCACCGCGACCAAAGATACCTATGATGCGCTGCATATGCAGGCGCTGCCGCCGCG*
*C*

SEQ ID NO: 101 L19.CD8αstalk.CD8αTM.OX40.ζ amino acid sequence
Bold: scFV L19
Dotted underline: CD8astalk.CD8aTM
Bold & italic: *OX40.zeta (OX40 underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKPAKPTTTPAPRPPTPAPTIASQPLSLRPEACRPAAGGAVHTRGL
DFACDIYIWAPLAGTCGVLLLSLVITLYCNHRN*RDQRLPPDAHKPPGGGSFRTPIQEEQADAHSTLAKIR*
*VKFSRSADAPAYQQGQNQLYNELNLGRREEYDVLDKRRGRDPEMGGKPRRKNPQEGLYNELQKDKMAEAY*
*SEIGMKGERRRGKGHDGLYQGLSTATKDTYDALHMQAL*PPR

Fig. 10AA

SEQ ID NO: 102 L19.CD8αstalk.CD8αTM.OX40.ζ DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGCCAGCCAAGCCCACCACAACCCCTGCTCCTAGACCTCCTACCCCAGCCCCTACCATTGCCTC
CCAGCCACTGTCTCTGAGGCCCGAGGCTTGTAGACCTGCTGCAGGCGGAGCCGTGCACACCAGAGGACTG
GATTTCGCCTGCGACATCTATATCTGGGCCCCTCTGGCCGGCACCTGTGGCGTGCTGCTGCTGTCACTCG
TGATCACCCTGTACTGCAACCACCGGAAC*CGCGATCAGCGCCTGCCGCCGGATGCGCATAAACCGCCGGG*
*CGGCGGCAGCTTTCGCACCCCGATTCAGGAAGAACAGGCGGATGCGCATAGCACCCTGGCGAAAATTCGC*
*GTGAAATTTAGCCGCAGCGCGGATGCGCCGGCGTATCAGCAGGGCCAGAACCAGCTGTATAACGAACTGA*
*ACCTGGGCCGCCGCGAAGAATATGATGTGCTGGATAAACGCCGCGGCCGCGATCCGGAAATGGGCGGCAA*
*ACCGCGCCGCAAAAACCCGCAGGAAGGCCTGTATAACGAACTGCAGAAAGATAAAATGGCGGAAGCGTAT*
*AGCGAAATTGGCATGAAAGGCGAACGCCGCCGCGGCAAAGGCCATGATGGCCTGTATCAGGGCCTGAGCA*
*CCGCGACCAAAGATACCTATGATGCGCTGCATATGCAGGCGCTG*CCGCCGCGC

SEQ ID NO: 103 L19.CD8αstalk.CD8αTM.MyD88.CD40.ζ amino acid sequence
Bold: scFV L19
Dotted underline: CD8astalk.CD8aTM
Bole&italic: *MyD88.CD40.zeta (MyD88.CD40 underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKPAKPTTTPAPRPPTPAPTIASQPLSLRPEACRPAAGGAVHTRGL
DFACDIYIWAPLAGTCGVLLLSLVITLYCNHRNV*AAGGPGAGSAAPVSSTSSLPLAALNMRVRRRLSLFL*
*NVRTQVAADWTALAEEMDFEYLEIRQLETQADPTGRLLDAWQGRPGASVGRLLELLTKLGRDDVLLELGP*
*SIEEDCQKYILKQQQEEAEKPLQVAAVDSSVPRTAELAGITTLDDPLGHMPERFDAFICYCPSDIVEKKV*
*AKKPTNKAPHPKQEPQEINFPDDLPGSNTAAPVQETLHGCQPVTQEDGKESRISVQERQRVKFSRSADAP*
*AYQQGQNQLYNELNLGRREEYDVLDKRRGRDPEMGGKPRRKNPQEGLYNELQKDKMAEAYSEIGMKGERR*
*RGKGHDGLYQGLSTATKDTYDALHMQALPPR*

Fig. 10BB

SEQ ID NO: 104 L19.CD8αstalk.CD8αTM.MyD88.CD40.ζ DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGCCAGCCAAGCCCACCACAACCCCTGCTCCTAGACCTCCTACCCCAGCCCCTACCATTGCCTC
CCAGCCACTGTCTCTGAGGCCCGAGGCTTGTAGACCTGCTGCAGGCGGAGCCGTGCACACCAGAGGACTG
GATTTCGCCTGCGACATCTATATCTGGGCCCCTCTGGCCGGCACCTGTGGCGTGCTGCTGCTGTCACTCG
TGATCACCCTGTACTGCAACCACCGGAAC*GCTGCTGGCGGACCTGGCGCCGGATCTGCTGCTCCTGTGTC
TAGCACAAGCAGCCTGCCTCTGGCCGCCCTGAACATGAGAGTGCGGAGAAGGCTGAGCCTGTTCCTGAAC
GTGCGGACACAGGTGGCCGCCGATTGGACAGCCCTGGCCGAGGAAATGGACTTCGAGTACCTGGAAATCC
GGCAGCTGGAAACCCAGGCCGACCCTACAGGCAGACTGCTGGATGCTTGGCAGGGCAGACCAGGCGCTTC
TGTGGGAAGGCTGCTGGAACTGCTGACCAAGCTGGGCAGGGACGACGTGCTGCTGGAACTGGGCCCTAGC
ATCGAAGAGGACTGCCAGAAGTACATCCTGAAGCAGCAGCAGGAAGAGGCCGAGAAGCCTCTGCAGGTGG
CAGCCGTGGATAGCAGCGTGCCAAGAACAGCCGAGCTGGCCGGCATCACCACCCTGGATGATCCTCTGGG
CCACATGCCCGAGAGATTCGACGCCTTCATCTGCTACTGCCCCAGCGACATC*GTGGAA**AAGAAGGTGGCC
AAGAAGCCCACCAACAAGGCCCCCACCCCAAGCAGGAACCCCAGGAAATCAACTTCCCCGACGACCTGC
CCGGCAGCAATACTGCTGCACCCGTGCAGGAAACCCTGCACGGCTGTCAGCCTGTGACCCAGGAAGATGG
CAAAGAAAGCCGGATCTCTGTGCAGGAACGCCAGAGAGTGAAGTTCAGCAGGAGCGCAGACGCCCCCGCG
TACCAGCAGGGCCAGAACCAGCTCTATAACGAGCTCAATCTAGGACGAAGAGAGGAGTACGATGTTTTGG
ACAAGAGACGTGGCCGGGACCCTGAGATGGGCGGCAAGCCCAGAAGAAAGAACCCCCAGGAAGGCCTGTA
TAACGAACTGCAGAAAGACAAGATGGCCGAGGCCTACAGCGAGATCGGCATGAAGGGCGAGCGGAGAAGA
GGCAAGGGCCACGATGGCCTGTACCAGGGACTGAGCACCGCCACCAAGGACACCTACGACGCCCTGCACA
TGCAGGCCCTGCCTCCAAGA*

SEQ ID NO: 105 L19.SH.CD28TM.41BB.ζ amino acid sequence
Bold: scFV L19
Dotted underline: IgG1 Short Hinge
Regular: additional amino acids before and after Hinge
Dashed underline: CD28 Transmembrane Domain
Bold & italic: *41BB.zeta (41BB underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKDLEPKSCDKTHTCPPCPDPKFWVLVVVGGVLACYSLLVTVAFII
FWV*KRGRKKLLYIFKQPFMRPVQTTQEEDGCSCRFPEEEEGGCELRVKFSRSADAPAYQQGQNQLYNELN*
*LGRREEYDVLDKRRGRDPEMGGKPRRKNPQEGLYNELQKDKMAEAYSEIGMKGERRRGKGHDGLYQGLST*
*ATKDTYDALHMQALPPR*

Fig. 10CC

SEQ ID NO: 106 L19.SH.CD28TM.41BB.ζ DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGGATCTCGAGCCCAAATCTTGTGACAAAACTCACACATGCCCACCGTGCCCGGATCCCAAGTT
CTGGGTGCTGGTGGTCGTGGGCGGAGTGCTGGCCTGTTACAGCCTGCTCGTGACCGTGGCCTTCATCATC
TTTTGGGTGAAACGCGGCCGCAAAAAACTGCTGTATATTTTTAAACAGCCGTTTATGCGCCCGGTGCAGA
CCACCCAGGAAGAAGATGGCTGCAGCTGCCGCTTTCCGGAAGAAGAAGAAGGCGGCTGCGAACTGCGCGT
GAAATTTAGCCGCAGCGCGGATGCGCCGGCGTATCAGCAGGGCCAGAACCAGCTGTATAACGAACTGAAC
CTGGGCCGCCGCGAAGAATATGATGTGCTGGATAAACGCCGCGGCCGCGATCCGGAAATGGGCGGCAAAC
CGCCGCGCAAAAACCCGCAGGAAGGCCTGTATAACGAACTGCAGAAAGATAAAATGGCGGAAGCGTATAG
CGAAATTGGCATGAAAGGCGAACGCCGCCGCGGCAAAGGCCATGATGGCCTGTATCAGGGCCTGAGCACC
GCGACCAAAGATACCTATGATGCGCTGCATATGCAGGCGCTGCCGCCGCGC

SEQ ID NO: 107 L19.SH.CD28TM.OX40.ζ amino acid sequence
Bold: scFV L19
Dotted underline: IgG1 Short Hinge
Regular: additional amino acids before and after Hinge
Dashed underline: CD28 Transmembrane Domain
Bold & italic: *OX40.zeta (OX40 underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKDLEPKSCDKTHTCPPCPDPKFWVLVVVGGVLACYSLLVTVAFII
FWV*RDQRLPPDAHKPPGGGSFRTPIQEEQADAHSTLAKIRVKFSRSADAPAYQQGQNQLYNELNLGRREE*
*YDVLDKRRGRDPEMGGKPRRKNPQEGLYNELQKDKMAEAYSEIGMKGERRRGKGHDGLYQGLSTATKDTY*
*DALHMQALPPR*

Fig. 10DD

SEQ ID NO: 108 L19.SH.CD28TM.OX40.ζ DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGGATCTCGAGCCCAAATCTTGTGACAAAACTCACACATGCCCACCGTGCCCGGATCCCAAGTT
CTGGGTGCTGGTGGTCGTGGGCGGAGTGCTGGCCTGTTACAGCCTGCTCGTGACCGTGGCCTTCATCATC
TTTTGGGTG*CGCGATCAGCGCCTGCCGCCGGATGCGCATAAACCGCCGGGCGGCGGCAGCTTTCGCACCC*
*CGATTCAGGAAGAACAGGCGGATGCGCATAGCACCCTGGCGAAAATTCGCGTGAAATTTAGCCGCAGCGC*
*GGATGCGCCGGCGTATCAGCAGGGCCAGAACCAGCTGTATAACGAACTGAACCTGGGCCGCCGCGAAGAA*
*TATGATGTGCTGGATAAACGCCGCGGCCGCGATCCGGAAATGGGCGGCAAACCGCGCCGCAAAAACCCGC*
*AGGAAGGCCTGTATAACGAACTGCAGAAAGATAAAATGGCGGAAGCGTATAGCGAAATTGGCATGAAAGG*
*CGAACGCCGCCGCGGCAAAGGCCATGATGGCCTGTATCAGGGCCTGAGCACCGCGACCAAAGATACCTAT*
*GATGCGCTGCATATGCAGGCGCTG*CCGCCGCGC

SEQ ID NO: 109 L19.SH.CD28TM.MyD88.CD40.ζ amino acid sequence
Bold: scFV L19
Dotted underline: IgG1 Short Hinge
Regular: additional amino acids
Dashed underline: CD28 Transmembrane Domain
Bold & italic: *MyD88.CD40.zeta* *(MyD88.CD40 underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKDLEPKSCDKTHTCPPCPDPKFWVLVVVGGVLACYSLLVTVAFII
FWV*AAGGPGAGSAAPVSSTSSLPLAALNMRVRRRLSLFLNVRTQVAADWTALAEEMDFEYLEIRQLETQA*
*DPTGRLLDAWQGRPGASVGRLLELLTKLGRDDVLLELGPSIEEDCQKYILKQQQEEAEKPLQVAAVDSSV*
*PRTAELAGITTLDDPLGHMPERFDAFICYCPSDI*VE*KKVAKKPTNKAPHPKQEPQEINFPDDLPGSNTAA*
*PVQETLHGCQPVTQEDGKESRISVQERQRVKFSRSADAPAYQQGQNQLYNELNLGRREEYDVLDKRRGRD*
*PEMGGKPRRKNPQEGLYNELQKDKMAEAYSEIGMKGERRRGKGHDGLYQGLSTATKDTYDALHMQALPPR*

Fig. 10EE

SEQ ID NO: 110 L19.SH.CD28TM.MyD88.CD40.ζ DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGGATCTCGAGCCCAAATCTTGTGACAAAACTCACACATGCCCACCGTGCCCGGATCCCAAGTT
CTGGGTGCTGGTGGTCGTGGGCGGAGTGCTGGCCTGTTACAGCCTGCTCGTGACCGTGGCCTTCATCATC
TTTTGGGGTG*GCTGCTGGCGGACCTGGCGCCGGATCTGCTGCTCCTGTGTCTAGCACAAGCAGCCTGCCTC*
*TGGCCGCCCTGAACATGAGAGTGCGGAGAAGGCTGAGCCTGTTCCTGAACGTGCGGACACAGGTGGCCGC*
*CGATTGGACAGCCCTGGCCGAGGAAATGGACTTCGAGTACCTGGAAATCCGGCAGCTGGAAACCCAGGCC*
*GACCCTACAGGCAGACTGCTGGATGCTTGGCAGGGCAGACCAGGCGCTTCTGTGGGAAGGCTGCTGGAAC*
*TGCTGACCAAGCTGGGCAGGGACGACGTGCTGCTGGAACTGGGCCCTAGCATCGAAGAGGACTGCCAGAA*
*GTACATCCTGAAGCAGCAGCAGGAAGAGGCCGAGAAGCCTCTGCAGGTGGCAGCCGTGGATAGCAGCGTG*
*CCAAGAACAGCCGAGCTGGCCGGCATCACCACCCTGGATGATCCTCTGGGCCACATGCCCGAGAGATTCG*
*ACGCCTTCATCTGCTACTGCCCCAGCGACATCGTGGAA*AAGAAGGTGGCCAAGAAGCCCACCAACAAGGC
CCCCCACCCCAAGCAGGAACCCCAGGAAATCAACTTCCCCGACGACCTGCCCGGCAGCAATACTGCTGCA
CCCGTGCAGGAAACCCTGCACGGCTGTCAGCCTGTGACCCAGGAAGATGGCAAAGAAAGCCGGATCTCTG
*TGCAGGAACGCCAGAGAGTGAAGTTCAGCAGGAGCGCAGACGCCCCCGCGTACCAGCAGGGCAGAACCA*
*GCTCTATAACGAGCTCAATCTAGGACGAAGAGAGGAGTACGATGTTTTGGACAAGAGACGTGGCCGGGAC*
*CCTGAGATGGGCGGCAAGCCCAGAAGAAAGAACCCCCAGGAAGGCCTGTATAACGAACTGCAGAAAGACA*
*AGATGGCCGAGGCCTACAGCGAGATCGGCATGAAGGGCGAGCGGAGAAGAGGCAAGGGCCACGATGGCCT*
*GTACCAGGGACTGAGCACCGCCACCAAGGACACCTACGACGCCCTGCACATGCAGGCCCTGCCTCCAAGA*

SEQ ID NO: 111 L19.CD28H/TM.CD28.ζ amino acid sequence
Bold: scFV L19
Dotted underline: CD28 Hinge
Dashed underline: CD28 Transmembrane Domain
Bold&italic: *CD28.zeta (CD28 underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKIEVMYPPPYLDNEKSNGTIIHVKGKHLCPSPLFPGPSKPFWVLV
VVGGVLACYSLLVTVAFIIFWV*RSKRSRLLHSDYMNMTPRRPGPTRKHYQPYAPPRDFAAYRSRVKFSRS*
*ADAPAYQQGQNQLYNELNLGRREEYDVLDKRRGRDPEMGGKPRRKNPQEGLYNELQKDKMAEAYSEIGMK*
*GERRRGKGHDGLYQGLSTATKDTYDALHMQALPPR*

Fig. 10FF

SEQ ID NO: 112 L19.CD28H/TM.CD28.ζ DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGATCGAAGTGATGTACCCGCCTCCTTACCTGGACAACGAGAAGTCCAACGGCACCATCATCCA
CGTGAAGGGAAAGCACCTGTGTCCTTCTCCACTGTTCCCCGGACCTAGCAAGCCTTCTGGGTGCTGGTGG
TCGTGGGCGGAGTGCTGGCCTGTTACAGCCTGCTCGTGACCGTGGCCTTCATCATCTTTTGGGTG*CGCAG*
*CAAGCGGAGCCGGCTGCTGCACAGCGACTACATGAACATGACCCCCAGACGGCCTGGCCCCACCAGAAAG*
*CACTACCAGCCTTACGCCCCTCCCAGAGACTTCGCCGCCTACCGGTCCAGAGTGAAGTTCAGCAGAAGCG*
*CCGACGCCCCTGCCTATCAGCAGGGCCAGAACCAGCTGTACAACGAGCTGAACCTGGGCAGACGGGAAGA*
*GTACGACGTGCTGGACAAGCGGAGAGGCAGGGACCCTGAGATGGGCGGCAAGCCCAGAAGAAAGAACCCC*
*CAGGAAGGCCTGTATAACGAACTGCAGAAAGACAAGATGGCCGAGGCCTACAGCGAGATCGGCATGAAGG*
*GCGAGCGGAGAAGAGGCAAGGGCCACGATGGCCTGTACCAGGGACTGAGCACCGCCACCAAGGACACCTA*
*CGACGCCCTGCACATGCAGGCCCTGCCTCCAAGA*

SEQ ID NO: 113 L19.CD28H/TM.41BB.ζ amino acid sequence
Bold: scFV L19
Dotted underline: CD28 Hinge
Dashed underline: CD28 Transmembrane Domain
Bold&italic: *41BB.zeta (41BB underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKIEVMYPPPYLDNEKSNGTIIHVKGKHLCPSPLFPGPSKPFWVLV
VVGGVLACYSLLVTVAFIIFWV*KRGRKKLLYIFKQPFMRPVQTTQEEDGCSCRFPEEEEGGCELRVKFSR*
*SADAPAYQQGQNQLYNELNLGRREEYDVLDKRRGRDPEMGGKPRRKNPQEGLYNELQKDKMAEAYSEIGM*
*KGERRRGKGHDGLYQGLSTATKDTYDALHMQALPPR*

Fig. 10GG

SEQ ID NO: 114 L19.CD28H/TM.41BB.ζ DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGATCGAAGTGATGTACCCGCCTCCTTACCTGGACAACGAGAAGTCCAACGGCACCATCATCCA
CGTGAAGGGAAAGCACCTGTGTCCTTCTCCACTGTTCCCCGGACCTAGCAAGCCTTCTGGGTGCTGGTGG
TCGTGGGCGGAGTGCTGGCCTGTTACAGCCTGCTCGTGACCGTGGCCTTCATCATCTTTTGGGTG*AAAC*
*GCGGCCGCAAAAAACTGCTGTATATTTTTAAACAGCCGTTTATGCGCCCGGTGCAGACCACCCA*
*GGAAGAAGATGGCTGCAGCTGCCGCTTTCCGGAAGAAGAAGAAGGCGGCTGCGAACTGCGCGTG*
*AAATTTAGCCGCAGCGCGGATGCGCCGGCGTATCAGCAGGGCCAGAACCAGCTGTATAACGAAC*
*TGAACCTGGGCCGCCGCAAGAATATGATGTGCTGGATAAACGCCGCGGCCGCGATCCGGAAAT*
*GGGCGGCAAACCGCGCCGCAAAAACCCGCAGGAAGGCCTGTATAACGAACTGCAGAAAGATAAA*
*ATGGCGGAAGCGTATAGCGAAATTGGCATGAAAGGCGAACGCCGCCGCGGCAAAGGCCATGATG*
*GCCTGTATCAGGGCCTGAGCACCGCGACCAAAGATACCTATGATGCTGCATATGCAGGCGCT*
*GCCGCCGCG*

SEQ ID NO: 115 L19.CD28H/TM.OX40.ζ amino acid sequence
Bold: scFV L19
Dotted underline: CD28 Hinge
Dashed underline: CD28 Transmembrane Domain
Bold&italic: *OX40.zeta (OX40 underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKIEVMYPPPYLDNEKSNGTIIHVKGKHLCPSPLFPGPSKPFWVLV
VVGGVLACYSLLVTVAFIIFWV*RDQRLPPDAHKPPGGGSFRTPIQEEQADAHSTLAKIRVKFSRSADAPA*
*YQQGQNQLYNELNLGRREEYDVLDKRRGRDPEMGGKPRRKNPQEGLYNELQKDKMAEAYSEIGMKGERRR*
*GKGHDGLYQGLSTATKDTYDALHMQALPPR*

Fig. 10HH

<u>SEQ ID NO: 116</u> L19.CD28H/TM.OX40.ζ DNA sequence
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGATCGAAGTGATGTACCCGCCTCCTTACCTGGACAACGAGAAGTCCAACGGCACCATCATCCA
CGTGAAGGGAAAGCACCTGTGTCCTTCTCCACTGTTCCCCGGACCTAGCAAGCCTTCTGGGTGCTGGTGG
TCGTGGGCGGAGTGCTGGCCTGTTACAGCCTGCTCGTGACCGTGGCCTTCATCATCTTTTGGGTG*CGCGA*
*TCAGCGCCTGCCGCCGGATGCGCATAAACCGCCGGGCGGCGGCAGCTTTC*
*GCACCCCGATTCAGGAAGAACAGGCGGATGCGCATAGCACCCTGGCGAAAATTCGCGTGAAATTTAGCCG*
*CAGCGCGGATGCGCCGGCGTATCAGCAGGGCCAGAACCAGCTGTATAACGAACTGAACCTGGGCCGCCGC*
*GAAGAATATGATGTGCTGGATAAACGCCGCGGCCGCGATCCGGAAATGGGCGGCAAACCGCGCCGCAAAA*
*ACCCGCAGGAAGGCCTGTATAACGAACTGCAGAAAGATAAAATGGCGGAAGCGTATAGCGAAATTGGCAT*
*GAAAGGCGAACGCCGCCGCGGCAAAGGCCATGATGGCCTGTATCAGGGCCTGAGCACCGCGACCAAAGAT*
*ACCTATGATGCGCTGCATATGCAGGCGCTG*CCGCCGCGC <u>SEQ ID NO: 117</u> L19.CD28H/TM.MyD88.CD40.ζ amino acid sequence
Bold: scFV L19
Dotted underline: CD28 Hinge
Regular: additional amino acids
Dashed underline: CD28 Transmembrane Domain
Bold & italic: *MyD88.CD40.zeta (MyD88.CD40 underlined)*
EVQLLESGGGLVQPGGSLRLSCAASGFTFSSFSMSWVRQAPGKGLEWVSSISGSSGTTYYADSVKGRFTI
SRDNSKNTLYLQMNSLRAEDTAVYYCAKPFPYFDYWGQGTLVTVSSGDGSSGGSGGASEIVLTQSPGTLS
LSPGERATLSCRASQSVSSSFLAWYQQKPGQAPRLLIYYASSRATGIPDRFSGSGSGTDFTLTISRLEPE
DFAVYYCQQTGRIPPTFGQGTKVEIKIEVMYPPPYLDNEKSNGTIIHVKGKHLCPSPLFPGPSKPFWVLV
VVGGVLACYSLLVTVAFIIFWV*AAGGPGAGSAAPVSSTSSLPLAALNMRVRRRLSLFLNVRTQVAADWTA*
*LAEEMDFEYLEIRQLETQADPTGRLLDAWQGRPGASVGRLLELLTKLGRDDVLLELGPSIEEDCQKYILK*
*QQQEEAEKPLQVAAVDSSVPRTAELAGITTLDDPLGHMPERFDAFICYCPSDI*VEKKVAKKPTNKAPHPK
QEPQEINFPDDLPGSNTAAPVQETLHGCQPVTQEDGKESRISVQERQRVKFSRSADAPAYQQGQNQLYNE
LNLGRREEYDVLDKRRGRDPEMGGKPRRKNPQEGLYNELQKDKMAEAYSEIGMKGERRRGKGHDGLYQGL
STATKDTYDALHMQALPPR

Fig. 10H

SEQ ID NO: 118 L19.CD28H/TM.MyD88.CD40.ζ DNA sequence

```
GAGGTTCAGCTTCTTGAGTCTGGGGGCGGCCTGGTGCAACCTGGTGGCAGTCTTAGGCTGAGTTGCGCCG
CGTCAGGGTTTACTTTTTCTTCCTTCAGCATGTCATGGGTCCGCCAGGCTCCAGGTAAGGGCCTGGAATG
GGTTAGTAGCATCAGTGGCAGTAGTGGTACAACATACTACGCTGATAGTGTTAAAGGGAGATTCACTATA
AGTAGGGATAATTCTAAAAATACCCTTTATCTGCAAATGAATTCTTTGAGGGCCGAAGATACTGCGGTCT
ATTACTGTGCCAAACCTTTTCCATACTTTGATTACTGGGGCCAGGGGACGCTTGTCACTGTCTCCTCTGG
CGACGGCTCCTCCGGCGGAAGTGGAGGCGCGTCAGAAATTGTACTGACTCAGTCCCCGGGCACGCTCTCA
CTCAGTCCAGGCGAAAGAGCTACGTTGTCTTGTCGCGCAAGCCAGTCCGTAAGCTCTAGCTTCCTCGCAT
GGTATCAACAAAGCCCGGGCAGGCTCCGCGGCTGCTCATTTACTATGCTAGTTCAAGGGCTACGGGAAT
TCCAGACCGATTTAGTGGATCTGGGAGTGGAACTGACTTCACACTTACGATCAGCAGGCTTGAGCCGGAA
GATTTTGCCGTGTACTACTGCCAGCAAACTGGAAGAATCCCCCCAACATTCGGACAAGGCACGAAGGTGG
AAATCAAGATCGAAGTGATGTACCCGCCTCCTTACCTGGACAACGAGAAGTCCAACGGCACCATCATCCA
CGTGAAGGGAAAGCACCTGTGTCCTTCTCCACTGTTCCCCGGACCTAGCAAGCCTTCTGGGTGCTGGTGG
TCGTGGGCGGAGTGCTGGCCTGTTACAGCCTGCTCGTGACCGTGGCCTTCATCATCTTTTGGGTGGCTGC
TGGCGGACCTGGCGCCGGATCTGCTGCTCCTGTGTCTAGCACAAGCAGCCTGCCTCTGGCCGCCCTGAAC
ATGAGAGTGCGGAGAAGGCTGAGCCTGTTCCTGAACGTGCGGACACAGGTGGCCGCCGATTGGACAGCCC
TGGCCGAGGAAATGGACTTCGAGTACCTGGAAATCCGGCAGCTGGAAACCCAGGCCGACCCTACAGGCAG
ACTGCTGGATGCTTGGCAGGGCAGACCAGGCGCTTCTGTGGGAAGGCTGCTGGAACTGCTGACCAAGCTG
GGCAGGGACGACGTGCTGCTGGAACTGGGCCCTAGCATCGAAGAGGACTGCCAGAAGTACATCCTGAAGC
AGCAGCAGGAAGAGGCCGAGAAGCCTCTGCAGGTGGCAGCCGTGGATAGCAGCGTGCCAAGAACAGCCGA
GCTGGCCGGCATCACCACCCTGGATGATCCTCTGGGCCACATGCCCGAGAGATTCGACGCCTTCATCTGC
TACTGCCCCAGCGACATCGTGGAAAAGAAGGTGGCCAAGAAGCCCACCAACAAGGCCCCCACCCCAAGC
AGGAACCCCAGGAAATCAACTTCCCCGACGACCTGCCCGGCAGCAATACTGCTGCACCCGTGCAGGAAAC
CCTGCACGGCTGTCAGCCTGTGACCCAGGAAGATGGCAAAGAAAGCCGGATCTCTGTGCAGGAACGCCAG
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGCGG
CAAGCCCAGAAGAAAGAACCCCCAGGAAGGCCTGTATAACGAACTGCAGAAAGACAAGATGGCCGAGGCC
TACAGCGAGATCGGCATGAAGGGCGAGCGGAGAAGAGGCAAGGGCCACGATGGCCTGTACCAGGGACTGA
GCACCGCCACCAAGGACACCTACGACGCCCTGCACATGCAGGCCCTGCCTCCAAGA
```

SEQ ID NO: 119 Leader.L19.SH.CD28TM.CD28.ζ CAR amino acid sequence
Italic: *Leader Sequence*
Bold: scFV L19
Dotted underline: IgG1 Short Hinge
Regular: additional amino acids before and after Hinge
Dashed underline: CD28 Transmembrane Domain
Bold & italic: *CD28.zeta (CD28 underlined)*

*MDWIWRILFLVGAATGAHS*EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPYFDYWGQGTLVTVSSGDGSS
GGSGGASEIVLTQSPGTLSLSPGERATLSCRASQSVSSSFLAWYQQKPGQAPRLLIYYASSRATGIPDRF
SGSGSGTDFTLTISRLEPEDFAVYYCQQTGRIPPTFGQGTKVEIKDLEPKSCDKTHTCPPCPDPKFWVLV
VVGGVLACYSLLVTVAFIIFWV*RSKRSRLLHSDYMNMTPRRPGPTRKHYQPYAPPRDFAAYRSRVKFSRS*
*ADAPAYQQGQNQLYNELNLGRREEYDVLDKRRGRDPEMGGKPRRKNPQEGLYNELQKDKMAEAYSEIGMK*
*GERRRGKGHDGLYQGLSTATKDTYDALHMQALPPR*

Fig. 10JJ

SEQ ID NO: 120 Leader.L19.SH.CD28TM.CD28.ζ CAR DNA sequence

*ATGGACTGGATCTGGCGCATCCTCTTCCTCGTCGGCGCTGCTACCGGCGCTCATTCTGAGGTTCAGCTTC*
TTGAGTCTGGGGGCGGCCTGGTGCAACCTGGTGGCAGTCTTAGGCTGAGTTGCGCCGCGTCAGGGTTTAC
TTTTTCTTCCTTCAGCATGTCATGGGTCCGCCAGGCTCCAGGTAAGGGCCTGGAATGGGTTAGTAGCATC
AGTGGCAGTAGTGGTACAACATACTACGCTGATAGTGTTAAAGGGAGATTCACTATAAGTAGGGATAATT
CTAAAAATACCCTTTATCTGCAAATGAATTCTTTGAGGGCCGAAGATACTGCGGTCTATTACTGTGCCAA
ACCTTTTCCATACTTTGATTACTGGGGCCAGGGGACGCTTGTCACTGTCTCCTCTGGCGACGGCTCCTCC
GGCGGAAGTGGAGGCGCGTCAGAAATTGTACTGACTCAGTCCCCGGGCACGCTCTCACTCAGTCCAGGCG
AAAGAGCTACGTTGTCTTGTCGCGCAAGCCAGTCCGTAAGCTCTAGCTTCCTCGCATGGTATCAACAAAA
GCCCGGGCAGGCTCCGCGGCTGCTCATTTACTATGCTAGTTCAAGGGCTACGGGAATTCCAGACCGATTT
AGTGGATCTGGGAGTGGAACTGACTTCACACTTACGATCAGCAGGCTTGAGCCGGAAGATTTTGCCGTGT
ACTACTGCCAGCAAACTGGAAGAATCCCCCCAACATTCGGACAAGGCACGAAGGTGGAAATCAAGGATCT
CGAGCCCAAATCTTGTGACAAAACTCACACATGCCCACCGTGCCCGGATCCCAAGTTCTGGGTGCTGGTG
GTCGTGGGCGGAGTGCTGGCCTGTTACAGCCTGCTCGTGACCGTGGCCTTCATCATCTTTTGGGTG*CGCA*
*GCAAGCGGAGCCGGCTGCTGCACAGCGACTACATGAACATGACCCCCAGACGGCCTGGCCCCACCAGAAA*
*GCACTACCAGCCTTACGCCCCTCCCAGAGACTTCGCCGCCTACCGGTCCAGAGTGAAGTTCAGCAGAAGC*
*GCCGACGCCCCTGCCTATCAGCAGGGCCAGAACCAGCTGTACAACGAGCTGAACCTGGGCAGACGGGAAG*
*AGTACGACGTGCTGGACAAGCGGAGAGGCAGGGACCCTGAGATGGGCGGCAAGCCCAGAAGAAAGAACCC*
*CCAGGAAGGCCTGTATAACGAACTGCAGAAAGACAAGATGGCCGAGGCCTACAGCGAGATCGGCATGAAG*
*GGCGAGCGGAGAAGAGGCAAGGGCCACGATGGCCTGTACCAGGGACTGAGCACCGCCACCAAGGACACCT*
*ACGACGCCCTGCACATGCAGGCCCTGCCTCCAAGA*

SEQ ID NO: 121 EDB-synNotch amino acid sequence
EVQLLESGGGLVQPGGSLRLSCAASGFTFSSFSMSWVRQAPGKGLEWVSSISGSSGTTYYADSVK
GRFTISRDNSKNTLYLQMNSLRAEDTAVYYCAKPFPYFDYWGQGTLVTVSSGDGSSGGSGGASE
IVLTQSPGTLSLSPGERATLSCRASQSVSSSFLAWYQQKPGQAPRLLIYYASSRATGIPDRFSGSGS
GTDFTLTISRLEPEDFAVYYCQQTGRIPPTFGQGTKVEIKILDYSFGGGAGRDIPPPLIEEACELPEC
QEDAGNKVCSLQCNNHACGWDGGDCSLNFNDPWKNCTQSLQCWKYFSDGHCDSQCNSAGCL
FDGFDCQRAEGQCNPLYDQYCKDHFSDGHCDQGCNSAECEWDGLDCAEHVPERLAAGTLVVV
VLMPPEQLRNSSFHFLRELSRVLHTNVVFKRDAHGQQMIFPYYGREEELRKHPIKRAAEGWAAP
DALLGQVKASLLPGGSEGGRRRRELDPMDVRGSIVYLEIDNRQCVQASSQCFQSATDVAAFLGA
LASLGSLNIPYKIEAVQSETVEPPPPAQLHFMYVAAAAFVLLFFVGCGVLLSRKRRRMKLLSSIEQ
ACDICRLKKLKCSKEKPKCAKCLKNNWECRYSPKTKRSPLTRAHLTEVESRLERLEQLFLLIFPRE
DLDMILKMDSLQDIKALLTGLFVQDNVNKDAVTDRLASVETDMPLTLRQHRISATSSSEESSNK
GQRQLTVSAAAGGSGGSGGSDALDDFDLDMLGSDALDDFDLDMLGSDALDDFDLDMLGSDAL
DDFDLDML

Fig. 10KK

SEQ ID NO: 122 EDB-synNotch DNA sequence
GAGGTTCAGCTTCTTGAGTCTGGGGGCGGCCTGGTGCAACCTGGTGGCAGTCTTAGGCTGAG
TTGCGCCGCGTCAGGGTTTACTTTTTCTTCCTTCAGCATGTCATGGGTCCGCCAGGCTCCAGG
TAAGGGCCTGGAATGGGTTAGTAGCATCAGTGGCAGTAGTGGTACAACATACTACGCTGAT
AGTGTTAAAGGGAGATTCACTATAAGTAGGGATAATTCTAAAAATACCCTTTATCTGCAAAT
GAATTCTTTGAGGGCCGAAGATACTGCGGTCTATTACTGTGCCAAACCTTTTCCATACTTTGA
TTACTGGGGCCAGGGGACGCTTGTCACTGTCTCCTCTGGCGACGGCTCCTCCGGCGGAAGTG
GAGGCGCGTCAGAAATTGTACTGACTCAGTCCCCGGGCACGCTCTCACTCAGTCCAGGCGAA
AGAGCTACGTTGTCTTGTCGCGCAAGCCAGTCCGTAAGCTCTAGCTTCCTCGCATGGTATCA
ACAAAAGCCCGGGCAGGCTCCGCGGCTGCTCATTTACTATGCTAGTTCAAGGGCTACGGGAA
TTCCAGACCGATTTAGTGGATCTGGGAGTGGAACTGACTTCACACTTACGATCAGCAGGCTT
GAGCCGGAAGATTTTGCCGTGTACTACTGCCAGCAAACTGGAAGAATCCCCCCAACATTCGG
ACAAGGCACGAAGGTGGAAATCAAGATTCTGGATTATAGCTTTGGCGGCGGCGCGGGCCGC
GATATTCCGCCGCCGCTGATTGAAGAAGCGTGCGAACTGCCGGAATGCCAGGAAGATGCGG
GCAACAAAGTGTGCAGCCTGCAGTGCAACAACCATGCGTGCGGCTGGGATGGCGGCGATTG
CAGCCTGAACTTTAACGATCCGTGGAAAAACTGCACCCAGAGCCTGCAGTGCTGGAAATATT
TTAGCGATGGCCATTGCGATAGCCAGTGCAACAGCGCGGGCTGCCTGTTTGATGGCTTTGAT
TGCCAGCGCGCGGAAGGCCAGTGCAACCCGCTGTATGATCAGTATTGCAAAGATCATTTTAG
CGATGGCCATTGCGATCAGGGCTGCAACAGCGCGGAATGCGAATGGGATGGCCTGGATTGC
GCGGAACATGTGCCGGAACGCCTGGCGGCGGGCACCCTGGTGGTGGTGGTGCTGATGCCGC
CGGAACAGCTGCGCAACAGCAGCTTTCATTTTCTGCGCGAACTGAGCCGCGTGCTGCATACC
AACGTGGTGTTTAAACGCGATGCGCATGGCCAGCAGATGATTTTTCCGTATTATGGCCGCGA
AGAAGAACTGCGCAAACATCCGATTAAACGCGCGGCGGAAGGCTGGGCGGCGCCGGATGCG
CTGCTGGGCCAGGTGAAAGCGAGCCTGCTGCCGGGCGGCAGCGAAGGCGGCCGCCGCCGCC
GCGAACTGGATCCGATGGATGTGCGCGGCAGCATTGTGTATCTGGAAATTGATAACCGCCAG
TGCGTGCAGGCGAGCAGCCAGTGCTTTCAGAGCGCGACCGATGTGGCGGCGTTTCTGGGCGC
GCTGGCGAGCCTGGGCAGCCTGAACATTCCGTATAAAATTGAAGCGGTGCAGAGCGAAACC
GTGGAACCGCCGCCGCCGGCGCAGCTGCATTTTATGTATGTGGCGGCGGCGGCGTTTGTGCT
GCTGTTTTTTGTGGGCTGCGGCGTGCTGCTGAGCCGCAAACGCCGCCGCATGAAACTGCTGA
GCAGCATTGAACAGGCGTGCGATATTTGCCGCCTGAAAAAACTGAAATGCAGCAAAGAAAA
ACCGAAATGCGCGAAATGCCTGAAAAACAACTGGGAATGCCGCTATAGCCCGAAAACCAAA
CGCAGCCCGCTGACCCGCGCGCATCTGACCGAAGTGGAAAGCCGCCTGGAACGCCTGGAAC
AGCTGTTTCTGCTGATTTTTCCGCGCGAAGATCTGGATATGATTCTGAAAATGGATAGCCTGC
AGGATATTAAAGCGCTGCTGACCGGCCTGTTTGTGCAGGATAACGTGAACAAAGATGCGGT
GACCGATCGCCTGGCGAGCGTGGAAACCGATATGCCGCTGACCCTGCGCCAGCATCGCATTA
GCGCGACCAGCAGCAGCGAAGAAAGCAGCAACAAAGGCCAGCGCCAGCTGACCGTGAGCG
CGGCGGCGGGCGGCAGCGGCGGCAGCGGCGGCAGCGATGCGCTGGATGATTTTGATCTGGA
TATGCTGGGCAGCGATGCGCTGGATGATTTTGATCTGGATATGCTGGGCAGCGATGCGCTGG
ATGATTTTGATCTGGATATGCTGGGCAGCGATGCGCTGGATGATTTTGATCTGGATATGCTG

SEQ ID NO: 123 CD3z signaling domain 1 DNA sequence
AGAGTGAAGTTCAGCAGGAGCGCAGACGCCCCCGCGTACCAGCAGGGCCAGAACCAGCTCT
ATAACGAGCTCAATCTAGGACGAAGAGAGGAGTACGATGTTTTGGACAAGAGACGTGGCCG
GGACCCTGAGATGGGGGGAAAGCCGAGAAGGAAGAACCCTCAGGAAGGCCTGTACAATGA
ACTGCAGAAAGATAAGATGGCGGAGGCCTACAGTGAGATTGGGATGAAAGGCGAGCGCCG
GAGGGGCAAGGGGCACGATGGCCTTTACCAGGGTCTCAGTACAGCCACCAAGGACACCTAC
GACGCCCTTCACATGCAGGCCCTGCCCCCTCGCTAA

Fig. 10LL

SEQ ID NO: 124 CD3z signaling domain 1 DNA sequence
AGAGTGAAGTTCAGCAGGAGCGCAGACGCCCCCGCGTACCAGCAGGGCCAGAACCAGCTCT
ATAACGAGCTCAATCTAGGACGAAGAGAGGAGTACGATGTTTTGGACAAGAGACGTGGCCG
GGACCCTGAGATGGGCGGCAAGCCCAGAAGAAAGAACCCCCAGGAAGGCCTGTATAACGA
ACTGCAGAAAGACAAGATGGCCGAGGCCTACAGCGAGATCGGCATGAAGGGCGAGCGGAG
AAGAGGCAAGGGCCACGATGGCCTGTACCAGGGACTGAGCACCGCCACCAAGGACACCTAC
GACGCCCTGCACATGCAGGCCCTGCCTCCAAGA

SEQ ID NO: 125 CD3z signaling domain 1 DNA sequence
AGAGTGAAGTTCAGCAGGAGCGCAGACGCCCCCGCGTACCAGCAGGGCCAGAACCAGCTCT
ATAACGAGCTCAATCTAGGACGAAGAGAGGAGTACGATGTTTTGGACAAGAGACGTGGCCG
GGACCCTGAGATGGGCGGCAAGCCCAGAAGAAAGAACCCCCAGGAAGGCCTGTATAACGA
ACTGCAGAAAGACAAGATGGCCGAGGCCTACAGCGAGATCGGCATGAAGGGCGAGCGGAG
AAGAGGCAAGGGCCACGATGGCCTGTACCAGGGACTGAGCACCGCCACCAAGGACACCTAC
GACGCCCTGCACATGCAGGCCCTGCCTCCAAGA

SEQ ID NO: 126 CD3z signaling domain 1 DNA sequence
CGCGTGAAATTTAGCCGCAGCGCGGATGCGCCGGCGTATCAGCAGGGCCAGAACCAGCTGT
ATAACGAACTGAACCTGGGCCGCCGCGAAGAATATGATGTGCTGGATAAACGCCGCGGCCG
CGATCCGGAAATGGGCGGCAAACCGCGCCGCAAAAACCCGCAGGAAGGCCTGTATAACGAA
CTGCAGAAAGATAAAATGGCGGAAGCGTATAGCGAAATTGGCATGAAAGGCGAACGCCGCC
GCGGCAAAGGCCATGATGGCCTGTATCAGGGCCTGAGCACCGCGACCAAAGATACCTATGA
TGCGCTGCATATGCAGGCGCTGCCGCCGCGC

SEQ ID NO: 127 OX40 costimulatory domain DNA sequence
CGCGATCAGCGCCTGCCGCCGGATGCGCATAAACCGCCGGGCGGCGGCAGCTTTCGCACCC
CGATTCAGGAAGAACAGGCGGATGCGCATAGCACCCTGGCGAAAATT

SEQ ID NO: 128 Leader sequence 1 DNA sequence
ATGGACTGGATCTGGCGCATCCTCTTCCTCGTCGGCGCTGCTACCGGCGCTCATTCT

SEQ ID NO: 129 scFV L19 DNA sequence
GAAGTGCAGCTGCTGGAAAGCGGCGGCGGCCTGGTGCAGCCGGGCGGCAGCCTGCGCCTGA
GCTGCGCGGCGAGCGGCTTTACCTTTAGCAGCTTTAGCATGAGCTGGGTGCGCCAGGCGCCG
GGCAAAGGCCTGGAATGGGTGAGCAGCATTAGCGGCAGCAGCGGCACCACCTATTATGCGG
ATAGCGTGAAAGGCCGCTTTACCATTAGCCGCGATAACAGCAAAAACACCCTGTATCTGCAG
ATGAACAGCCTGCGCGCGGAAGATACCGCGGTGTATTATTGCGCGAAACCGTTTCGTATTT
TGATTATTGGGGCCAGGGCACCCTGGTGACCGTGAGCAGCGGCGATGGCAGCAGCGGCGGC
AGCGGCGGCGCGAGCGAAATTGTGCTGACCCAGAGCCCGGGCACCCTGAGCCTGAGCCCGG
GCGAACGCGCGACCCTGAGCTGCCGCGCGAGCCAGAGCGTGAGCAGCAGCTTTCTGGCGTG
GTATCAGCAGAAACCGGGCCAGGCGCCGCGCCTGCTGATTTATTATGCGAGCAGCCGCGCG
ACCGGCATTCCGGATCGCTTTAGCGGCAGCGGCAGCGGCACCGATTTTACCCTGACCATTAG
CCGCCTGGAACCGGAAGATTTTGCGGTGTATTATTGCCAGCAGACCGGCCGCATTCCGCCGA
CCTTTGGCCAGGGCACCAAAGTGGAAATTAAA

CHIMERIC ANTIGEN RECEPTORS FOR DIRECT AND INDIRECT TARGETING OF FIBRONECTIN-POSITIVE TUMORS

CROSS-REFERENCE TO RELATED APPLICATIONS

This application is a National Stage Application of International Application No. PCT/US2020/042565, filed Jul. 17, 2020 which claims priority to U.S. Provisional Application No. 62/876,158, filed Jul. 19, 20219, all of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Jul. 15, 2020, is named 243734_000137_SL.txt and is 242,572 bytes in size.

FIELD

The application relates to chimeric antigen receptors (CARs), particularly CARs with improved antitumor properties (e.g., CARs the directly and/or indirectly target cells), and their uses in tumor immunotherapy (e.g., adoptive cell therapy). The application further relates to methods for activating T-cells and other lymphocytes resulting in an immune response against a target antigen. The application further relates to therapeutic cells that express said CARs and methods for treating patients using the modified therapeutic cells.

BACKGROUND

The outcome of recurrent/refractory solid tumor and brain tumors remains poor despite aggressive multimodal therapy. Cell therapy with genetically modified T-cells expressing chimeric antigen receptors (CARs) hold the promise to improve outcomes since they kill tumor cells through mechanisms that are distinct from conventional therapies such a chemotherapy and radiation. While CAR T-cell therapy has been successful for hematological malignancies, leading to the FDA approval of two CD19-CAR T-cell products, the antitumor activity of CAR T-cells for solid tumors and brain tumors have been limited.[5-8] For example, in a Phase I clinical study in which 16 patients with osteosarcoma were infused with up to $1 \times 10^8/m^2$ HER2-CAR T-cells.[5] HER2-CAR T-cells trafficked to tumor sites and persisted at low levels for >6 weeks without evident toxicities. Four patients had stable disease for up to 14 months; of these, three are alive with no evidence of disease after tumor removal with median follow up of three to five years.

The lack of efficacy of CAR T-cell therapy for solid tumors is most likely multifactorial, including heterogeneous expression of a limited array of tumor associated antigens (TAAs), loss of TAAs following natural or therapy-induced selective pressure, limited homing of T-cells to solid tumors, concerns about on-target/off target toxicity, and the hostile tumor micro-environment (TM).[9-11] In addition, non-malignant cells present in the tumor stroma that support tumor growth such as vascular endothelial cells and cancer associated fibroblasts are not targeted by standard CAR T-cells.

While adult solid tumors and brain tumors express unique neoantigens, they use is problematic since most are private and rarely shared between patients, making it almost impossible to generate a CAR T-cell product that could be used for multiple patients.[58] In addition, pediatric solid tumors and brain tumors carry a low neoantigen load, which precludes its targeting with neoantigen-specific CARs. To increase CAR T-cell specificity when targeting solid and brain tumors, the unique extracellular matrix (ECM) within the tumor micro-environment (TME) may serve as a target as it is an environment that is distinct to tumors alone.

Fibronectin is a major component of the ECM. Tumor cells as well as tumor endothelial cell express a unique variant of fibronectin called FN-EDB, EDB, or EIIIB. Several monoclonal antibodies have been developed for targeting and imaging of EDB+ positive tumors.[27-29]

SUMMARY OF THE INVENTION

As specified in the Background section above, there is a great need in the art for CARs that target new antigens in solid tumors and brain tumors. EDB is an ideal target, since it is a major component of the tumor's ECM that is produced by tumor cells as well as endothelial cells of the tumor neovasculature. The present application addresses these and other needs.

In one aspect provided herein is a polynucleotide encoding a first chimeric antigen receptor (CAR) comprising: (a) an extracellular target-binding domain comprising a Fibronectin Extradomain B (FN-EDB)-binding moiety, (b) a hinge domain, (c) a transmembrane domain, and (d) a cytoplasmic domain comprising (i) optionally one or more costimulatory domains, (ii) a signaling domain.

In some embodiments, the FN-EDB-binding moiety is an anti-FN-EDB single chain variable fragment (scFv). In some embodiments, the anti-FN-EDB scFv is derived from antibody L19 (L19 scFv). In some embodiments, the L19 scFv comprises the amino acid sequence set forth in SEQ ID NO: 25, or an amino acid sequence having at least 80% identity thereof. In some embodiments, the nucleotide sequence encoding the L19 scFV comprises the sequence set forth in SEQ ID NO: 26, or a nucleotide sequence having at least 80% identity thereof.

In some embodiments, the extracellular target-binding domain further comprises a leader sequence. In some embodiments, the leader sequence comprises the amino acid sequence set forth in SEQ ID NO: 61, or an amino acid sequence having at least 80% identity thereof. In some embodiments, the nucleotide sequence encoding the leader sequence comprises the sequence set forth in SEQ ID NO: 62, or a nucleotide sequence having at least 80% identity thereof.

In some embodiments, the hinge domain is derived from IgG1, CD8a stalk, or CD28.

In some embodiments, the hinge domain comprises the amino acid sequence set forth in SEQ ID NO: 91, or an amino acid sequence having at least 80% identity thereof. In some embodiments, the nucleotide sequence encoding the hinge domain comprises the sequence set forth in SEQ ID NO: 92, or a nucleotide sequence having at least 80% identity thereof.

In some embodiments, the transmembrane domain is derived from CD28, CD8a, CD4, or CD3.

In some embodiments, the transmembrane domain comprises the amino acid sequence set forth in SEQ ID NO: 36, or an amino acid sequence having at least 80% identity thereof. In some embodiments, the nucleotide sequence encoding the transmembrane domain comprises the sequence set forth in SEQ ID NO: 37, or a nucleotide sequence having at least 80% identity thereof.

In some embodiments, the costimulatory domain is derived from CD28, CD27, CD40, CD134, CD137, CD226, CD79A, ICOS, or MyD88.

In some embodiments, the costimulatory domain comprises the amino acid sequence set forth SEQ ID NO: 40, or an amino acid sequence having at least 80% identity thereof. In some embodiments, the nucleotide sequence encoding the costimulatory domain comprises the sequence set forth in SEQ ID NO: 41, or a nucleotide sequence having at least 80% identity thereof.

In some embodiments, the lymphocyte activation domain is derived from CD3ζ, DAP10, DAP12, Fc epsilon receptor I γ chain (FCER1G), CD3δ, CD3ε, CD3γ, CD226, or CD79A.

In some embodiments, the CD3 signaling domain comprises the amino acid sequence set forth in SEQ ID NO: 57, or an amino acid sequence having at least 80% identity thereof. In some embodiments, the nucleotide sequence encoding the signaling domain comprises the sequence set forth in SEQ ID NO: 58, or a nucleotide sequence having at least 80% identity thereof.

In some embodiments, the CAR encoded by the polynucleotide comprises the amino acid sequence as set forth in SEQ ID NO: 95, or an amino acid sequence having at least 80% identity thereof. In some embodiments, the polynucleotide encoding the CAR comprises the nucleotide sequence as set forth in SEQ ID NO: 2, 96 or 120, or a nucleotide sequence having at least 80% identity thereof.

In some embodiments, the polynucleotide comprises at least one additional polynucleotide sequence encoding a second gene.

In some embodiments, the second gene encodes a truncated CD19 (tCD19) polypeptide. In some embodiments, the tCD19 comprises the amino acid sequence set forth in SEQ ID NO: 65, or an amino acid sequence having at least 80% identity thereof. In some embodiments, the nucleotide sequence encoding the tCD19 comprises the sequence set forth in SEQ ID NO: 66, or a nucleotide sequence having at least 80% identity thereof.

In some embodiments, the second gene encodes a synthetic notch (synNotch) receptor. In some embodiments, the synNotch receptor comprises the amino acid sequence set forth in SEQ ID NO: 67, or an amino acid sequence having at least 80% identity thereof. In some embodiments, the nucleotide sequence encoding the synNotch receptor comprises the sequence set forth in SEQ ID NO: 68, or a nucleotide sequence having at least 80% identity thereof.

In some embodiments, the polynucleotide further comprises a polynucleotide that encodes an additional antigen binding moiety. In some embodiments, the antigen-binding moiety is an anti-FN-EDB binding moiety. In some embodiments, the FN-EDB-binding moiety is an anti-FN-EDB single chain variable fragment (scFv). In some embodiments, the anti-FN-EDB scFv is derived from antibody L19 (L19 scFv). In some embodiments, the L19 scFv comprises the amino acid sequence set forth in SEQ ID NO: 25, or an amino acid sequence having at least 80% identity thereof. In some embodiments, the nucleotide sequence encoding the L19 scFV comprises the sequence set forth in SEQ ID NO: 26, or a nucleotide sequence having at least 80% identity thereof.

In some embodiments, the at least one additional polynucleotide sequence is operably linked to the sequence encoding a CAR via a sequence encoding a self-cleaving peptide and/or an internal ribosomal entry site (IRES).

In some embodiments, the self-cleaving peptide is a 2A peptide. In some embodiments, the 2A peptide is T2A, P2A, E2A, or F2A peptide. In some embodiments, the self-cleaving 2A peptide encoded comprises the amino acid sequence set forth in SEQ ID NO: 69, or an amino acid sequence having at least 80% identity thereof. In some embodiments, the sequence encoding the self-cleaving 2A peptide comprises the nucleotide sequence set forth in SEQ ID NO: 70, or a nucleotide sequence having at least 80% identity thereof.

In one aspect provided herein is a polynucleotide encoding a synthetic notch (synNotch) receptor operably linked to at an antigen targeting moiety. In certain embodiments, the antigen targeting moiety can be, but is not limited to, a chimeric antigen receptors (CAR), bispecific T-cell engager (BiTE), or an antibody. In certain embodiments, the synNotch receptor is operably linked to the antigen targeting moiety via a sequence encoding a self-cleaving peptide and/or an internal ribosomal entry site (IRES). In some embodiments, the synNotch receptor comprises the amino acid sequence set forth in SEQ ID NO: 67, or an amino acid sequence having at least 80% identity thereof. In some embodiments, the nucleotide sequence encoding the synNotch receptor comprises the sequence set forth in SEQ ID NO: 68, or a nucleotide sequence having at least 80% identity thereof.

In some embodiments, the polynucleotide is a DNA molecule. In other embodiments, the polynucleotide is an RNA molecule.

In another aspect provided herein is a recombinant vector comprising a polynucleotide described herein. In some embodiments, the vector is a viral vector. In some embodiments, the viral vector is a retroviral vector, a lentiviral vector, an adenoviral vector, an adeno-associated virus vector, an alphaviral vector, a herpes virus vector, or a vaccinia virus vector. In some embodiments, the viral vector is a retroviral vector. In some embodiments, the vector is a non-viral vector.

In another aspect provided herein is a chimeric antigen receptor (CAR) encoded by a polynucleotide described herein.

In another aspect provided herein is an isolated host cell comprising a polynucleotide described herein or a recombinant vector described herein. In some embodiments, host cell comprises a CAR as described herein.

In some embodiments, the host cell is an immune cell. In some embodiments, the immune cell is a T-cell, a NK cell, or a macrophage. In some embodiments, the T-cell is selected from a CD8+ T-cell, a CD4+ T-cell, a cytotoxic T-cell, an αβ T-cell receptor (TCR) T-cell, an invariant natural killer T (iNKT) cell, a γδ T-cell, a memory T-cell including memory stem T-cell (TSCM), a naïve T-cell, an effector T-cell, a T-helper cell, and a regulatory T-cell (Treg).

In some embodiments, the host cell further comprises a second CAR or a bispecific molecule and wherein the expression of the second CAR or the bispecific molecule is induced by the activation of the first CAR. In some embodiments, the expression of the second CAR or bispecific molecule is induced using a synthetic Notch (synNotch) receptor. In some embodiments, the expression of the second CAR or bispecific molecule is induced using at least one nuclear factor of activated T-cells (NFAT) dependent-promoter.

In some embodiments, the bispecific molecule is a bispecific T-cell engager (BiTE) or a bispecific antibody.

In some embodiments, the second CAR or the bispecific molecule targets a tumor associated antigen.

In some embodiments, the tumor associated antigen is 5T4, $\alpha v\beta 6$ integrin, B7-H3, B7-H6, CAIX, CD19, CD20, CD22, CD30, CD33, CD44, CD44v6, CD44v7/8, CD70, CD123, CD138, CD171, CEA, Claudin-6 or -18, CSPG4, EGFR, EGFR family including ErbB2 (HER2), EGFRvIII, EGP2, EGP40, EPCAM, EphA2, EpCAM, FAP, fetal AchR, FR$\alpha$, GD2, GD3, MAGE1, NY-ESO-1, IL-11R$\alpha$, IL-13R$\alpha$2, Lambda, Lewis-Y, Kappa, Mesothelin, Muc1, Muc16, NCAM, NKG2D Ligands, NY-ESO-1, PRAME, PSCA, PSMA, ROR1, Survivin, TAG72, TEMs, or VEGFR2.

In some embodiments, the host cell has been activated and/or expanded ex vivo. In some embodiments, wherein the host cell is an allogeneic cell. In some embodiments, the host cell is an autologous cell.

In some embodiments, the host cell is isolated from a subject having a tumor, wherein one or more cells of the tumor express FN-EDB. In some embodiments, the tumor is a solid tumor. In some embodiments, the tumor is selected from breast cancer, prostate cancer, bladder cancer, oral squamous cell carcinoma, head and neck squamous cell carcinoma, colorectal cancer, lung cancer, brain tumors, melanoma, bone, pediatric solid tumors and brain tumors, and lymphoma.

In some embodiments, the host cell is derived from a blood, marrow, tissue, or a tumor sample.

In another aspect provided herein is a pharmaceutical composition comprising a host cell described herein and a pharmaceutically acceptable carrier and/or excipient.

In another aspect provided herein is a method of generating an isolated host cell described herein, said method comprising genetically modifying the host cell with a polynucleotide described herein or a recombinant vector described herein.

In some embodiments, the method comprises a vector. In some embodiments, the vector is a viral vector and the genetic modification is conducted by a transduction using said vector.

In some embodiments, the method comprises a genetic modification conducted ex vivo.

In some embodiments, the method further comprises activation and/or expansion of the host cell ex vivo before, after and/or during said genetic modification.

In another aspect provided herein is a method for killing a tumor cell expressing FN-EDB, said method comprising contacting the cell with a host cell described herein or a pharmaceutical composition described herein.

In another aspect provided herein is a method for indirectly killing a tumor cell expressing a tumor associated antigen, said method comprising contacting said cell with a host cell described herein or a pharmaceutical composition described herein.

In another aspect provided herein is a method for treating a tumor in a subject in need thereof, wherein one or more cells of the tumor express FN-EDB, said method comprising administering to the subject a therapeutically effective amount of host cells described herein or a pharmaceutical composition described herein.

In another aspect provided herein is a method for treating a tumor and/or inhibiting tumor neovascularization in a subject in need thereof, wherein one or more cells of the tumor or non-tumor cells within the tumor micro-environment express FN-EDB and the tumor cell expresses a tumor associated antigen, said method comprising administering to the subject a therapeutically effective amount of host cells described herein or a pharmaceutical composition described herein.

In some embodiments, the non-tumor cells within the tumor micro-environment are vascular endothelial cells and/or tumor stroma. In some embodiments, the tumor is a solid tumor. In some embodiments, the tumor is selected from breast cancer, prostate cancer, bladder cancer, oral squamous cell carcinoma, head and neck squamous cell carcinoma, colorectal cancer, lung cancer, brain tumors, melanoma, bone, pediatric solid tumors and brain tumors, and lymphoma.

In another aspect provided herein is a method comprising: a) isolating T-cells, NK cells, iNKT cells or macrophages from the subject or generating T-cells, NK cells, iNKT cells or macrophages from stem cells including induced pluripotent stem cells (IPS cells); b) genetically modifying said T-cells, NK cells, iNKT cells, macrophages or stem cells including IPS cells ex vivo with a polynucleotide described herein or a vector described herein; c) optionally, expanding and/or activating said T-cells, NK cells, iNKT cells or macrophages before, after or during step b); and d) introducing the genetically modified T-cells, NK cells, iNKT cells or macrophages into the subject.

In some embodiments, the subject is human. In some embodiments, the subject is an adult. In some embodiments, the subject is a child.

These and other aspects of the present invention will be apparent to those of ordinary skill in the art in the following description, claims and drawings.

BRIEF DESCRIPTION OF THE DRAWINGS

FIG. 1A). As EDB is secreted, it is also an ideal target for indirect targeting of tumor cells, an approach in which T-cells are genetically modified to express an EDB-specific SynNotch (EDB-SynNotch) receptor. Once EDB-SynNotch T-cells encounter EDB within the extracellular matrix (ECM; FIG. 1B), the EDB-SynNotch receptor induces the expression of a tumor associated antigen (TAA)-specific CAR or bispecific T-cell engage (BiTE).

FIGS. 3A-3C demonstrates that EDB-CAR T-cells recognize and kill FN-EDB+ tumor cells. A retroviral vector was designed encoding an EDB-specific CAR (EDB-CAR) using the EDB-specific L19 scFv, a short IgG 1 hinge, a CD28 transmembrane domain and a CD28. $\zeta$ signaling domain; in addition, the retroviral vector encoded a 2A sequence and truncated CD19 (FIG. 3A). FACS analysis of CAR expression on transduced T-cells (FIG. 3B). Only EDB-CAR T-cells secrete IFN$\gamma$ in the presence of recombinant (rh) FN-EDB; non-transduced (NT) T-cells do not (n=3) (FIG. 3C).

FIGS. 4A-4D demonstrate that EDB-CAR T-cells recognize and kill EDB-positive tumor cells. Tumor cells (LM7, A549, U87) express EDB in contrast to normal fibroblasts (FIG. 4A). EDB-CAR T-cells (FIG. 4B) secrete IFN$\gamma$ and kill EDB+ tumor cells in contrast to NT T-cells (FIG. 4C) (n=3). EDB-CAR T cells do not kill EDB-fibroblasts in contrast to EDB+ A549 tumor cells (FIG. 4D).

FIGS. 8A-8C demonstrate utilization of the synNotch system. FIG. 8A depicts a scheme of a vector that encodes an EDB-synNotch receptor, which will induce the expression of a TAA-specific CAR or BiTE molecule. FIG. 8B depicts how EDB-synNotch receptor induce the expression of a TAA-specific CAR or BiTE molecule. FIG. 8C depicts a vector for combined indirect and direct targeting of tumor cells encoding an EDB-CAR T-cells, an EDB-SynNotch receptor, and an inducible gene encoding for a TAA-specific CAR or BiTE molecule. DBD—DNA binding domain. MND—a promoter that comprising the modified LTR U3 region of MoMuLV (Moloney Murine Leukemia Virus), in which the enhancer sequence is replaced by myeloproliferative sarcoma virus enhancer and the negative control region is deleted. VP—viral protein sequence.

FIGS. 9A-9B present additional EDB-CARs.

FIGS. 10A-10LL presents exemplary sequences of the disclosure.

DETAILED DESCRIPTION

Figure 1A:
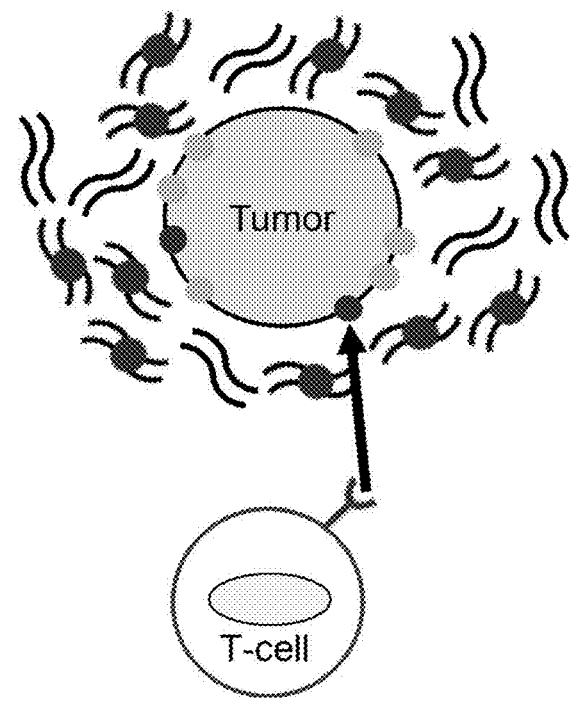
FIGS. 1A-1B show schematics of direct or indirect targeting of tumor cells with EDB-CAR T-cells. While FN-EDB is a secreted protein, it plays a major role in cellular adhesion, allowing EDB-CAR T-cells to directly recognize EDB-producing tumor cells (Direct targeting.
Figure 1A:
Figure 1B:
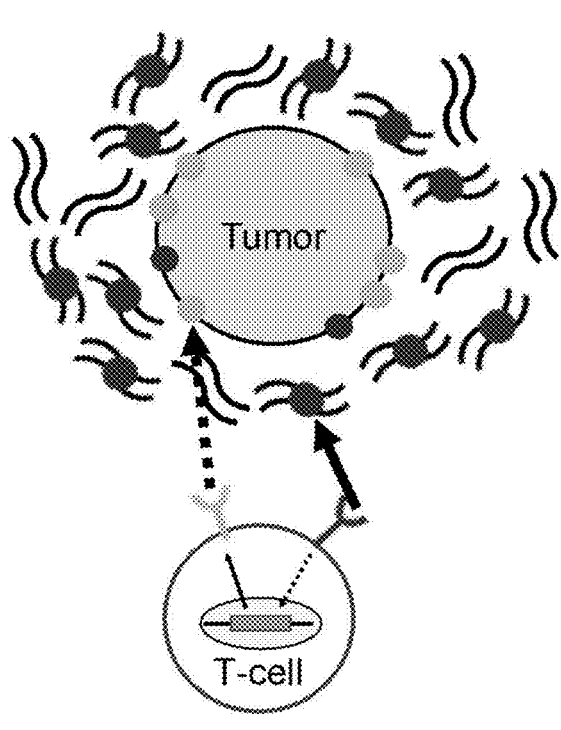

The present disclosure provides chimeric antigen receptors (CARs) and T-cells and other lymphocytes expressing said CARs that target antigens located on the target tumor cell and/or the extracellular matrix (ECM) within the tumor micro-environment (TME) (e.g., targeting vascular endothelial cells and/or tumor stroma) with special focus on fibronectin-EDB (oncofetal fibronectin, FN-EDB, EDB, EIIIB). In certain embodiments, the CAR T-cells directly target tumor cells (see e.g., FIG. 1A; i.e., EDB-specific CAR T-cells recognize an antigen that is also present on the cell surface of tumor cells and kill it). In certain embodiments, the EDB-specific T-cells indirectly target tumor cells (see e.g., FIG. 1B; i.e., synthetic Notch (synNotch)-receptor T-cells recognize an antigen that is present in the tumor ECM). Upon recognition, the synNotch receptor induces the expression of a second molecule (e.g., a second transgene)

within the T-cells or other lymphocytes that enables tumor cell killing. By way of example and not limitation, the second molecule includes a tumor-specific CAR, bispecific T-cell engager (BiTE), dual affinity retargeting (DART) antibody, or bispecific antibodies that redirect other immune cells (for example, but not limited to macrophages, NK cells) to kill tumor cells.

The TME contains the ECM, which is formed through the secretion of distinct proteins while the tumors develop. This ECM possesses molecules that are tumor specific. One example of such an ECM molecule is fibronectin-EDB (oncofetal fibronectin, FN-EDB, EDB, EIIIB), which is a splice variant of fibronectin and a major component of the ECM in solid tumors. EDB expression is limited to fetal cells, tumor cells, endothelial of the tumor neovasculature and not found in either the plasma or normal healthy tissue in adults.[14,22] Further, EDB is homologous across multiple species including mouse, rabbit, and human.[23,24] These tumor-specific attributes and the shared homology make EDB a promising target for both pre-clinical and clinical studies to reduce off-target toxicity in patients that can be caused by widespread cytokine release leading to potential organ failure. A high affinity EDB-specific monoclonal antibody (MAb), L19, was successfully tested in 40 patients demonstrating localization to the tumor site.[27-29] While EDB is secreted, Example 1 demonstrates that it is arrayed on the cell surface since EDB-CAR T-cells have antitumor activity in preclinical in vitro and in vivo (FIGS. 3 to 8). In addition, the Example 3 demonstrates that EDB-CAR T-cells target the tumor vasculature (FIG. 5). Other examples of splice variants within the ECM that could be targeted with this approach include the EDA domain of fibronectin, and splice variants of other proteins, but not limited to, tenascin-C, -N and -R, SPARC (Secreted Protein Acidic And Cysteine Rich), and the CCN (Cellular Communication Network) family (see e.g., Yoshida et al., Cell Adh Migr. 2015, 9(1-2): 96-104) and Viloria and Hill, Biomol Concepts, 2016, 7(2): 117-32; both of which are incorporated herein by reference in their entirety for all purposes).

Figure 8A:
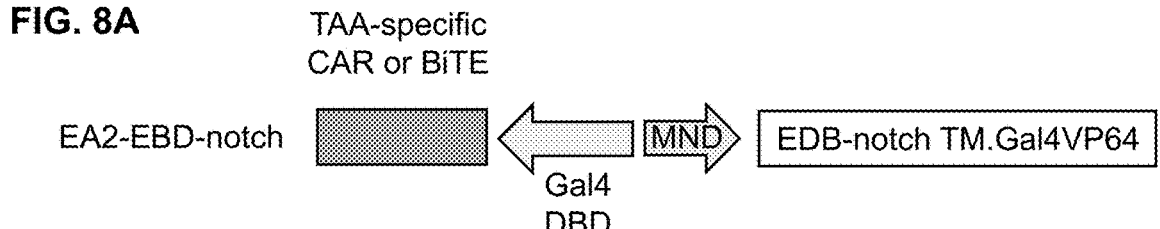

Targeting a single tumor associated antigen (TAA) carries the risk of selecting immune escape mutants, which no longer express the targeted TAA,[11,36,47] and/or in some instances can cause on-target/off target toxicity. Both limitations can be addressed with the approaches described herein. For example, in certain aspects of the present disclosure, EDB-SynNotch (e.g., SEQ ID NO: 67, 93, or 121) expressed in T-cells or other lymphocytes can be used to induce the expression of a second antigen targeting molecule (e.g., a second CAR or the bispecific molecule (e.g., bispecific T-cell engager (BiTE) or bispecific antibody)) that targets a TAA expressed on the target tumor cell (FIG. 8A,B).

This allows for targeting TAA that are potentially expressed in normal tissues since the TAA-specific molecule is only expressed by the T-cells in the EDB+ tumor microenvironment. The selection of immune escape variants can be prevented by combining the EDB-CAR and EDB-SynNotch receptor approach and a representative vector for this combined approach is shown in FIG. 8C. Thus, advantageously, only the CAR T-cells activated by the antigen present on the surrounding stroma will be induced to express the TAA targeting construct.

Figure 8B:
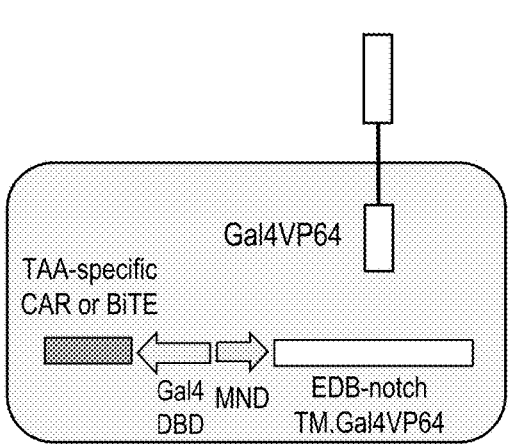
Figure 8B:
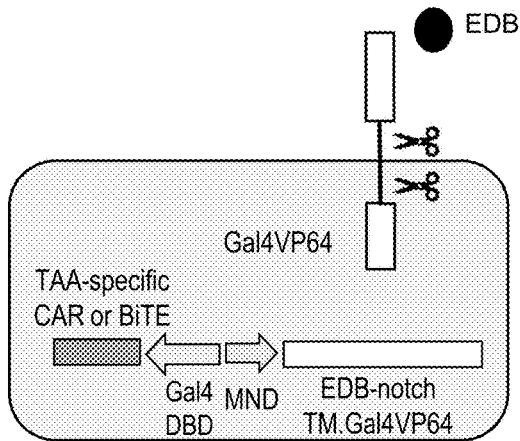
Figure 8B:
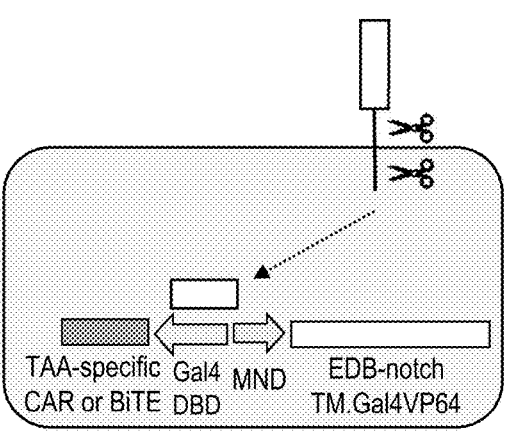
Figure 8B:
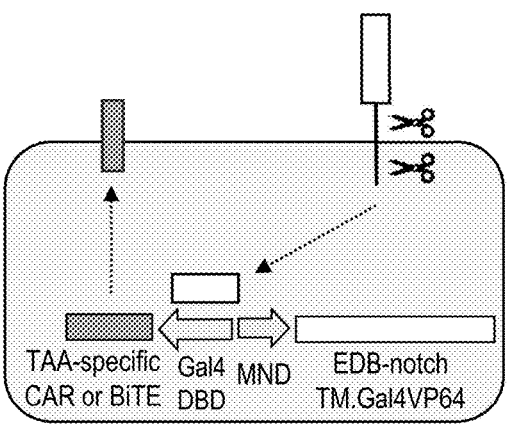
Figure 8C:
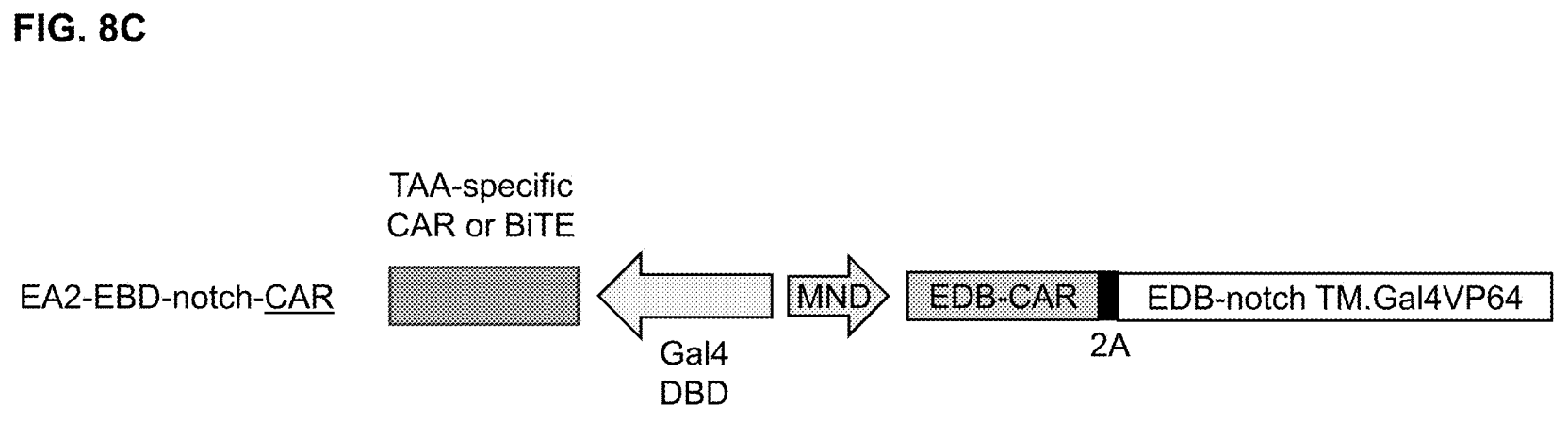

The synNotch receptor system is ideal to couple T-cell or other lymphocyte activation to expression of a protein since in contrast to other activating T-cell or other lymphocyte promoters, synNotch receptors have no baseline activity as they do not share any common signaling intermediates, making them an attractive option for the current approach. SynNotch receptors contain its core regulatory domain from the cell-cell signaling receptor Notch, but it further comprises a synthetic extracellular recognition domain (e.g., EDB scFv) and a synthetic transcriptional domain that will induce the expression of a desired target gene (e.g., second CAR or bispecific molecule (e.g., BiTE or bispecific antibody)). When the synNotch receptor engages with its cognate antigen (e.g., EDB), the synNotch receptor undertakes induced transmembrane cleavage that releases the intracellular transcriptional domain to enter the nucleus and induces the expression of the target gene via an upstream promoter (FIG. 8B).

Alternatively, the expression of the second antigen targeting molecule can be under the control of at least one nuclear factor of activated T-cells (NFAT) dependent-promoter, which results in the expression of the second antigen targeting molecule is tightly linked to T-cell activation (e.g., but not limited to Th1 and Th2 cytokines or cell surface molecules (e.g., PD-1, CD137)).

In certain embodiments, the present disclosure provides CARs and T-cells or other lymphocytes expressing said CARs that target FN-EDB located on the target tumor cell (see FIG. 1A) and/or the ECM within the TME. In certain embodiments, the CARs that target FN-EDB on the ECM enable the activation of CAR T-cells or other lymphocytes within the tumors that are not in direct contact with tumor cells (see FIG. 1B). The activation of the CAR T-cells or other lymphocytes induces the expression of a second antigen targeting molecule (e.g., a second CAR or a bispecific molecule (e.g., BiTE or bispecific antibody)) that targets a tumor associated antigen expressed on the target tumor cell. At that point, the CAR T-cell or other lymphocyte will then become in direct contact with the target tumor cell to induce death of the tumor cell or secrete a molecule (e.g. BiTE or bispecific antibody) that will induce tumor cell killing.

In certain embodiments, a tumor associated antigen can be, but not limited to, 5T4, $\alpha_v\beta_6$ integrin, B7-H3, B7-H6, CAIX, CD19, CD20, CD22, CD30, CD33, CD44, CD44v6, CD44v7/8, CD70, CD123, CD138, CD171, CEA, Claudin-6 or -18, CSPG4, EGFR, EGFR family including ErbB2 (HER2), EGFRvIII, EGP2, EGP40, EPCAM, EphA2, EpCAM, FAP, fetal AchR, FRα, GD2, GD3, MAGE1, NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, Survivin, TAG72, TEMs, or VEGFR2.

CARs are primarily comprised of 1) an antigen-binding moiety, such as but not limited to a single-chain variable fragment (scFv) derived from an antigen-specific monoclonal antibody, and 2) a lymphocyte activation domain, such as but not limited to the ζ-chain from the T-cell receptor CD3. These two regions are fused together via a transmembrane domain. A hinge domain is usually required to provide more flexibility and accessibility between the antigen-binding moiety and the transmembrane domain. Upon transduction, the lymphocyte expresses the CAR on its surface, and upon contact and ligation with the target antigen, it signals through the lymphocyte activation domain (e.g., CD3ζ chain) inducing cytotoxicity and cellular activation.

CAR constructs may also include co-stimulatory polypeptides to boost the CAR-induced immune response. The most commonly used co-stimulating molecules include CD28 and 4-1BB, which promotes both T-cell proliferation and cell survival. Another example of co-stimulatory domains is a MyD88/CD40 molecule that can be used with or without the use of a separate dimerization agent. Additional CAR constructs may also include three signaling domains (e.g., CD3ζ, CD28, and 4-1BB), which further improves lymphocyte cell survival and efficacy.

In certain embodiments, the polynucleotide encoding the CAR is further operably linked to a second gene. In certain embodiments, the second gene encodes a truncated CD19 (tCD19) polypeptide. In certain embodiments, the second gene encodes a synthetic notch (synNotch) receptor.

Definitions

The term "chimeric antigen receptor" or "CAR" as used herein is defined as a cell-surface receptor comprising an extracellular target-binding domain, a transmembrane domain and a cytoplasmic domain, comprising a lymphocyte activation domain and optionally at least one co-stimulatory signaling domain, all in a combination that is not naturally found together on a single protein. This particularly includes receptors wherein the extracellular domain and the cytoplasmic domain are not naturally found together on a single receptor protein. The chimeric antigen receptors of the present disclosure are intended primarily for use with lymphocyte such as T-cells and natural killer (NK) cells.

The terms "T cell" and "T lymphocyte" are interchangeable and used synonymously herein. As used herein, T-cell includes thymocytes, naive T lymphocytes, immature T lymphocytes, mature T lymphocytes, resting T lymphocytes, or activated T lymphocytes. A T-cell can be a T helper (Th) cell, for example a T helper 1 (Th1) or a T helper 2 (Th2) cell. The T-cell can be a helper T-cell (HTL; CD4+ T-cell) CD4+ T-cell, a cytotoxic T-cell (CTL; CD8+ T-cell), a tumor infiltrating cytotoxic T-cell (TIL; CD8+ T-cell), CD4+CD8+ T-cell, or any other subset of T-cells. Other illustrative populations of T-cells suitable for use in particular embodiments include naive T-cells and memory T-cells. Also included are "NKT cells", which refer to a specialized population of T-cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T-cells (γδ T-cells)," which refer to a specialized population that to a small subset of T-cells possessing a distinct TCR on their surface, and unlike the majority of T-cells in which the TCR is composed of two glycoprotein chains designated α- and β-TCR chains, the TCR in γδ T-cells is made up of a γ-chain and a δ-chain. γδ T-cells can play a role in immunosurveillance and immunoregulation, and were found to be an important source of IL-17 and to induce robust CD8+ cytotoxic T-cell response. Also included are "regulatory T-cells" or "Tregs" refers to T-cells that suppress an abnormal or excessive immune response and play a role in immune tolerance. Tregs cells are typically transcription factor Foxp3-positive CD4+ T cells and can also include transcription factor Foxp3-negative regulatory T-cells that are IL-10-producing CD4+ T cells.

The terms "natural killer cell" and "NK cell" are used interchangeable and used synonymously herein. As used herein, NK cell refers to a differentiated lymphocyte with a CD 16+CD56+ and/or CD57+ TCR− phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

As used herein, the term "antigen" refers to any agent (e.g., protein, peptide, polysaccharide, glycoprotein, glycolipid, nucleic acid, portions thereof, or combinations thereof) molecule capable of being bound by a T-cell receptor. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components, organisms, subunits of proteins/antigens, killed or inactivated whole cells or lysates.

The term "antigen-binding moiety" refers to a target-specific binding element that may be any ligand that binds to the antigen of interest or a polypeptide or fragment thereof, wherein the ligand is either naturally derived or synthetic. Examples of antigen-binding moieties include, but are not limited to, antibodies; polypeptides derived from antibodies, such as, for example, single chain variable fragments (scFv), Fab, Fab', F(ab')2, and Fv fragments; polypeptides derived from T-cell receptors, such as, for example, TCR variable domains; secreted factors (e.g., cytokines, growth factors) that can be artificially fused to signaling domains (e.g., "zytokines"); and any ligand or receptor fragment (e.g., CD27, NKG2D) that binds to the antigen of interest. Combinatorial libraries could also be used to identify peptides binding with high affinity to the therapeutic target.

Terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotypic (anti-Id) antibodies (including, e.g., anti-Id antibodies to antigen-specific TCR), and epitope-binding fragments of any of the above. The terms "antibody" and "antibodies" also refer to covalent diabodies such as those disclosed in U.S. Pat. Appl. Pub. 2007/0004909 and Ig-DARTS such as those disclosed in U.S. Pat. Appl. Pub. 2009/0060910. Antibodies useful as a TCR-binding molecule include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgM1, IgM2, IgA1 and IgA2) or subclass.

The term "host cell" means any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5α, JM109, and KCB, SURE® Competent Cells, and SOLO-PACK Gold Cells, can be used as host cells for vector replication and/or expression. Additionally, bacterial cells such as E. coli LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, CHO, Saos, and PC12. In certain embodiments, the host cell is autologous. In certain embodiments, the host cell is allogenic.

Host cells of the present disclosure include T-cells and natural killer cells that contain the DNA or RNA sequences encoding the CAR and express the CAR on the cell surface. Host cells may be used for enhancing T-cell activity, natural killer cell activity, treatment of tumors, and treatment of autoimmune disease.

The terms "activation" or "stimulation" means to induce a change in their biologic state by which the cells (e.g., T-cells and NK cells) express activation markers, produce cytokines, proliferate and/or become cytotoxic to target cells. All these changes can be produced by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T-cell and/or NK cell proliferation and/or upregulation or downregulation of key molecules.

The term "proliferation" refers to an increase in cell division, either symmetric or asymmetric division of cells. The term "expansion" refers to the outcome of cell division and cell death.

The term "differentiation" refers to a method of decreasing the potency or proliferation of a cell or moving the cell to a more developmentally restricted state.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or transmembrane.

The term "transfection" means the introduction of a "foreign" (i.e., extrinsic or extracellular) nucleic acid into a cell using recombinant DNA technology. The term "genetic modification" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to polynucleotide encoding the chimeric antigen receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "genetically engineered." The DNA or RNA introduced to a host cell can come from any source, including cells of the same genus or species as the host cell, or from a different genus or species.

The term "transduction" means the introduction of a foreign nucleic acid into a cell using a viral vector.

The terms "genetically modified" or "genetically engineered" refers to the addition of extra genetic material in the form of DNA or RNA into a cell.

As used herein, the term "derivative" or "variant" in the context of proteins or polypeptides (e.g., CAR constructs or domains thereof) refer to: (a) a polypeptide that has at least 40%, 45%, 50%, 55%, 60%, 65%, 70%, 75%, 80%, 85%, 90%, 95%, 98% or 99% sequence identity to the polypeptide it is a derivative or variant of, (b) a polypeptide encoded by a nucleotide sequence that has at least 40%, 45%, 50%, 55%, 60%, 65%, 70%, 75%, 80%, 85%, 90%, 95%, 98% or 99% sequence identity to a nucleotide sequence encoding the polypeptide it is a derivative or variant of; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to the polypeptide it is a derivative or variant of; (d) a polypeptide encoded by nucleic acids can hybridize under high, moderate or typical stringency hybridization conditions to nucleic acids encoding the polypeptide it is a derivative or variant of, (e) a polypeptide encoded by a nucleotide sequence that can hybridize under high, moderate or typical stringency hybridization conditions to a nucleotide sequence encoding a fragment of the polypeptide, it is a derivative or variant of, of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids; or (f) a fragment of the polypeptide it is a derivative or variant of.

Percent sequence identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wisconsin). Information regarding hybridization conditions (e.g., high, moderate, and typical stringency conditions) have been described, see, e.g., U.S. Patent Application Publication No. US 2005/0048549 (e.g., paragraphs 72-73).

The terms "vector", "cloning vector" and "expression vector" mean the vehicle by which a DNA or RNA sequence (e.g., a foreign gene) can be introduced into a host cell, so as to genetically modify the host and promote expression (e.g., transcription and translation) of the introduced sequence. Vectors include plasmids, synthesized RNA and DNA molecules, phages, viruses, etc. In certain embodiments, the vector is a viral vector such as, but not limited to, viral vector is an adenoviral, adeno-associated, alphaviral, herpes, lentiviral, retroviral, or vaccinia vector.

The term "regulatory element" refers to any cis-acting genetic element that controls some aspect of the expression of nucleic acid sequences. In some embodiments, the term "promoter" comprises essentially the minimal sequences required to initiate transcription. In some embodiments, the term "promoter" includes the sequences to start transcription, and in addition, also include sequences that can upregulate or downregulate transcription, commonly termed "enhancer elements" and "repressor elements", respectively.

As used herein, the term "operatively linked," and similar phrases, when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

By "enhance" or "promote," or "increase" or "expand" or "improve" refers generally to the ability of a composition contemplated herein to produce, elicit, or cause a greater physiological response (i.e., downstream effects) compared to the response caused by either vehicle or a control molecule/composition. A measurable physiological response may include an increase in T-cell expansion, activation, effector function, persistence, and/or an increase in tumor cell death killing ability, among others apparent from the understanding in the art and the description herein. In certain embodiments, an "increased" or "enhanced" amount can be a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. In certain embodiments, a "decrease" or "reduced" amount can be a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise. By a "nucleic acid sequence" or "nucleotide sequence" is meant the nucleic acid sequence encoding an amino acid, the term may also refer to the nucleic acid sequence including the portion coding for any amino acids added as an artifact of cloning, including any amino acids coded for by linkers The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

If aspects of the disclosure are described as "comprising" a feature, or versions there of (e.g., comprise), embodiments also are contemplated "consisting of" or "consisting essentially of" the feature.

The practice of the present disclosure employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ Additional techniques are explained, e.g., in U.S. Pat. No. 7,912,698 and U.S. Patent Appl. Pub. Nos. 2011/0202322 and 2011/0307437.

The technology illustratively described herein suitably may be practiced in the absence of any element(s) not specifically disclosed herein.

The terms and expressions which have been employed are used as terms of description and not of limitation, and use of such terms and expressions do not exclude any equivalents of the features shown and described or portions thereof, and various modifications are possible within the scope of the technology claimed.

Chimeric Antigen Receptors

In certain aspects, the disclosure provides a CAR that targets antigens located on the target tumor cell and/or the ECM within the TME to allow for direct targeting of the tumor cell and/or ECM (e.g., neovasculature, stromal cells such as cancer associated fibroblasts, etc.).

In other aspects, the disclosure provides a CAR that targets antigens located on the ECM within the TME to allow for indirect targeting of the tumor cell. In particular, the CAR is co-expressed with a second antigen targeting molecule (e.g., a second CAR or a bispecific molecule (e.g., a BiTE or bispecific antibody)) that targets a TAA expressed on the target tumor cell. In certain embodiments, activation of the lymphocyte expressing the CAR induces the expression of the second antigen targeting molecule. In certain embodiments, the expression of the second antigen targeting molecule is induced by a second molecule. In certain embodiments, the second molecule can be a synNotch receptor. In certain embodiments, the synNotch receptor is operably linked to the polynucleotide encoding the CAR. In some embodiments, the second molecule can be an NFAT that is activated by the activation of the T-cell or other lymphocyte.

In certain aspects, the present disclosure provides a polynucleotide encoding a first chimeric antigen receptor (CAR) comprising: (a) an extracellular target-binding domain, (b) a hinge domain, (c) a transmembrane domain, and (d) a cytoplasmic domain comprising (i) optionally one or more costimulatory domains, and (ii) a signaling domain.

In certain aspects, the present disclosure provides a polynucleotide encoding a first chimeric antigen receptor (CAR)

comprising (a) an extracellular target-binding domain comprising a Fibronectin Extradomain B (FN-EDB)-binding moiety, (b) a hinge domain, (c) a transmembrane domain, (d) a cytoplasmic domain comprising (i) optionally one or more costimulatory domains, (ii) a signaling domain.

In certain aspects, the present disclosure provides a polynucleotide encoding a first chimeric antigen receptor (CAR) comprising (a) an extracellular target-binding domain comprising a Fibronectin Extradomain B (FN-EDB)-binding moiety, (b) a hinge domain, (c) a transmembrane domain, (d) a cytoplasmic domain comprising (i) optionally one or more costimulatory domains, (ii) a signaling domain, and (e) a second gene.

Extracellular Target-Binding Domain

In certain aspects, the CARs of the present disclosure comprise an extracellular target-binding domain, wherein the extracellular target-binding domain comprises an antigen-binding moiety.

The choice of antigen-binding moiety depends upon the type and number of antigens that define the surface of a target cell. For example, the antigen-binding moiety may be chosen to recognize an antigen that acts as a cell surface marker on target cells associated with a particular disease state. In certain embodiments, the CARs of the present disclosure can be genetically modified to target a tumor antigen of interest by way of engineering a desired antigen-binding moiety that specifically binds to an antigen (e.g., on a tumor cell). Non-limiting examples of cell surface markers that may act as targets for the antigen-binding moiety in the CAR of the disclosure include those associated with tumor cells.

Examples of antigens that may be targeted by the extracellular target-binding domains include, but are not limited to, carbonic anhydrase EX, alpha-fetoprotein, A3, antigen specific for A33 antibody, Ba 733, BrE3-antigen, CA125, CD1, CD1a, CD3, CD5, CD15, CD16, CD19, CD20, CD21, CD22, CD23, CD25, CD30, CD33, CD38, CD45, CD74, CD79a, CD80, CD123, CD138, colon-specific antigen-p (CSAp), CEA (CEACAM5), CEACAM6, EGFR, EGP-I, EGP-2, Ep-CAM, EphA1, EphA2, EphA3, EphA4, EphA5, EphA6, EphA7, EphA8, EphA10, EphB1, EphB2, EphB3, EphB4, EphB6, Flt-I, Flt-3, folate receptor, HLA-DR, human chorionic gonadotropin (HCG) and its subunits, HER2/neu, hypoxia inducible factor (HIF-I), Ia, IL-2, IL-6, IL-8, interleukin 13 receptor $\alpha 2$ (IL13R$\alpha$2), insulin growth factor-1 (IGF-I), KC4-antigen, KS-1-antigen, KS1-4, Le-Y, macrophage inhibition factor (MIF), MAGE, MUC1, MUC2, MUC3, MUC4, NCA66, NCA95, NCA90, antigen specific for PAM-4 antibody, placental growth factor, p53, prostatic acid phosphatase, PSA, PSMA, RSS, 5100, TAC, TAG-72, tenascin, TRAIL receptors, Tn antigen, Thomson-Friedenreich antigens, tumor necrosis antigens, VEGF, or fibronectin-EDB (oncofetal fibronectin, FN-EDB, EDB).

In certain embodiments, the antigen that is targeted by the extracellular target-binding domain is FN-EDB or a variant of FN-EDB.

In certain embodiments, the antigen-binding moiety can be monomeric or multimeric (e.g., homodimeric or heterodimeric), or associated with multiple proteins in a non-covalent complex. In some embodiments, the antigen-binding moiety comprises an antigen-binding polypeptide or functional variant thereof that binds to an antigen. In some embodiments, the antigen-binding polypeptide is an antibody or an antibody fragment that binds to an antigen. Antigen-binding moieties may comprise antibodies and/or antibody fragments such as monoclonal antibodies, multi-specific antibodies, chimeric antibodies, single-chain Fvs (scFv), single chain antibodies, Fab fragments, F(ab') fragments, disulfide-linked Fvs (sdFv), intrabodies, minibodies, single domain antibody variable domains, nanobodies (VHHs), diabodies and anti-idiotypic (anti-Id) antibodies (including, e.g., anti-Id antibodies to antigen-specific TCR), and epitope-binding fragments of any of the above. Antibodies and/or antibody fragments may be derived from murine antibodies, rabbit antibodies, human antibodies, fully humanized antibodies, camelid antibody variable domains and humanized versions, shark antibody variable domains and humanized versions, and camelized antibody variable domains.

In certain embodiments, the antigen-binding moiety comprises an FN-EDB-binding polypeptide or functional variant thereof. In certain embodiments, the antigen-binding moiety is an antibody or an antibody fragment that binds to FN-EDB. In certain embodiments, the FN-EDB-binding moiety is an anti-FN-EDB single chain variable fragment (scFv). In some embodiments, the anti-FN-EDB is derived from an FN-EDB specific MAb (EDB-specific scFv). In some embodiments, the anti-FN-EDB is derived from an FN-EDB specific Mab L19 (L19 scFv). The L19 antibody is a specific FN-EDB antibody described in U.S. Pat. No. 8,455,625, which is herein incorporated by reference in its entirety for all purposes. In some embodiments, the anti-FN-EDB is derived from EBD-specific antibodies such as, but not limited to, bc-1 and NJB2 (see www.abcam.com/fibronectin-antibody-bc-1-ab154210; which incorporated herein by reference in their entirety for all purposes).

In some embodiments, L19 scFV comprises the amino acid sequence set forth in SEQ ID NO: 25, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 25. In certain embodiments, the nucleotide sequence that encodes the L19 scFV comprises the nucleotide sequence that encodes the amino acid sequence of SEQ ID NO: 25, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 25. In certain embodiments, the nucleotide sequence that encodes the L19 scFV comprises the nucleotide sequence set forth in SEQ ID: 26, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 26 or 129. In certain embodiments, the L19 scFV comprises the amino acid sequence set forth in SEQ ID NO: 25. In certain embodiments, the nucleotide sequence that encodes the L19 scFV comprises the nucleotide sequence set forth in SEQ ID: 26 or 129.

In certain embodiments, the extracellular target-binding domain of the CAR is a ligand for a target cell antigen or receptor. In certain embodiments, the ligand is a natural ligand of the antigen or receptor.

Linker Region and Hinge Domain

In certain embodiments, the CAR further comprises a linker region between the extracellular antigen-binding domain and the transmembrane domain, wherein the antigen-binding moiety, linker, and the transmembrane domain are in frame with each other.

The term "linker region" as used herein generally means any oligo- or polypeptide that functions to link the antigen-binding moiety to the transmembrane domain. A linker region can be used to provide more flexibility and accessibility for the antigen-binding moiety. A linker region may comprise up to 300 amino acids, preferably 10 to 100 amino acids and most preferably 25 to 50 amino acids. A linker region may be derived from all or part of naturally occurring molecules, such as from all or part of the extracellular region of CD8, CD4 or CD28, or from all or part of an antibody constant region. Alternatively, the linker region may be a synthetic sequence that corresponds to a naturally occurring linker region sequence, or may be an entirely synthetic linker region sequence. Non-limiting examples of linker regions which may be used in accordance to the disclosure include a part of human CD8a chain, partial extracellular domain of CD28, FcγRIIIa receptor, IgG, IgM, IgA, IgD, IgE, an Ig hinge, or functional fragment thereof. In some embodiments, additional linking amino acids are added to the linker region to ensure that the antigen-binding moiety is an optimal distance from the transmembrane domain. In some embodiments, when the linker is derived from an Ig, the linker may be mutated to prevent Fc receptor binding.

In some embodiments, the linker domain comprises a hinge domain. The hinge domain may be derived from CD8a, CD28, or an immunoglobulin (IgG). For example, the IgG hinge may be from IgG1, IgG2, IgG3, IgG4, IgM1, IgM2, IgA1, IgA2, IgD, IgE, or a chimera thereof.

In certain embodiments, the linker domain comprises an immunoglobulin IgG hinge or functional fragment thereof. In certain embodiments, the IgG hinge is from IgG1, IgG2, IgG3, IgG4, IgM1, IgM2, IgA1, IgA2, IgD, IgE, or a chimera thereof. In certain embodiments, the linker domain comprises the CH1, CH2, CH3 and/or hinge region of the immunoglobulin. In certain embodiments, the linker domain comprises the core hinge region of the immunoglobulin. The term "core hinge" can be used interchangeably with the term "short hinge" (a.k.a "SH"). Non-limiting examples of suitable linker domains are the core immunoglobulin hinge regions listed in Table 1 (see also Wypych et al., *JBC* 2008 283(23): 16194-16205, which is incorporated herein by reference in its entirety for all purposes). In certain embodiments, the linker domain is a fragment of the immunoglobulin hinge.

TABLE 1

| Amino Acid Sequence of Short Hinge Regions of IgG Immunoglobulins | | |
|---|---|---|
| IgG Subtype | Short Hinge Sequence | SEQ ID NO |
| IgG1 | EPKSCDKTHTCPPCP | SEQ ID NO: 27 |
| IgG1 | DLEPKSCDKTHTCPPCPDPK | SEQ ID NO: 91 |
| IgG2 | ERKCCVECPPCP | SEQ ID NO: 29 |
| IgG3 | ELKTPLGDTTHTCPRCP (EPKSCDTPPPCPRCP)$_3$ | SEQ ID NO: 30 |
| IgG4 | ESKYGPPCPSCP | SEQ ID NO: 31 |

In certain embodiments, the hinge domain comprises an IgG1 hinge, or a variant thereof. In certain embodiments, the hinge domain comprises the short hinge structure of IgG1, IgG2, IgG3, or IgG4 or a variant thereof. In certain embodiments, hinge domain comprises a short hinge region and comprises the amino acid sequence set forth in SEQ ID NO: 27, 29, 30, 31, or 91, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 27, 29, 30, 31, or 91. In certain embodiments, the nucleotide sequence encoding the hinge comprising the short hinge region comprises the nucleotide sequence that encodes the amino acid sequence of SEQ ID NO: 27, 29, 30, 31, or 91, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 27, 29, 30, 31, or 91. In certain embodiments, the nucleotide sequence encoding the hinge comprising the short hinge region comprises the nucleotide sequence of SEQ ID NO: 28 or 92, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 28 or 92. In certain embodiments, hinge domain comprises a short hinge region and comprises the amino acid sequence set forth in SEQ ID NO: 27, 29, 30, 31, or 91. In certain embodiments, the nucleotide sequence encoding the hinge comprising the short hinge region comprises the nucleotide sequence of SEQ ID NO: 28 or 92. In certain embodiments, hinge domain is a short hinge region comprising the amino acid sequence set forth in SEQ ID NO: 27 or 91 or a variant thereof. In certain embodiments, the nucleotide sequence encoding the short hinge region comprises the nucleotide sequence of SEQ ID: 28 or 92 or a variant thereof.

In some embodiments, the hinge domain is derived from CD8a stalk or complete or partial sequences of the CD8a stalk, which are also called CD8a hinge. In some embodiments, the hinge domain derived from CD8a stalk comprises the amino acid sequence set forth in SEQ ID NO: 32, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 32. In certain embodiments, the nucleotide sequence that encodes the CD8a stalk hinge domain comprises the nucleotide sequence that encodes the amino acid sequence of SEQ ID NO: 32, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 32. In certain embodiments, the nucleotide sequence that encodes the CD8a stalk hinge domain comprises the nucleotide sequence set forth in SEQ ID NO: 33, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 33. In certain embodiments, the CD8a stalk hinge domain comprises the amino acid sequence set forth in SEQ ID NO: 32. In certain embodiments, the nucleotide sequence that encodes the CD8a stalk hinge domain comprises the nucleotide sequence set forth in SEQ ID NO: 33.

In some embodiments, the hinge domain is derived from CD28. In some embodiments, the hinge domain derived from CD28 hinge domain comprises the amino acid sequence set forth in SEQ ID NO: 34, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 34. In certain embodiments, the nucleotide sequence that encodes the CD28 hinge domain comprises the nucleotide sequence that encodes the amino acid sequence of SEQ ID NO: 34, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 34. In certain embodiments, the nucleotide sequence that encodes the CD28 hinge domain comprises the nucleotide sequence set forth in SEQ ID NO: 35, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 35. In certain embodiments, the CD28 hinge domain comprises the amino acid sequence set forth in SEQ ID NO: 34. In certain embodiments, the nucleotide sequence that encodes the CD28 hinge domain comprises the nucleotide sequence set forth in SEQ ID NO: 35.

In some embodiments, in addition to the hinge domain, the linker region comprises additional linker amino acids to allow for extra flexibility and/or accessibility.

Transmembrane Domain

In certain aspects, the CARs of the present disclosure comprise a transmembrane domain, fused in frame between the extracellular target-binding domain and the cytoplasmic domain.

The transmembrane domain may be derived from the protein contributing to the extracellular target-binding domain, the protein contributing the signaling or co-signaling domain, or by a totally different protein. In some instances, the transmembrane domain can be selected or modified by amino acid substitution, deletions, or insertions to minimize interactions with other members of the CAR complex. In some instances, the transmembrane domain can be selected or modified by amino acid substitution, deletions, or insertions to avoid-binding of proteins naturally associated with the transmembrane domain. In certain embodiments, the transmembrane domain includes additional amino acids to allow for flexibility and/or optimal distance between the domains connected to the transmembrane domain.

The transmembrane domain may be derived either from a natural or from a synthetic source. Where the source is natural, the domain may be derived from any membrane-bound or transmembrane protein. Non-limiting examples of transmembrane domains of particular use in this disclosure may be derived from (i.e. comprise at least the transmembrane region(s) of) the α, β or ζ chain of the T-cell receptor, CD28, CD3 epsilon, CD45, CD4, CD5, CD8, CD8a, CD9, CD16, CD22, CD33, CD37, CD40, CD64, CD80, CD86, CD134, CD137, CD154. Alternatively, the transmembrane domain may be synthetic, in which case it will comprise predominantly hydrophobic residues such as leucine and valine. For example, a triplet of phenylalanine, tryptophan and/or valine can be found at each end of a synthetic transmembrane domain.

In certain embodiments, it will be desirable to utilize the transmembrane domain of the ζ, η or FcεR1γ chains which contain a cysteine residue capable of disulfide bonding, so that the resulting chimeric protein will be able to form disulfide linked dimers with itself, or with unmodified versions of the ζ, η or FcεR1γ chains or related proteins. In some instances, the transmembrane domain will be selected or modified by amino acid substitution to avoid-binding of such domains to the transmembrane domains of the same or different surface membrane proteins to minimize interactions with other members of the receptor complex. In other cases, it will be desirable to employ the transmembrane domain of ζ, η or FcεR1γ and -β, MB1 (Igα), B29 or CD3-γ, ζ, or η, in order to retain physical association with other members of the receptor complex.

In certain embodiments, the transmembrane domain in the CAR of the disclosure is derived from the CD28 transmembrane domain. In certain embodiments, the CD28 transmembrane domain comprises the amino acid sequence set forth in SEQ ID NO: 36, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO:36. In certain embodiments, the nucleotide sequence that encodes the CD28 transmembrane domain comprises the nucleotide sequence that encodes the amino acid sequence of SEQ ID NO: 36, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO:36. In certain embodiments, the nucleotide sequence that encodes the CD28 transmembrane domain comprises the nucleotide sequence set forth in SEQ ID NO: 37, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 37. In certain embodiments, the CD28 transmembrane domain comprises the amino acid sequence set forth in SEQ ID NO: 36. In certain embodiments, the nucleotide sequence that encodes the CD28 transmembrane domain comprises the nucleotide sequence set forth in SEQ ID NO: 37.

In certain embodiments, the transmembrane domain in the CAR of the disclosure is derived from the CD8a transmembrane domain. In certain embodiments, the CD8a transmembrane domain comprises the amino acid sequence set forth in SEQ ID NO: 38, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 38. In certain embodiments, the nucleotide sequence that encodes the CD8a transmembrane domain comprises the nucleotide sequence that encodes the amino acid sequence of SEQ ID NO: 38, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 38. In certain embodiments, the nucleotide sequence that encodes the CD8a transmembrane domain comprises the nucleotide sequence set forth in SEQ ID NO: 39, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 39. In certain embodiments, the CD8a transmembrane domain comprises the amino acid sequence set forth in SEQ ID NO: 38. In certain embodiments, the nucleotide sequence that encodes the CD8a transmembrane domain comprises the nucleotide sequence set forth in SEQ ID NO: 39.

Cytoplasmic Domain

In certain aspects, CARs of the present disclosure comprise a cytoplasmic domain, which comprises one or more costimulatory domains and one or more signaling domains. The cytoplasmic domain, which comprises one or more costimulatory domains and one or more signaling domains, is responsible for activation of at least one of the normal effector functions of the lymphocyte in which the CAR has been placed in. The term "effector function" refers to a specialized function of a cell. Effector function of a T-cell, for example, may be cytolytic activity or helper activity including the secretion of cytokines. Thus, the term "signaling domain" refers to the portion of a protein which transduces the effector function signal and directs the cell to perform a specialized function. While usually the entire signaling domain is present, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the signaling domain sufficient to transduce the effector function signal.

Non-limiting examples of signaling domains which can be used in the CARs of the present disclosure include, e.g., signaling domains derived from DAP10, DAP12, Fc epsilon receptor I γ chain (FCER1G), FcR β, CD3δ, CD3ε, CD3γ, CD3 CD5, CD22, CD226, CD66d, CD79A, and CD79B. In some embodiments, the CAR of the present disclosure comprises a signaling domain derived from CD3ζ.

In certain embodiments, the lymphocyte activation domain in the CAR of the disclosure is designed to comprise the signaling domain of CD3ζ. In certain embodiments, the CD3ζ signaling domain comprises the amino acid sequence set forth in SEQ ID NO: 57 or 59 or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 57 or 59. In certain embodiments, the nucleotide sequence that encodes the CD3ζ signaling domain comprises the nucleotide sequence that encodes the amino acid sequence of SEQ ID NO: 57 or 59, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 57 or 59. In certain embodiments, the nucleotide sequence that encodes the CD3ζ signaling domain comprises the nucleotide sequence set forth in SEQ ID NO: 58, 60, or 123-126, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 58, 60, or 123-126. In certain embodiments, the CD3 signaling domain comprises the amino acid sequence set forth in SEQ ID NO: 57 or 59. In certain embodiments, the nucleotide sequence that encodes the CD3ζ signaling domain comprises the nucleotide sequence set forth in SEQ ID NO: 58, 60, or 123-126.

Non-limiting examples of costimulatory domains which can be used in the CARs of the present disclosure include, those derived from 4-1BB (CD137), CD28, CD40, ICOS, CD134 (OX-40), BTLA, CD27, CD30, GITR, CD226, CD79A, and HVEM. In some embodiments, the CAR of the present disclosure comprises one costimulatory domain. In some embodiments, the CAR of the present disclosure comprises a costimulatory domain derived from 4-1BB. In some embodiments, the CAR of the present disclosure comprises a costimulatory domain derived from CD28.

In some embodiments, the CAR of the present disclosure comprises two or more costimulatory domains. In certain embodiments, the CAR of the present disclosure comprises two, three, four, five, six or more costimulatory domains. In some embodiments, the CAR of the present disclosure comprises a costimulatory domain derived from 4-1BB and a costimulatory domain derived from CD28.

In certain aspects, the CARs of the present disclosure comprise a cytoplasmic domain, which comprises a lymphocyte activation domain, a MyD88 polypeptide or functional fragment thereof, and a CD40 cytoplasmic polypeptide region or a functional fragment thereof. In certain embodiments, the CAR lacks the CD40 transmembrane and/or CD40 extracellular domains. In certain embodiments, the CAR includes the CD40 transmembrane domain. In certain embodiments, the CAR includes the CD40 transmembrane domain and a portion of the CD40 extracellular domain, wherein the CD40 extracellular domain does not interact with natural or synthetic ligands of CD40.

In certain embodiments, the lymphocyte activation domain is separated from the MyD88 polypeptide or functional fragment thereof and/or the CD40 cytoplasmic polypeptide region or a functional fragment thereof. In certain embodiments, the lymphocyte activation domain is separated from the MyD88 polypeptide or functional fragment thereof and/or the CD40 cytoplasmic polypeptide region or a functional fragment thereof by at least 1, 2, 3, 4, 5, 6, 7, 8, 9, 10, 11, 12, 13, 14, or 15 amino acids.

In some embodiments, the signaling domain(s) and costimulatory domain(s) can be in any order. In some embodiments, the signaling domain is upstream of the costimulatory domains. In some embodiments, the signaling domain is downstream from the costimulatory domains. In the cases where two or more costimulatory domains are included, the order of the costimulatory domains could be switched.

In some embodiments, the costimulatory domain derived from CD28 comprises the amino acid sequence set forth in SEQ ID NO: 40, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 40. In certain embodiments, the nucleotide sequence that encodes the CD28 costimulatory domain comprises the nucleotide sequence that encodes the amino acid sequence of SEQ ID NO: 40, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 40. In certain embodiments, the nucleotide sequence that encodes the CD28 costimulatory domain comprises the nucleotide sequence set forth in SEQ ID NO: 41, 42, 43, or 44, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 41, 42, 43, or 44. In certain embodiments, the CD28 costimulatory domain comprises the amino acid sequence set forth in SEQ ID NO: 40. In certain embodiments, the nucleotide sequence that encodes the CD28 costimulatory domain comprises the nucleotide sequence set forth in SEQ ID NO: 41, 42, 43, or 44.

In some embodiments, the costimulatory domain derived from 4-1BB comprises the amino acid sequence set forth in SEQ ID NO: 45, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 45. In certain embodiments, the nucleotide sequence that encodes the 4-1BB costimulatory domain comprises the nucleotide sequence that encodes the amino acid sequence of SEQ ID NO: 45, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 45. In certain embodiments, the nucleotide sequence that encodes the 4-1BB costimulatory domain comprises the nucleotide sequence set forth in SEQ ID NO: 46, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 46. In certain embodiments, the 4-1BB costimulatory domain comprises the amino acid sequence set forth in SEQ ID NO: 45. In certain embodiments, the nucleotide sequence that encodes the 4-1BB costimulatory domain comprises the nucleotide sequence set forth in SEQ ID NO: 46.

In some embodiments, the costimulatory domain derived from OX40 comprises the amino acid sequence set forth in SEQ ID NO: 47, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 47. In certain embodiments, the nucleotide sequence that encodes the OX40 costimulatory domain comprises the nucleotide sequence that encodes the amino acid sequence of SEQ ID NO: 47, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 47. In certain embodiments, the nucleotide sequence that encodes the OX40 costimulatory domain comprises the nucleotide sequence set forth in SEQ ID NO: 48 or 127, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 48 or 127. In certain embodiments, the OX40 costimulatory domain comprises the amino acid sequence set forth in SEQ ID NO: 47. In certain embodiments, the nucleotide sequence that encodes the OX40 costimulatory domain comprises the nucleotide sequence set forth in SEQ ID NO: 48 or 127.

In certain embodiments, the MyD88 polypeptide or functional fragment thereof in the CAR of the disclosure is designed to comprise the co-stimulatory domain of MyD88, or variant thereof. In certain embodiments, the MyD88 functional fragment comprises the amino acid sequence set forth in SEQ ID NO: 49, 51, or 53, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 49, 51, or 53. In certain embodiments, the nucleotide sequence encoding the MyD88 functional fragment comprises the nucleotide sequence that encodes the amino acid sequence of SEQ ID NO: 49, 51, or 53, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 49, 51, or 53. In certain embodiments, the nucleotide sequence encoding the MyD88 functional fragment comprises the nucleotide sequence set forth in SEQ ID NO: 50, 52, or 54, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 50, 52, or 54. In certain embodiments, the MyD88 functional fragment comprises the amino acid sequence set forth in SEQ ID NO: 49, 51, or 53. In certain embodiments, the nucleotide sequence that encodes the MyD88 functional fragment comprises the nucleotide sequence set forth in SEQ ID NO: 50, 52, or 54.

In certain embodiments, the CD40 polypeptide or functional fragment thereof in the CAR of the disclosure is designed to comprise the CD40 cytoplasmic polypeptide region. In certain embodiments, the CD40 cytoplasmic polypeptide region comprises the amino acid sequence set forth in SEQ ID NO: 55 or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 55. In certain embodiments, the nucleotide sequence encoding the CD40 cytoplasmic polypeptide region comprises the nucleotide sequence that encodes the amino acid sequence of SEQ ID NO: 55, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 55. In certain embodiments, the nucleotide sequence encoding the CD40 cytoplasmic polypeptide region comprises the nucleotide sequence set forth in SEQ ID NO: 56, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 56. In certain embodiments, the CD40 cytoplasmic polypeptide region comprises the amino acid sequence of SEQ ID NO: 55. In certain embodiments, the nucleotide sequence encoding the CD40 cytoplasmic polypeptide region comprises the nucleotide sequence set forth in SEQ ID NO: 56.

Leader Sequence

In certain aspects, the CAR of the present disclosure comprises a leader sequence. The leader sequence may be positioned amino-terminal to the extracellular target-binding domain. The leader sequence may be optionally cleaved from the antigen-binding moiety during cellular processing and localization of the CAR to the cellular membrane.

In some embodiments, the leader sequence may be derived from human immunoglobulin heavy chain variable region. In some embodiments, the leader sequence comprises the amino acid sequence set forth in SEQ ID NO: 61 or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 61. In certain embodiments, the nucleotide sequence encoding the leader sequence comprises the nucleotide sequence that encodes the amino acid sequence of SEQ ID NO: 61, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 61. In certain embodiments, the nucleotide sequence encoding the leader sequence comprises the sequence set forth in SEQ ID: 62, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 62 or 128. In certain embodiments, the leader sequence comprises the amino acid sequence of SEQ ID NO: 61. In certain embodiments, the nucleotide sequence encoding the leader sequence comprises the nucleotide sequence set forth in SEQ ID NO: 62 or 128.

In some embodiments, the leader sequence may be derived from CD8a. In some embodiments, the leader sequence comprises the amino acid sequence set forth in SEQ ID NO: 63 or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 63. In certain embodiments, the nucleotide sequence encoding the leader sequence comprises the nucleotide sequence that encodes the amino acid sequence of SEQ ID NO: 63, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 63. In certain embodiments, the nucleotide sequence encoding the leader sequence comprises the sequence set forth in SEQ ID NO: 64, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 64. In certain embodiments, the leader sequence comprises the amino acid sequence of SEQ ID NO: 63. In certain embodiments, the nucleotide sequence encoding the leader sequence comprises the nucleotide sequence set forth in SEQ ID NO: 64.

Additional Genes

In addition to the CAR construct, the CAR may further comprise at least one additional gene that encodes an additional peptide. Examples of additional genes can include a transduced host cell selection marker, an in vivo tracking marker, a cytokine, a suicide gene, or some other functional gene. In certain embodiments, the functional additional gene can induce the expression of another molecule. In certain embodiments, the functional additional gene can increase the safety of the CAR. For example, the CAR construct may comprise an additional gene which is truncated CD19 (tCD19). The tCD19 can be used as a tag. Expression of tCD19 may also help determine transduction efficiency. As another example, the CAR construct may comprise an additional gene which is a synNotch receptor. Once activated, the synNotch receptor can induce the expression of a target gene (e.g., a second CAR and/or bispecific molecule).

Other examples of additional genes include genes that encode polypeptides with a biological function; examples include, but are not limited to, cytokines, chimeric cytokine receptors, dominant negative receptors, safety switches (CD20, truncated EGFR or HER2, inducible caspase 9 molecules).

In certain embodiments, the CAR comprises at least one additional gene (i.e., a second gene). In certain embodiments, the CAR comprises one second gene. In other embodiments, the CAR comprises two additional genes (i.e., a third gene). In yet another embodiment, the CAR comprises three additional genes (i.e., a fourth gene). In certain embodiments, the additional genes are separated from each other and the CAR construct. For example, they may be separated by 2A sequences and/or an internal ribosomal entry sites (IRES). In certain examples, the CAR can be at any position of the polynucleotide chain (for example construct A: CAR, second gene, third gene, fourth gene; construct B: second gene, CAR, third gene, fourth gene; etc)

Non-limiting examples of classes of additional genes that can be used to increase the effector function of CAR containing host cells, include (a) secretable cytokines (e.g., but not limited to, IL-7, IL-12, IL-15, IL-18), (b) membrane bound cytokines (e.g., but not limited to, IL-15), (c) chimeric cytokine receptors (e.g., but not limited to, IL-2/IL-7, IL-4/IL-7), (d) constitutive active cytokine receptors (e.g., but not limited to, C7R), (e) dominant negative receptors (DNR; e.g., but not limited to TGFRII DNR), (f) ligands of costimulatory molecules (e.g., but not limited to, CD80, 4-1BBL), (g) nuclear factor of activated T-cells (NFATs) (e.g., NFATc1, NFATc2, NFATc3, NFATc4, and NFATS), (h) antibodies, including fragments thereof and bispecific antibodies (e.g., but not limited to, bispecific T-cell engagers (BiTEs)), or (i) a second CAR.

In some embodiments, the additional gene sequence may be derived from tCD19. In some embodiments, the tCD19 sequence comprises the amino acid sequence set forth in SEQ ID NO: 65 or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 65. In certain embodiments, the nucleotide sequence encoding the tCD19 sequence comprises the nucleotide sequence that encodes the amino acid sequence of SEQ ID NO: 65, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 65. In certain embodiments, the nucleotide sequence encoding the tCD19 sequence comprises the sequence set forth in SEQ ID NO: 66, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 66. In certain embodiments, the tCD19 sequence comprises the amino acid sequence of SEQ ID NO: 65. In certain embodiments, the nucleotide sequence encoding the tCD19 sequence comprises the nucleotide sequence set forth in SEQ ID NO: 66.

In some embodiments, the additional gene sequence may be a synNotch receptor. Example 4 provides a non-limiting example of a synNotch receptor, wherein the receptor comprises the transcription factor Gal4-VP64 as an intracellular domain. In other non-limiting embodiments, other intracellular domains include Gal4-KRAB, FFHD1-VP64, or tTA.

In some embodiments, the synNotch receptor sequence comprises the amino acid sequence set forth in SEQ ID NO: 67, 93, or 121, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 67, 93, or 121. In certain embodiments, the nucleotide sequence encoding the synNotch receptor sequence comprises the nucleotide sequence that encodes the amino acid sequence of SEQ ID NO: 67, 93, or 121, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 67, 93, or 121. In certain embodiments, the nucleotide sequence encoding the synNotch receptor sequence comprises the sequence set forth in SEQ ID NO: 68, 94, or 122, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 68, 95, or 122. In certain embodiments, the synNotch receptor sequence comprises the amino acid sequence of SEQ ID NO: 67, 93, or 121. In certain embodiments, the nucleotide sequence encoding the synNotch receptor sequence comprises the nucleotide sequence set forth in SEQ ID NO: 68, 95, or 122. An antigen-binding moiety (e.g., anti-EDB scFv (SEQ ID NO: 25)) is attached to the synNotch receptor, which will bind to the target antigen.

In certain embodiments, the additional gene may be regulated by an NFAT dependent-promoter. Activation of the T-cell or other lymphocyte leads to activation of the transcription factor NFAT resulting in the induction of the expression of the protein encoded by the gene linked with the NFAT dependent promoter. One or more members of the NFAT family (i.e., NFATc1, NFATc2, NFATc3, NFATc4, and

29

NFAT5) is expressed in most cells of the immune system. NFAT-dependent promoters and enhancers tend to have three to five NFAT binding sites In certain embodiments, the functional additional gene can be a suicide gene. A suicide gene is a recombinant gene that will cause the host cell that the gene is expressed in to undergo programmed cell death or antibody mediated clearance at a desired time. Suicide genes can function to increase the safety of the CAR. In another embodiment, the additional gene is an inducible suicide gene. Non-limiting examples of suicide genes include i) molecules that are expressed on the cell surface and can be targeted with a clinical grade monoclonal antibody including CD20, EGFR or a fragment thereof, HER2 or a fragment thereof, and ii) inducible suicide genes (e.g., but not limited to inducible caspase 9 (see Straathof et al. (2005) *Blood.* 105(11): 4247-4254; US Publ. No. 2011/0286980, each of which are incorporated herein by reference in their entirety for all purposes)).

In certain aspects, CARs of the present disclosure may be regulated by a safety switch. As used herein, the term "safety switch" refers to any mechanism that is capable of removing or inhibiting the effect of a CAR from a system (e.g., a culture or a subject). Safety switches can function to increase the safety of the CAR.

The function of the safety switch may be inducible. Non-limiting examples of safety switches include (a) molecules that are expressed on the cell surface and can be targeted with a clinical grade monoclonal antibody including CD20, EGFR or a fragment thereof, HER2 or a fragment thereof, and (b) inducible suicide genes (e.g., but not limited to herpes simplex virus thymidine kinase (HSV-TK) and inducible caspase 9 (see Straathof et al. (2005) *Blood.* 105(11): 4247-4254; US Publ. No. 2011/0286980, each of which are incorporated herein by reference in their entirety for all purposes).

In some embodiments, the safety switch is a CD20 polypeptide. Expression of human CD20 on the cell surface presents an attractive strategy for a safety switch. The inventors and others have shown that cells that express CD20 can be rapidly eliminated with the FDA approved monoclonal antibody rituximab through complement-mediated cytotoxicity and antibody-dependent cell-mediated cytotoxicity (see e.g., Griffioen, M., et al. *Haematologica* 94, 1316-1320 (2009), which is incorporated herein by reference in its entirety for all purposes). Rituximab is an anti-CD20 monoclonal antibody that has been FDA approved for Chronic Lymphocytic Leukemia (CLL) and Non-Hodgkin's Lymphoma (NHL), among others (Storz, U. *MAbs* 6, 820-837 (2014), which is incorporated herein by reference in its entirety for all purposes). The CD20 safety switch is non-immunogenic and can function as a reporter/selection marker in addition to a safety switch (Bonifant, C. L., et al. *Mol Ther* 24, 1615-1626 (2016); van Loenen, M. M., et al. *Gene Ther* 20, 861-867 (2013); each of which is incorporated herein by reference in its entirety for all purposes).

Accordingly, in some embodiments, the polynucleotide encoding a CAR of the present disclosure further comprises a sequence encoding a CD20 polypeptide. In some embodiments, the CD20 polypeptide comprises the amino acid sequence set forth in SEQ ID NO: 84, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 84. In certain embodiments, the nucleotide sequence that encodes the CD20 polypeptide comprises the nucleotide sequence that encodes the amino acid sequence of SEQ ID NO: 84, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 84. In certain embodiments, the nucleotide sequence that encodes the CD20 polypeptide comprises the nucleotide sequence set forth in SEQ ID NO: 85 or 86, or a nucleotide sequence having at least 50, at least 55, at least 60, at least 65, at least 70, at least 75, at least 80, at least 85, at least 90, at least 95, at least 96, at least 97, at least 98 or at least 99%, sequence identity with SEQ ID NO: 85 or 86. In certain embodiments, the CD20 polypeptide comprises the amino acid sequence set forth in SEQ ID NO: 84. In certain embodiments, the nucleotide sequence that encodes the CD20 polypeptide comprises the nucleotide sequence set forth in SEQ ID NO.: 85 or 86.

In some embodiments, the sequence encoding an additional gene is operably linked to the sequence encoding CAR via a sequence encoding a self-cleaving peptide and/or an Internal Ribosome Entry Site (IRES) as disclosed herein.

Non-limiting examples of self-cleaving peptide sequences includes Thoseaasigna virus 2A (T2A; AEGRGSLLTCGD-VEENPGP, SEQ ID NO: 69, EGRGSLLTCGDVEENPGP, SEQ ID NO: 71, or GSGEGRGSLLTCGDVEENPGP, SEQ ID NO: 73); the foot and mouth disease virus (FMDV) 2A sequence (F2A; GSGSRVTELLYRMKRAETYCPRPL-LAIHPTEARHKQKIVAPVKQLLNFDLLKLAGDV ESNPGP, SEQ ID NO: 74), Sponge (*Amphimedon queens-landica*) 2A sequence (LLCFLLLLLSGDVELNPGP, SEQ ID NO: 75; or HHFMFLLLLLAGDIELNPGP, SEQ ID NO: 76); acorn worm 2A sequence (*Saccoglossus kowalevskii*) (WFLVLLSFILSGDIEVNPGP, SEQ ID NO: 77); amphioxus (*Branchiostoma floridae*) 2A sequence (KN-CAMYMLLLSGDVETNPGP, SEQ ID NO: 78; or MVISQLMLKLAGDVEENPGP, SEQ ID NO: 79); porcine teschovirus-1 2A sequence (P2A; GSGATNFSLLKQAGD-VEENPGP, SEQ ID NO: 80); and equine rhinitis A virus 2A sequence (E2A; GSGQCTNYALLKLAGDVESNPGP, SEQ ID NO: 81). In some embodiments, the separation sequence is a naturally occurring or synthetic sequence. In certain embodiments, the separation sequence includes the 2A consensus sequence D-X-E-X-NPGP (SEQ ID NO: 82), in which X is any amino acid residue.

Alternatively, an Internal Ribosome Entry Site (IRES) may be used to link the CAR and the additional gene. IRES is an RNA element that allows for translation initiation in a cap-independent manner. IRES can link two coding sequences in one bicistronic vector and allow the translation of both proteins in cells.

In some embodiments, the self-cleaving 2A peptide is a T2A peptide and comprises the amino acid sequence set forth in SEQ ID NO: 69 or 71. In some embodiments, the sequence encoding the T2A peptide comprises the nucleotide sequence SEQ ID NO: 70, 72 or 83.

In certain embodiments, the host cells can be genetically modified to express not only CARs as disclosed herein but to also express fusion protein with signaling activity (e.g., costimulation, T-cell activation). These fusion proteins can improve host cell activation and/or responsiveness. In certain embodiments, the fusion protein can enhance the host cell's response to the target antigen. In certain embodiments, the fusion protein can impart resistance to suppression signals.

In certain embodiments, fusion proteins can comprise portions of CD4, CD8a, CD28, portions of a T-cell receptor, or an antigen-binding moiety (e.g., scFv) linked to a MyD88, CD40, and/or other signaling molecules.

In certain embodiments, the fusion protein comprises an extracellular target-binding domain (as disclosed above), a transmembrane domain (as described above) and a cytoplas- mic domain, wherein the cytoplasmic domain comprises at least one co-stimulatory protein (as described above). In certain embodiments, the co-stimulatory fusion protein does not comprise a lymphocyte activation domain (e.g., Cd3ζ). In certain embodiments, the at least one co-stimulatory protein can be a MyD88 polypeptide or functional fragment thereof (as described above), and/or a CD40 cytoplasmic polypeptide region or a functional fragment thereof (as described above).

In certain embodiments, the fusion protein comprises an extracellular domain (such as, but not limited to CD19, CD34), a transmembrane domain (as described above) and a cytoplasmic domain, wherein the cytoplasmic domain comprises at least one co-stimulatory protein (as described above). In certain embodiments, the fusion protein does not comprise a lymphocyte activation domain (e.g., Cd3ζ). In certain embodiments, the at least one portion of the fusion protein can be a MyD88 polypeptide or functional fragment thereof (as described above), and/or a CD40 cytoplasmic polypeptide region or a functional fragment thereof (as described above).

Non-limiting examples of fusion proteins include, but are not limited to, the constructs in the publication of PCT/US19/32786 and WO2016073875, which are incorporated herein by reference in its entirety for all purposes.

In certain embodiments, the fusion proteins are intro- duced into the host cell on a separate vector from the CAR. In certain embodiments, the fusion proteins are introduced into the host cell on the same vector as the CAR. In certain embodiments, the fusion proteins are introduced into the host cell on the same vector as the CAR but separated by a separation sequence such as 2A.

Non-Limited Examples of CARs

In certain embodiments, the CAR can be encoded by one polypeptide chain. In certain embodiments, the CAR of the disclosure is encoded by a nucleotide sequence comprising the nucleotides sequence of SEQ ID NO: 2, 4, 6, 8, 10, 12, 14, 16, 18, 20, 22, 24, 96, 98, 100, 102, 104, 106, 108, 110, 112, 114, 116, 118, or 120, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 2, 4, 6, 8, 10, 12, 14, 16, 18, 20, 22, 24, 96, 98, 100, 102, 104, 106, 108, 110, 112, 114, 116, 118, or 120. In certain embodiments, the CAR is encoded by the nucleotide sequence that encodes the amino acid sequence of SEQ ID NO: 1, 3, 5, 7, 9, 11, 13, 15, 17, 19, 21, 23, 95, 97, 99, 101, 103, 105, 107, 109, 111, 113, 115, 117, or 119. In another embodiment, the CAR comprises the amino acid sequence of SEQ ID NO: 1, 3, 5, 7, 9, 11, 13, 15, 17, 19, 21, 23, 95, 97, 99, 101, 103, 105, 107, 109, 111, 113, 115, 117, or 119, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 1, 3, 5, 7, 9, 11, 13, 15, 17, 19, 21, 23, 95, 97, 99, 101, 103, 105, 107, 109, 111, 113, 115, 117, or 119. In another embodiment, the CAR comprises the amino acid sequence of SEQ ID NO: 1, 3, 5, 7, 9, 11, 13, 15, 17, 19, 21, 23, 95, 97, 99, 101, 103, 105, 107, 109, 111, 113, 115, 117, or 119.

In certain embodiments, the CAR can be encoded by two polypeptide chains. For example, the first polypeptide chain can encode an extracellular target-binding domain compris- ing an FN-EDB-binding moiety, a transmembrane domain, and a short cytoplasmic tail, and the second polypeptide chain can encode a short extracellular domain, a transmem- brane domain, and a cytoplasmic domain comprising a lymphocyte activation domain, a MyD88 polypeptide or functional fragment thereof, and a CD40 cytoplasmic poly- peptide region or a functional fragment thereof. Each domain is described in greater detail above. In certain embodiments, both polypeptides can interact via their respective transmembrane domain.

In various embodiments, the polynucleotide encoding a CAR is a DNA molecule. In various embodiments, the polynucleotide encoding a CAR is an RNA molecule.

In one aspect, the present disclosure provides CAR poly- peptides encoded by a polynucleotide described above.

Vectors

The present disclosure provides recombinant vectors comprising a polynucleotide encoding a CAR comprising polynucleotides encoding the proteins disclosed above. In certain embodiments, the polynucleotide is operatively linked to at least one regulatory element for expression of the chimeric antigen receptor.

In certain embodiments, recombinant vectors of the dis- closure comprise the nucleotide sequence of SEQ ID NO: 2, 4, 6, 8, 10, 12, 14, 16, 18, 20, 22, 24, 96, 98, 100, 102, 104, 106, 108, 110, 112, 114, 116, 118, or 120, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 2, 4, 6, 8, 10, 12, 14, 16, 18, 20, 22, 24, 96, 98, 100, 102, 104, 106, 108, 110, 112, 114, 116, 118, or 120. In certain embodiments, recombinant vectors comprise a nucleotide sequence that encodes the amino acid sequence of SEQ ID NO: 1, 3, 5, 7, 9, 11, 13, 15, 17, 19, 21, 23, 95, 97, 99, 101, 103, 105, 107, 109, 111, 113, 115, 117, or 119, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 1, 3, 5, 7, 9, 11, 13, 15, 17, 19, 21, 23, 95, 97, 99, 101, 103, 105, 107, 109, 111, 113, 115, 117, or 119.

In certain embodiments, the recombinant vector com- prises a polynucleotide encoding a CAR, wherein the poly- nucleotide is operatively linked to at least one additional gene. In some embodiments, the additional gene is a syn- Notch receptor. In some embodiments, the additional gene is a tCD19.

In certain embodiments, the vector is a viral vector. In certain embodiments, the viral vector can be, but is not limited to, a retroviral vector, an adenoviral vector, an adeno-associated virus vector, an alphaviral vector, a herpes virus vector, and a vaccinia virus vector. In some embodi- ments, the viral vector is a lentiviral vector.

In some embodiments, the vector is a non-viral vector. The viral vector may be a plasmid or a transposon (such as a PiggyBac- or a Sleeping Beauty transposon).

In certain embodiments, the polynucleotide encoding the CAR is operably linked to at least a regulatory element. The regulatory element can be capable of mediating expression of the CAR in the host cell. Regulatory elements include, but are not limited to, promoters, enhancers, initiation sites, polyadenylation (polyA) tails, IRES elements, response ele- ments, and termination signals. In certain embodiments, the regulatory element regulates CAR expression. In certain embodiments, the regulatory element increased the expres- sion of the CAR. In certain embodiments, the regulatory element increased the expression of the CAR once the host cell is activated. In certain embodiments, the regulatory element decreases expression of the CAR. In certain embodiments, the regulatory element decreases expression of the CAR once the host cell is activated.

CAR-Modified Host Cells

In one aspect, the present disclosure provides an isolated host cell comprising a polynucleotide or a recombinant vector described herein. In one aspect, the present disclosure provides an isolated host cell comprising a CAR described herein. In various embodiments, the isolated host cell further comprises a second antigen targeting molecule (e.g., a second CAR or a bispecific molecule) that targets a TAA expressed on the target tumor cell. In certain embodiments, the isolated host cell further comprises a second CAR that targets a TAA expressed on the target tumor cell. In certain embodiments, the isolated host cell further comprises a bispecific molecule that targets a TAA expressed on the target tumor cell. In certain embodiments, the bispecific molecule is a bispecific T-cell engager (BiTE) or a bispecific antibody.

In certain embodiments, the TAA is 5T4, $\alpha_v\beta_6$ integrin, B7-H3, B7-H6, CAIX, CD19, CD20, CD22, CD30, CD33, CD44, CD44v6, CD44v7/8, CD70, CD123, CD138, CD171, CEA, Claudin-6 or -18, CSPG4, EGFR, EGFR family including ErbB2 (HER2), EGFRvIII, EGP2, EGP40, EPCAM, EphA2, EpCAM, FAP, fetal AchR, FR$\alpha$, GD2, GD3, MAGE1, NY-ESO-1, IL-11R$\alpha$, IL-13R$\alpha$2, Lambda, Lewis-Y, Kappa, Mesothelin, Muc1, Muc16, NCAM, NKG2D Ligands, NY-ESO-1, PRAME, PSCA, PSMA, ROR1, Survivin, TAG72, TEMs, or VEGFR2.

In various embodiments, the host cell is an immune cell. The immune cell may be a T-cell or a natural killer (NK) cell.

In various embodiments, the host cell is a T-cell. T-cells may include, but are not limited to, thymocytes, naive T lymphocytes, immature T lymphocytes, mature T lymphocytes, resting T lymphocytes, or activated T lymphocytes. A T-cell can be a T helper (Th) cell, for example a T helper 1 (Th1) or a T helper 2 (Th2) cell. The T-cell can be a helper T-cell (HTL; CD4+ T-cell) CD4+ T-cell, a cytotoxic T-cell (CTL; CD8+ T-cell), a tumor infiltrating cytotoxic T-cell (TIL; CD8+ T-cell), CD4+CD8+ T-cell, or any other subset of T-cells. Other illustrative populations of T-cells suitable for use in particular embodiments include naive T-cells memory T-cells, and NKT cells.

In some embodiments, the T-cell is selected from a CD8+ T-cell, a CD4+ T-cell, a cytotoxic T-cell, an $\alpha\beta$ T-cell receptor (TCR) T-cell, a natural killer T (NKT) cell, a $\gamma\delta$ T-cell, a memory T-cell, a T-helper cell, and a regulatory T-cell (Treg).

In various embodiments, the host cell is a NK cell. NK cell refers to a differentiated lymphocyte with a CD3– CD16+, CD3–CD56+, CD16+CD56+ and/or CD57+ TCR-phenotype.

In various embodiments, the host cell has been activated and/or expanded ex vivo.

In various embodiments, the host cell is an allogeneic cell. In various embodiments, the host cell is an autologous cell.

In some embodiments, the host cell is isolated from a subject having a tumor. In some embodiments, the tumor can be found within, but not limited to, breast tissue, prostate tissue, bladder tissue, oral and/or dental tissue, head and/or neck tissue, colorectal tissue, lung tissue, brain tissue, skin, lymph nodes, and bone. In some embodiments, the tumor is a cancer. In some embodiments, the cancer can be, but not limited to, breast cancer, prostate cancer, bladder cancer, oral squamous cell carcinoma, head and/or neck squamous cell carcinoma, colorectal cancer, lung cancer, brain tumors, melanoma, bone, pediatric solid tumors and brain tumors, and/or lymphoma.

In certain embodiments, the host cell is isolated from a subject having a tumor, wherein one or more cells of the tumor cells express FN-EDB. Non-limiting examples of tumor cells that express FN-EDB include breast tumor cells, prostate tumor cells, bladder tumor cells, oral squamous cell carcinoma, head and neck squamous cell carcinoma, colorectal tumor cells, lung tumor cells, brain tumors, melanoma, bone, pediatric solid tumors and brain tumors, lymphoma, plasmacytoma, mantel cell lymphoma, lymphocytic lymphoma, marginal zone lymphoma, lymphoplasmocytic lymphoma, follicular lymphoma, diffuse large B-cell lymphoma (DLBCL), B-lymphoblastic lymphoma, anaplastic large T-cell lymphoma, T lymphoblastic lymphoma, peripheral T-NHL (NOS), classical Hodgkin lymphoma (cHL), chronic myelogenous leukemia, chronic idiopathic myelofibrosis, essential thrombocythemia, polycythemia vera, and/or acute myeloblastic leukemia.

In some embodiments, the host cell is derived from a blood, marrow, tissue, or a tumor sample.

In one aspect, the present disclosure provides a method of generating an isolated host cell described herein. The method includes genetically modifying the host cell with a polynucleotide encoding a CAR and optionally an additional gene (e.g., synNotch, tCD19), and/or the recombinant vector comprising the polynucleotide encoding a CAR and optionally a safety switch (e.g., CD20 polypeptide). The genetically modifying step may be conducted in vivo or ex vivo. In some embodiments, the genetically modifying step is conducted ex vivo. The method may further include activation and/or expansion of the host cell ex vivo before, after and/or during the genetic modification.

Isolation/Enrichment

The host cells may be autologous/autogeneic ("self") or non-autologous ("non-self," e.g., allogeneic, syngeneic or xenogeneic). In certain embodiments, the host cells are obtained from a mammalian subject. In other embodiments, the host cells are obtained from a primate subject. In certain embodiments, the host cells are obtained from a human subject.

Lymphocytes can be obtained from sources such as, but not limited to, peripheral blood mononuclear cells, bone marrow, lymph nodes tissue, cord blood, thymus issue, tissue from a site of infection, ascites, pleural effusion, spleen tissue, and tumors. Lymphocytes may also be generated by differentiation of stem cells. In certain embodiments, lymphocytes can be obtained from blood collected from a subject using techniques generally known to the skilled person, such as sedimentation, e.g., FICOLL™ separation.

In certain embodiments, cells from the circulating blood of a subject are obtained by apheresis. An apheresis device typically contains lymphocytes, including T-cells, monocytes, granulocytes, B cells, other nucleated white blood cells, red blood cells, and platelets. In certain embodiments, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. A washing step may be accomplished by methods known to those in the art, such as, but not limited to, using a semiautomated flowthrough centrifuge (e.g., Cobe 2991 cell processor, or the Baxter CytoMate). After washing, the cells may be resuspended in a variety of biocompatible buffers, cell culture medias, or other saline solution with or without buffer.

In certain embodiments, host cells can be isolated from peripheral blood mononuclear cells (PBMCs) by lysing the red blood cells and depleting the monocytes. As an example, the cells can be sorted by centrifugation through a PER-COLL™ gradient. In certain embodiments, after isolation of PBMC, both cytotoxic and helper T lymphocytes can be sorted into naive, memory, and effector T-cell subpopulations either before or after activation, expansion, and/or genetic modification.

In certain embodiments, T lymphocytes can be enriched. For example, a specific subpopulation of T lymphocytes, expressing one or more markers such as, but not limited to, CD3, CD4, CD8, CD14, CD15, CD16, CD19, CD27, CD28, CD34, CD36, CD45RA, CD45RO, CD56, CD62, CD62L, CD122, CD123, CD127, CD235a, CCR7, HLA-DR or a combination thereof using either positive or negative selection techniques. In certain embodiments, the T lymphocytes for use in the compositions of the disclosure do not express or do not substantially express one or more of the following markers: CD57, CD244, CD160, PD-1, CTLA4, TIM3, and LAG3.

In certain embodiments, NK cells can be enriched. For example, a specific subpopulation of T lymphocytes, expressing one or more markers such as, but not limited to, CD2, CD16, CD56, CD57, CD94, CD122 or a combination thereof using either positive or negative selection techniques.

Stimulation/Activation

In order to reach sufficient therapeutic doses of host cell compositions, host cells are often subjected to one or more rounds of stimulation/activation. In certain embodiments, a method of producing host cells for administration to a subject comprises stimulating the host cells to become activated in the presence of one or more stimulatory signals or agents (e.g., compound, small molecule, e.g., small organic molecule, nucleic acid, polypeptide, or a fragment, isoform, variant, analog, or derivative thereof). In certain embodiments, a method of producing host cells for administration to a subject comprises stimulating the host cells to become activated and to proliferate in the presence of one or more stimulatory signals or agents.

Host cells (e.g., T lymphocytes and NK cells) can be activated by inducing a change in their biologic state by which the cells express activation markers, produce cytokines, proliferate and/or become cytotoxic to target cells. All these changes can be produced by primary stimulatory signals. Co-stimulatory signals amplify the magnitude of the primary signals and suppress cell death following initial stimulation resulting in a more durable activation state and thus a higher cytotoxic capacity.

T cells can be activated generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety.

In certain embodiments, the T-cell based host cells can be activated by binding to an agent that activates CD3.

In other embodiments, a CD2-binding agent may be used to provide a primary stimulation signal to the T-cells. For example, and not by limitation, CD2 agents include, but are not limited to, CD2 ligands and anti-CD2 antibodies, e.g., the Tl 1.3 antibody in combination with the Tl 1.1 or Tl 1.2 antibody (Meuer, S. C. et al. (1984) Cell 36:897-906) and the 9.6 antibody (which recognizes the same epitope as TI 1.1) in combination with the 9-1 antibody (Yang, S. Y. et al. (1986) J. Immunol. 137:1097-1100). Other antibodies which bind to the same epitopes as any of the above described antibodies can also be used.

In certain embodiments, the host cells are activated by administering phorbol myristate acetate (PMA) and ionomycine. In certain embodiments, the host cells are activated by administering an appropriate antigen that induces activation and then expansion. In certain embodiments, PMA, ionomycin, and/or appropriate antigen are administered with CD3 induce activation and/or expansion.

In general, the activating agents used in the present disclosure includes, but is not limited to, an antibody, a fragment thereof and a proteinaceous binding molecule with antibody-like functions. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). The divalent antibody fragment may be an (Fab)2'-fragment, or a divalent single-chain Fv fragment while the monovalent antibody fragment may be selected from the group consisting of a Fab fragment, a Fv fragment, and a single-chain Fv fragment (scFv).

In certain embodiments, one or more binding sites of the CD3 agents may be a bivalent proteinaceous artificial binding molecule such as a dimeric lipocalin mutein (i.e., duocalin). In certain embodiments the receptor binding reagent may have a single second binding site, (i.e., monovalent). Examples of monovalent agents include, but are not limited to, a monovalent antibody fragment, a proteinaceous binding molecule with antibody-like binding properties or an MHC molecule. Examples of monovalent antibody fragments include, but are not limited to a Fab fragment, a Fv fragment, and a single-chain Fv fragment (scFv), including a divalent single-chain Fv fragment.

The agent that specifically binds CD3 includes, but is not limited to, an anti-CD3-antibody, a divalent antibody fragment of an anti-CD3 antibody, a monovalent antibody fragment of an anti-CD3-antibody, and a proteinaceous CD3-binding molecule with antibody-like binding properties. A proteinaceous CD3-binding molecule with antibody-like binding properties can be an aptamer, a mutein based on a polypeptide of the lipocalin family, a glubody, a protein based on the ankyrin scaffold, a protein based on the crystalline scaffold, an adnectin, and an avimer. It also can be coupled to a bead.

In certain embodiments, the activating agent (e.g., CD3-binding agents) can be present in a concentration of about 0.1 to about 10 μg/ml. In certain embodiments, the activating agent (e.g., CD3-binding agents) can be present in a concentration of about 0.2 μg/ml to about 9 μg/ml, about 0.3 μg/ml to about 8 μg/ml, about 0.4 μg/ml to about 7 μg/ml, about 0.5 μg/ml to about 6 μg/ml, about 0.6 μg/ml to about 5 μg/ml, about 0.7 μg/ml to about 4 μg/ml, about 0.8 μg/ml to about 3 μg/ml, or about 0.9 μg/ml to about 2 μg/ml. In certain embodiments, the activating agent (e.g., CD3-binding agents) is administered at a concentration of about 0.1 μg/ml, about 0.2 μg/ml, about 0.3 μg/ml, about 0.4 μg/ml, about 0.5 μg/ml, about 0.6 μg/ml, about 0.7 μg/ml, about 0.8 μM, about 0.9 μg/ml, about 1 μg/ml, about 2 μg/ml, about 3

µg/ml, about 4 µM, about 5 µg/ml, about 6 µg/ml, about 7 µg/ml, about 8 µg/ml, about 9 µg/ml, or about 10 µg/ml. In certain embodiments, the CD3-binding agents can be present in a concentration of 1 µg/ml.

NK cells can be activated generally using methods as described, for example, in U.S. Pat. Nos. 7,803,376, 6,949, 520, 6,693,086, 8,834,900, 9,404,083, 9,464,274, 7,435,596, 8,026,097, 8,877,182; U.S. Patent Applications US2004/ 0058445, US2007/0160578, US2013/0011376, US2015/ 0118207, US2015/0037887; and PCT Patent Application WO2016/122147, each of which is incorporated herein by reference in its entirety.

In certain embodiments, the NK based host cells can be activated by, for example and not limitation, inhibition of inhibitory receptors on NK cells (e.g., KIR2DL1, KIR2DL2/ 3, KIR2DL4, KIR2DL5A, KIR2DL5B, KIR3DL1, KIR3DL2, KIR3DL3, LILRB1, NKG2A, NKG2C, NKG2E or LILRB5 receptor).

In certain embodiments, the NK based host cells can be activated by, for example and not limitation, feeder cells (e.g., native K562 cells or K562 cells that are genetically modified to express 4-1BBL and cytokines such as IL15 or IL21).

In other embodiments, interferons or macrophage-derived cytokines can be used to activate NK cells. For example and not limitation, such interferons include but are not limited to interferon alpha and interferon gamma, and such cytokines include but are not limited to IL-15, IL-2, IL-21.

In certain embodiments, the NK activating agent can be present in a concentration of about 0.1 to about 10 µg/ml. In certain embodiments, the NK activating agent can be present in a concentration of about 0.2 µg/ml to about 9 µg/ml, about 0.3 µg/ml to about 8 µg/ml, about 0.4 µg/ml to about 7 µg/ml, about 0.5 µg/ml to about 6 µg/ml, about 0.6 µg/ml to about 5 µg/ml, about 0.7 µg/ml to about 4 µg/ml, about 0.8 µg/ml to about 3 µg/ml, or about 0.9 µg/ml to about 2 µg/ml. In certain embodiments, the NK activating agent is administered at a concentration of about 0.1 µg/ml, about 0.2 µg/ml, about 0.3 µg/ml, about 0.4 µg/ml, about 0.5 µg/ml, about 0.6 µg/ml, about 0.7 µg/ml, about 0.8 µM, about 0.9 µg/ml, about 1 µg/ml, about 2 µg/ml, about 3 µg/ml, about 4 µM, about 5 µg/ml, about 6 µg/ml, about 7 µg/ml, about 8 µg/ml, about 9 µg/ml, or about 10 µg/ml. In certain embodiments, the NK activating agent can be present in a concentration of 1 µg/ml.

In certain embodiments, the activating agent is attached to a solid support such as, but not limited to, a bead, an absorbent polymer present in culture plate or well or other matrices such as, but not limited to, Sepharose or glass; may be expressed (such as in native or recombinant forms) on cell surface of natural or recombinant cell line by means known to those skilled in the art.

Polynucleotide Transfer

In certain embodiments, the host cells are genetically modified to express a CAR described above. The host cells can be genetically modified after stimulation/activation. In certain embodiments, the host cells are modified within 12 hours, 16 hours, 24 hours, 36 hours, or 48 hours of stimulation/activation. In certain embodiments, the cells are modified within 16 to 24 hours after stimulation/activation. In certain embodiments, the host cells are modified within 24 hours.

In order to genetically modify the host cell to express the CAR, the CAR polynucleotide construct must be transferred into the host cell. Polynucleotide transfer may be via viral or non-viral gene methods. Suitable methods for polynucleotide delivery for use with the current methods include any method known by those of skill in the art, by which a polynucleotide can be introduced into an organelle, cell, tissue or organism.

In some embodiments, polynucleotides are transferred to the cell in a non-viral vector. In some embodiments, the non-viral vector is a transposon. Exemplary transposons hat can be used in the present disclosure include, but are not limited to, a sleeping beauty transposon and a PiggyBac transposon.

Nucleic acid vaccines can be used to transfer CAR polynucleotides into the host cells. Such vaccines include, but are not limited to non-viral polynucleotide vectors, "naked" DNA and RNA, and viral vectors. Methods of genetically modifying cells with these vaccines, and for optimizing the expression of genes included in these vaccines are known to those of skill in the art.

In certain embodiments, the host cells can be genetically modified by methods ordinarily used by one of skill in the art. In certain embodiments, the host cells can be transduced via retroviral transduction. References describing retroviral transduction of genes are Anderson et al., U.S. Pat. No. 5,399,346; Mann et al., Cell 33:153 (1983); Temin et al., U.S. Pat. No. 4,650,764; Temin et al., U.S. Pat. No. 4,980, 289; Markowitz et al., J. Virol. 62:1120 (1988); Temin et al., U.S. Pat. No. 5,124,263; International Patent Publication No. WO 95/07358, published Mar. 16, 1995, by Dougherty et al.; and Kuo et al., Blood 82:845 (1993), each of which is incorporated herein by reference in its entirety.

One method of genetic modification includes ex vivo modification. Various methods are available for transfecting cells and tissues removed from a subject via ex vivo modification. For example, retroviral gene transfer in vitro can be used to genetically modified cells removed from the subject and the cell transferred back into the subject. See e.g., Wilson et al., Science, 244:1344-1346, 1989 and Nabel et al., Science, 244(4910):1342-1344, 1989, both of which are incorporated herein by reference in their entity. In certain embodiments, the host cells may be removed from the subject and transfected ex vivo using the polynucleotides (e.g., expression vectors) of the disclosure. In certain embodiments, the host cells obtained from the subject can be transfected or transduced with the polynucleotides (e.g., expression vectors) of the disclosure and then administered back to the subject.

Another method of gene transfer includes injection. In certain embodiments, a cell or a polynucleotide or viral vector may be delivered to a cell, tissue, or organism via one or more injections (e.g., a needle injection). Non-limiting methods of injection include injection of a composition (e.g., a saline based composition). Polynucleotides can also be introduced by direct microinjection. Non-limiting sites of injection include, subcutaneous, intradermal, intramuscular, intranodal (allows for direct delivery of antigen to lymphoid tissues). intravenous, intraprotatic, intratumor, intralymphatic (allows direct administration of DCs) and intraperitoneal. It is understood that proper site of injection preparation is necessary (e.g., shaving of the site of injection to observe proper needle placement).

Electroporation is another method of polynucleotide delivery. See e.g., Potter et al., (1984) Proc. Nat'l Acad. Sci. USA, 81, 7161-7165 and Tur-Kaspa et al., (1986) Mol. Cell Biol., 6, 716-718, both of which are incorporated herein in their entirety for all purposes. Electroporation involves the exposure of a suspension of cells and DNA to a high-voltage electric discharge. In certain embodiments, cell wall-degrading enzymes, such as pectin-degrading enzymes, can be employed to render the host cells more susceptible to genetic modification by electroporation than untreated cells. See e.g., U.S. Pat. No. 5,384,253, incorporated herein by reference in its entirety for all purposes.

In vivo electroporation involves a basic injection technique in which a vector is injected intradermally in a subject. Electrodes then apply electrical pulses to the intradermal site causing the cells localized there (e.g., resident dermal dendritic cells), to take up the vector. These tumor antigen-expressing dendritic cells activated by local inflammation can then migrate to lymph-nodes.

Methods of electroporation for use with this disclosure include, for example, Sardesai, N. Y., and Weiner, D. B., *Current Opinion in Immunotherapy* 23:421-9 (2011) and Ferraro, B. et al., *Human Vaccines* 7:120-127 (2011), both of which are hereby incorporated by reference herein in their entirety for all purposes.

Additional methods of polynucleotide transfer include liposome-mediated transfection (e.g., polynucleotide entrapped in a lipid complex suspended in an excess of aqueous solution. See e.g., Ghosh and Bachhawat, (1991) In: *Liver Diseases, Targeted Diagnosis and Therapy Using Specific Receptors and Ligands*. pp. 87-104). Also contemplated is a polynucleotide complexed with Lipofectamine, or Superfect); DEAE-dextran (e.g., a polynucleotide is delivered into a cell using DEAE-dextran followed by polyethylene glycol. See e.g., Gopal, T. V., *Mol Cell Biol.* 1985 May; 5(5):1188-90); calcium phosphate (e.g., polynucleotide is introduced to the cells using calcium phosphate precipitation. See e.g., Graham and van der Eb, (1973) *Virology*, 52, 456-467; Chen and Okayama, *Mol. Cell Biol.*, 7(8):2745-2752, 1987), and Rippe et al., *Mol. Cell Biol.*, 10:689-695, 1990); sonication loading (introduction of a polynucleotide by direct sonic loading. See e.g., Fechheimer et al., (1987) *Proc. Nat'l Acad. Sci. USA*, 84, 8463-8467); microprojectile bombardment (e.g., one or more particles may be coated with at least one polynucleotide and delivered into cells by a propelling force. See e.g., U.S. Pat. Nos. 5,550,318; 5,538,880; 5,610,042; and PCT Application WO 94/09699; Klein et al., (1987) *Nature*, 327, 70-73, Yang et al., (1990) *Proc. Nat'l Acad. Sci. USA*, 87, 9568-9572); and receptor-mediated transfection (e.g., selective uptake of macromolecules by receptor-mediated endocytosis that will be occurring in a target cell using cell type-specific distribution of various receptors. See e.g., Wu and Wu, (1987) *J. Biol. Chem.*, 262, 4429-4432; Wagner et al., *Proc. Natl. Acad. Sci. USA*, 87(9):3410-3414, 1990; Perales et al., *Proc. Natl. Acad. Sci. USA*, 91:4086-4090, 1994; Myers, EPO 0273085; Wu and Wu, *Adv. Drug Delivery Rev.*, 12:159-167, 1993; Nicolau et al., (1987) *Methods Enzymol.*, 149, 157-176), each reference cited here is incorporated by reference in their entirety for all purposes.

In further embodiments, host cells are genetically modified using gene editing with homology-directed repair (HDR). Homology-directed repair (HDR) is a mechanism used by cells to repair double strand DNA breaks. In HDR, a donor polynucleotide with homology to the site of the double strand DNA break is used as a template to repair the cleaved DNA sequence, resulting in the transfer of genetic information from the donor polynucleotide to the DNA. As such, new nucleic acid material may be inserted or copied into a target DNA cleavage site. Double strand DNA breaks in host cells may be induced by a site-specific nuclease. The term "site-specific nuclease" as used herein refers to a nuclease capable of specifically recognizing and cleaving a nucleic acid (DNA or RNA) sequence. Suitable site-specific nucleases for use in the present disclosure include, but are not limited to, RNA-guided endonuclease (e.g., CRISPR-associated (Cas) proteins), zinc finger nuclease, a TALEN nuclease, or mega-TALEN nuclease. For example, a site-specific nuclease (e.g., a Cas9+guide RNA) capable of inducing a double strand break in a target DNA sequence is introduced to a host cell, along with a donor polynucleotide encoding a CAR of the present disclosure and optionally an additional protein (e.g., synNotch or tCD19).

Expansion/Proliferation

After the host cells are activated and transduced, the cells are cultured to proliferate. T-cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

Agents that can be used for the expansion of T-cells can include interleukins, such as IL-2, IL-7, IL-15, or IL-21 (see for example Cornish et al. 2006, Blood. 108(2):600-8, Bazdar and Sieg, 2007, Journal of Virology, 2007, 81(22): 12670-12674, Battalia et al, 2013, Immunology, 139(1):109-120). Other illustrative examples for agents that may be used for the expansion of T-cells are agents that bind to CD8, CD45 or CD90, such as αCD8, αCD45 or αCD90 antibodies. Illustrative examples of T-cell population including antigen-specific T-cells, T helper cells, cytotoxic T-cells, memory T-cell (an illustrative example of memory T-cells are CD62L|CD8| specific central memory T-cells) or regulatory T-cells (an illustrative example of Treg are CD4+ CD25+CD45RA+ Treg cells).

Additional agents that can be used to expand T lymphocytes includes methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety.

In certain embodiments, the agent(s) used for expansion (e.g., IL-2) are administered at about 20 units/ml to about 200 units/ml. In certain embodiments, the agent(s) used for expansion (e.g., IL-2) are administered at about 25 units/ml to about 190 units/ml, about 30 units/ml to about 180 units/ml, about 35 units/ml to about 170 units/ml, about 40 units/ml to about 160 units/ml, about 45 units/ml to about 150 units/ml, about 50 units/ml to about 140 units/ml, about 55 units/ml to about 130 units/ml, about 60 units/ml to about 120 units/ml, about 65 units/ml to about 110 units/ml, about 70 units/ml to about 100 units/ml, about 75 units/ml to about 95 units/ml, or about 80 units/ml to about 90 units/ml. In certain embodiments, the agent(s) used for expansion (e.g., IL-2) are administered at about 20 units/ml, about 25 units/ml, about 30 units/ml, 35 units/ml, 40 units/ml, 45 units/ml, about 50 units/ml, about 55 units/ml, about 60 units/ml, about 65 units/ml, about 70 units/ml, about 75 units/ml, about 80 units/ml, about 85 units/ml, about 90 units/ml, about 95 units/ml, about 100 units/ml, about 105 units/ml, about 110 units/ml, about 115 units/ml, about 120 units/ml, about 125 units/ml, about 130 units/ml, about 135 units/ml, about 140 units/ml, about 145 units/ml, about 150 units/ml, about 155 units/ml, about 160 units/ml, about 165 units/ml, about 170 units/ml, about 175 units/ml, about 180 units/ml, about 185 units/ml, about 190 units/ml, about 195 units/ml, or about 200 units/ml. In certain embodiments, the agent(s) used for expansion (e.g., IL-2) are administered at about 5 mg/ml to about 10 ng/ml. In certain embodiments, the agent(s) used for expansion (e.g., IL-2) are administered at about 5.5 ng/ml to about 9.5 ng/ml, about 6 ng/ml to about 9 ng/ml, about 6.5 ng/ml to about 8.5 ng/ml, or about 7 ng/ml to about 8 ng/ml. In certain embodiments, the agent(s)

used for expansion (e.g., IL-2) are administered at about 5 ng/ml, 6 ng/ml, 7 ng/ml, 8 ng/ml, 9, ng/ml, or 10 ng/ml.

After the host cells are activated and transduced, the cells are cultured to proliferate. NK cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

Agents that can be used for the expansion of natural killer cells can include agents that bind to CD16 or CD56, such as for example αCD16 or αCD56 antibodies. In certain embodiments, the binding agent includes antibodies (see for example Hoshino et al, Blood. 1991 Dec. 15; 78(12):3232-40.). Other agents that may be used for expansion of NK cells may be IL-15 (see for example Vitale et al. 2002. The Anatomical Record. 266:87-92, which is hereby incorporated by reference in its entirety for all purposes).

Conditions appropriate for T-cell culture include an appropriate media (e.g., Minimal Essential Media (MEM), RPMI Media 1640, Lonza RPMI 1640, Advanced RPMI, Clicks, AIM-V, DMEM, a-MEM, F-12, TexMACS, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion).

Examples of other additives for host cell expansion include, but are not limited to, surfactant, piasmanate, pH buffers such as HEPES, and reducing agents such as N-acetyl-cysteine and 2-mercaptoethanol, Antibiotics (e.g., penicillin and streptomycin), are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2).

In certain embodiments, host cells of the present disclosure may be modified such that the expression of an endogenous TCR, MHC molecule, or other immunogenic molecule is decreased or eliminated. When allogeneic cells are used, rejection of the therapeutic cells may be a concern as it may cause serious complications such as the graft-versus-host disease (GvHD). Although not wishing to be bound by theory, immunogenic molecules (e.g., endogenous TCRs and/or MHC molecules) are typically expressed on the cell surface and are involved in self vs non-self discrimination. Decreasing or eliminating the expression of such molecules may reduce or eliminate the ability of the therapeutic cells to cause GvHD.

In certain embodiments, expression of an endogenous TCR in the host cells is decreased or eliminated. In a particular embodiment, expression of an endogenous TCR (e.g., αβ TCR) in the host cells is decreased or eliminated. Expression of the endogenous TCR may be decreased or eliminated by disrupting the TRAC locus, TCR beta constant locus, and/or CD3 locus. In certain embodiments, expression of an endogenous TCR may be decreased or eliminated by disrupting one or more of the TRAC, TRBC1, TRBC2, CD3E, CD3G, and/or CD3D locus.

In certain embodiments, expression of one or more endogenous MHC molecules in the host cells is decreased or eliminated. Modified MHC molecule may be an MHC class I or class II molecule. In certain embodiments, expression of an endogenous MHC molecule may be decreased or eliminated by disrupting one or more of the MHC, β2M, TAP1, TAP2, CIITA, RFX5, RFXAP and/or RFXANK locus.

Expression of the endogenous TCR, an MHC molecule, and/or any other immunogenic molecule in the host cell can be disrupted using genome editing techniques such as Clustered regularly interspaced short palindromic repeats (CRISPR)/Cas, zinc finger nucleases (ZFNs), transcription activator-like effector nucleases (TALENs), and Meganucleases. These genome editing methods may disrupt a target gene by entirely knocking out all of its output or partially knocking down its expression. In a particular embodiment, expression of the endogenous TCR, an MHC molecule and/or any other immunogenic molecule in the host cell is disrupted using the CRISPR/Cas technique.

Pharmaceutical Compositions

In some embodiments, the compositions comprise one or more polypeptides of the CARs and other related molecules (e.g., synNotch receptor, second CAR or bispecific molecule), polynucleotides, vectors comprising same, and cell compositions, as disclosed herein. Compositions of the present disclosure include, but are not limited to pharmaceutical compositions.

In one aspect, the present disclosure provides a pharmaceutical composition comprising a polynucleotide or a recombinant vector described herein, and a pharmaceutically accepted carrier and/or excipient.

In another aspect, the present disclosure provides pharmaceutical composition comprising the CAR-modified host cells described herein and a pharmaceutically acceptable carrier and/or excipient.

Examples of pharmaceutical carriers include but are not limited to sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

Compositions comprising CAR-modified host cells disclosed herein may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions comprising CAR-modified host cells disclosed herein may comprise one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose.

In some embodiments, the compositions are formulated for parenteral administration, e.g., intravascular (intravenous or intraarterial), intraperitoneal, intratumoral, intraventricular, intrapleural or intramuscular administration. The parenteral preparation can be enclosed in ampoules, disposable syringes or multiple dose vials made of glass or plastic. An injectable pharmaceutical composition is preferably sterile. In some embodiments, the composition is reconstituted from a lyophilized preparation prior to administration.

In some embodiments, the CAR-modified host cells may be mixed with substances that adhere or penetrate then prior to their administration, e.g., but not limited to, nanoparticles.

Therapeutic Methods

In one aspect, the present disclosure provides a method for treating a tumor in a subject in need thereof. A therapeutically effective amount of the CAR-modified host cells described herein or the pharmaceutical composition comprising the host cells is administered to the subject.

The term "tumor" refers to a benign or malignant abnormal growth of tissue. The term "tumor" includes cancer. Examples of tumors are, but not limited to, the soft tissue tumors (e.g., lymphomas), and tumors of the blood and blood-forming organs (e.g., leukemias), and solid tumors, which is one that grows in an anatomical site outside the bloodstream (e.g., carcinomas). Examples of cancer include, but are not limited to, carcinoma, lymphoma, blastoma, sarcoma (e.g., osteosarcoma or rhabdomyosarcoma), and leukemia or lymphoid malignancies. More particular examples of such cancers include squamous cell cancer (e.g., epithelial squamous cell cancer), adenosquamous cell carcinoma, lung cancer (e.g., including small-cell lung cancer, non-small cell lung cancer, adenocarcinoma of the lung, squamous carcinoma of the lung), cancer of the peritoneum, hepatocellular cancer, gastric or stomach cancer (e.g., including gastrointestinal cancer, pancreatic cancer), cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, primary or metastatic melanoma, multiple myeloma and B-cell lymphoma, non-Hodgkin's lymphoma, Hodgkin's lymphoma, brain (e.g., high grade glioma, diffuse pontine glioma, ependymoma, neuroblastoma, or glioblastoma), as well as head and neck cancer, and associated metastases. Additional examples of tumors can be found in The Merck Manual of Diagnosis and Therapy, 19th Edition, § on Hematology and Oncology, published by Merck Sharp & Dohme Corp., 2011 (ISBN 978-0-911910-19-3); The Merck Manual of Diagnosis and Therapy, 20th Edition, § on Hematology and Oncology, published by Merck Sharp & Dohme Corp., 2018 (ISBN 978-0-911-91042-1) (2018 digital online edition at internet website of Merck Manuals); and SEER Program Coding and Staging Manual 2016, each of which are incorporated by reference in their entirety for all purposes.

In some embodiments, host cells modified with a FN-EDB-binding CAR, or pharmaceutical compositions thereof, are administered to a subject to treat a tumor expressing FN-EDB.

In some embodiments, host cells modified with an TAA-binding CAR, or pharmaceutical compositions thereof, are administered to a subject to treat a tumor expressing the TAA.

In some embodiments, host cells modified with an TAA-binding bispecific molecule (e.g., a BiTE or bispecific antibody), or pharmaceutical compositions thereof, are administered to a subject to treat a tumor expressing the TAA.

In cases where the CAR-modified host cells also express a CD20 polypeptide, the method may further include administering an anti-CD20 antibody to the subject for removal of the isolated host cells. The anti-CD20 antibody is administered in an amount effective for sufficient removal of the isolated host cells from the subject. In some embodiments, the anti-CD20 antibody is administered in an amount effective for removal of more than 50% of the isolated host cells from the subject. For example, the anti-CD20 antibody may be administered in an amount effective for removal of more than 55%, more than 60%, more than 65%, more than 70%, more than 75%, more than 80%, more than 85%, more than 90%, more than 95%, more than 98%, more than 99%, or about 100% of the isolated host cells from the subject. The anti-CD20 antibody may be administered in an amount effective for removal of about 50% to about 70%, about 60% to about 80%, about 70% to about 90%, or about 80% to about 100% of the isolated host cells from the subject.

Non-limiting examples of anti-CD20 antibodies that can be used for removal the isolated host cells include Rituximab, Ibritumomab tiuxetan, Tositumomab, Ofatumumab, Ocrelizumab, TRU-015, Veltuzumab, AME-133v, PRO131921, and Obinutuzumab. In some embodiments, the anti-CD20 antibody is Rituximab.

In some embodiments, the therapeutic method of the present disclosure includes one or more of the following steps: (a) isolating immune cells from the subject or donor; (b) modifying the immune cells ex vivo with a polynucleotide encoding a CAR and optionally an additional protein, a second CAR and/or a bispecific molecule, or a recombinant vector comprising the same; (c) optionally, expanding and/or activating the modified immune cells before, after and/or during step (b); (d) introducing a therapeutically effective amount of the modified immune cells into the subject, and (e) in cases when the modified immune cells comprise the CD20 suicide switch, optionally, administering an anti-CD20 antibody to the subject, wherein the anti-CD20 antibody is administered in an amounts effective for removal of the modified immune cells from the subject. The immune cells may be T-cells and/or NK cells.

In some embodiments, the modified host cell is an autologous cell. In some embodiments, the modified host cell is an allogeneic cell. In cases where the host cell is isolated from a donor, the method may further include a method to prevent graft vs host disease (GVHD) and the host cell rejection.

In some embodiments of any of the therapeutic methods described above, the composition is administered in a therapeutically effective amount. The dosages of the composition administered in the methods of the disclosure will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve in vivo persistence of modified host cells. It is also contemplated that a variety of doses will be effective to improve in vivo effector function of modified host cells.

In some embodiments, composition comprising the modified host cells manufactured by the methods described herein may be administered at a dosage of $10^2$ to $10^{10}$ cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or $10^7$ to $10^8$. cells/kg body weight, including all integer values within those ranges. The number of modified host cells will depend on the therapeutic use for which the composition is intended for.

Modified host cells may be administered multiple times at dosages listed above. The modified host cells may be allogeneic, syngeneic, xenogeneic, or autologous to the patient undergoing therapy.

The compositions and methods described in the present disclosure may be utilized in conjunction with other types of therapy for tumors, such as chemotherapy, surgery, radiation, gene therapy, and so forth.

It is also contemplated that when used to treat various diseases/disorders, the compositions and methods of the present disclosure can be utilized with other therapeutic methods/agents suitable for the same or similar diseases/ disorders. Such other therapeutic methods/agents can be co-administered (simultaneously or sequentially) to generate additive or synergistic effects. Suitable therapeutically effective dosages for each agent may be lowered due to the additive action or synergy.

In some embodiments of any of the above therapeutic methods, the method further comprises administering to the subject one or more additional compounds selected from the group consisting of immuno-suppressives, biologicals, probiotics, prebiotics, and cytokines (e.g., IFN or IL-2).

As a non-limiting example, the disclosure can be combined with other therapies that block inflammation (e.g., via blockage of IL', INFα/β, IL6, TNF, IL23, etc.).

The methods and compositions of the disclosure can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 4-1BB, OX40, etc.). The methods of the disclosure can be also combined with other treatments that possess the ability to modulate NKT function or stability, including but not limited to CD1d, CD1d-fusion proteins, CD dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e). The methods of the disclosure can also be combined with other treatments such as midostaurin, enasidenib, or a combination thereof.

Therapeutic methods of the disclosure can be combined with additional immunotherapies and therapies. For example, when used for treating tumors, the compositions of the disclosure can be used in combination with conventional therapies, such as, e.g., surgery, radiotherapy, chemotherapy or combinations thereof, depending on type of the tumor, patient condition, other health issues, and a variety of factors. In certain aspects, other therapeutic agents useful for combination tumor therapy with the inhibitors of the disclosure include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the modified host cells of the disclosure can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the present disclosure include, for example, aminoglutethimide, amsacrine, anastrozole, asparaginase, azacitidine, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, decitabine, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-tumor agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopi-dine, clopidogrel, abciximab; antimigratory agents; antise-cretory agents (breveldin); immunosuppressives (cy-closporine, tacrolimus (FK-506), sirolimus (rapamycin), azathioprine, mycophenolate mofetil); anti-angiogenic com-pounds (e.g., TNP-470, genistein, bevacizumab) and growth factor inhibitors (e.g., fibroblast growth factor (FGF) inhibi-tors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dac-tinomycin, eniposide, epirubicin, etoposide, idarubicin and mitoxantrone, topotecan, irinotecan), corticosteroids (corti-sone, dexamethasone, hydrocortisone, methylpednisolone, prednisone, and prenisolone); growth factor signal transduc-tion kinase inhibitors; mitochondrial dysfunction inducers and caspase activators; and chromatin disruptors.

In various embodiments of the methods described herein, the subject is a human. The subject may be a juvenile or an adult, of any age or sex.

In accordance with the present disclosure there may be numerous tools and techniques within the skill of the art, such as those commonly used in molecular biology, phar-macology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Proto-cols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ.

EXAMPLES

The present invention is also described and demonstrated by way of the following examples. However, the use of these and other examples anywhere in the specification is illus-trative only and in no way limits the scope and meaning of the invention or of any exemplified term. Likewise, the invention is not limited to any particular preferred embodi-ments described here. Indeed, many modifications and varia-tions of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

The following materials and methods were used in Examples 1-3.

Tumor Cell Lines

The U87 (glioma), A549 (lung cancer), and A673 (Ewing sarcoma) cell lines were purchased from the American Type Tissue Collection (ATCC). The lung metastatic osteosar-coma cell line LM7 was provided by Dr. Eugenie Kleiner-man (MD Anderson Cancer Center, Houston, TX). Primary fibroblast cell lines have been previously established (62). The generation of the A549 cell line expressing an enhanced green fluorescence protein firefly luciferase fusion gene (GFP.ffluc) was previously described (61). All cell lines were grown in DMEM or RPMI (GE Healthcare Life Sciences HyClone Laboratories) supplemented with 10% fetal bovine serum (FBS; GE Healthcare Life Sciences HyClone) and 2 mM Glutamax (Invitrogen). Cell lines were authenticated using the ATCC's human STR profiling cell authentication service and routinely checked for *Myco-plasma* by the MycoAlert *Mycoplasma* Detection Kit (Lonza).

Generation of CAR T-Cells

The generation of the SFG retroviral vectors encoding the EphA2-CAR with a CD28 costimulatory domain, or GFP.f-fluc have been previously described (38). In-Fusion cloning (Takara Bio) was used to generate the EDB-CAR with a CD28 costimulatory domain. This retroviral vector contains a CAR.CD2ζ expression cassette, a 2A sequence, and trun-cated CD19 (38). The EDB-specific single chain variable fragment (scFv) was derived from the human MAb L19 (28) and synthesized by GeneArt (Thermo Fisher Scientific). RD114-pseudotyped retroviral particles were generated by transient transfection of 293T cells as previously described (38). Supernatants were collected 48 hours after transfec-tion, filtered, and snap frozen for later transduction of T-cells.

Human peripheral blood mononuclear cells (PBMCs) were obtained from whole blood of healthy donors under IRB-approved protocols at SJCRH. CAR T-cells were gen-erated as described in (61). Briefly, Lymphoprep (Abbott Laboratories) isolated PBMCs were stimulated on treated non-tissue culture 24-well plates, which were precoated with CD3 and CD28 antibodies (BD). Recombinant human IL-7 and IL-15 (IL-7: 10 ng/mL; IL-15: 5 ng/mL; PeproTech) were added to cultures the next day. On day 2, CD3/CD28-stimulated T-cells ($2.5 \times 10^5$ cells/well) were transduced with RD114-pseudotyped retroviral particles on RetroNectin (Clontech)-coated plates in the presence of IL-7 and IL-15. On day 5, transduced T-cells were transferred into new tissue culture 24-well plates and subsequently expanded with IL-7 and IL-15. Non-transduced (NT) T-cells were prepared in the same way except for no retrovirus was added. For the generation of GFP.ffluc-expressing EDB-CAR T-cells, acti-vated T-cells were transduced with two retroviral vectors. All experiments were performed 7-14 days post-transduc-tion. Biological replicates were performed using PBMCs from different healthy donors.

Flow Cytometry

A FACSCanto II (BD) instrument was used to acquire flow cytometry data, which was analyzed using FlowJo v10 (FlowJo). For surface staining, samples were washed with and stained in PBS (Lonza) with 1% FBS (HyClone). For all experiments, matched isotypes or known negatives (e.g. NT T-cells) served as gating controls. LIVE/DEAD® Fixable Aqua Dead Cell Stain Kit (Invitrogen) was used as a viability dye. T-cells were evaluated for CAR expression at multiple time points post-transduction with an anti-human IgG, F(ab')2 fragment specific-AF647 (Jackson ImmunoRe-search). Transduction was also confirmed with anti-CD19-PE (clone J3-119, Beckman Coulter). T-cells phenotype was established with several different panels using combinations of antibodies that are listed in the supplemental data section.

The following antibodies were used for FACS analysis: CD3-APC (clone UTCH1, Beckman Coulter), CD4-Pacific Blue (clone SK3, BioLegend) CD8-PerCPCy5.5 (clone SK1, BioLegend), CD19-PE (clone J3-119, Beckman Coulter), CD19-BV421 (clone HIB19, BD), CCR7-AF488 (clone G043H7, BioLegend), CD45RA-APC-H7 (clone HI100, BD), LAG3-FITC (clone 11C3C65, BioLegend), TIM3-PE-Cy7 (clone F38-2E2, BioLegend), PD1-PE (clone EH12.2H7, BioLegend), and F(ab') Goat IgG (AF647: 005600003, Jackson Labs).

Real-Time PCR mRNA extraction from $1 \times 10^6$ to $1 \times 10^7$ cells was performed using the Maxwell RSC SimplyRNA Blood kit (Promega AS1380) on a Maxwell RSC. RT-qPCR was performed according to the manufacturer's instruction using a one-step kit (ThermoFisher). Previously published sequences were used for EDB PCR primers (63), and GAPDH PCR primers were purchased from Life Technologies. Reactions were completed on the Applied Bioscience QuantStudio 6 Flex and analyzed using QuantStudio software.

Co-Culture Assay $1 \times 10^6$ T-cells were co-cultured with no tumor cells or $5 \times 10^5$ LM7, U87, or A549 cells without the provision of exogenous cytokine. For recombinant protein studies, rhFN-EDB (Abcam) was incubated at decreasing concentrations for 3 hours at 37° C. Plates were washed and $5 \times 10^5$ T-cells were plated. 24 and 48 hours later, supernatant was collected and frozen for later analysis. Cytokines were measured using IFNγ and IL-2 ELISA kits (R&D Systems).

MTS Assay

A CellTiter96® AQueous One Solution Cell Proliferation Assay (Promega) was utilized to assess CAR T-cell cytotoxicity. In a tissue culture-treated 96-well plate, 12,500 U87, and A549, or 15,000 LM7 cells and primary fibroblasts were co-cultured with serial dilutions of T-cells. Media and tumor cells alone served as controls. Each condition was plated in triplicate. After 5 days, the media and T-cells were removed by gently pipetting up and down to avoid disrupting adherent tumor cells. CellTiter96® AQueous One Solution Reagent (phenazine ethosulfate) in RPMI-10% FBS was added to each well and incubated at 37° C., 5% $CO_2$ for 2 hours. The absorbance at 492 nm was measured using an Infinite® 200 Pro MPlex plate reader (Tecan) to assess the number of viable cells in each well. Percent live tumor cells were determined by the following formula: (sample-media alone)/(tumor alone-media alone)*100.

Xenograft Mouse Models

Animal experiments followed a protocol approved by SJCRH Institutional Animal Care and Use Committee. All experiments utilized 6-8-week NOD-scid IL2Rgammanull (NSG) mice obtained from SJCRH NSG colony. Subcutaneous tumor models: Mice were injected s.c. with $2 \times 10^6$ tumor cells in Matrigel (Corning; 1:1 diluted in PBS). On day 7, mice received a single i.v. dose of $1 \times 10^6$ T-cells via tail vein injection. Tumor growth was assessed by serial caliper measurements. Mice were euthanized when i) they met physical euthanasia criteria (significant weight loss, signs of distress), ii) the tumor burden was approximately 3,000 $mm^3$, or iii) recommended by St. Jude veterinary staff. Intravenous tumor models: Mice were injected i.v. with $2 \times 10^6$ tumor cells via tail vein injection, and on day 7 received a single i.v. dose of $1 \times 10^6$ T-cells. Mice were euthanized when they reached i) the bioluminescence Flux endpoint of $2 \times 10^{10}$ on two consecutive measurements, and/ or ii) the above-mentioned general euthanasia criteria. For T-cell experiments in non-tumor bearing mice, mice received a single i.v. dose of $1 \times 10^7$ NT or $1 \times 10^6$ or $1 \times 10^7$ CAR T-cells expressing GFP.ffLuc.

Bioluminescence Imaging

Mice were injected i.p. with 150 mg/kg of D-luciferin 5-10 minutes before imaging, anesthetized with isoflurane, and imaged with a Xenogen IVIS-200 imaging system. The photons emitted from the luciferase-expressing tumor cells were quantified using Living Image software (Caliper Life Sciences). Mice were imaged once per week to track tumor burden, or 1-5 times per week to track T-cells.

Angiosense Imaging

Mice where anesthetized with isoflurane and received a single i.v. dose of Angiosense 750 (PerkinElmer; NEV10011EX) via tail vain injection as recommended by the manufacturer. Administered Angiosense 750 was allowed to equilibrate in mice for 24 hours before imaging using a Xenogen IVIS-200 imaging system. Fluorescence signals were quantified using Living Image software (Caliper Life). Relative fluorescent units (RFU) where calculated by measuring tumor fluorescence subtracted from the background of mouse auto-fluorescence divided by tumor volume.

Immunohistochemistry

Immunohistochemistry (IHC) was performed in collaboration with the SJCRH Veterinary Pathology Core Facility. After fixation, the tumor samples were embedded in paraffin and 8 μm sections were cut and mounted on slides. The sections were then processed and analyzed using immunohistochemistry with CD31 (Dianova, clone SZ31, cat. DIA 310). CD31 was only scored on those tumors+/-700 $mm^3$ from the average tumor size in order to best control for the impact tumor size variation has on vascularization. CD31 levels where calculated by independent blind-scoring and images were acquired at the St. Jude Cell & Tissue Imaging Center using the Axio Scan Z.1.

Statistical Analysis

All experiments were performed at least in triplicates. For comparison between two groups, two-tailed t-test was used. For comparisons of three or more groups, values were log transformed as needed and analyzed by ANOVA with Tukey's post-test. Survival was analyzed by Kaplan-Meier method and by the log-rank test. Bioluminescence imaging data were analyzed using either ANOVA, t-test, or area under the curve (AUC).

Figure 2:
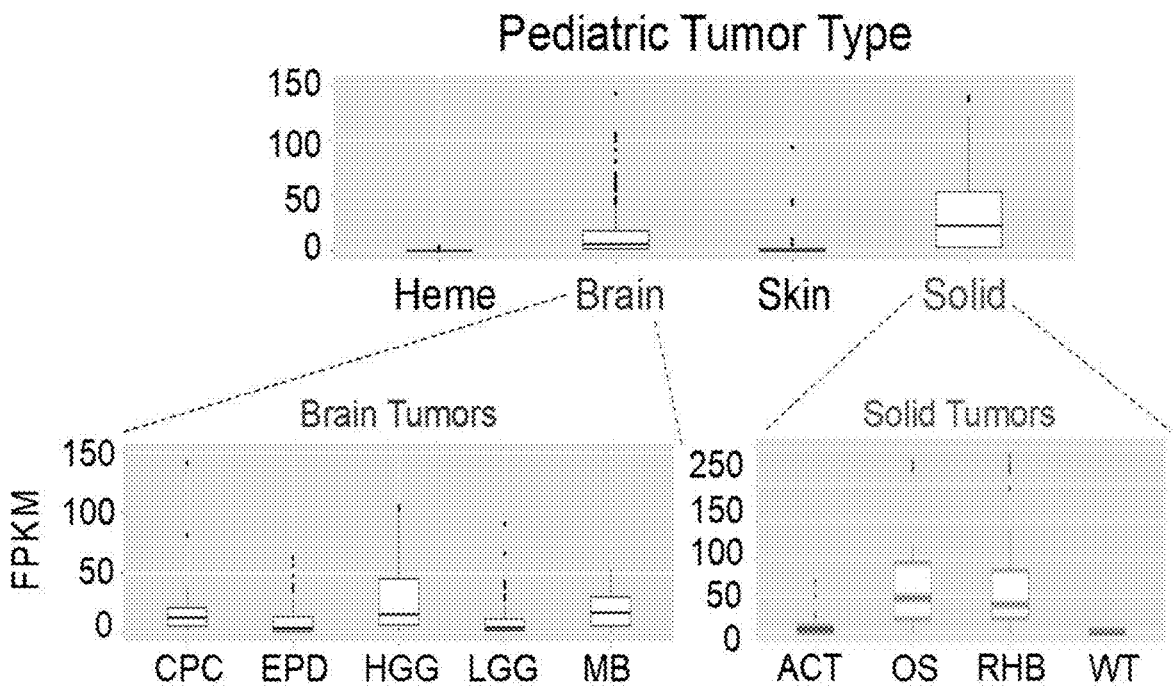
FIG. 2 shows expression of FN-EDB in pediatric solid tumors and brain tumors including sarcoma using the Pediatric Cancer Genome Project (PCGP) dataset. Fragments Per Kilobase Million (FPKM) and t-Distributed Stochastic Neighbor Embedding (t-SNE) plots show expression in pediatric solid tumors and brain tumors.

Example 1. Expression of FN-EDB in Pediatric Solid Tumors and Brain Tumors Including Sarcoma FN-EDB is expressed in a broad range of adult solid tumors, but little is known about expression in the pediatric solid tumors and brain tumors. The expression of FN-EDB was analyzed using the Pediatric Cancer Genome Project (PCGP) dataset, which includes 31 osteosarcoma (OS), 51 rhabdo-myosarcoma (RHB), 85 high grade glioma (HGG), 78 low grade gliomas (LGG) and 82 ependymomas (EPD). As shown in FIG. 2, FN-EDB is expressed in OS and RHB. Thus, this data demonstrates that FN-EDB is expressed in pediatric solid tumors as well as brain tumors.

Example 2. Generation of EDB-CAR T-Cells

While FN-EDB is a secreted protein, it plays a major role in cellular adhesion,[35] making it likely that FN-EDB-producing tumor cells (EDB+ tumor cells) can be targeted with EDB-CAR T-cells. To test this hypothesis a retroviral vector was designed encoding an EDB-specific CAR (EDB-CAR) using the EDB-specific scFv that has shown tumor specificity in imaging studies in humans (L19), a CD28hinge/ transmembrane domain (CD28H/TM) and a CD28. ζ signaling domain (FIG. 3A). EDB-CAR T-cells were generated by retroviral transduction of CD3/CD28-activated T-cells in the presence of IL7 (10 ng/ml) and IL15 (10 ng/ml). CAR expression was readily detected on transduced T-cells by FACS analysis (FIG. 3B). In brief, cells were harvested, washed, and stained with isotype control or a Fab antibody to detect the CAR. Cells were analyzed on a BD Canto cell analyzer. Retroviral T-cell transduction was confirmed using anti-CD19. EDB-CAR T-cells contained a mixture of CD4- and CD8-positive T-cell, and further T-cell subset analysis revealed the presence of naïve, central memory, effector memory, and terminally differentiated memory T-cells. To confirm the specificity of EDB-CAR T-cells, CAR T-cells and non-transduced T-cells (NT T-cells) were incubated with increasing concentration of recombinant EDB protein (purchased from Abcam) (0 ng, 0.5 ng, 1 ng, or 10 ng). Only, EDB-CAR T-cells produced significant amount IFNγ, indicating specific EDB-CAR T-cell activation (FIG. 3C).

To evaluate if EDB-CAR T-cells recognize and kill EDB+ tumor cells, three EDB+ tumor cells (LM7: osteosarcoma, A549: lung cancer, U87: high grade glioma) were used (FIG. 4A). To measure IFNγ secretion, $5 \times 10^5$ tumor cells and $1 \times 10^6$ T-cells were cocultured in wells of a 24 well tissue culture plate. After 24 hours media was harvested and IFNγ production was determined by ELISA. EDB-CAR T-cells readily recognized EDB+ tumor cells as judged by IFNγ secretion (FIG. 4B) in contrast to NT T-cells. To determine the cytolytic activity of CAR and NT T-cells, standard MTS (3-(4,5-dimethylthiazol-2-yl)-5-(3-carboxymethoxyphe-nyl)-2-(4-sulfophenyl)-2H-tetrazolium) assays were performed. Briefly, tumor cells and T-cells were plated in wells of 96 well plates at a T-cell to tumor cell ratio of 8:1. After 3 days T-cells were gently removed and viable tumor cells were quantified using the MTS reagent according to the manufacturer's instructions. EDB-CAR T-cells killed EDB+ tumor cells in contrast to NT T-cells (FIG. 4C). In contrast, EDB-CAR T-cells had no cytolytic activity against primary human fibroblasts even at high effector to target (E:T) ratios of 16:1 (FIG. 4D).

Example 3. EDB-CAR T-Cells have Antitumor Activity In Vivo

In this example, three studies were performed to determine if EDB-CAR T-cells have antitumor activity in vivo.

Figure 5A:
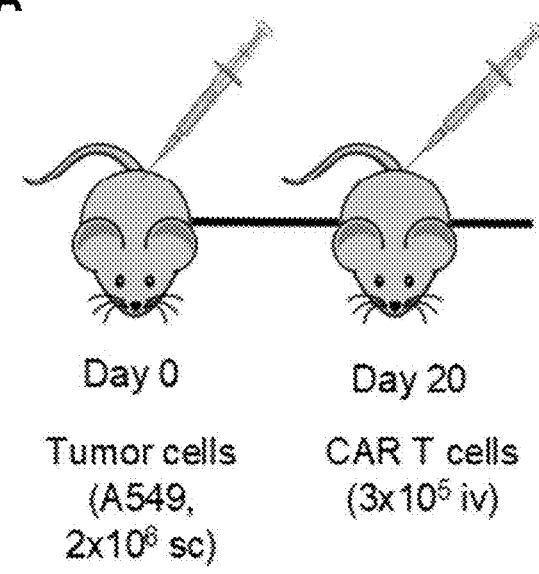
FIGS. 5A-5D demonstrate that EDB-CAR T-cells have antitumor activity in the A549 subcutaneous tumor model in vivo. To determine if EDB-CAR T-cells have antitumor activity in vivo, $2\times10^6$ A549 cells were injected s.c. into immunodeficient NSG mice. On day 20, mice received a single iv of $3\times10^5$ T-cells (FIG. 5A). Mice received either NT, EphA2-CAR, or EDB-CAR T-cells. Tumor growth was followed by caliper measurements (FIG. 5B). Tumors were stained for CD31 (FIG. 5C; representative images). Vessel density was quantified (n=4 tumors; dots represent average of 3 blind scores per tumor; 2 fields of view per tumor) (FIG. 5D).
Figure 5B:
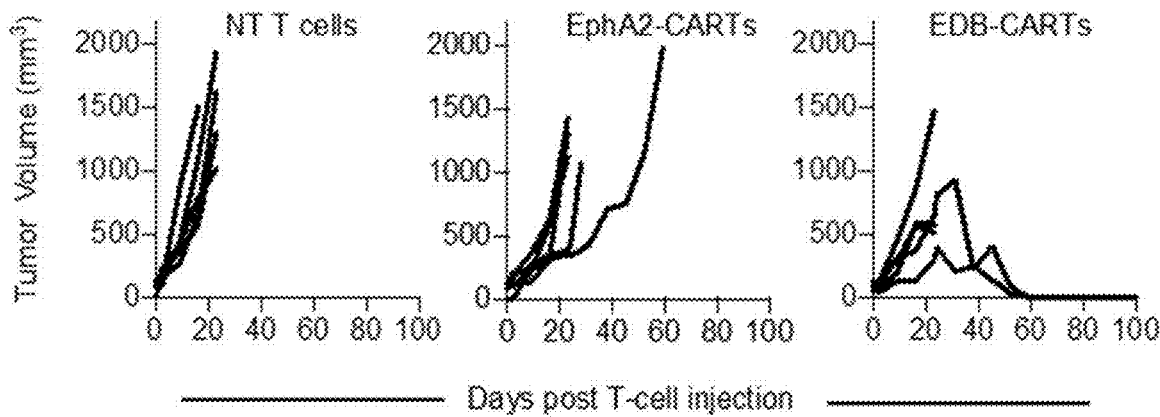
Figure 5C:
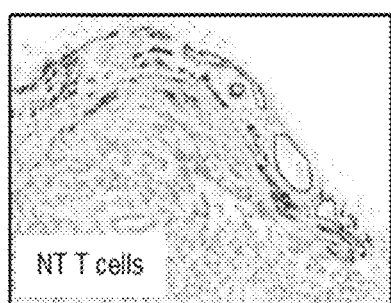
Figure 5C:
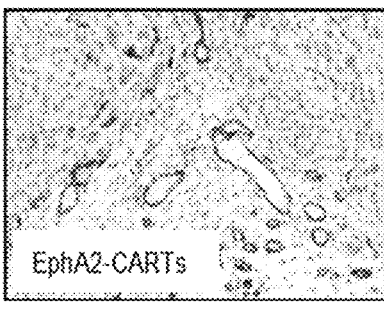
Figure 5C:
Figure 5D:
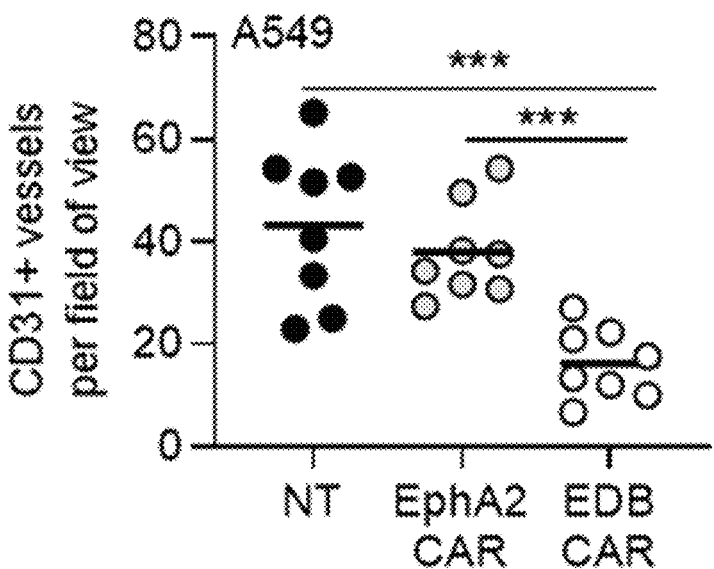

In the first experiment, $2 \times 10^6$ A549 cells were injected subcutaneously into immunodeficient NSG mice, and on day 20, mice received a single intravenous injection of $3 \times 10^5$ T-cells (FIG. 5A), a cell dose which 10× fold less than is normally used in preclinical models. Mice received EDB-CAR T-cells, EphA2-CAR (as a positive control for a CAR T-cells that work well at T-cell doses of $3 \times 10^6$) or NT T-cells. Tumor growth was measured by serial caliper measurements. While NT- and EphA2-CAR T-cells had no or very limited antitumor activity, 4 out of 5 mice treated with EDB-CAR T-cells had tumor regression (FIG. 5B). Of these, two mice required euthanasia due to skin necrosis covering their small tumor, and two mice achieved a long-lasting CR (>100 days post CAR T-cell injection). The tumors of euthanized mice were examined for the presence to blood vessels (CD31 staining) and compared to untreated tumors and tumors treated with EphA2-CAR T-cells (FIG. 5C, FIG. 5D). EDB-CAR treated tumors had a reduced vessel density as judged by CD31 staining. This data demonstrates that EDB-CAR T-cells have antitumor activity in subcutaneous tumor model in vivo.

Figure 6A:
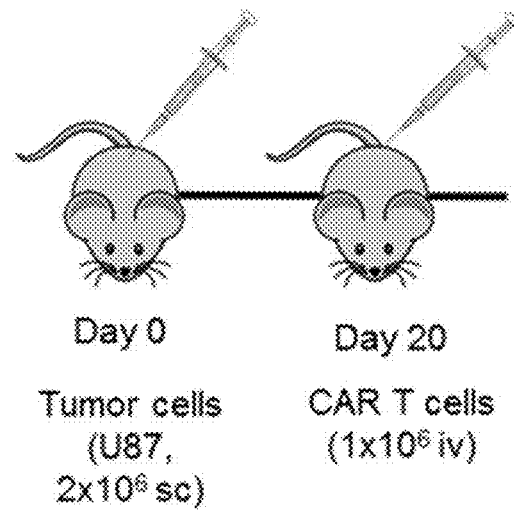
FIGS. 6A-6C demonstrate that EDB-CAR T-cells have antitumor activity in the U87 subcutaneous tumor model in vivo; $2\times10^6$ U87 cells were injected subcutaneously, and on day 7, mice received a single intravenous injection of $1\times10^6$ EDB-CAR or NT T-cells (n=10 per group) (FIG. 6A). Tumor growth was measured by serial caliper measurements. EDB-CAR T-cells had potent antitumor activity (FIG. 6B) that translated into a significant survival advantage (FIG. 6C).
Figure 6B:
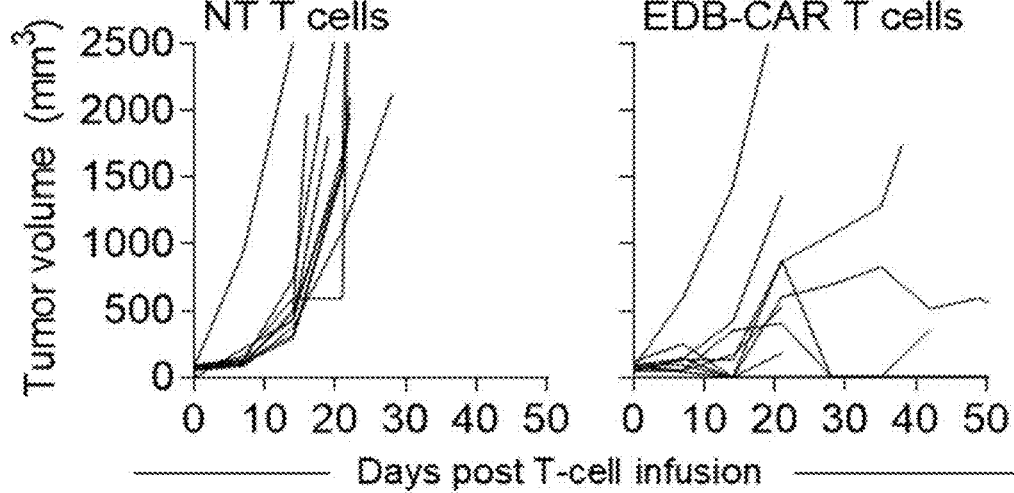
Figure 6C:
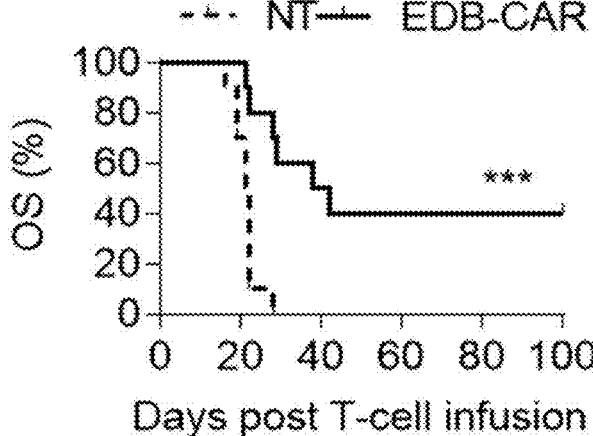

In the second experiment, $2 \times 10^6$ U87 cells were injected subcutaneously into immunodeficient NSG mice, and on day 7, mice received a single intravenous injection of $1 \times 10^6$ EDB-CAR or NT T-cells (n=5 per group). Tumor growth was measured by serial caliper measurements. EDB-CAR T-cells had potent antitumor activity (FIG. 6A) that translated into a significant survival advantage (FIG. 6B).

Figure 7A:
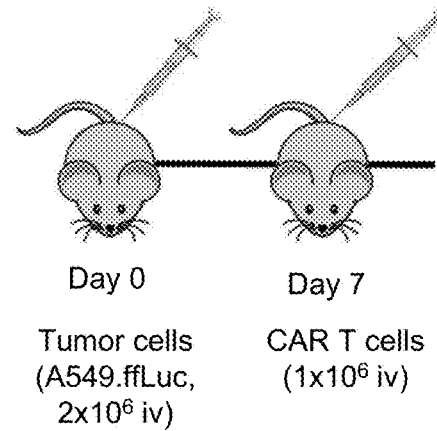
FIGS. 7A-7B demonstrate that EDB-CAR T-cells have antitumor activity in systemic tumor model in vivo. $2\times10^6$ GFP-ffluc-expressing A549 cells were injected i.v. into immunodeficient NSG mice, and on day 7 mice received i.v. $1\times10^6$ NT or EDB-CAR T-cells (FIG. 7A). Tumor growth was followed by bioluminescence imaging (FIG. 7B).
Figure 7B:
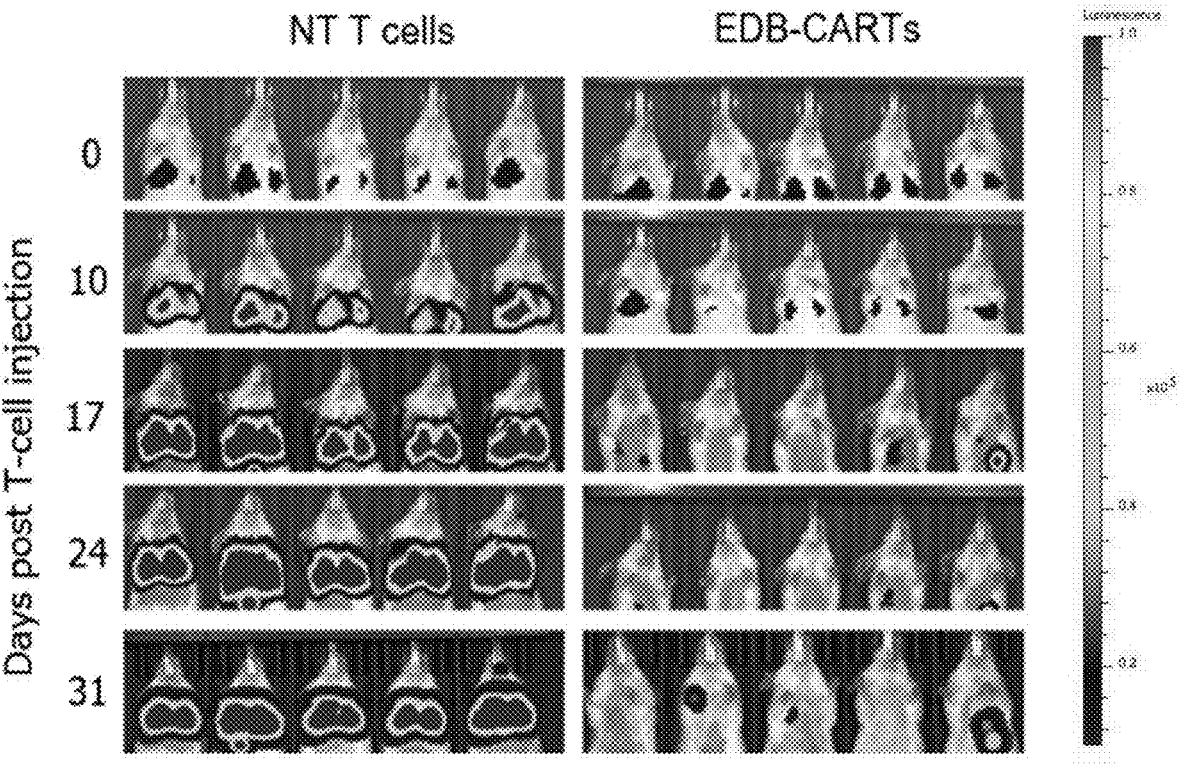

In the third experiment, $2 \times 10^6$ GFP-ffluc-expressing A549 cells were injected intravenously into immunodeficient NSG mice, and on day 7 mice received iv $1 \times 10^6$ NT or EDB-CAR T-cells (FIG. 7A). Tumor growth was followed by serial bioluminescence imaging using an IVIS imager and luciferase as a substrate. EDB-CAR T-cells had significant antitumor activity as judged by bioluminescence imaging in comparison to NT T-cells with a follow up of 31 days post T-cell injection (FIG. 7B).

Thus, these studies indicate that EDB-CAR T-cells have potent antitumor activity. Of note, toxicity was not observed as judged by the lack of weight loss, change in appearance, and/or activity. Since human and murine EDB is 100% identical, these studies thus highlight an encouraging safety profile of EDB-CAR T-cells.

The L19-based CAR not only recognized and killed L19-CAR T-cells EDB+ tumor cells in cell culture experiments, but it surprisingly also had potent antitumor activity in two immunodeficient mouse models, demonstrating that EDB-CAR T-cells do not need other immune cells in vivo to exert their antitumor activity.

Example 4. Indirect Targeting of Tumor Cells

FIG. 8A depicts an exemplary scheme of a vector that encodes an EDB-specific synNotch receptor, which will induce the expression of a TAA-specific CAR or BiTE molecule. FIG. 8C depicts a vector for combined indirect and direct targeting of tumor cells with EDB-CAR T-cells, wherein T-cell activation via the EDB-CAR.synNotch interacting with the EDB located on the tumor stroma induces expression of a second CAR (e.g., TAA-specific CAR) or BiTE that directly targets the tumor cells.

A synNotch inducible lentiviral vector is generated to link the expression of a second CAR or BiTE molecule to the recognition of EDB by T-cells expressing an EDB-specific SynNotch receptor; see FIG. 8B). T-cell expressing the synNotch receptor alone will not be able to directly kill the tumor cells, even those expressing the cognate antigen. Thus, this synNotch receptor construct is used to only induce the expression of the second CAR or BiTE in the tumor ECM in which EDB in present.

Next, a second lentiviral vector is generated that encodes a constitutive EDB-CAR in addition to the synNotch receptor (i.e., EDB-notch-CAR; see FIG. 8C).

An example of how the indirect approach will be tested in vitro and in vivo is provided below. A lentiviral vector will be generated that encodes the EDB-specific SynNotch receptor and a bispecific T-cell engager BiTE) that recognizes the TAA EphA2 (EA2-ENG).

In vitro analysis. Three T-cell populations: i) EphA2-specific BiTE-Notch T-cells) (EA2-ENG.EDB-Notch T-cells), ii) EA2-ENG T-cells, and iii) NT T-cells are tested. The ability of each cell population to recognize EDB+ target cells and secrete EA2-ENG will be assessed. The same tumor cells U87, A549, LM7) and assays that were used in the in vitro experiment shown in FIG. 3 (Example 2) for EDB-CAR T-cells will be used; in addition, an ELISA to determine the concentration of EA2-ENG will be used.

In vivo analysis. The same experimental set up as shown for the analysis of EDB-CAR T-cells in vivo (FIGS. 4 to 7; Example 3) will be used. Immunodeficient NSG mice will be injected subcutaneously with U87 or A549 cells and will received a single dose of EA2-ENG.EDB-Notch T-cells, EA2-ENG T-cells, or NT T-cells. Tumor cell growth will be measured by caliper measurement. The anti-vascular activity of T-cells will be determined by IHC for CD31. The antitumor activity of EA2-ENG.EDB-Notch T-cells in the systemic tumor cell model in which A549 cells are injected intravenously as shown in FIG. 7 will also be assessed.

For the BiTE molecule approach, a lentiviral vector in which the inducible, tumor-specific molecule is an EA2-specific CAR will be constructed an evaluated as described above, wherein the only difference is that CAR expression will be measured by FACS analysis and not EA2-ENG production by ELISA. In addition, the indirect approach for other TAAs for which CARs and/or engager molecules are available (e.g., HER2, GD2, IL13Rα2, or B7-H3) will be tested.

Example 5. Additional EDB-CAR T-Cells

Additional retroviral constructs (FIG. 9) are generated by cloning the EDB-specific scFv into CAR expression cassettes, such as but not limited to the expression cassettes discussed in Krenciute et al., *Cancer Immunology Research*, (2017) 5:571-81; Yi et al., *Mol. Ther. Methods Clin. Dev.* (2018) 9:70-80; or Mata et al., *Cancer Discovery* (2017) 7:1306-19, each of which are incorporated herein by reference in their entirety. RD114-pseudotyped retroviral vectors are generated by standard methods and EDB-CAR T-cells are generated as outlined in Example 2.

REFERENCES

1. Maude S L, Laetsch T W, Buechner J, et al. Tisagenlecleucel in Children and Young Adults with B-Cell Lymphoblastic Leukemia. The New England journal of medicine 2018; 378:439-48.
2. Park J H, Riviere I, Gonen M, et al. Long-Term Follow-up of CD19 CAR Therapy in Acute Lymphoblastic Leukemia. The New England journal of medicine 2018; 378:449-59.
3. Kochenderfer J N, Dudley M E, Kassim S H, et al. Chemotherapy-refractory diffuse large B-cell lymphoma and indolent B-cell malignancies can be effectively treated with autologous T cells expressing an anti-CD19 chimeric antigen receptor. Journal of clinical oncology: official journal of the American Society of Clinical Oncology 2015; 33:540-9.
4. Gardner R A, Finney O, Annesley C, et al. Intent-to-treat leukemia remission by CD19 CAR T cells of defined formulation and dose in children and young adults. Blood 2017; 129:3322-31.
5. Ahmed N, Brawley V S, Hegde M, et al. Human Epidermal Growth Factor Receptor 2 (HER2)-Specific Chimeric Antigen Receptor-Modified T Cells for the Immunotherapy of HER2-Positive Sarcoma. Journal of clinical oncology: official journal of the American Society of Clinical Oncology 2015; 33:1688-96.
6. Heczey A, Louis C U, Savoldo B, et al. CAR T Cells Administered in Combination with Lymphodepletion and PD-1 Inhibition to Patients with Neuroblastoma. Molecular therapy: the journal of the American Society of Gene Therapy 2017; 25:2214-24.
7. Zhang C, Wang Z, Yang Z, et al. Phase I Escalating-Dose Trial of CAR-T Therapy Targeting CEA(+) Metastatic Colorectal Cancers. Molecular therapy: the journal of the American Society of Gene Therapy 2017; 25:1248-58.
8. Thistlethwaite F C, Gilham D E, Guest R D, et al. The clinical efficacy of first-generation carcinoembryonic antigen (CEACAM5)-specific CAR T cells is limited by poor persistence and transient pre-conditioning-dependent respiratory toxicity. Cancer immunology, immunotherapy: CII 2017; 66:1425-36.
9. Knochelmann H M, Smith A S, Dwyer C J, Wyatt M M, Mehrotra S, Paulos C M. CAR T Cells in Solid Tumors: Blueprints for Building Effective Therapies. Frontiers in immunology 2018; 9:1740.
10. Long K B, Young R M, Boesteanu A C, et al. CAR T Cell Therapy of Non-hematopoietic Malignancies: Detours on the Road to Clinical Success. Frontiers in immunology 2018; 9:2740.
11. O'Rourke D M, Nasrallah M P, Desai A, et al. A single dose of peripherally infused EGFRvIII-directed CAR T cells mediates antigen loss and induces adaptive resistance in patients with recurrent glioblastoma. Science translational medicine 2017; 9.
12. Sauer S, Erba P A, Petrini M, et al. Expression of the oncofetal ED-B-containing fibronectin isoform in hematologic tumors enables ED-B-targeted 131I-L19SIP radioimmunotherapy in Hodgkin lymphoma patients. Blood 2009; 113:2265-74.
13. Santimaria M, Moscatelli G, Viale G L, et al. Immunoscintigraphic detection of the ED-B domain of fibronectin, a marker of angiogenesis, in patients with cancer. Clinical cancer research: an official journal of the American Association for Cancer Research 2003; 9:571-9.
14. Fukuda T, Yoshida N, Kataoka Y, et al. Mice lacking the EDB segment of fibronectin develop normally but exhibit reduced cell growth and fibronectin matrix assembly in vitro. Cancer research 2002; 62:5603-10.
15. Velasquez M P, Tones D, Iwahori K, et al. T cells expressing CD19-specific Engager Molecules for the Immunotherapy of CD19-positive Malignancies. Scientific reports 2016; 6:27130.
16. Iwahori K, Kakarla S, Velasquez M P, et al. Engager T cells: a new class of antigen-specific T cells that redirect bystander T cells. Molecular therapy: the journal of the American Society of Gene Therapy 2015; 23:171-8.
17. Skapek S X, Ferrari A, Gupta A A, et al. Rhabdomyosarcoma. Nat Rev Dis Primers 2019; 5:1.
18. Grunewald T G P, Cidre-Aranaz F, Surdez D, et al. Ewing sarcoma. Nat Rev Dis Primers 2018; 4:5.
19. Saraf A J, Fenger J M, Roberts R D. Osteosarcoma: Accelerating Progress Makes for a Hopeful Future. Front Oncol 2018; 8:4.
20. Dotti G, Gottschalk S, Savoldo B, Brenner M K. Design and development of therapies using chimeric antigen receptor-expressing T cells. Immunol Rev 2014; 257:107-26.
21. June C H, Sadelain M. Chimeric Antigen Receptor Therapy. The New England journal of medicine 2018; 379:64-73.
22. Ongaro T, Matasci M, Cazzamalli S, et al. A novel anti-cancer L19-interleukin-12 fusion protein with an optimized peptide linker efficiently localizes in vivo at the site of tumors. J Biotechnol 2019; 291:17-25.
23. White E S, Baralle F E, Muro A F. New insights into form and function of fibronectin splice variants. J Pathol 2008; 216:1-14.
24. White E S, Muro A F. Fibronectin splice variants: understanding their multiple roles in health and disease using engineered mouse models. IUBMB Life 2011; 63:538-46.
25. Mariani G, Lasku A, Pau A, et al. A pilot pharmacokinetic and immunoscintigraphic study with the technetium-99m-labeled monoclonal antibody BC-1 directed against oncofetal fibronectin in patients with brain tumors. *Cancer* 1997; 80:2484-9.

26. Berndorff D, Borkowski S, Moosmayer D, et al. Imaging of tumor angiogenesis using 99mTc-labeled human recombinant anti-ED-B fibronectin antibody fragments. J Nucl Med 2006; 47:1707-16.

27. Borsi L, Balza E, Bestagno M, et al. Selective targeting of tumoral vasculature: comparison of different formats of an antibody (L19) to the ED-B domain of fibronectin. Int J Cancer 2002; 102:75-85.

28. Pini A, Viti F, Santucci A, et al. Design and use of a phage display library. Human antibodies with subnanomolar affinity against a marker of angiogenesis eluted from a two-dimensional gel. J Biol Chem 1998; 273: 21769-76.

29. Tijink B M, Perk L R, Budde M, et al. (124)I-L19-SIP for immuno-PET imaging of tumour vasculature and guidance of (131)I-L19-SIP radioimmunotherapy. Eur J Nucl Med Mol Imaging 2009; 36:1235-44.

30. Xie Y J, Dougan M, Jailkhani N, et al. Nanobody-based CAR T cells that target the tumor microenvironment inhibit the growth of solid tumors in immunocompetent mice. Proceedings of the National Academy of Sciences of the United States of America 2019; 116:7624-31.

31. Posthumadeboer J, Piersma S R, Pham T V, et al. Surface proteomic analysis of osteosarcoma identifies EPHA2 as receptor for targeted drug delivery. British journal of cancer 2013; 109:2142-54.

32. Nordberg J, Mpindi J P, Iljin K, et al. Systemic analysis of gene expression profiles identifies ErbB3 as a potential drug target in pediatric alveolar rhabdomyosarcoma. PloS one 2012; 7:e50819.

33. Morsut L, Roybal K T, Xiong X, et al. Engineering Customized Cell Sensing and Response Behaviors Using Synthetic Notch Receptors. Cell 2016; 164:780-91.

34. Roybal K T, Williams J Z, Morsut L, et al. Engineering T Cells with Customized Therapeutic Response Programs Using Synthetic Notch Receptors. Cell 2016; 167:419-32 e16.

35. To W S, Midwood K S. Plasma and cellular fibronectin: distinct and independent functions during tissue repair. Fibrogenesis Tissue Repair 2011; 4:21.

36. Krenciute G, Prinzing B L, Yi Z, et al. Transgenic Expression of IL15 Improves Antiglioma Activity of IL13Ralpha2-CAR T Cells but Results in Antigen Loss Variants. Cancer immunology research 2017; 5:571-81.

37. Krenciute G, Krebs S, Torres D, et al. Characterization and Functional Analysis of scFv-based Chimeric Antigen Receptors to Redirect T Cells to IL13Ralpha2-positive Glioma. Molecular therapy: the journal of the American Society of Gene Therapy 2016; 24:354-63.

38. Yi Z, Prinzing B L, Cao F, Gottschalk S, Krenciute G. Optimizing EphA2-CAR T Cells for the Adoptive Immunotherapy of Glioma. Mol Ther Methods Clin Dev 2018; 9:70-80.

39. Mata M, Gerken C, Nguyen P, Krenciute G, Spencer D M, Gottschalk S. Inducible Activation of MyD88 and CD40 in CAR T Cells Results in Controllable and Potent Antitumor Activity in Preclinical Solid Tumor Models. Cancer discovery 2017; 7:1306-19.

40. Koneru M, Purdon T J, Spriggs D, Koneru S, Brentjens R J. IL-12 secreting tumor-targeted chimeric antigen receptor T cells eradicate ovarian tumors in vivo. Oncoimmunology 2015; 4: e994446.

41. Chmielewski M, Abken H. CART Cells Releasing I L-18 Convert to T-Bet(high) FoxOl(low) Effectors that Exhibit Augmented Activity against Advanced Solid Tumors. Cell reports 2017; 21:3205-19.

42. Zhao S, Kurenbekova L, Gao Y, et al. NKD2, a negative regulator of Wnt signaling, suppresses tumor growth and metastasis in osteosarcoma. Oncogene 2015; 34:5069-79.

43. Di Stasi A, Tey S K, Dotti G, et al. Inducible apoptosis as a safety switch for adoptive cell therapy. NEnglJMed 2011; 365:1673-83.

44. Falcon C, Al-Obaidi M, Di Stasi A. Exploiting Cell Death Pathways for Inducible Cell Elimination to Modulate Graft-versus-Host-Disease. Biomedicines 2017; 5.

45. Bonifant C L, Szoor A, Torres D, et al. CD123-Engager T Cells as a Novel Immunotherapeutic for Acute Myeloid Leukemia. Molecular therapy: the journal of the American Society of Gene Therapy 2016; 24:1615-26.

46. Hedeker D, Gibbons R, Waternaux C. Sample size estimation for longitudinal designs with attrition: comparing time-related contrasts between two groups. Journal of Educational and Behavioral Statistics 1999:70-93.

47. Orlando E J, Han X, Tribouley C, et al. Genetic mechanisms of target antigen loss in CAR19 therapy of acute lymphoblastic leukemia. Nature medicine 2018; 24:1504-6.

48. Yoshida T, Akatsuka T, Imanaka-Yoshida K. Tenascin-C and integrins in cancer. Cell Adh Migr 2015; 9:96-104.

49. Spenle C, Saupe F, Midwood K, Burckel H, Noel G, Orend G. Tenascin-C: Exploitation and collateral damage in cancer management. Cell Adh Migr 2015; 9:141-53.

50. Allen-Rhoades W, Whittle S B, and Rainusso N. Pediatric Solid Tumors in Children and Adolescents: An Overview. Pediatr Rev. 2018; 39(9):444-53.

51. Ostrom Q T, Gittleman H, Xu J, Kromer C, Wolinsky Y, Kruchko C, et al. CBTRUS Statistical Report: Primary Brain and Other Central Nervous System Tumors Diagnosed in the United States in 2009-2013. Neuro Oncol. 2016; 18(suppl_5):v1-v75.

52. Ostrom Q T, Gittleman H, Liao P, Vecchione-Koval T, Wolinsky Y, Kruchko C, et al. CBTRUS Statistical Report: Primary brain and other central nervous system tumors diagnosed in the United States in 2010-2014. Neuro Oncol. 2017; 19(suppl_5):v1-v88.

53. Mackay A, Burford A, Carvalho D, Izquierdo E, Fazal-Salom J, Taylor K R, et al. Integrated Molecular Meta-Analysis of 1,000 Pediatric High-Grade and Diffuse Intrinsic Pontine Glioma. Cancer Cell. 2017; 32(4):520-37.e5.

54. Jones C, Karajannis M A, Jones D T W, Kieran M W, Monje M, Baker S J, et al. Pediatric high-grade glioma: biologically and clinically in need of new thinking. Neuro Oncol. 2017; 19(2):153-61.

55. Sadelain M, Brentjens R, and Riviére I. The basic principles of chimeric antigen receptor design. Cancer Discov. 2013; 3(4):388-98.

56. Muhammad N, Mao Q, and Xia H. CAR T-cells for cancer therapy. Biotechnol Genet Eng Rev. 2017; 33(2): 190-226.

57. Brocker T, and Karjalainen K. Signals through T cell receptor-zeta chain alone are insufficient to prime resting T lymphocytes. J Exp Med. 1995; 181(5):1653-9.

58. Segal N H, Parsons D W, Peggs K S, Velculescu V, Kinzler K W, Vogelstein B, et al. Epitope landscape in breast and colorectal cancer. Cancer Res. 2008; 68(3): 889-92.

59. Brudno J N, and Kochenderfer J N. Toxicities of chimeric antigen receptor T cells: recognition and management. Blood. 2016; 127(26):3321-30.

60. J. P. Connelly, S. M. Pruett-Miller, CRIS.py: A Versatile and High-throughput Analysis Program for CRISPR-based Genome Editing. Sci Rep 9, 4194 (2019).

61. S. Kakarla et al., Antitumor effects of chimeric receptor engineered human T cells directed to tumor stroma. Mol Ther 21, 1611-1620 (2013).

62. S. Gottschalk et al., Generating CTLs against the subdominant Epstein-Barr virus LMP1 antigen for the adoptive immunotherapy of EBV-associated malignancies. Blood 101, 1905-1912 (2003).

63. M. Midulla et al., Source of oncofetal ED-B-containing fibronectin: implications of production by both tumor and endothelial cells. Cancer Res 60, 164-169 (2000).

64. S. A. Grupp et al., Chimeric antigen receptor-modified T cells for acute lymphoid leukemia. N Engl J Med 368, 1509-1518 (2013).

65. T. J. Fry et al., CD22-targeted CAR T cells induce remission in B-ALL that is naive or resistant to CD19-targeted CAR immunotherapy. Nat Med 24, 20-28 (2018).

66. C. A. Ramos et al., Clinical and immunological responses after CD30-specific chimeric antigen receptor-redirected lymphocytes. J Clin Invest 127, 3462-3471 (2017).

67. M. Martinez, E. K. Moon, CAR T Cells for Solid Tumors: New Strategies for Finding, Infiltrating, and Surviving in the Tumor Microenvironment. Front Immunol 10, 128 (2019).

68. D. Hanahan, R. A. Weinberg, Hallmarks of cancer: the next generation. Cell 144, 646-674 (2011).

69. M. Kaspar, L. Zardi, D. Neri, Fibronectin as target for tumor therapy. Int J Cancer 118, 1331-1339 (2006).

70. Z. A. Khan et al., EDB fibronectin and angiogenesis—a novel mechanistic pathway. Angiogenesis 8, 183-196 (2005).

71. E. El-Emir et al., Characterisation and radioimmunotherapy of L19-SIP, an anti-angiogenic antibody against the extra domain B of fibronectin, in colorectal tumour models. Br J Cancer 96, 1862-1870 (2007).

72. D. Moosmayer et al., Bispecific antibody pretargeting of tumor neovasculature for improved systemic radiotherapy of solid tumors. Clin Cancer Res 12, 5587-5595 (2006).

73. S. P. Santoro et al., T cells bearing a chimeric antigen receptor against prostate-specific membrane antigen mediate vascular disruption and result in tumor regression. Cancer Immunol Res 3, 68-84 (2015).

74. W. Wang et al., Specificity redirection by CAR with human VEGFR-1 affinity endows T lymphocytes with tumor-killing ability and anti-angiogenic potency. Gene Ther 20, 970978 (2013).

75. K. Petrovic et al., TEM8/ANTXR1-specific CAR T cells mediate toxicity in vivo. PLoS One 14, e0224015 (2019).

76. J. P. Venables, Aberrant and alternative splicing in cancer. Cancer Res 64, 7647-7654 (2004).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A polynucleotide encoding a first chimeric antigen receptor (CAR):

targeting a Fibronectin Extradomain B (FN-EDB) comprising the nucleotide sequence SEQ ID NO: 96, or a nucleotide sequence having at least 80% identity thereof.

2. The polynucleotide of claim 1, wherein the polynucleotide further comprises a leader sequence.

3. The polynucleotide of claim 1, wherein the polynucleotide comprises at least one additional polynucleotide sequence encoding a second gene.

4. The polynucleotide of claim 3, wherein the second gene encodes a truncated CD19 (tCD19) polypeptide.

5. The polynucleotide of claim 3, wherein the second gene encodes a synthetic notch (synNotch) receptor.

6. The polynucleotide of claim 5, wherein the synNotch receptor encoded by the polynucleotide comprises the amino acid sequence SEQ ID NO: 67, or an amino acid sequence having at least 80% identity thereof.

7. A polynucleotide encoding a chimeric antigen receptor (CAR) and at least one additional polynucleotide sequence encoding a synthetic notch (synNotch) receptor, wherein the CAR comprises:

(a) an extracellular target-binding domain comprising a Fibronectin Extradomain B (FN-EDB)-binding moiety, (b) a hinge domain, (c) a transmembrane domain, and (d) a cytoplasmic domain comprising (i) optionally one or more costimulatory domains, and (ii) a lymphocyte activation domain; and wherein the polynucleotide sequence encoding the synNotch receptor comprises the nucleotide sequence SEQ ID NO: 68, or a nucleotide sequence having at least 80% identity thereof.

8. The polynucleotide of claim 6, wherein the synNotch receptor is operably linked to a polynucleotide that encodes an antigen binding moiety.

9. The polynucleotide of claim 8, wherein the antigen-binding moiety is an anti-FN-EDB binding moiety.

10. The polynucleotide of claim 9, wherein the FN-EDB-binding moiety is an anti-FN-EDB single chain variable fragment (scFv).

11. The polynucleotide of claim 10, wherein the anti-FN-EDB scFv is derived from antibody L19 (L19 scFv).

12. The polynucleotide of claim 3, wherein the at least one additional polynucleotide sequence is operably linked to the sequence encoding CAR via a sequence encoding a self-cleaving peptide and/or an internal ribosomal entry site (IRES).

13. A recombinant vector comprising the polynucleotide of claim 1.

14. A chimeric antigen receptor (CAR) encoded by the polynucleotide of claim 1.

15. An isolated host cell comprising the polynucleotide of claim 1.

16. The isolated host cell of claim 15, wherein the host cell further comprises a second CAR or a bispecific molecule, and wherein the expression of the second CAR or the bispecific molecule is induced by the activation of the first CAR.

17. The isolated host cell of claim 16, wherein the expression of the second CAR or bispecific molecule is induced using a synthetic Notch (synNotch) receptor or at least one nuclear factor of activated T cells (NFAT) dependent promoter.

18. The isolated host cell of claim 16, wherein the bispecific molecule is a bispecific T-cell engager (BiTE) or a bispecific antibody.

19. The isolated host cell of claim 16, wherein the second CAR or the bispecific molecule targets a tumor associated antigen.

20. The isolated host cell of claim 15, wherein the host cell is an allogeneic or autologous cell.

21. A pharmaceutical composition comprising the host cell of claim 15 and a pharmaceutically acceptable carrier and/or excipient.

22. A method of generating an isolated host cell, said method comprising genetically modifying the host cell with the polynucleotide of claim 1.

23. A method for indirectly killing a tumor cell expressing a tumor associated antigen, said method comprising contacting said cell with host cell(s) comprising the polynucleotide of claim 1, wherein the host cell(s) further comprises a second CAR or a bispecific molecule, wherein the expression of the second CAR or the bispecific molecule is induced by the activation of the first CAR, and wherein the second CAR or the bispecific molecule targets the tumor associated antigen.

24. A method for treating a tumor in a subject in need thereof, wherein one or more cells of the tumor express FN-EDB, said method comprising administering to the subject a therapeutically effective amount of host cells comprising the polynucleotide of claim 1.

25. A method for treating a tumor and/or inhibiting tumor neovascularization in a subject in need thereof, wherein one or more cells of the tumor or non-tumor cells within the tumor micro-environment express FN-EDB and one or more cells of the tumor express a tumor associated antigen, said method comprising administering to the subject a therapeutically effective amount of host cells of comprising the polynucleotide of claim 1, wherein the host cells further comprise a second CAR or a bispecific molecule, wherein the expression of the second CAR or the bispecific molecule is induced by the activation of the first CAR, and wherein the second CAR or the bispecific molecule targets the tumor associated antigen.

26. The polynucleotide of claim 5, wherein the nucleotide sequence encoding the synNotch receptor comprises the nucleotide sequence SEQ ID NO: 68, or a nucleotide sequence having at least 80% identity thereof.

27. The polynucleotide of claim 7, wherein the FN-EDB-binding moiety is an anti-FN-EDB single chain variable fragment (scFv).

28. The polynucleotide of claim 27, wherein the anti-FN-EDB scFv is derived from antibody L19 (L19 scFv).

29. The polynucleotide of claim 28, wherein the L19 scFv encoded by the polynucleotide comprises the amino acid sequence SEQ ID NO: 25, or an amino acid sequence having at least 80% identity thereof.

30. The polynucleotide of claim 7, wherein the extracellular target-binding domain further comprises a leader sequence.

31. The polynucleotide of claim 7, wherein the hinge domain is derived from IgG1, CD8a stalk, or CD28.

32. The polynucleotide of claim 7, wherein the transmembrane domain is derived from CD28, CD8a, CD4, or CD35.

33. The polynucleotide of claim 7, wherein the costimulatory domain is derived from CD28, CD27, CD40, CD134, CD137, CD226, CD79A, ICOS, or MyD88.

34. The polynucleotide of claim 7, wherein the lymphocyte activation domain is derived from CD32, DAP10, DAP12, Fc epsilon receptor I γ chain (FCER1G), CD3δ, CD3ε, CD3γ, CD226, or CD79A.

35. The polynucleotide of claim 7, wherein the CAR comprises the amino acid sequence SEQ ID NO: 95, or an amino acid sequence having at least 80% identity thereof.

36. The polynucleotide of claim 7, wherein the CAR comprises the nucleotide sequence SEQ ID NO: 96, or a nucleotide sequence having at least 80% identity thereof.

37. The polynucleotide of claim 7, wherein the synNotch receptor is operably linked to a polynucleotide that encodes an antigen binding moiety.

38. The polynucleotide of claim 37, wherein the antigen-binding moiety is an anti-FN-EDB binding moiety.

39. The polynucleotide of claim 38, wherein the FN-EDB-binding moiety is an anti-FN-EDB single chain variable fragment (scFv).

40. The polynucleotide of claim 39, wherein the anti-FN-EDB scFv is derived from antibody L19 (L19 scFv).

41. The polynucleotide of claim 7, wherein the at least one additional polynucleotide sequence is operably linked to the sequence encoding CAR via a sequence encoding a self-cleaving peptide and/or an internal ribosomal entry site (IRES).

42. A method for indirectly killing a tumor cell expressing a tumor associated antigen, said method comprising contacting said cell with host cell(s) comprising the polynucleotide of claim 7, wherein the host cell(s) further comprises a second CAR or a bispecific molecule, wherein the expression of the second CAR or the bispecific molecule is induced by the activation of the first CAR, and wherein the second CAR or the bispecific molecule targets the tumor associated antigen.

43. A method for treating a tumor in a subject in need thereof, wherein one or more cells of the tumor express FN-EDB, said method comprising administering to the subject a therapeutically effective amount of host cells comprising the polynucleotide of claim 7.

44. A method for treating a tumor and/or inhibiting tumor neovascularization in a subject in need thereof, wherein one or more cells of the tumor or non-tumor cells within the tumor micro-environment express FN-EDB and one or more cells of the tumor express a tumor associated antigen, said method comprising administering to the subject a therapeutically effective amount of host cells of comprising the polynucleotide of claim 7, wherein the host cells further comprise a second CAR or a bispecific molecule, wherein the expression of the second CAR or the bispecific molecule is induced by the activation of the first CAR, and wherein the second CAR or the bispecific molecule targets the tumor associated antigen.

45. A recombinant vector comprising the polynucleotide of claim 7.

46. A chimeric antigen receptor (CAR) encoded by the polynucleotide of claim 7.

47. The polynucleotide of claim 1, wherein the CAR targeting FN-EDB comprises the nucleotide sequence SEQ ID NO: 96.

48. The polynucleotide of claim 7, wherein the polynucleotide sequence encoding the synNotch receptor comprises the nucleotide sequence SEQ ID NO: 68.

* * * * *

SEQUENCE LISTING

```
<160> NUMBER OF SEQ ID NOS: 129

<210> SEQ ID NO 1
<211> LENGTH: 807
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ser Met Ser Trp Val Arg Gln Ala Pro Gly Lys Gly Leu
    50                  55                  60

Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
            85                  90                  95

Thr Leu Tyr Leu Gln Met Asn Ser Leu Arg Ala Glu Asp Thr Ala Val
            100                 105                 110

Tyr Tyr Cys Ala Lys Pro Phe Pro Tyr Phe Asp Tyr Trp Gly Gln Gly
            115                 120                 125
```

```
Thr Leu Val Thr Val Ser Ser Gly Asp Gly Ser Ser Gly Gly Ser Gly
    130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
                180                 185                 190

Arg Leu Leu Ile Tyr Tyr Ala Ser Ser Arg Ala Thr Gly Ile Pro Asp
            195                 200                 205

Arg Phe Ser Gly Ser Gly Ser Gly Thr Asp Phe Thr Leu Thr Ile Ser
    210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Asp
                245                 250                 255

Leu Glu Pro Lys Ser Cys Asp Lys Thr His Thr Cys Pro Pro Cys Pro
                260                 265                 270

Asp Pro Lys Phe Trp Val Leu Val Val Val Gly Gly Val Leu Ala Cys
            275                 280                 285

Tyr Ser Leu Leu Val Thr Val Ala Phe Ile Ile Phe Trp Val Arg Ser
    290                 295                 300

Lys Arg Ser Arg Leu Leu His Ser Asp Tyr Met Asn Met Thr Pro Arg
305                 310                 315                 320

Arg Pro Gly Pro Thr Arg Lys His Tyr Gln Pro Tyr Ala Pro Pro Arg
                325                 330                 335

Asp Phe Ala Ala Tyr Arg Ser Arg Val Lys Phe Ser Arg Ser Ala Asp
            340                 345                 350

Ala Pro Ala Tyr Gln Gln Gly Gln Asn Gln Leu Tyr Asn Glu Leu Asn
    355                 360                 365

Leu Gly Arg Arg Glu Glu Tyr Asp Val Leu Asp Lys Arg Arg Gly Arg
    370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Gly Lys Gly His Asp Gly Leu
            420                 425                 430

Tyr Gln Gly Leu Ser Thr Ala Thr Lys Asp Thr Tyr Asp Ala Leu His
            435                 440                 445

Met Gln Ala Leu Pro Pro Arg Ala Glu Gly Arg Gly Ser Leu Leu Thr
    450                 455                 460

Cys Gly Asp Val Glu Glu Asn Pro Gly Pro Met Pro Pro Pro Arg Leu
465                 470                 475                 480

Leu Phe Phe Leu Leu Phe Leu Thr Pro Met Glu Val Arg Pro Glu Glu
                485                 490                 495

Pro Leu Val Val Lys Val Glu Glu Gly Asp Asn Ala Val Leu Gln Cys
            500                 505                 510

Leu Lys Gly Thr Ser Asp Gly Pro Thr Gln Gln Leu Thr Trp Ser Arg
            515                 520                 525

Glu Ser Pro Leu Lys Pro Phe Leu Lys Leu Ser Leu Gly Leu Pro Gly
    530                 535                 540

Leu Gly Ile His Met Arg Pro Leu Ala Ile Trp Leu Phe Ile Phe Asn
```

```
545             550             555             560

Val Ser Gln Gln Met Gly Gly Phe Tyr Leu Cys Gln Pro Gly Pro Pro
                565             570             575

Ser Glu Lys Ala Trp Gln Pro Gly Trp Thr Val Asn Val Glu Gly Ser
            580             585             590

Gly Glu Leu Phe Arg Trp Asn Val Ser Asp Leu Gly Gly Leu Gly Cys
            595             600             605

Gly Leu Lys Asn Arg Ser Ser Glu Gly Pro Ser Ser Pro Ser Gly Lys
        610             615             620

Leu Met Ser Pro Lys Leu Tyr Val Trp Ala Lys Asp Arg Pro Glu Ile
    625             630             635             640

Trp Glu Gly Glu Pro Pro Cys Leu Pro Pro Arg Asp Ser Leu Asn Gln
                645             650             655

Ser Leu Ser Gln Asp Leu Thr Met Ala Pro Gly Ser Thr Leu Trp Leu
            660             665             670

Ser Cys Gly Val Pro Pro Asp Ser Val Ser Arg Gly Pro Leu Ser Trp
            675             680             685

Thr His Val His Pro Lys Gly Pro Lys Ser Leu Leu Ser Leu Glu Leu
        690             695             700

Lys Asp Asp Arg Pro Ala Arg Asp Met Trp Val Met Glu Thr Gly Leu
    705             710             715             720

Leu Leu Pro Arg Ala Thr Ala Gln Asp Ala Gly Lys Tyr Tyr Cys His
                725             730             735

Arg Gly Asn Leu Thr Met Ser Phe His Leu Glu Ile Thr Ala Arg Pro
                740             745             750

Val Leu Trp His Trp Leu Leu Arg Thr Gly Gly Trp Lys Val Ser Ala
            755             760             765

Val Thr Leu Ala Tyr Leu Ile Phe Cys Leu Cys Ser Leu Val Gly Ile
            770             775             780

Leu His Leu Gln Arg Ala Leu Val Leu Arg Arg Lys Arg Lys Arg Met
    785             790             795             800

Thr Asp Pro Thr Arg Arg Phe
                805
```

```
<210> SEQ ID NO 2
<211> LENGTH: 2421
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac tttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa acctttccca     360
tactttgatt actggggcca ggggacgctt gtcactgtct cctctggcga cggctcctcc     420
ggcggaagtg gaggcgcgtc agaaattgta ctgactcagt ccccgggcac gctctcactc     480
agtccaggcg aaagagctac gttgtcttgt cgcgcaagcc agtccgtaag ctctagcttc     540
```

```
ctcgcatggt atcaacaaaa gcccgggcag gctccgcggc tgctcattta ctatgctagt     600
tcaagggcta cgggaattcc agaccgattt agtggatctg ggagtggaac tgacttcaca     660
cttacgatca gcaggcttga gccggaagat tttgccgtgt actactgcca gcaaactgga     720
agaatccccc caacattcgg acaaggcacg aaggtggaaa tcaaggatct cgagcccaaa     780
tcttgtgaca aaactcacac atgcccaccg tgcccggatc ccaagttctg ggtgctggtg     840
gtcgtgggcg gagtgctggc ctgttacagc ctgctcgtga ccgtggcctt catcatcttt     900
tgggtgcgca gcaagcggag ccggctgctg cacagcgact acatgaacat gacccccaga     960
cggcctggcc ccaccagaaa gcactaccag ccttacgccc tcccagaga cttcgccgcc    1020 taccggtcca gagtgaagtt cagcagaagc gccgacgccc ctgcctatca gcagggccag    1080
aaccagctgt acaacgagct gaacctgggc agacgggaag agtacgacgt gctggacaag    1140
cggagaggca gggaccctga gatgggcggc aagcccagaa gaaagaaccc ccaggaaggc    1200
ctgtataacg aactgcagaa agacaagatg gccgaggcct acagcgagat cggcatgaag    1260
ggcgagcgga gaagaggcaa gggccacgat ggcctgtacc agggactgag caccgccacc    1320
aaggacacct acgacgccct gcacatgcag gccctgcctc caagagccga gggcagaggc    1380
agcctgctga catgtggcga cgtggaagag aacccaggcc ccatgcctcc ccccagactg    1440
ctgttcttcc tgctgttcct gacccctatg gaagtgcggc ccgaggaacc cctggtcgtg    1500
aaagtggaag agggcgacaa cgccgtgctg cagtgtctga agggcacctc cgatggccct    1560
acccagcagc tgacctggtc cagagagagc cccctgaagc ccttcctgaa gctgtctctg    1620
ggcctgcctg gcctgggcat ccatatgagg ccactggcca tctggctgtt catcttcaac    1680
gtgtcccagc agatgggagg cttctacctg tgccagcctg gcccaccttc tgagaaggct    1740
tggcagcctg gctggaccgt gaacgtggaa ggatctggcg agctgttccg gtggaacgtg    1800
tccgatctgg gcggcctggg atgcggcctg aagaacagat ctagcgaggg ccccagcagc    1860
cccagcggca aactgatgag ccccaagctg tacgtgtggg ccaaggacag acccgagatt    1920
tgggagggcg agccccttg cctgcccct agagatagcc tgaaccagag cctgagccag    1980
gacctgacaa tggcccctgg cagcacactg tggctgagct gtggcgtgcc acccgactct    2040
gtgtctagag gccctctgag ctggacccac gtgcaccta agggccctaa gagcctgctg    2100
tccctggaac tgaaggacga caggcccgcc agagatatgt gggtcatgga aaccggcctg    2160
ctgctgccta gagccacagc ccaggatgcc ggcaagtact actgccacag aggcaacctg    2220
accatgagct ccacctgga aatcaccgcc agaccgtgc tgtggcactg gctgctgaga    2280
accggcggat ggaaagtgtc cgccgtgact ctggcctacc tgatcttctg cctgtgctcc    2340
ctcgtgggca tcctgcatct gcagagggct ctggtgctgc ggcggaagcg gaagagaatg    2400
accgacccta cccggcggtt c                                               2421
```

```
<210> SEQ ID NO 3
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
```

-continued

```
                20              25              30

Pro Gly Gly Ser Leu Arg Leu Ser Cys Ala Ala Ser Gly Phe Thr Phe
            35              40              45

Ser Ser Phe Ser Met Ser Trp Val Arg Gln Ala Pro Gly Lys Gly Leu
        50              55              60

Glu Trp Val Ser Ser Ile Ser Gly Ser Ser Gly Thr Thr Tyr Tyr Ala
65              70              75              80

Asp Ser Val Lys Gly Arg Phe Thr Ile Ser Arg Asp Asn Ser Lys Asn
                85              90              95

Thr Leu Tyr Leu Gln Met Asn Ser Leu Arg Ala Glu Asp Thr Ala Val
            100             105             110

Tyr Tyr Cys Ala Lys Pro Phe Pro Tyr Phe Asp Tyr Trp Gly Gln Gly
            115             120             125

Thr Leu Val Thr Val Ser Ser Gly Asp Gly Ser Ser Gly Gly Ser Gly
            130             135             140

Gly Ala Ser Glu Ile Val Leu Thr Gln Ser Pro Gly Thr Leu Ser Leu
145             150             155             160

Ser Pro Gly Glu Arg Ala Thr Leu Ser Cys Arg Ala Ser Gln Ser Val
                165             170             175

Ser Ser Ser Phe Leu Ala Trp Tyr Gln Gln Lys Pro Gly Gln Ala Pro
            180             185             190

Arg Leu Leu Ile Tyr Tyr Ala Ser Ser Arg Ala Thr Gly Ile Pro Asp
            195             200             205

Arg Phe Ser Gly Ser Gly Ser Gly Thr Asp Phe Thr Leu Thr Ile Ser
    210             215             220

Arg Leu Glu Pro Glu Asp Phe Ala Val Tyr Tyr Cys Gln Gln Thr Gly
225             230             235             240

Arg Ile Pro Pro Thr Phe Gly Gln Gly Thr Lys Val Glu Ile Lys Pro
            245             250             255

Ala Lys Pro Thr Thr Thr Pro Ala Pro Arg Pro Pro Thr Pro Ala Pro
            260             265             270

Thr Ile Ala Ser Gln Pro Leu Ser Leu Arg Pro Glu Ala Cys Arg Pro
            275             280             285

Ala Ala Gly Gly Ala Val His Thr Arg Gly Leu Asp Phe Ala Cys Asp
    290             295             300

Ile Tyr Ile Trp Ala Pro Leu Ala Gly Thr Cys Gly Val Leu Leu Leu
305             310             315             320

Ser Leu Val Ile Thr Leu Tyr Cys Asn His Arg Asn Arg Ser Lys Arg
            325             330             335

Ser Arg Leu Leu His Ser Asp Tyr Met Asn Met Thr Pro Arg Arg Pro
            340             345             350

Gly Pro Thr Arg Lys His Tyr Gln Pro Tyr Ala Pro Pro Arg Asp Phe
            355             360             365

Ala Ala Tyr Arg Ser Arg Val Lys Phe Ser Arg Ser Ala Asp Ala Pro
    370             375             380

Ala Tyr Gln Gln Gly Gln Asn Gln Leu Tyr Asn Glu Leu Asn Leu Gly
385             390             395             400

Arg Arg Glu Glu Tyr Asp Val Leu Asp Lys Arg Arg Gly Arg Asp Pro
                405             410             415

Glu Met Gly Gly Lys Pro Arg Arg Lys Asn Pro Gln Glu Gly Leu Tyr
            420             425             430

Asn Glu Leu Gln Lys Asp Lys Met Ala Glu Ala Tyr Ser Glu Ile Gly
            435             440             445
```

```
Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485
```

<210> SEQ ID NO 4
<211> LENGTH: 1455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac tttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa accttttcca     360
tactttgatt actggggcca ggggacgctt gtcactgtct cctctggcga cggctcctcc     420
ggcggaagtg gaggcgcgtc agaaattgta ctgactcagt ccccgggcac gctctcactc     480
agtccaggcg aaagagctac gttgtcttgt cgcgcaagcc agtccgtaag ctctagcttc     540
ctcgcatggt atcaacaaaa gcccgggcag gctccgcggc tgctcattta ctatgctagt     600
tcaagggcta cgggaattcc agaccgattt agtggatctg ggagtggaac tgacttcaca     660
cttacgatca gcaggcttga gccggaagat tttgccgtgt actactgcca gcaaactgga     720
agaatccccc caacattcgg acaaggcacg aaggtggaaa tcaagccagc caagcccacc     780
acaacccctg ctcctagacc tcctacccca gcccctacca ttgcctccca gccactgtct     840
ctgaggcccg aggcttgtag acctgctgca ggcggagccg tgcacaccag aggactggat     900
ttcgcctgcg acatctatat ctgggcccct ctgccggca cctgtggcgt gctgctgctg     960
tcactcgtga tcaccctgta ctgcaaccac cggaaccgca gcaagcggag ccggctgctg    1020
cacagcgact acatgaacat gacccccaga cggcctggcc ccaccagaaa gcactaccag    1080
ccttacgccc tcccagaga cttcgccgcc taccggtcca gagtgaagtt cagcagaagc    1140
gccgacgccc tgcctatca gcagggccag aaccagctgt acaacgagct gaacctgggc    1200
agacgggaag agtacgacgt gctggacaag cggagaggca gggaccctga gatgggcggc    1260
aagcccagaa gaaagaaccc ccaggaaggc ctgtataacg aactgcagaa agacaagatg    1320
gccgaggcct acagcgagat cggcatgaag gcgagcgga gaagaggcaa gggccacgat    1380
ggcctgtacc agggactgag caccgccacc aaggacacct acgacgccct gcacatgcag    1440
gccctgcctc caaga                                                     1455
```

<210> SEQ ID NO 5
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 5

```
Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Ser Phe Ser Met Ser Trp Val Arg Gln Ala Pro Gly Lys Gly Leu
        50                  55                  60

Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Pro Phe Pro Tyr Phe Asp Tyr Trp Gly Gln Gly
            115                 120                 125

Thr Leu Val Thr Val Ser Ser Gly Asp Gly Ser Ser Gly Gly Ser Gly
            130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
            180                 185                 190

Arg Leu Leu Ile Tyr Tyr Ala Ser Ser Arg Ala Thr Gly Ile Pro Asp
            195                 200                 205

Arg Phe Ser Gly Ser Gly Ser Gly Thr Asp Phe Thr Leu Thr Ile Ser
        210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Pro
                245                 250                 255

Ala Lys Pro Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
            290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Asn His Arg Asn Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
            370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
```

```
                  405                 410                 415
Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

```
<210> SEQ ID NO 6
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac ttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa accttttcca     360
tactttgatt actggggcca ggggacgctt gtcactgtct cctctggcga cggctcctcc     420
ggcggaagtg gaggcgcgtc agaaattgta ctgactcagt ccccgggcac gctctcactc     480
agtccaggcg aaagagctac gttgtcttgt cgcgcaagcc agtccgtaag ctctagcttc     540
ctcgcatggt atcaacaaaa gcccgggcag gctccgcggc tgctcattta ctatgctagt     600
tcaagggcta cgggaattcc agaccgattt agtggatctg ggagtggaac tgacttcaca     660
cttacgatca gcaggcttga gccggaagat tttgccgtgt actactgcca gcaaactgga     720 agaatcccc caacattcgg acaaggcacg aaggtggaaa tcaagccagc caagcccacc     780
acaacccctg ctcctagacc tcctaccca gcccctacca ttgcctccca gccactgtct     840
ctgaggcccg aggcttgtag acctgctgca ggcggagccg tgcacaccag aggactggat     900
ttcgcctgcg acatctatat ctgggcccct ctggccggca cctgtggcgt gctgctgctg     960
tcactcgtga tcaccctgta ctgcaaccac cggaacaaac gcggccgcaa aaaactgctg    1020 tatatttta aacagccgtt tatgcgcccg gtgcagacca cccaggaaga agatggctgc    1080
agctgccgct ttccggaaga agaagaaggc ggctgcgaac tgcgcgtgaa atttagccgc    1140
agcgcggatg cgccggcgta tcagcagggc cagaaccagc tgtataacga actgaacctg    1200
ggccgccgcg aagaatatga tgtgctggat aaacgccgcg gccgcgatcc ggaaatgggc    1260
ggcaaaccgc gccgcaaaaa cccgcaggaa ggcctgtata cgaactgca gaaagataaa     1320 atggcggaag cgtatagcga aattggcatg aaaggcgaac gccgccgcgg caaaggccat    1380
gatggcctgt atcagggcct gagcaccgcg accaaagata cctatgatgc gctgcatatg    1440
caggcgctgc cgccgcgc                                                   1458
```

<210> SEQ ID NO 7
<211> LENGTH: 480
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 7

Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Phe Ser Met Ser Trp Val Arg Gln Ala Pro Gly Lys Gly Leu
        50                  55                  60

Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Pro Phe Pro Tyr Phe Asp Tyr Trp Gly Gln Gly
        115                 120                 125

Thr Leu Val Thr Val Ser Ser Gly Asp Gly Ser Ser Gly Gly Ser Gly
    130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
            180                 185                 190

Arg Leu Leu Ile Tyr Tyr Ala Ser Ser Arg Ala Thr Gly Ile Pro Asp
        195                 200                 205

Arg Phe Ser Gly Ser Gly Ser Gly Thr Asp Phe Thr Leu Thr Ile Ser
    210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Pro
                245                 250                 255

Ala Lys Pro Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Asn His Arg Asn Arg Asp Gln Arg
                325                 330                 335

Leu Pro Pro Asp Ala His Lys Pro Pro Gly Gly Gly Ser Phe Arg Thr
            340                 345                 350

Pro Ile Gln Glu Glu Gln Ala Asp Ala His Ser Thr Leu Ala Lys Ile
        355                 360                 365

-continued

```
Arg Val Lys Phe Ser Arg Ser Ala Asp Ala Pro Ala Tyr Gln Gln Gly
    370             375             380
```

```
Gln Asn Gln Leu Tyr Asn Glu Leu Asn Leu Gly Arg Arg Glu Glu Tyr
385             390             395             400
```

```
Asp Val Leu Asp Lys Arg Arg Gly Arg Asp Pro Glu Met Gly Gly Lys
            405             410             415
```

```
Pro Arg Arg Lys Asn Pro Gln Glu Gly Leu Tyr Asn Glu Leu Gln Lys
            420             425             430
```

```
Asp Lys Met Ala Glu Ala Tyr Ser Glu Ile Gly Met Lys Gly Glu Arg
            435             440             445
```

```
Arg Arg Gly Lys Gly His Asp Gly Leu Tyr Gln Gly Leu Ser Thr Ala
    450             455             460
```

```
Thr Lys Asp Thr Tyr Asp Ala Leu His Met Gln Ala Leu Pro Pro Arg
465             470             475             480
```

```
<210> SEQ ID NO 8
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac tttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa accttttcca     360
tactttgatt actggggcca ggggacgctt gtcactgtct cctctggcga cggctcctcc     420
ggcggaagtg gaggcgcgtc agaaattgta ctgactcagt ccccgggcac gctctcactc     480
agtccaggcg aaagagctac gttgtcttgt cgcgcaagcc agtccgtaag ctctagcttc     540
ctcgcatggt atcaacaaaa gcccgggcag gctccgcggc tgctcattta ctatgctagt     600
tcaagggcta cgggaattcc agaccgattt agtggatctg ggagtggaac tgacttcaca     660
cttacgatca gcaggcttga gccggaagat tttgccgtgt actactgcca gcaaactgga     720
agaatccccc caacattcgg acaaggcacg aaggtggaaa tcaagccagc caagcccacc     780
acaacccctg ctcctagacc tcctaccccca gcccctacca ttgcctccca gccactgtct     840
ctgaggcccg aggcttgtag acctgctgca ggcggagccg tgcacaccag aggactggat     900
ttcgcctgcg acatctatat ctgggcccct ctggccggca cctgtggcgt gctgctgctg     960
tcactcgtga tcaccctgta ctgcaaccac cggaaccgcg atcagcgcct gccgccggat    1020
gcgcataaac cgccgggcgg cggcagcttt cgcacccga ttcaggaaga acaggcggat     1080
gcgcatagca ccctggcgaa aattcgcgtg aaatttagcc gcagcgcgga tgcgccggcg    1140
tatcagcagg gccagaacca gctgtataac gaactgaacc tgggccgccg cgaagaatat    1200
gatgtgctgg ataaacgccg cggccgcgat ccggaaatgg gcggcaaacc gcgccgcaaa    1260
aacccgcagg aaggcctgta taacgaactg cagaaagata aaatggcgga agcgtatagc    1320
gaaattggca tgaaaggcga acgccgccgc ggcaaaggcc atgatggcct gtatcagggc    1380
ctgagcaccg cgaccaaaga tacctatgat gcgctgcata tgcaggcgct gccgccgcgc    1440
```

```
<210> SEQ ID NO 9
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ser Met Ser Trp Val Arg Gln Ala Pro Gly Lys Gly Leu
    50                  55                  60

Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Pro Phe Pro Tyr Phe Asp Tyr Trp Gly Gln Gly
            115                 120                 125

Thr Leu Val Thr Val Ser Ser Gly Asp Gly Ser Ser Gly Gly Ser Gly
    130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
            180                 185                 190

Arg Leu Leu Ile Tyr Tyr Ala Ser Ser Arg Ala Thr Gly Ile Pro Asp
            195                 200                 205

Arg Phe Ser Gly Ser Gly Ser Gly Thr Asp Phe Thr Leu Thr Ile Ser
    210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Pro
                245                 250                 255

Ala Lys Pro Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Asn His Arg Asn Val Ala Ala Gly
                325                 330                 335

Gly Pro Gly Ala Gly Ser Ala Ala Pro Val Ser Ser Thr Ser Ser Leu
            340                 345                 350

Pro Leu Ala Ala Leu Asn Met Arg Val Arg Arg Arg Leu Ser Leu Phe
```

```
        355                 360                 365
```

Leu Asn Val Arg Thr Gln Val Ala Ala Asp Trp Thr Ala Leu Ala Glu
    370                 375                 380

Glu Met Asp Phe Glu Tyr Leu Glu Ile Arg Gln Leu Glu Thr Gln Ala
385                 390                 395                 400

Asp Pro Thr Gly Arg Leu Leu Asp Ala Trp Gln Gly Arg Pro Gly Ala
                405                 410                 415

Ser Val Gly Arg Leu Leu Glu Leu Leu Thr Lys Leu Gly Arg Asp Asp
                420                 425                 430

Val Leu Leu Glu Leu Gly Pro Ser Ile Glu Glu Asp Cys Gln Lys Tyr
                435                 440                 445

Ile Leu Lys Gln Gln Gln Glu Glu Ala Glu Lys Pro Leu Gln Val Ala
    450                 455                 460

Ala Val Asp Ser Ser Val Pro Arg Thr Ala Glu Leu Ala Gly Ile Thr
465                 470                 475                 480

Thr Leu Asp Asp Pro Leu Gly His Met Pro Glu Arg Phe Asp Ala Phe
                485                 490                 495

Ile Cys Tyr Cys Pro Ser Asp Ile Val Glu Lys Lys Val Ala Lys Lys
                500                 505                 510

Pro Thr Asn Lys Ala Pro His Pro Lys Gln Glu Pro Gln Glu Ile Asn
                515                 520                 525

Phe Pro Asp Asp Leu Pro Gly Ser Asn Thr Ala Ala Pro Val Gln Glu
    530                 535                 540

Thr Leu His Gly Cys Gln Pro Val Thr Gln Glu Asp Gly Lys Glu Ser
545                 550                 555                 560

Arg Ile Ser Val Gln Glu Arg Gln Arg Val Lys Phe Ser Arg Ser Ala
                565                 570                 575

Asp Ala Pro Ala Tyr Gln Gln Gly Gln Asn Gln Leu Tyr Asn Glu Leu
                580                 585                 590

Asn Leu Gly Arg Arg Glu Glu Tyr Asp Val Leu Asp Lys Arg Arg Gly
                595                 600                 605

Arg Asp Pro Glu Met Gly Gly Lys Pro Arg Arg Lys Asn Pro Gln Glu
    610                 615                 620

Gly Leu Tyr Asn Glu Leu Gln Lys Asp Lys Met Ala Glu Ala Tyr Ser
625                 630                 635                 640

Glu Ile Gly Met Lys Gly Glu Arg Arg Arg Gly Lys Gly His Asp Gly
                645                 650                 655

Leu Tyr Gln Gly Leu Ser Thr Ala Thr Lys Asp Thr Tyr Asp Ala Leu
                660                 665                 670

His Met Gln Ala Leu Pro Pro Arg
    675                 680

<210> SEQ ID NO 10
<211> LENGTH: 2037
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggactgga tctggcgcat cctcttcctc gtcggcgctg ctaccggcgc tcattctgag        60
gttcagcttc ttgagtctgg gggcggcctg gtgcaacctg gtggcagtct taggctgagt       120
tgcgccgcgt cagggtttac ttttttcttcc ttcagcatgt catgggtccg ccaggctcca       180

-continued

```
ggtaagggcc tggaatgggt tagtagcatc agtggcagta gtggtacaac atactacgct       240
gatagtgtta aagggagatt cactataagt agggataatt ctaaaaatac cctttatctg       300
caaatgaatt ctttgagggc cgaagatact gcggtctatt actgtgccaa accttttcca       360
tactttgatt actggggcca ggggacgctt gtcactgtct cctctggcga cggctcctcc       420
ggcggaagtg gaggcgcgtc agaaattgta ctgactcagt ccccgggcac gctctcactc       480
agtccaggcg aaagagctac gttgtcttgt cgcgcaagcc agtccgtaag ctctagcttc       540
ctcgcatggt atcaacaaaa gcccgggcag gctccgcggc tgctcattta ctatgctagt       600
tcaagggcta cgggaattcc agaccgattt agtggatctg ggagtggaac tgacttcaca       660
cttacgatca gcaggcttga gccggaagat tttgccgtgt actactgcca gcaaactgga       720
agaatccccc caacattcgg acaaggcacg aaggtggaaa tcaagccagc caagcccacc       780 acaccctg ctcctagacc tcctacccca gcccctacca ttgcctccca gccactgtct       840
ctgaggcccg aggcttgtag acctgctgca ggcggagccg tgcacaccag aggactggat       900
ttcgcctgcg acatctatat ctgggcccct ctggccggca cctgtggcgt gctgctgctg       960
tcactcgtga tcaccctgta ctgcaaccac cggaacgctg ctggcggacc tggcgccgga      1020
tctgctgctc ctgtgtctag cacaagcagc ctgcctctgg ccgccctgaa catgagagtg      1080
cggagaaggc tgagcctgtt cctgaacgtg cggacacagg tggccgccga ttggacagcc      1140
ctggccgagg aaatggactt cgagtacctg gaaatccggc agctggaaac ccaggccgac      1200
cctacaggca gactgctgga tgcttggcag ggcagaccag cgcttctgt gggaaggctg      1260 ctggaactgc tgaccaagct gggcagggac gacgtgctgc tggaactggg ccctagcatc      1320
gaagaggact gccagaagta catcctgaag cagcagcagg aagaggccga gaagcctctg      1380
caggtggcag ccgtggatag cagcgtgcca agaacagccg agctggccgg catcaccacc      1440
ctggatgatc tctgggcca catgcccgag agattcgacg ccttcatctg ctactgcccc      1500
agcgacatcg tggaaaagaa ggtggccaag aagcccacca caaggcccc ccaccccaag      1560 caggaacccc aggaaatcaa cttccccgac gacctgcccg gcagcaatac tgctgcaccc      1620
gtgcaggaaa ccctgcacgg ctgtcagcct gtgacccagg aagatggcaa agaaagccgg      1680
atctctgtgc aggaacgcca gagagtgaag ttcagcagga gcgcagacgc ccccgcgtac      1740
cagcagggcc agaaccagct ctataacgag ctcaatctag gacgaagaga ggagtacgat      1800
gttttggaca gagacgtgg ccgggaccct gagatgggcg gcaagcccag aagaaagaac      1860
ccccaggaag gcctgtataa cgaactgcag aaagacaaga tggccgaggc ctacagcgag      1920
atcggcatga gggcgagcg gagaagaggc aagggccacg atggcctgta ccagggactg      1980
agcaccgcca ccaaggacac ctacgacgcc ctgcacatgc aggccctgcc tccaaga      2037
```

<210> SEQ ID NO 11
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
            20                  25                  30
```

-continued

```
Pro Gly Gly Ser Leu Arg Leu Ser Cys Ala Ala Ser Gly Phe Thr Phe
        35              40              45

Ser Ser Phe Ser Met Ser Trp Val Arg Gln Ala Pro Gly Lys Gly Leu
    50              55              60

Glu Trp Val Ser Ser Ile Ser Gly Ser Ser Gly Thr Thr Tyr Tyr Ala
65              70              75              80

Asp Ser Val Lys Gly Arg Phe Thr Ile Ser Arg Asp Asn Ser Lys Asn
                85              90              95

Thr Leu Tyr Leu Gln Met Asn Ser Leu Arg Ala Glu Asp Thr Ala Val
            100             105             110

Tyr Tyr Cys Ala Lys Pro Phe Pro Tyr Phe Asp Tyr Trp Gly Gln Gly
        115             120             125

Thr Leu Val Thr Val Ser Ser Gly Asp Gly Ser Ser Gly Gly Ser Gly
    130             135             140

Gly Ala Ser Glu Ile Val Leu Thr Gln Ser Pro Gly Thr Leu Ser Leu
145             150             155             160

Ser Pro Gly Glu Arg Ala Thr Leu Ser Cys Arg Ala Ser Gln Ser Val
                165             170             175

Ser Ser Ser Phe Leu Ala Trp Tyr Gln Gln Lys Pro Gly Gln Ala Pro
            180             185             190

Arg Leu Leu Ile Tyr Tyr Ala Ser Ser Arg Ala Thr Gly Ile Pro Asp
        195             200             205

Arg Phe Ser Gly Ser Gly Ser Gly Thr Asp Phe Thr Leu Thr Ile Ser
    210             215             220

Arg Leu Glu Pro Glu Asp Phe Ala Val Tyr Tyr Cys Gln Gln Thr Gly
225             230             235             240

Arg Ile Pro Pro Thr Phe Gly Gln Gly Thr Lys Val Glu Ile Lys Asp
                245             250             255

Leu Glu Pro Lys Ser Cys Asp Lys Thr His Thr Cys Pro Pro Cys Pro
            260             265             270

Asp Pro Lys Phe Trp Val Leu Val Val Val Gly Gly Val Leu Ala Cys
        275             280             285

Tyr Ser Leu Leu Val Thr Val Ala Phe Ile Ile Phe Trp Val Lys Arg
290             295             300

Gly Arg Lys Lys Leu Leu Tyr Ile Phe Lys Gln Pro Phe Met Arg Pro
305             310             315             320

Val Gln Thr Thr Gln Glu Glu Asp Gly Cys Ser Cys Arg Phe Pro Glu
                325             330             335

Glu Glu Glu Gly Gly Cys Glu Leu Arg Val Lys Phe Ser Arg Ser Ala
            340             345             350

Asp Ala Pro Ala Tyr Gln Gln Gly Gln Asn Gln Leu Tyr Asn Glu Leu
        355             360             365

Asn Leu Gly Arg Arg Glu Glu Tyr Asp Val Leu Asp Lys Arg Arg Gly
    370             375             380

Arg Asp Pro Glu Met Gly Gly Lys Pro Arg Arg Lys Asn Pro Gln Glu
385             390             395             400

Gly Leu Tyr Asn Glu Leu Gln Lys Asp Lys Met Ala Glu Ala Tyr Ser
                405             410             415

Glu Ile Gly Met Lys Gly Glu Arg Arg Arg Gly Lys Gly His Asp Gly
            420             425             430

Leu Tyr Gln Gly Leu Ser Thr Ala Thr Lys Asp Thr Tyr Asp Ala Leu
        435             440             445

His Met Gln Ala Leu Pro Pro Arg
```

-continued

```
450                455
```

```
<210> SEQ ID NO 12
<211> LENGTH: 1368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac tttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa accttttcca     360
tactttgatt actggggcca ggggacgctt gtcactgtct cctctggcga cggctcctcc     420
ggcggaagtg gaggcgcgtc agaaattgta ctgactcagt ccccgggcac gctctcactc     480
agtccaggcg aaagagctac gttgtcttgt cgcgcaagcc agtccgtaag ctctagcttc     540
ctcgcatggt atcaacaaaa gcccgggcag gctccgcggc tgctcattta ctatgctagt     600
tcaagggcta cgggaattcc agaccgattt agtggatctg ggagtggaac tgacttcaca     660
cttacgatca gcaggcttga gccggaagat tttgccgtgt actactgcca gcaaactgga     720
agaatccccc caacattcgg acaaggcacg aaggtggaaa tcaaggatct cgagcccaaa     780
tcttgtgaca aaactcacac atgcccaccg tgcccggatc ccaagttctg ggtgctggtg     840
gtcgtgggcg gagtgctggc ctgttacagc ctgctcgtga ccgtggcctt catcatcttt     900
tgggtgaaac gcggccgcaa aaaactgctg tatattttta acagccgtt tatgcgcccg     960 gtgcagacca cccaggaaga agatggctgc agctgccgct tccggaaga agaagaaggc    1020 ggctgcgaac tgcgcgtgaa atttagccgc agcgcggatg cgccggcgta tcagcagggc    1080
cagaaccagc tgtataacga actgaacctg gccgccgcg aagaatatga tgtgctggat    1140
aaacgccgcg gccgcgatcc ggaaatgggc ggcaaaccgc gccgcaaaaa cccgcaggaa    1200
ggcctgtata cgaactgca gaaagataaa atggcggaag cgtatagcga aattggcatg    1260
aaaggcgaac gccgccgcgg caaaggccat gatggcctgt atcagggcct gagcaccgcg    1320
accaaagata cctatgatgc gctgcatatg caggcgctgc cgccgcgc                1368

<210> SEQ ID NO 13
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45
```

-continued

```
Ser Ser Phe Ser Met Ser Trp Val Arg Gln Ala Pro Gly Lys Gly Leu
    50              55                  60

Glu Trp Val Ser Ser Ile Ser Gly Ser Ser Gly Thr Thr Tyr Tyr Ala
65              70                  75                  80

Asp Ser Val Lys Gly Arg Phe Thr Ile Ser Arg Asp Asn Ser Lys Asn
            85                  90                  95

Thr Leu Tyr Leu Gln Met Asn Ser Leu Arg Ala Glu Asp Thr Ala Val
            100                 105                 110

Tyr Tyr Cys Ala Lys Pro Phe Pro Tyr Phe Asp Tyr Trp Gly Gln Gly
            115                 120                 125

Thr Leu Val Thr Val Ser Ser Gly Asp Gly Ser Ser Gly Gly Ser Gly
    130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
            165                 170                 175

Ser Ser Ser Phe Leu Ala Trp Tyr Gln Gln Lys Pro Gly Gln Ala Pro
            180                 185                 190

Arg Leu Leu Ile Tyr Tyr Ala Ser Ser Arg Ala Thr Gly Ile Pro Asp
            195                 200                 205

Arg Phe Ser Gly Ser Gly Ser Gly Thr Asp Phe Thr Leu Thr Ile Ser
    210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Asp
            245                 250                 255

Leu Glu Pro Lys Ser Cys Asp Lys Thr His Thr Cys Pro Pro Cys Pro
            260                 265                 270

Asp Pro Lys Phe Trp Val Leu Val Val Val Gly Gly Val Leu Ala Cys
            275                 280                 285

Tyr Ser Leu Leu Val Thr Val Ala Phe Ile Ile Phe Trp Val Arg Asp
    290                 295                 300

Gln Arg Leu Pro Pro Asp Ala His Lys Pro Pro Gly Gly Gly Ser Phe
305                 310                 315                 320

Arg Thr Pro Ile Gln Glu Glu Gln Ala Asp Ala His Ser Thr Leu Ala
            325                 330                 335

Lys Ile Arg Val Lys Phe Ser Arg Ser Ala Asp Ala Pro Ala Tyr Gln
            340                 345                 350

Gln Gly Gln Asn Gln Leu Tyr Asn Glu Leu Asn Leu Gly Arg Arg Glu
            355                 360                 365

Glu Tyr Asp Val Leu Asp Lys Arg Arg Gly Arg Asp Pro Glu Met Gly
    370                 375                 380

Gly Lys Pro Arg Arg Lys Asn Pro Gln Glu Gly Leu Tyr Asn Glu Leu
385                 390                 395                 400

Gln Lys Asp Lys Met Ala Glu Ala Tyr Ser Glu Ile Gly Met Lys Gly
            405                 410                 415

Glu Arg Arg Arg Gly Lys Gly His Asp Gly Leu Tyr Gln Gly Leu Ser
            420                 425                 430

Thr Ala Thr Lys Asp Thr Tyr Asp Ala Leu His Met Gln Ala Leu Pro
            435                 440                 445

Pro Arg
    450
```

<210> SEQ ID NO 14
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac tttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa accttttcca     360
tactttgatt actggggcca ggggacgctt gtcactgtct cctctggcga cggctcctcc     420
ggcggaagtg gaggcgcgtc agaaattgta ctgactcagt ccccgggcac gctctcactc     480
agtccaggcg aaagagctac gttgtcttgt cgcgcaagcc agtccgtaag ctctagcttc     540
ctcgcatggt atcaacaaaa gcccgggcag gctccgcggc tgctcattta ctatgctagt     600
tcaagggcta cgggaattcc agaccgattt agtggatctg ggagtggaac tgacttcaca     660
cttacgatca gcaggcttga gccggaagat tttgccgtgt actactgcca gcaaactgga     720
agaatccccc caacattcgg acaaggcacg aaggtggaaa tcaaggatct cgagcccaaa     780
tcttgtgaca aaactcacac atgcccaccg tgcccggatc ccaagttctg ggtgctggtg     840
gtcgtgggcg gagtgctggc ctgttacagc ctgctcgtga ccgtggcctt catcatcttt     900
tgggtgcgcg atcagcgcct gccgccggat gcgcataaac cgccgggcgg cggcagcttt     960 cgcacccga ttcaggaaga acaggcggat gcgcatagca ccctggcgaa aattcgcgtg    1020
aaatttagcc gcagcgcgga tgcgccggcg tatcagcagg gccagaacca gctgtataac    1080
gaactgaacc tgggccgccg cgaagaatat gatgtgctgg ataaacgccg cggccgcgat    1140
ccggaaatgg gcggcaaacc gcgccgcaaa aacccgcagg aaggcctgta taacgaactg    1200
cagaaagata aaatggcgga agcgtatagc gaaattggca tgaaaggcga acgccgccgc    1260
ggcaaaggcc atgatggcct gtatcagggc ctgagcaccg cgaccaaaga tacctatgat    1320
gcgctgcata tgcaggcgct gccgccgcgc                                     1350

<210> SEQ ID NO 15
<211> LENGTH: 649
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ser Met Ser Trp Val Arg Gln Ala Pro Gly Lys Gly Leu
    50                  55                  60

```
Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Pro Phe Pro Tyr Phe Asp Tyr Trp Gly Gln Gly
        115                 120                 125

Thr Leu Val Thr Val Ser Ser Gly Asp Gly Ser Ser Gly Gly Ser Gly
    130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
            180                 185                 190

Arg Leu Leu Ile Tyr Tyr Ala Ser Ser Arg Ala Thr Gly Ile Pro Asp
            195                 200                 205

Arg Phe Ser Gly Ser Gly Ser Gly Thr Asp Phe Thr Leu Thr Ile Ser
    210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Asp
                245                 250                 255

Leu Glu Pro Lys Ser Cys Asp Lys Thr His Thr Cys Pro Pro Cys Pro
            260                 265                 270

Asp Pro Lys Phe Trp Val Leu Val Val Gly Gly Val Leu Ala Cys
            275                 280                 285

Tyr Ser Leu Leu Val Thr Val Ala Phe Ile Ile Phe Trp Val Ala Ala
    290                 295                 300

Gly Gly Pro Gly Ala Gly Ser Ala Ala Pro Val Ser Ser Thr Ser Ser
305                 310                 315                 320

Leu Pro Leu Ala Ala Leu Asn Met Arg Val Arg Arg Arg Leu Ser Leu
            325                 330                 335

Phe Leu Asn Val Arg Thr Gln Val Ala Ala Asp Trp Thr Ala Leu Ala
            340                 345                 350

Glu Glu Met Asp Phe Glu Tyr Leu Glu Ile Arg Gln Leu Glu Thr Gln
            355                 360                 365

Ala Asp Pro Thr Gly Arg Leu Leu Asp Ala Trp Gln Gly Arg Pro Gly
    370                 375                 380

Ala Ser Val Gly Arg Leu Leu Glu Leu Leu Thr Lys Leu Gly Arg Asp
385                 390                 395                 400

Asp Val Leu Leu Glu Leu Gly Pro Ser Ile Glu Glu Asp Cys Gln Lys
                405                 410                 415

Tyr Ile Leu Lys Gln Gln Gln Glu Glu Ala Glu Lys Pro Leu Gln Val
            420                 425                 430

Ala Ala Val Asp Ser Ser Val Pro Arg Thr Ala Glu Leu Ala Gly Ile
            435                 440                 445

Thr Thr Leu Asp Asp Pro Leu Gly His Met Pro Glu Arg Phe Asp Ala
    450                 455                 460

Phe Ile Cys Tyr Cys Pro Ser Asp Ile Val Glu Lys Lys Val Ala Lys
465                 470                 475                 480

Lys Pro Thr Asn Lys Ala Pro His Pro Lys Gln Glu Pro Gln Glu Ile
```

|     |     |     | 485 |     |     |     | 490 |     |     |     | 495 |     |     |     |
| --- | --- | --- | --- | --- | --- | --- | --- | --- | --- | --- | --- | --- | --- | --- |

Asn Phe Pro Asp Asp Leu Pro Gly Ser Asn Thr Ala Ala Pro Val Gln
         500             505            510

Glu Thr Leu His Gly Cys Gln Pro Val Thr Gln Glu Asp Gly Lys Glu
      515            520            525

Ser Arg Ile Ser Val Gln Glu Arg Gln Arg Val Lys Phe Ser Arg Ser
      530            535            540

Ala Asp Ala Pro Ala Tyr Gln Gln Gly Gln Asn Gln Leu Tyr Asn Glu
545              550            555            560

Leu Asn Leu Gly Arg Arg Glu Glu Tyr Asp Val Leu Asp Lys Arg Arg
         565             570            575

Gly Arg Asp Pro Glu Met Gly Gly Lys Pro Arg Arg Lys Asn Pro Gln
         580             585            590

Glu Gly Leu Tyr Asn Glu Leu Gln Lys Asp Lys Met Ala Glu Ala Tyr
       595             600            605

Ser Glu Ile Gly Met Lys Gly Glu Arg Arg Arg Gly Lys Gly His Asp
      610            615            620

Gly Leu Tyr Gln Gly Leu Ser Thr Ala Thr Lys Asp Thr Tyr Asp Ala
625              630            635            640

Leu His Met Gln Ala Leu Pro Pro Arg
         645

<210> SEQ ID NO 16
<211> LENGTH: 1947
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 16

```
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac tttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa accttttcca     360
tactttgatt actggggcca ggggacgctt gtcactgtct cctctggcga cggctcctcc     420
ggcggaagtg gaggcgcgtc agaaattgta ctgactcagt ccccgggcac gctctcactc     480
agtccaggcg aaagagctac gttgtcttgt cgcgcaagcc agtccgtaag ctctagcttc     540
ctcgcatggt atcaacaaaa gcccgggcag gctccgcggc tgctcattta ctatgctagt     600
tcaagggcta cgggaattcc agaccgattt agtggatctg ggagtggaac tgacttcaca     660
cttacgatca gcaggcttga gccggaagat tttgccgtgt actactgcca gcaaactgga     720
agaatccccc caacattcgg acaaggcacg aaggtggaaa tcaaggatct cgagcccaaa     780
tcttgtgaca aaactcacac atgcccaccg tgcccggatc ccaagttctg ggtgctggtg     840
gtcgtgggcg gagtgctggc ctgttacagc ctgctcgtga ccgtggcctt catcatcttt     900
tgggtggctg ctggcggacc tggcgccgga tctgctgctc ctgtgtctag cacaagcagc     960
ctgcctctgg ccgccctgaa catgagagtg cggagaaggc tgagcctgtt cctgaacgtg    1020
cggacacagg tggccgccga ttggacagcc ctggccgagg aaatggactt cgagtacctg    1080
```

-continued

```
gaaatccggc agctggaaac ccaggccgac cctacaggca gactgctgga tgcttggcag    1140
ggcagaccag gcgcttctgt gggaaggctg ctggaactgc tgaccaagct gggcagggac    1200
gacgtgctgc tggaactggg ccctagcatc gaagaggact gccagaagta catcctgaag    1260
cagcagcagg aagaggccga gaagcctctg caggtggcag ccgtggatag cagcgtgcca    1320
agaacagccg agctggccgg catcaccacc ctggatgatc tctgggcca catgcccgag    1380 agattcgacg ccttcatctg ctactgcccc agcgacatcg tggaaaagaa ggtggccaag    1440
aagcccacca acaaggcccc ccacccaag caggaacccc aggaaatcaa cttccccgac    1500
gacctgcccg gcagcaatac tgctgcaccc gtgcaggaaa ccctgcacgg ctgtcagcct    1560
gtgacccagg aagatggcaa agaaagccgg atctctgtgc aggaacgcca gagagtgaag    1620
ttcagcagga gcgcagacgc ccccgcgtac cagcagggcc agaaccagct ctataacgag    1680
ctcaatctag gacgaagaga ggagtacgat gtttttggaca agagacgtgg ccgggaccct    1740
gagatgggcg gcaagcccag aagaaagaac ccccaggaag gcctgtataa cgaactgcag    1800
aaagacaaga tggccgaggc ctacagcgag atcggcatga agggcgagcg gagaagaggc    1860
aagggccacg atggcctgta ccagggactg agcaccgcca ccaaggacac ctacgacgcc    1920
ctgcacatgc aggccctgcc tccaaga    1947
```

```
<210> SEQ ID NO 17
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ser Met Ser Trp Val Arg Gln Ala Pro Gly Lys Gly Leu
    50                  55                  60

Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Pro Phe Pro Tyr Phe Asp Tyr Trp Gly Gln Gly
        115                 120                 125

Thr Leu Val Thr Val Ser Ser Gly Asp Gly Ser Ser Gly Gly Ser Gly
    130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
            180                 185                 190

Arg Leu Leu Ile Tyr Tyr Ala Ser Ser Arg Ala Thr Gly Ile Pro Asp
        195                 200                 205
```

```
Arg Phe Ser Gly Ser Gly Ser Gly Thr Asp Phe Thr Leu Thr Ile Ser
    210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Ile
                245                 250                 255

Glu Val Met Tyr Pro Pro Pro Tyr Leu Asp Asn Glu Lys Ser Asn Gly
                260                 265                 270

Thr Ile Ile His Val Lys Gly Lys His Leu Cys Pro Ser Pro Leu Phe
                275                 280                 285

Pro Gly Pro Ser Lys Pro Phe Trp Val Leu Val Val Val Gly Gly Val
    290                 295                 300

Leu Ala Cys Tyr Ser Leu Leu Val Thr Val Ala Phe Ile Ile Phe Trp
305                 310                 315                 320

Val Arg Ser Lys Arg Ser Arg Leu Leu His Ser Asp Tyr Met Asn Met
                325                 330                 335

Thr Pro Arg Arg Pro Gly Pro Thr Arg Lys His Tyr Gln Pro Tyr Ala
                340                 345                 350

Pro Pro Arg Asp Phe Ala Ala Tyr Arg Ser Arg Val Lys Phe Ser Arg
                355                 360                 365

Ser Ala Asp Ala Pro Ala Tyr Gln Gln Gly Gln Asn Gln Leu Tyr Asn
    370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
                420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470
```

<210> SEQ ID NO 18
<211> LENGTH: 1421
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac tttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa accttttcca     360
tactttgatt actggggcca ggggacgctt gtcactgtct cctctggcga cggtcctcc      420 ggcggaagtg gaggcgcgtc agaaattgta ctgactcagt ccccgggcac gctctcactc     480
```

```
agtccaggcg aaagagctac gttgtcttgt cgcgcaagcc agtccgtaag ctctagcttc      540
ctcgcatggt atcaacaaaa gcccgggcag gctccgcggc tgctcattta ctatgctagt      600
tcaagggcta cgggaattcc agaccgattt agtggatctg ggagtggaac tgacttcaca      660
cttacgatca gcaggcttga gccggaagat tttgccgtgt actactgcca gcaaactgga      720
agaatccccc caacattcgg acaaggcacg aaggtggaaa tcaagatcga agtgatgtac      780
ccgcctcctt acctggacaa cgagaagtcc aacggcacca tcatccacgt gaagggaaag      840
cacctgtgtc cttctccact gttccccgga cctagcaagc cttctgggtg ctggtggtcg      900
tgggcggagt gctggcctgt tacagcctgc tcgtgaccgt ggccttcatc atcttttggg      960
tgcgcagcaa gcggagccgg ctgctgcaca gcgactacat gaacatgacc cccagacggc     1020
ctggccccac cagaaagcac taccagcctt acgcccctcc cagagacttc gccgcctacc     1080
ggtccagagt gaagttcagc agaagcgccg acgcccctgc ctatcagcag ggccagaacc     1140
agctgtacaa cgagctgaac ctgggcagac gggaagagta cgacgtgctg gacaagcgga     1200
gaggcaggga ccctgagatg ggcggcaagc cccagaagaaa gaaccccag gaaggcctgt     1260 ataacgaact gcagaaagac aagatggccg aggcctacag cgagatcggc atgaagggcg     1320
agcggagaag aggcaagggc cacgatggcc tgtaccaggg actgagcacc gccaccaagg     1380
acacctacga cgccctgcac atgcaggccc tgcctccaag a                          1421
```

<210> SEQ ID NO 19
<211> LENGTH: 475
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 19

```
Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Phe Ser Met Ser Trp Val Arg Gln Ala Pro Gly Lys Gly Leu
        50                  55                  60

Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
                100                 105                 110

Tyr Tyr Cys Ala Lys Pro Phe Pro Tyr Phe Asp Tyr Trp Gly Gln Gly
            115                 120                 125

Thr Leu Val Thr Val Ser Ser Gly Asp Gly Ser Ser Gly Gly Ser Gly
            130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
                180                 185                 190
```

-continued

```
Arg Leu Leu Ile Tyr Tyr Ala Ser Ser Arg Ala Thr Gly Ile Pro Asp
        195                 200                 205

Arg Phe Ser Gly Ser Gly Ser Gly Thr Asp Phe Thr Leu Thr Ile Ser
        210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Ile
                245                 250                 255

Glu Val Met Tyr Pro Pro Pro Tyr Leu Asp Asn Glu Lys Ser Asn Gly
                260                 265                 270

Thr Ile Ile His Val Lys Gly Lys His Leu Cys Pro Ser Pro Leu Phe
                275                 280                 285

Pro Gly Pro Ser Lys Pro Phe Trp Val Leu Val Val Val Gly Gly Val
        290                 295                 300

Leu Ala Cys Tyr Ser Leu Leu Val Thr Val Ala Phe Ile Ile Phe Trp
305                 310                 315                 320

Val Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
                340                 345                 350

Phe Pro Glu Glu Glu Glu Gly Gly Cys Glu Leu Arg Val Lys Phe Ser
        355                 360                 365

Arg Ser Ala Asp Ala Pro Ala Tyr Gln Gln Gly Gln Asn Gln Leu Tyr
        370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
                420                 425                 430

Ala Tyr Ser Glu Ile Gly Met Lys Gly Glu Arg Arg Arg Gly Lys Gly
                435                 440                 445

His Asp Gly Leu Tyr Gln Gly Leu Ser Thr Ala Thr Lys Asp Thr Tyr
        450                 455                 460

Asp Ala Leu His Met Gln Ala Leu Pro Pro Arg
465                 470                 475
```

```
<210> SEQ ID NO 20
<211> LENGTH: 1424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac tttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa acctttccca     360
tactttgatt actggggcca ggggacgctt gtcactgtct cctctggcga cggctcctcc     420
```

-continued

```
ggcggaagtg gaggcgcgtc agaaattgta ctgactcagt ccccgggcac gctctcactc      480
agtccaggcg aaagagctac gttgtcttgt cgcgcaagcc agtccgtaag ctctagcttc      540
ctcgcatggt atcaacaaaa gcccgggcag gctccgcggc tgctcattta ctatgctagt      600
tcaagggcta cgggaattcc agaccgattt agtggatctg ggagtggaac tgacttcaca      660
cttacgatca gcaggcttga gccggaagat tttgccgtgt actactgcca gcaaactgga      720
agaatccccc caacattcgg acaaggcacg aaggtggaaa tcaagatcga agtgatgtac      780
ccgcctcctt acctggacaa cgagaagtcc aacggcacca tcatccacgt gaagggaaag      840
cacctgtgtc cttctccact gttccccgga cctagcaagc cttctgggtg ctggtggtcg      900
tgggcggagt gctggcctgt tacagcctgc tcgtgaccgt ggccttcatc atcttttggg      960
tgaaacgcgg ccgcaaaaaa ctgctgtata tttttaaaca gccgtttatg cgcccggtgc     1020
agaccaccca ggaagaagat ggctgcagct gccgctttcc ggaagaagaa gaaggcggct     1080
gcgaactgcg cgtgaaattt agccgcagcg cggatgcgcc ggcgtatcag cagggccaga     1140
accagctgta taacgaactg aacctgggcc gccgcgaaga atatgatgtg ctggataaac     1200
gccgcggccg cgatccggaa atgggcggca aaccgcgccg caaaaacccg caggaaggcc     1260
tgtataacga actgcagaaa gataaaatgg cggaagcgta tagcgaaatt ggcatgaaag     1320
gcgaacgccg ccgcggcaaa ggccatgatg gcctgtatca gggcctgagc accgcgacca     1380
aagataccta tgatgcgctg catatgcagg cgctgccgcc gcgc                     1424
```

```
<210> SEQ ID NO 21
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ser Met Ser Trp Val Arg Gln Ala Pro Gly Lys Gly Leu
    50                  55                  60

Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Pro Phe Pro Tyr Phe Asp Tyr Trp Gly Gln Gly
        115                 120                 125

Thr Leu Val Thr Val Ser Ser Gly Asp Gly Ser Ser Gly Gly Ser Gly
    130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
```

-continued

```
              180              185              190
Arg Leu Leu Ile Tyr Tyr Ala Ser Ser Arg Ala Thr Gly Ile Pro Asp
         195              200              205

Arg Phe Ser Gly Ser Gly Ser Gly Thr Asp Phe Thr Leu Thr Ile Ser
     210              215              220

Arg Leu Glu Pro Glu Asp Phe Ala Val Tyr Tyr Cys Gln Gln Thr Gly
225              230              235              240

Arg Ile Pro Pro Thr Phe Gly Gln Gly Thr Lys Val Glu Ile Lys Ile
              245              250              255

Glu Val Met Tyr Pro Pro Pro Tyr Leu Asp Asn Glu Lys Ser Asn Gly
              260              265              270

Thr Ile Ile His Val Lys Gly Lys His Leu Cys Pro Ser Pro Leu Phe
         275              280              285

Pro Gly Pro Ser Lys Pro Phe Trp Val Leu Val Val Val Gly Gly Val
     290              295              300

Leu Ala Cys Tyr Ser Leu Leu Val Thr Val Ala Phe Ile Ile Phe Trp
305              310              315              320

Val Arg Asp Gln Arg Leu Pro Pro Asp Ala His Lys Pro Pro Gly Gly
              325              330              335

Gly Ser Phe Arg Thr Pro Ile Gln Glu Glu Gln Ala Asp Ala His Ser
              340              345              350

Thr Leu Ala Lys Ile Arg Val Lys Phe Ser Arg Ser Ala Asp Ala Pro
         355              360              365

Ala Tyr Gln Gln Gly Gln Asn Gln Leu Tyr Asn Glu Leu Asn Leu Gly
     370              375              380

Arg Arg Glu Glu Tyr Asp Val Leu Asp Lys Arg Arg Gly Arg Asp Pro
385              390              395              400

Glu Met Gly Gly Lys Pro Arg Arg Lys Asn Pro Gln Glu Gly Leu Tyr
              405              410              415

Asn Glu Leu Gln Lys Asp Lys Met Ala Glu Ala Tyr Ser Glu Ile Gly
              420              425              430

Met Lys Gly Glu Arg Arg Arg Gly Lys Gly His Asp Gly Leu Tyr Gln
         435              440              445

Gly Leu Ser Thr Ala Thr Lys Asp Thr Tyr Asp Ala Leu His Met Gln
     450              455              460

Ala Leu Pro Pro Arg
465
```

```
<210> SEQ ID NO 22
<211> LENGTH: 1406
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac ttttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa accttttcca     360
```

-continued

```
tactttgatt actggggcca ggggacgctt gtcactgtct cctctggcga cggctcctcc        420
ggcggaagtg gaggcgcgtc agaaattgta ctgactcagt ccccgggcac gctctcactc        480
agtccaggcg aaagagctac gttgtcttgt cgcgcaagcc agtccgtaag ctctagcttc        540
ctcgcatggt atcaacaaaa gcccgggcag gctccgcggc tgctcattta ctatgctagt        600
tcaagggcta cgggaattcc agaccgattt agtggatctg ggagtggaac tgacttcaca        660
cttacgatca gcaggcttga gccggaagat tttgccgtgt actactgcca gcaaactgga        720
agaatccccc caacattcgg acaaggcacg aaggtggaaa tcaagatcga agtgatgtac        780
ccgcctcctt acctggacaa cgagaagtcc aacggcacca tcatccacgt gaagggaaag        840
cacctgtgtc cttctccact gttccccgga cctagcaagc cttctgggtg ctggtggtcg        900
tgggcggagt gctggcctgt tacagcctgc tcgtgaccgt ggccttcatc atcttttggg        960
tgcgcgatca gcgcctgccg ccggatgcgc ataaaccgcc gggcggcggc agctttcgca       1020
ccccgattca ggaagaacag gcggatgcgc atagcaccct ggcgaaaatt cgcgtgaaat       1080
ttagccgcag cgcggatgcg ccggcgtatc agcagggcca gaaccagctg tataacgaac       1140
tgaacctggg ccgccgcgaa gaatatgatg tgctggataa acgccgcggc cgcgatccgg       1200
aaatgggcgg caaaccgcgc cgcaaaaacc cgcaggaagg cctgtataac gaactgcaga       1260
aagataaaat ggcggaagcg tatagcgaaa ttggcatgaa aggcgaacgc cgccgcggca       1320
aaggccatga tggcctgtat cagggcctga gcaccgcgac caaagatacc tatgatgcgc       1380
tgcatatgca ggcgctgccg ccgcgc                                          1406
```

<210> SEQ ID NO 23
<211> LENGTH: 668
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Phe Ser Met Ser Trp Val Arg Gln Ala Pro Gly Lys Gly Leu
        50                  55                  60

Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
                100                 105                 110

Tyr Tyr Cys Ala Lys Pro Phe Pro Tyr Phe Asp Tyr Trp Gly Gln Gly
            115                 120                 125

Thr Leu Val Thr Val Ser Ser Gly Asp Gly Ser Ser Gly Gly Ser Gly
        130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175
```

```
Ser Ser Ser Phe Leu Ala Trp Tyr Gln Gln Lys Pro Gly Gln Ala Pro
        180                 185                 190

Arg Leu Leu Ile Tyr Tyr Ala Ser Ser Arg Ala Thr Gly Ile Pro Asp
        195                 200                 205

Arg Phe Ser Gly Ser Gly Ser Gly Thr Asp Phe Thr Leu Thr Ile Ser
    210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Ile
                245                 250                 255

Glu Val Met Tyr Pro Pro Pro Tyr Leu Asp Asn Glu Lys Ser Asn Gly
            260                 265                 270

Thr Ile Ile His Val Lys Gly Lys His Leu Cys Pro Ser Pro Leu Phe
            275                 280                 285

Pro Gly Pro Ser Lys Pro Phe Trp Val Leu Val Val Val Gly Gly Val
    290                 295                 300

Leu Ala Cys Tyr Ser Leu Leu Val Thr Val Ala Phe Ile Ile Phe Trp
305                 310                 315                 320

Val Ala Ala Gly Gly Pro Gly Ala Gly Ser Ala Ala Pro Val Ser Ser
                325                 330                 335

Thr Ser Ser Leu Pro Leu Ala Ala Leu Asn Met Arg Val Arg Arg Arg
            340                 345                 350

Leu Ser Leu Phe Leu Asn Val Arg Thr Gln Val Ala Ala Asp Trp Thr
            355                 360                 365

Ala Leu Ala Glu Glu Met Asp Phe Glu Tyr Leu Glu Ile Arg Gln Leu
    370                 375                 380

Glu Thr Gln Ala Asp Pro Thr Gly Arg Leu Leu Asp Ala Trp Gln Gly
385                 390                 395                 400

Arg Pro Gly Ala Ser Val Gly Arg Leu Leu Glu Leu Leu Thr Lys Leu
                405                 410                 415

Gly Arg Asp Asp Val Leu Leu Glu Leu Gly Pro Ser Ile Glu Glu Asp
            420                 425                 430

Cys Gln Lys Tyr Ile Leu Lys Gln Gln Gln Glu Glu Ala Glu Lys Pro
            435                 440                 445

Leu Gln Val Ala Ala Val Asp Ser Ser Val Pro Arg Thr Ala Glu Leu
    450                 455                 460

Ala Gly Ile Thr Thr Leu Asp Asp Pro Leu Gly His Met Pro Glu Arg
465                 470                 475                 480

Phe Asp Ala Phe Ile Cys Tyr Cys Pro Ser Asp Ile Val Glu Lys Lys
                485                 490                 495

Val Ala Lys Lys Pro Thr Asn Lys Ala Pro His Pro Lys Gln Glu Pro
            500                 505                 510

Gln Glu Ile Asn Phe Pro Asp Asp Leu Pro Gly Ser Asn Thr Ala Ala
            515                 520                 525

Pro Val Gln Glu Thr Leu His Gly Cys Gln Pro Val Thr Gln Glu Asp
    530                 535                 540

Gly Lys Glu Ser Arg Ile Ser Val Gln Glu Arg Gln Arg Val Lys Phe
545                 550                 555                 560

Ser Arg Ser Ala Asp Ala Pro Ala Tyr Gln Gln Gly Gln Asn Gln Leu
                565                 570                 575

Tyr Asn Glu Leu Asn Leu Gly Arg Arg Glu Glu Tyr Asp Val Leu Asp
            580                 585                 590
```

```
Lys Arg Arg Gly Arg Asp Pro Glu Met Gly Gly Lys Pro Arg Arg Lys
        595                 600                 605

Asn Pro Gln Glu Gly Leu Tyr Asn Glu Leu Gln Lys Asp Lys Met Ala
        610                 615                 620

Glu Ala Tyr Ser Glu Ile Gly Met Lys Gly Glu Arg Arg Arg Gly Lys
625                 630                 635                 640

Gly His Asp Gly Leu Tyr Gln Gly Leu Ser Thr Ala Thr Lys Asp Thr
                645                 650                 655

Tyr Asp Ala Leu His Met Gln Ala Leu Pro Pro Arg
            660                 665
```

<210> SEQ ID NO 24
<211> LENGTH: 2003
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac ttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa accttttcca     360
tactttgatt actggggcca ggggacgctt gtcactgtct cctctggcga cggctcctcc     420
ggcggaagtg gaggcgcgtc agaaattgta ctgactcagt ccccgggcac gctctcactc     480
agtccaggcg aaagagctac gttgtcttgt cgcgcaagcc agtccgtaag ctctagcttc     540
ctcgcatggt atcaacaaaa gcccgggcag gctccgcggc tgctcattta ctatgctagt     600
tcaagggcta cgggaattcc agaccgattt agtggatctg ggagtggaac tgacttcaca     660
cttacgatca gcaggcttga gccggaagat tttgccgtgt actactgcca gcaaactgga     720
agaatccccc caacattcgg acaaggcacg aaggtggaaa tcaagatcga agtgatgtac     780
ccgcctcctt acctggacaa cgagaagtcc aacggcacca tcatccacgt gaagggaaag     840
cacctgtgtc cttctccact gttccccgga cctagcaagc cttctgggtg ctggtggtcg     900
tgggcggagt gctggcctgt tacagcctgc tcgtgaccgt ggccttcatc atcttttggg     960
tggctgctgg cggacctggc gccggatctg ctgctcctgt gtctagcaca agcagcctgc    1020
ctctggccgc cctgaacatg agagtgcgga gaaggctgag cctgttcctg aacgtgcgga    1080
cacaggtggc cgccgattgg acagccctgg ccgaggaaat ggacttcgag tacctggaaa    1140
tccggcagct ggaaacccag gccgacccta caggcagact gctggatgct tggcagggca    1200
gaccaggcgc ttctgtggga aggctgctgg aactgctgac caagctgggc agggacgacg    1260
tgctgctgga actgggccct agcatcgaag aggactgcca gaagtacatc ctgaagcagc    1320
agcaggaaga ggccgagaag cctctgcagg tggcagccgt ggatagcagc gtgccaagaa    1380
cagccgagct ggccggcatc accaccctgg atgatcctct gggccacatg cccgagagat    1440
tcgacgcctt catctgctac tgccccagcg acatcgtgga aaagaaggtg gccaagaagc    1500
ccaccaacaa ggcccccac cccaagcagg aaccccagga aatcaacttc cccgacgacc    1560
tgcccggcag caatactgct gcacccgtgc aggaaaccct gcacggctgt cagcctgtga    1620
```

-continued

```
cccaggaaga tggcaaagaa agccggatct ctgtgcagga acgccagaga gtgaagttca      1680
gcaggagcgc agacgccccc gcgtaccagc agggccagaa ccagctctat aacgagctca      1740
atctaggacg aagagaggag tacgatgttt tggacaagag acgtggccgg gaccctgaga      1800
tgggcggcaa gcccagaaga aagaacccc aggaaggcct gtataacgaa ctgcagaaag        1860
acaagatggc cgaggcctac agcgagatcg gcatgaaggg cgagcggaga agaggcaagg      1920
gccacgatgg cctgtaccag ggactgagca ccgccaccaa ggacacctac gacgccctgc      1980
acatgcaggc cctgcctcca aga                                               2003
```

```
<210> SEQ ID NO 25
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys
225                 230                 235

<210> SEQ ID NO 26
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide
```

-continued

<400> SEQUENCE: 26

```
gaggttcagc ttcttgagtc tggggggcggc ctggtgcaac ctggtggcag tcttaggctg      60
agttgcgccg cgtcagggtt tactttttct tccttcagca tgtcatgggt ccgccaggct     120
ccaggtaagg gcctggaatg ggttagtagc atcagtggca gtagtggtac aacatactac     180
gctgatagtg ttaaagggag attcactata agtagggata attctaaaaa tacccttat     240 ctgcaaatga attctttgag ggccgaagat actgcggtct attactgtgc caaacctttt     300
ccatactttg attactgggg ccaggggacg cttgtcactg tctcctctgg cgacggctcc     360
tccggcggaa gtggaggcgc gtcagaaatt gtactgactc agtccccggg cacgctctca     420
ctcagtccag gcgaaagagc tacgttgtct tgtcgcgcaa gccagtccgt aagctctagc     480
ttcctcgcat ggtatcaaca aaagcccggg caggctccgc ggctgctcat ttactatgct     540
agttcaaggg ctacgggaat tccagaccga tttagtggat ctgggagtgg aactgacttc     600
acacttacga tcagcaggct tgagccggaa gattttgccg tgtactactg ccagcaaact     660
ggaagaatcc ccccaacatt cggacaaggc acgaaggtgg aaatcaag               708
```

```
<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Pro Lys Ser Cys Asp Lys Thr His Thr Cys Pro Pro Cys Pro
1               5                   10                  15
```

```
<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gagcccaaat cttgtgacaa aactcacaca tgcccaccgt gcccg                    45
```

```
<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Arg Lys Cys Cys Val Glu Cys Pro Pro Cys Pro
1               5                   10
```

```
<210> SEQ ID NO 30
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30
```

-continued

```
Glu Leu Lys Thr Pro Leu Gly Asp Thr Thr His Thr Cys Pro Arg Cys
1               5                  10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro
    50                  55                  60
```

```
<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Ser Lys Tyr Gly Pro Pro Cys Pro Ser Cys Pro
1               5                  10
```

```
<210> SEQ ID NO 32
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Pro Ala Lys Pro Thr Thr Thr Pro Ala Pro Arg Pro Pro Thr Pro Ala
1               5                  10                  15

Pro Thr Ile Ala Ser Gln Pro Leu Ser Leu Arg Pro Glu Ala Cys Arg
            20                  25                  30

Pro Ala Ala Gly Gly Ala Val His Thr Arg Gly Leu Asp Phe Ala
        35                  40                  45
```

```
<210> SEQ ID NO 33
<211> LENGTH: 231
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
ccagccaagc ccaccacaac ccctgctcct agacctccta ccccagcccc taccattgcc      60
tcccagccac tgtctctgag gcccgaggct tgtagacctg ctgcaggcgg agccgtgcac     120
accagaggac tggatttcgc ctgcgacatc tatatctggg cccctctggc cggcacctgt     180
ggcgtgctgc tgctgtcact cgtgatcacc ctgtactgca accaccggaa c              231
```

```
<210> SEQ ID NO 34
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ile Glu Val Met Tyr Pro Pro Pro Tyr Leu Asp Asn Glu Lys Ser Asn
1               5                  10                  15
```

Gly Thr Ile Ile His Val Lys Gly Lys His Leu Cys Pro Ser Pro Leu
                20                      25                      30

Phe Pro Gly Pro Ser Lys Pro
        35

<210> SEQ ID NO 35
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atcgaagtga tgtacccgcc tccttacctg gacaacgaga agtccaacgg caccatcatc        60
cacgtgaagg gaaagcacct gtgtccttct ccactgttcc ccggacctag caagcc          116

<210> SEQ ID NO 36
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Trp Val Leu Val Val Val Gly Gly Val Leu Ala Cys Tyr Ser Leu
1               5                       10                      15

Leu Val Thr Val Ala Phe Ile Ile Phe Trp Val
                20                      25

<210> SEQ ID NO 37
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttctgggtgc tggtggtcgt gggcggagtg ctggcctgtt acagcctgct cgtgaccgtg        60
gccttcatca tcttttgggt g                                                  81

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Cys Asp Ile Tyr Ile Trp Ala Pro Leu Ala Gly Thr Cys Gly Val Leu
1               5                       10                      15

Leu Leu Ser Leu Val Ile Thr Leu Tyr Cys Asn His Arg Asn
                20                      25                      30

<210> SEQ ID NO 39
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgcgacatct acatctgggc ccctctggcc ggcacatgtg gcgtgctgct gctgagcctc     60
gtgatcaccc tgtactgcaa ccaccggaac                                      90

<210> SEQ ID NO 40
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 41
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
cgcagcaagc ggagccggct gctgcacagc gactacatga acatgacccc cagacggcct     60
ggccccacca gaaagcacta ccagccttac gcccctccca gagacttcgc cgcctaccgg    120
tccag                                                                125

<210> SEQ ID NO 42
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
cgaagcaagc ggagccggct gctgcacagc gactacatga acatgacccc tagacggccc     60
ggaccaacca gaaagcacta ccagccttac gctcctccta gagatttcgc cgcctaccgg    120
tcc                                                                  123

<210> SEQ ID NO 43
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
cggtccaaga gaagcagact gctgcacagc gactacatga acatgacccc tagacggccc     60
ggacctacca gaaagcacta ccagccttac gctcctccta gagatttcgc cgcctaccgg    120
tcc                                                                  123

<210> SEQ ID NO 44

<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
aggagtaaga ggagcaggct cctgcacagt gactacatga acatgactcc ccgccgcccc      60
gggcccaccc gcaagcatta ccagccctat gccccaccac gcgacttcgc agcctatcgc      120
tcc                                                                    123

<210> SEQ ID NO 45
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 46
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
aaacggggca gaaagaaact cctgtatata ttcaaacaac catttatgag accagtacaa      60
actactcaag aggaagatgg ctgtagctgc cgatttccag aagaagaaga aggaggatgt      120
gaactg                                                                 126

<210> SEQ ID NO 47
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile
        35

<210> SEQ ID NO 48
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48
agggaccaga ggctgccccc cgatgcccac aagccccctg ggggaggcag tttccggacc        60
cccatccaag aggagcaggc cgacgcccac tccaccctgg ccaagatc        108

<210> SEQ ID NO 49
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Ala Gly Gly Pro Gly Ala Gly Ser Ala Ala Pro Val Ser Ser Thr
1               5                   10                  15

Ser Ser Leu Pro Leu Ala Ala Leu Asn Met Arg Val Arg Arg Arg Leu
            20                  25                  30

Ser Leu Phe Leu Asn Val Arg Thr Gln Val Ala Ala Asp Trp Thr Ala
        35                  40                  45

Leu Ala Glu Glu Met Asp Phe Glu Tyr Leu Glu Ile Arg Gln Leu Glu
    50                  55                  60

Thr Gln Ala Asp Pro Thr Gly Arg Leu Leu Asp Ala Trp Gln Gly Arg
65                  70                  75                  80

Pro Gly Ala Ser Val Gly Arg Leu Leu Glu Leu Leu Thr Lys Leu Gly
                85                  90                  95

Arg Asp Asp Val Leu Leu Glu Leu Gly Pro Ser Ile Glu Glu Asp Cys
            100                 105                 110

Gln Lys Tyr Ile Leu Lys Gln Gln Gln Glu Glu Ala Glu Lys Pro Leu
        115                 120                 125

Gln Val Ala Ala Val Asp Ser Ser Val Pro Arg Thr Ala Glu Leu Ala
    130                 135                 140

Gly Ile Thr Thr Leu Asp Asp Pro Leu Gly His Met Pro Glu Arg Phe
145                 150                 155                 160

Asp Ala Phe Ile Cys Tyr Cys Pro Ser Asp Ile
                165                 170

<210> SEQ ID NO 50
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gctgctggcg gacctggcgc cggatctgct gctcctgtgt ctagcacaag cagcctgcct        60
ctggccgccc tgaacatgag agtgcggaga aggctgagcc tgttcctgaa cgtgcggaca       120
caggtggccg ccgattggac agccctggcc gaggaaatgg acttcgagta cctggaaatc       180
cggcagctgg aaacccaggc cgaccctaca ggcagactgc tggatgcttg cagggcagga       240
ccaggcgctt ctgtgggaag gctgctggaa ctgctgacca agctgggcag ggacgacgtg       300
ctgctggaac tgggccctag catcgaagag gactgccaga gtacatcct gaagcagcag        360 caggaagagg ccgagaagcc tctgcaggtg gcagccgtgg atagcagcgt gccaagaaca       420
gccgagctgg ccggcatcac caccctggat gatcctctgg gccacatgcc cgagagattc       480

-continued gacgccttca tctgctactg ccccagcgac atc                                          513

<210> SEQ ID NO 51
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 52
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
atggccgctg ggggcccagg cgccggatca gctgctcccg tatcttctac ttcttctttg        60
ccgctggctg ctctgaacat gcgcgtgaga agacgcctct ccctgttcct taacgttcgc       120
acacaagtcg ctgccgattg gaccgccctt gccgaagaaa tggactttga atacctggaa       180
attagacaac ttgaaacaca ggccgacccc actggcagac tcctggacgc atggcaggga       240
agacctggtg caagcgttgg acggctcctg gatctcctga caaaactggg acgcgacgac       300
gtactgcttg aactcggacc tagcattgaa gaagactgcc aaaaatatat cctgaaacaa       360
caacaagaag aagccgaaaa acctctccaa gtcgcagcag tggactcatc agtaccccga       420
acagctgagc ttgctgggat tactacactc gacgacccac tcggacatat gcctgaaaga       480
ttcgacgctt tcatttgcta ttgcccctct gacata                                516

<210> SEQ ID NO 53
<211> LENGTH: 171
<212> TYPE: PRT

<213> ORGANISM: Artificial Sequence
<220> FEATURE:
<223> OTHER INFORMATION: Description of Artificial Sequence: Synthetic
     polypeptide

<400> SEQUENCE: 53

```
Ala Ala Gly Gly Pro Gly Ala Gly Ser Ala Ala Pro Val Ser Ser Thr
1               5                   10                  15

Ser Ser Leu Pro Leu Ala Ala Leu Asn Met Arg Val Arg Arg Arg Leu
            20                  25                  30

Ser Leu Phe Leu Asn Val Arg Thr Gln Val Ala Ala Asp Trp Thr Ala
        35                  40                  45

Leu Ala Glu Glu Met Asp Phe Glu Tyr Leu Glu Ile Arg Gln Leu Glu
    50                  55                  60

Thr Gln Ala Asp Pro Thr Gly Arg Leu Leu Asp Ala Trp Gln Gly Arg
65                  70                  75                  80

Pro Gly Ala Ser Val Gly Arg Leu Leu Asp Leu Leu Thr Lys Leu Gly
                85                  90                  95

Arg Asp Asp Val Leu Leu Glu Leu Gly Pro Ser Ile Glu Glu Asp Cys
            100                 105                 110

Gln Lys Tyr Ile Leu Lys Gln Gln Gln Glu Glu Ala Glu Lys Pro Leu
        115                 120                 125

Gln Val Ala Ala Val Asp Ser Ser Val Pro Arg Thr Ala Glu Leu Ala
    130                 135                 140

Gly Ile Thr Thr Leu Asp Asp Pro Leu Gly His Met Pro Glu Arg Phe
145                 150                 155                 160

Asp Ala Phe Ile Cys Tyr Cys Pro Ser Asp Ile
                165                 170
```

<210> SEQ ID NO 54
<211> LENGTH: 513
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 54

```
gccgctgggg gcccaggcgc cggatcagct gctcccgtat cttctacttc ttctttgccg      60
ctggctgctc tgaacatgcg cgtgagaaga cgcctctccc tgttccttaa cgttcgcaca     120
caagtcgctg ccgattggac cgcccttgcc gaagaaatgg actttgaata cctggaaatt     180
agacaacttg aaacacaggc cgaccccact ggcagactcc tggacgcatg cagggaaga     240 cctggtgcaa gcgttggacg gctcctggat ctcctgacaa aactgggacg cgacgacgta     300
ctgcttgaac tcggacctag cattgaagaa gactgccaaa aatatatcct gaaacaacaa     360
caagaagaag ccgaaaaacc tctccaagtc gcagcagtgg actcatcagt accccgaaca     420
gctgagcttg ctgggattac tacactcgac gacccactcg gacatatgcc tgaaagattc     480
gacgctttca tttgctattg cccctctgac ata                                  513
```

<210> SEQ ID NO 55
<211> LENGTH: 62
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 55

```
Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
                20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60
```

```
<210> SEQ ID NO 56
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
aagaaggtgg ccaagaagcc caccaacaag gcccccacc ccaagcagga accccaggaa        60
atcaacttcc ccgacgacct gcccggcagc aatactgctg cacccgtgca ggaaaccctg      120
cacggctgtc agcctgtgac ccaggaagat ggcaaagaaa gccggatctc tgtgcaggaa      180
cgccag                                                                186
```

```
<210> SEQ ID NO 57
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```

```
<210> SEQ ID NO 58
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
agagtgaagt tcagcagaag cgccgacgcc cctgcctatc agcagggcca gaaccagctg        60
tacaacgagc tgaacctggg cagacgggaa gagtacgacg tgctggacaa gcggagaggc      120
```

```
agggaccctg agatgggcgg caagcccaga agaaagaacc cccaggaagg cctgtataac        180
gaactgcaga aagacaagat ggccgaggcc tacagcgaga tcggcatgaa gggcgagcgg        240
agaagaggca agggccacga tggcctgtac cagggactga gcaccgccac caaggacacc        300
tacgacgccc tgcacatgca ggccctgcct ccaaga                                  336
```

```
<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Arg Arg Gly Arg Asp Pro
        35                  40                  45

Glu Met Gly Gly Lys Pro Arg Arg Lys Asn Pro Gln Glu Gly Leu Tyr
    50                  55                  60

Asn Glu Leu Gln Lys Asp Lys Met Ala Glu Ala Tyr Ser Glu Ile Gly
65                  70                  75                  80

Met Lys Gly Glu Arg Arg Arg Gly Lys Gly His Asp Gly Leu Tyr Gln
                85                  90                  95

Gly Leu Ser Thr Ala Thr Lys Asp Thr Tyr Asp Ala Leu His Met Gln
            100                 105                 110

Ala Leu Pro Pro Arg
        115
```

```
<210> SEQ ID NO 60
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
agagtgaagt tcagcaggag cgcagacgcc cccgcgtacc agcagggcca gaaccagctc         60
tataacgagc tcaatctagg acgaagagag gagtacgatg ttttggacaa gagacgtggc        120
cgggacagac gtggccggga ccctgagatg gggggaaagc cgagaaggaa gaaccctcag        180
gaaggcctgt acaatgaact gcagaaagat aagatggcgg aggcctacag tgagattggg        240
atgaaaggcg agcgccggag gggcaagggg cacgatggcc tttaccaggg tctcagtaca        300
gccaccaagg acacctacga cgcccttcac atgcaggccc tgccccctcg c                 351
```

```
<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Asp Trp Ile Trp Arg Ile Leu Phe Leu Val Gly Ala Ala Thr Gly
1               5                   10                  15
```

Ala His Ser

<210> SEQ ID NO 62
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
atggactgga tctggcgcat cctcttcctc gtcggcgctg ctaccggcgc tcattct          57

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Ala Leu Pro Val Thr Ala Leu Leu Leu Pro Leu Ala Leu Leu Leu
1               5                   10                  15

His Ala Ala Arg Pro
            20

<210> SEQ ID NO 64
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
atggccttac cagtgaccgc cttgctcctg ccgctggcct tgctgctcca cgccgccagg          60
ccg                                                                       63

<210> SEQ ID NO 65
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

-continued

```
Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe
            325                 330
```

<210> SEQ ID NO 66
<211> LENGTH: 999
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 66

```
atgcctcccc ccagactgct gttcttcctg ctgttcctga cccctatgga agtgcggccc      60
gaggaacccc tggtcgtgaa agtggaagag ggcgacaacg ccgtgctgca gtgtctgaag     120
ggcacctccg atggccctac ccagcagctg acctggtcca gagagagccc cctgaagccc     180
ttcctgaagc tgtctctggg cctgcctggc ctgggcatcc atatgaggcc actggccatc     240
tggctgttca tcttcaacgt gtcccagcag atgggaggct ctacctgtg ccagcctggc     300 ccaccttctg agaaggcttg gcagcctggc tggaccgtga acgtggaagg atctggcgag     360
ctgttccggt ggaacgtgtc cgatctgggc ggcctgggat gcggcctgaa gaacagatct     420
agcgagggcc ccagcagccc cagcggcaaa ctgatgagcc caagctgta cgtgtgggcc     480 aaggacagac ccgagatttg ggagggcgag ccccttgcc tgccccctag agatagcctg     540
aaccagagcc tgagccagga cctgacaatg gcccctggca cacactgtg ctgagctgt     600 ggcgtgccac ccgactctgt gtctagaggc cctctgagct ggaccacgt gcaccctaag     660 ggccctaaga gctgctgtc cctggaactg aaggacgaca gcccgccag agatatgtgg     720 gtcatggaaa ccggcctgct gctgcctaga gccacagccc aggatgccgg caagtactac     780
```

-continued

```
tgccacagag gcaacctgac catgagcttc cacctggaaa tcaccgccag acccgtgctg      840
tggcactggc tgctgagaac cggcggatgg aaagtgtccg ccgtgactct ggcctacctg      900
atcttctgcc tgtgctccct cgtgggcatc ctgcatctgc agagggctct ggtgctgcgg      960
cggaagcgga agagaatgac cgaccctacc cggcggttc                            999
```

```
<210> SEQ ID NO 67
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ile Leu Asp Tyr Ser Phe Gly Gly Gly Ala Gly Arg Asp Ile Pro Pro
1               5                   10                  15

Pro Leu Ile Glu Glu Ala Cys Glu Leu Pro Glu Cys Gln Glu Asp Ala
                20                  25                  30

Gly Asn Lys Val Cys Ser Leu Gln Cys Asn Asn His Ala Cys Gly Trp
            35                  40                  45

Asp Gly Gly Asp Cys Ser Leu Asn Phe Asn Asp Pro Trp Lys Asn Cys
        50                  55                  60

Thr Gln Ser Leu Gln Cys Trp Lys Tyr Phe Ser Asp Gly His Cys Asp
65                  70                  75                  80

Ser Gln Cys Asn Ser Ala Gly Cys Leu Phe Asp Gly Phe Asp Cys Gln
                85                  90                  95

Arg Ala Glu Gly Gln Cys Asn Pro Leu Tyr Asp Gln Tyr Cys Lys Asp
            100                 105                 110

His Phe Ser Asp Gly His Cys Asp Gln Gly Cys Asn Ser Ala Glu Cys
            115                 120                 125

Glu Trp Asp Gly Leu Asp Cys Ala Glu His Val Pro Glu Arg Leu Ala
        130                 135                 140

Ala Gly Thr Leu Val Val Val Val Leu Met Pro Pro Glu Gln Leu Arg
145                 150                 155                 160

Asn Ser Ser Phe His Phe Leu Arg Glu Leu Ser Arg Val Leu His Thr
                165                 170                 175

Asn Val Val Phe Lys Arg Asp Ala His Gly Gln Gln Met Ile Phe Pro
            180                 185                 190

Tyr Tyr Gly Arg Glu Glu Glu Leu Arg Lys His Pro Ile Lys Arg Ala
            195                 200                 205

Ala Glu Gly Trp Ala Ala Pro Asp Ala Leu Leu Gly Gln Val Lys Ala
        210                 215                 220

Ser Leu Leu Pro Gly Gly Ser Glu Gly Gly Arg Arg Arg Arg Glu Leu
225                 230                 235                 240

Asp Pro Met Asp Val Arg Gly Ser Ile Val Tyr Leu Glu Ile Asp Asn
                245                 250                 255

Arg Gln Cys Val Gln Ala Ser Ser Gln Cys Phe Gln Ser Ala Thr Asp
            260                 265                 270

Val Ala Ala Phe Leu Gly Ala Leu Ala Ser Leu Gly Ser Leu Asn Ile
            275                 280                 285

Pro Tyr Lys Ile Glu Ala Val Gln Ser Glu Thr Val Glu Pro Pro Pro
        290                 295                 300

Pro Ala Gln Leu His Phe Met Tyr Val Ala Ala Ala Ala Phe Val Leu
305                 310                 315                 320
```

Leu Phe Phe Val Gly Cys Gly Val Leu Leu Ser Arg Lys Arg Arg Arg
                325                 330                 335

<210> SEQ ID NO 68
<211> LENGTH: 1008
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
attctggatt atagctttgg cggcggcgcg ggccgcgata ttccgccgcc gctgattgaa        60
gaagcgtgcg aactgccgga atgccaggaa gatgcgggca acaaagtgtg cagcctgcag       120
tgcaacaacc atgcgtgcgg ctgggatggc ggcgattgca gcctgaactt taacgatccg       180
tggaaaaact gcacccagag cctgcagtgc tggaaatatt ttagcgatgg ccattgcgat       240
agccagtgca acagcgcggg ctgcctgttt gatggctttg attgccagcg cgcggaaggc       300
cagtgcaacc cgctgtatga tcagtattgc aaagatcatt ttagcgatgg ccattgcgat       360
cagggctgca acagcgcgga atgcgaatgg gatggcctgg attgcgcgga acatgtgccg       420
gaacgcctgg cggcgggcac cctggtggtg gtggtgctga tgccgccgga acagctgcgc       480
aacagcagct tcatttct gcgcgaactg agccgcgtgc tgcataccaa cgtggtgttt       540
aaacgcgatg cgcatggcca gcagatgatt tttccgtatt atggccgcga agaagaactg       600
cgcaaacatc cgattaaacg cgcggcggaa ggctgggcgg cgccggatgc gctgctgggc       660
caggtgaaag cgagcctgct gccgggcggc agcgaaggcg gccgccgccg ccgcgaactg       720
gatccgatgg atgtgcgcgg cagcattgtg tatctggaaa ttgataaccg ccagtgcgtg       780
caggcgagca gccagtgctt tcagagcgcg accgatgtgg cggcgtttct gggcgcgctg       840
gcgagcctgg cagcctgaa cattccgtat aaaattgaag cggtgcagag cgaaaccgtg       900
gaaccgccgc cgccggcgca gctgcatttt atgtatgtgg cggcggcggc gtttgtgctg       960
ctgttttttg tgggctgcgg cgtgctgctg agccgcaaac gccgccgc                  1008

<210> SEQ ID NO 69
<211> LENGTH: 19
<212> TYPE: PRT
<213> ORGANISM: Thosea asigna virus

<400> SEQUENCE: 69

Ala Glu Gly Arg Gly Ser Leu Leu Thr Cys Gly Asp Val Glu Glu Asn
1               5                   10                  15

Pro Gly Pro

<210> SEQ ID NO 70
<211> LENGTH: 57
<212> TYPE: DNA
<213> ORGANISM: Thosea asigna virus

<400> SEQUENCE: 70
gccgagggca gaggcagcct gctgacatgt ggcgacgtgg aagagaaccc aggcccc           57

<210> SEQ ID NO 71
<211> LENGTH: 18
<212> TYPE: PRT
<213> ORGANISM: Thosea asigna virus

<400> SEQUENCE: 71

-continued

```
Glu Gly Arg Gly Ser Leu Leu Thr Cys Gly Asp Val Glu Glu Asn Pro
1               5                   10                  15

Gly Pro

<210> SEQ ID NO 72
<211> LENGTH: 54
<212> TYPE: DNA
<213> ORGANISM: Thosea asigna virus

<400> SEQUENCE: 72
gaaggcagag gatcactgct gacatgcggc gacgtggaag agaaccctgg accc          54

<210> SEQ ID NO 73
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 74
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Ser Gly Ser Arg Val Thr Glu Leu Leu Tyr Arg Met Lys Arg Ala
1               5                   10                  15

Glu Thr Tyr Cys Pro Arg Pro Leu Leu Ala Ile His Pro Thr Glu Ala
            20                  25                  30

Arg His Lys Gln Lys Ile Val Ala Pro Val Lys Gln Leu Leu Asn Phe
        35                  40                  45

Asp Leu Leu Lys Leu Ala Gly Asp Val Glu Ser Asn Pro Gly Pro
    50                  55                  60

<210> SEQ ID NO 75
<211> LENGTH: 19
<212> TYPE: PRT
<213> ORGANISM: Amphimedon queenslandica

<400> SEQUENCE: 75

Leu Leu Cys Phe Leu Leu Leu Leu Leu Ser Gly Asp Val Glu Leu Asn
1               5                   10                  15

Pro Gly Pro

<210> SEQ ID NO 76
<211> LENGTH: 20
<212> TYPE: PRT
<213> ORGANISM: Amphimedon queenslandica

<400> SEQUENCE: 76

His His Phe Met Phe Leu Leu Leu Leu Leu Ala Gly Asp Ile Glu Leu
1               5                   10                  15
```

Asn Pro Gly Pro
        20

<210> SEQ ID NO 77
<211> LENGTH: 20
<212> TYPE: PRT
<213> ORGANISM: Saccoglossus kowalevskii

<400> SEQUENCE: 77

Trp Phe Leu Val Leu Leu Ser Phe Ile Leu Ser Gly Asp Ile Glu Val
1               5                   10                  15

Asn Pro Gly Pro
        20

<210> SEQ ID NO 78
<211> LENGTH: 20
<212> TYPE: PRT
<213> ORGANISM: Branchiostoma floridae

<400> SEQUENCE: 78

Lys Asn Cys Ala Met Tyr Met Leu Leu Leu Ser Gly Asp Val Glu Thr
1               5                   10                  15

Asn Pro Gly Pro
        20

<210> SEQ ID NO 79
<211> LENGTH: 20
<212> TYPE: PRT
<213> ORGANISM: Branchiostoma floridae

<400> SEQUENCE: 79

Met Val Ile Ser Gln Leu Met Leu Lys Leu Ala Gly Asp Val Glu Glu
1               5                   10                  15

Asn Pro Gly Pro
        20

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Ser Gly Ala Thr Asn Phe Ser Leu Leu Lys Gln Ala Gly Asp Val
1               5                   10                  15

Glu Glu Asn Pro Gly Pro
        20

<210> SEQ ID NO 81
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ser Gly Gln Cys Thr Asn Tyr Ala Leu Leu Lys Leu Ala Gly Asp
1               5                   10                  15

Val Glu Ser Asn Pro Gly Pro
        20

<210> SEQ ID NO 82
<211> LENGTH: 8
<212> TYPE: PRT
<213> ORGANISM: Unknown
<220> FEATURE:
<223> OTHER INFORMATION: Description of Unknown:
      2A consensus sequence
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 82

Asp Xaa Glu Xaa Asn Pro Gly Pro
1               5

<210> SEQ ID NO 83
<211> LENGTH: 54
<212> TYPE: DNA
<213> ORGANISM: Thosea asigna virus

<400> SEQUENCE: 83
gagggcagag gcagcctgct gacatgtggc gacgtggaag agaacccagg cccc                54

<210> SEQ ID NO 84
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 85
<211> LENGTH: 891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
atgaccacac ctcggaacag cgtgaacggc acatttcccg ccgagcctat gaagggccct      60
atcgccatgc agtctggccc caagcctctg ttcagacgga tgtctagcct cgtgggcccc     120
acacagagct tttcatgag agagagcaag accctgggcg ccgtgcagat catgaacggc      180
ctgtttcaca ttgccctcgg cggcctgctg atgatccctg ccggaatcta tgcccctatc     240
tgcgtgaccg tgtggtatcc tctgtggggc ggcatcatgt acatcatctc tggatctctg     300
ctggccgcca ccgagaagaa cagcagaaag tgtctggtca agggcaagat gatcatgaat     360
agcctgagcc tgttcgccgc catcagcggc atgatcctga gcatcatgga tatcctgaat     420
atcaagatca gccacttcct gaagatggaa agcctgaact tcatcagggc ccacacacct     480
tacatcaaca tctacaactg cgagcccgcc aatcctagcg agaagaatag ccccagcaca     540
cagtactgct actctatcca gagcctgttt ctgggcatcc tgagcgtgat gctgatcttc     600
gcattcttcc aagagctggt tatcgccggc atcgtggaaa acgagtggaa gcggacctgc     660
agcagaccca gagcaacat cgtgctgctg agcgccgagg aaaagaaaga gcagaccatc     720
gagatcaaag aggaagtcgt cggcctgacc gagacaagca gccagcctaa gaacgaagag     780
gacattgaga tcatccccat ccaagaagag gaagaagaag agactgagac aaacttcccc     840
gagcctcctc aggaccaaga gagcagcccc attgagaacg atagcagccc t             891

<210> SEQ ID NO 86
<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
atgaccaccc ccagaaacag cgtgaacggc accttccccg ccgagcctat gaagggccct      60
atcgccatgc agagcggccc caagcccctg ttcagacgga tgtctagcct cgtgggcccct    120 acccagagct tcttcatgag agagagcaag accctgggcg ccgtgcagat catgaacggc     180

```
ctgttccaca ttgccctggg cggcctgctg atgatccctg ccggaatcta cgcccccatc        240
tgcgtgaccg tgtggtatcc tctgtggggc ggcatcatgt acatcatcag cggcagcctg        300
ctggccgcca ccgagaagaa cagcagaaag tgcctcgtga agggcaagat gatcatgaat        360
agcctgagcc tgttcgccgc catctccggc atgatcctga gcatcatgga tatcctgaat        420
atcaagatca gccacttcct gaagatggaa agcctgaact tcatccgggc ccacacccc         480 tacatcaaca tctacaactg cgagcccgcc aaccccagcg agaagaatag ccccagcacc        540
cagtactgct actctatcca gtccctgttc ctgggcatcc tgagcgtgat gctgatcttc        600 gcatttttc aagagctcgt gatcgccggc atcgtggaaa cgagtggaa gcggacctgc          660 agccggccca agagcaacat cgtgctgctg agcgccgagg aaaagaaaga gcagaccatc        720
gagatcaaag aggaagtcgt gggcctgacc gagacaagct cccagcccaa gaacgaagag        780
gacattgaga tcatcccaat ccaggaagaa gaggaagagg aaaccgagac taacttcccc        840 gagcccccc aggaccagga aagcagcccc atcgagaacg acagcagccc ctga              894
```

```
<210> SEQ ID NO 87
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ala Ala Ala Gly Gly Ser Gly Gly Ser Gly Gly Ser
145                 150                 155
```

```
<210> SEQ ID NO 88
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
atgaaactgc tgagcagcat tgaacaggcg tgcgatattt gccgcctgaa aaaactgaaa        60
```

-continued

```
tgcagcaaag aaaaaccgaa atgcgcgaaa tgcctgaaaa acaactggga atgccgctat     120
agcccgaaaa ccaaacgcag cccgctgacc cgcgcgcatc tgaccgaagt ggaaagccgc     180
ctggaacgcc tggaacagct gtttctgctg attttttccgc gcgaagatct ggatatgatt     240
ctgaaaatgg atagcctgca ggatattaaa gcgctgctga ccggcctgtt tgtgcaggat     300
aacgtgaaca aagatgcggt gaccgatcgc ctggcgagcg tggaaaccga tatgccgctg     360
accctgcgcc agcatcgcat tagcgcgacc agcagcagcg aagaaagcag caacaaaggc     420
cagcgccagc tgaccgtgag cgcggcggcg ggcggcagcg gcggcagcgg cggcagc       477
```

```
<210> SEQ ID NO 89
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu
    50
```

```
<210> SEQ ID NO 90
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
gatgcgctgg atgattttga tctggatatg ctgggcagcg atgcgctgga tgattttgat     60
ctggatatgc tgggcagcga tgcgctggat gattttgatc tggatatgct gggcagcgat    120
gcgctggatg attttgatct ggatatgctg                                     150
```

```
<210> SEQ ID NO 91
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Leu Glu Pro Lys Ser Cys Asp Lys Thr His Thr Cys Pro Pro Cys
1               5                   10                  15

Pro Asp Pro Lys
            20
```

```
<210> SEQ ID NO 92
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 92
gatctcgagc ccaaatcttg tgacaaaact cacacatgcc caccgtgccc ggatcccaag        60

<210> SEQ ID NO 93
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Met Asp Trp Ile Trp Arg Ile Leu Phe Leu Val Gly Ala Ala Thr Gly
1               5                   10                  15

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ser Met Ser Trp Val Arg Gln Ala Pro Gly Lys Gly Leu
    50                  55                  60

Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Pro Phe Pro Tyr Phe Asp Tyr Trp Gly Gln Gly
            115                 120                 125

Thr Leu Val Thr Val Ser Ser Gly Asp Gly Ser Ser Gly Gly Ser Gly
        130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
            180                 185                 190

Arg Leu Leu Ile Tyr Tyr Ala Ser Ser Arg Ala Thr Gly Ile Pro Asp
            195                 200                 205

Arg Phe Ser Gly Ser Gly Ser Gly Thr Asp Phe Thr Leu Thr Ile Ser
        210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Ile
                245                 250                 255

Leu Asp Tyr Ser Phe Gly Gly Gly Ala Gly Arg Asp Ile Pro Pro Pro
            260                 265                 270

Leu Ile Glu Glu Ala Cys Glu Leu Pro Glu Cys Gln Glu Asp Ala Gly
            275                 280                 285

Asn Lys Val Cys Ser Leu Gln Cys Asn Asn His Ala Cys Gly Trp Asp
        290                 295                 300

Gly Gly Asp Cys Ser Leu Asn Phe Asn Asp Pro Trp Lys Asn Cys Thr
305                 310                 315                 320

Gln Ser Leu Gln Cys Trp Lys Tyr Phe Ser Asp Gly His Cys Asp Ser
            325                 330                 335
```

```
Gln Cys Asn Ser Ala Gly Cys Leu Phe Asp Gly Phe Asp Cys Gln Arg
            340                 345                 350

Ala Glu Gly Gln Cys Asn Pro Leu Tyr Asp Gln Tyr Cys Lys Asp His
            355                 360                 365

Phe Ser Asp Gly His Cys Asp Gln Gly Cys Asn Ser Ala Glu Cys Glu
            370                 375                 380

Trp Asp Gly Leu Asp Cys Ala Glu His Val Pro Glu Arg Leu Ala Ala
385                 390                 395                 400

Gly Thr Leu Val Val Val Val Leu Met Pro Pro Glu Gln Leu Arg Asn
                405                 410                 415

Ser Ser Phe His Phe Leu Arg Glu Leu Ser Arg Val Leu His Thr Asn
            420                 425                 430

Val Val Phe Lys Arg Asp Ala His Gly Gln Gln Met Ile Phe Pro Tyr
            435                 440                 445

Tyr Gly Arg Glu Glu Glu Leu Arg Lys His Pro Ile Lys Arg Ala Ala
            450                 455                 460

Glu Gly Trp Ala Ala Pro Asp Ala Leu Leu Gly Gln Val Lys Ala Ser
465                 470                 475                 480

Leu Leu Pro Gly Gly Ser Glu Gly Gly Arg Arg Arg Arg Glu Leu Asp
                485                 490                 495

Pro Met Asp Val Arg Gly Ser Ile Val Tyr Leu Glu Ile Asp Asn Arg
            500                 505                 510

Gln Cys Val Gln Ala Ser Ser Gln Cys Phe Gln Ser Ala Thr Asp Val
            515                 520                 525

Ala Ala Phe Leu Gly Ala Leu Ala Ser Leu Gly Ser Leu Asn Ile Pro
            530                 535                 540

Tyr Lys Ile Glu Ala Val Gln Ser Glu Thr Val Glu Pro Pro Pro Pro
545                 550                 555                 560

Ala Gln Leu His Phe Met Tyr Val Ala Ala Ala Ala Phe Val Leu Leu
                565                 570                 575

Phe Phe Val Gly Cys Gly Val Leu Leu Ser Arg Lys Arg Arg Arg Met
                580                 585                 590

Lys Leu Leu Ser Ser Ile Glu Gln Ala Cys Asp Ile Cys Arg Leu Lys
            595                 600                 605

Lys Leu Lys Cys Ser Lys Glu Lys Pro Lys Cys Ala Lys Cys Leu Lys
            610                 615                 620

Asn Asn Trp Glu Cys Arg Tyr Ser Pro Lys Thr Lys Arg Ser Pro Leu
625                 630                 635                 640

Thr Arg Ala His Leu Thr Glu Val Glu Ser Arg Leu Glu Arg Leu Glu
                645                 650                 655

Gln Leu Phe Leu Leu Ile Phe Pro Arg Glu Asp Leu Asp Met Ile Leu
            660                 665                 670

Lys Met Asp Ser Leu Gln Asp Ile Lys Ala Leu Leu Thr Gly Leu Phe
            675                 680                 685

Val Gln Asp Asn Val Asn Lys Asp Ala Val Thr Asp Arg Leu Ala Ser
            690                 695                 700

Val Glu Thr Asp Met Pro Leu Thr Leu Arg Gln His Arg Ile Ser Ala
705                 710                 715                 720

Thr Ser Ser Ser Glu Glu Ser Ser Asn Lys Gly Gln Arg Gln Leu Thr
                725                 730                 735

Val Ser Ala Ala Ala Gly Gly Ser Gly Gly Ser Gly Gly Ser Asp Ala
            740                 745                 750

Leu Asp Asp Phe Asp Leu Asp Met Leu Gly Ser Asp Ala Leu Asp Asp
```

```
        755              760              765

Phe Asp Leu Asp Met Leu Gly Ser Asp Ala Leu Asp Asp Phe Asp Leu
    770              775              780

Asp Met Leu Gly Ser Asp Ala Leu Asp Asp Phe Asp Leu Asp Met Leu
785              790              795              800

<210> SEQ ID NO 94
<211> LENGTH: 2400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
atggactgga tctggcgcat cctcttcctc gtcggcgctg ctaccggcgc tcattctgag      60
gttcagcttc ttgagtctgg gggcggcctg gtgcaacctg gtggcagtct taggctgagt     120
tgcgccgcgt cagggtttac tttttcttcc ttcagcatgt catgggtccg ccaggctcca     180
ggtaagggcc tggaatgggt tagtagcatc agtggcagta gtggtacaac atactacgct     240
gatagtgtta aagggagatt cactataagt agggataatt ctaaaaatac cctttatctg     300
caaatgaatt ctttgagggc cgaagatact gcggtctatt actgtgccaa accttttcca     360
tactttgatt actggggcca ggggacgctt gtcactgtct cctctggcga cggctcctcc     420
ggcggaagtg gaggcgcgtc agaaattgta ctgactcagt ccccgggcac gctctcactc     480
agtccaggcg aaagagctac gttgtcttgt cgcgcaagcc agtccgtaag ctctagcttc     540
ctcgcatggt atcaacaaaa gcccgggcag gctccgcggc tgctcattta ctatgctagt     600
tcaagggcta cggggaattcc agaccgattt agtggatctg ggagtggaac tgacttcaca     660
cttacgatca gcaggcttga gccggaagat tttgccgtgt actactgcca gcaaactgga     720
agaatccccc caacattcgg acaaggcacg aaggtggaaa tcaagattct ggattatagc     780
tttggcggcg gcgcgggccg cgatattccg ccgccgctga ttgaagaagc gtgcgaactg     840
ccggaatgcc aggaagatgc gggcaacaaa gtgtgcagcc tgcagtgcaa caaccatgcg     900
tgcggctggg atggcggcga ttgcagcctg aactttaacg atccgtggaa aaactgcacc     960
cagagcctgc agtgctggaa atattttagc gatggccatt gcgatagcca gtgcaacagc    1020
gcgggctgcc tgtttgatgg ctttgattgc agcgcgcgg aaggccagtg caacccgctg    1080
tatgatcagt attgcaaaga tcattttagc gatggccatt gcgatcaggg ctgcaacagc    1140
gcggaatgcg aatgggatgg cctggattgc gcggaacatg tgccggaacg cctggcggcg    1200
ggcaccctgg tggtggtggt gctgatgccg ccggaacagc tgcgcaacag cagctttcat    1260
tttctgcgcg aactgagccg cgtgctgcat accaacgtgg tgtttaaacg cgatgcgcat    1320
ggccagcaga tgattttttcc gtattatggc cgcgaagaag aactgcgcaa acatccgatt    1380
aaacgcgcgg cggaaggctg ggcggcgccg gatgcgctgc tgggccaggt gaaagcgagc    1440
ctgctgccgg cggcagcga aggcggccgc cgccgccgcg aactggatcc gatggatgtg    1500
cgcggcagca ttgtgtatct ggaaattgat aaccgccagt gcgtgcaggc gagcagccag    1560
tgctttcaga gcgcgaccga tgtggcggcg tttctgggcg cgctggcgag cctgggcagc    1620
ctgaacattc cgtataaaat tgaagcggtg cagagcgaaa ccgtggaacc gccgccgccg    1680
gcgcagctgc attttatgta tgtggcggcg cggcgtttg tgctgctgtt ttttgtgggc    1740
tgcggcgtgc tgctgagccg caaacgccgc cgcatgaaac tgctgagcag cattgaacag    1800
```

-continued

```
gcgtgcgata tttgccgcct gaaaaaactg aaatgcagca agaaaaaacc gaaatgcgcg    1860
aaatgcctga aaacaactg ggaatgccgc tatagcccga aaccaaacg cagcccgctg     1920 acccgcgcgc atctgaccga agtggaaagc cgcctggaac gcctggaaca gctgtttctg    1980 ctgattttc cgcgcgaaga tctggatatg attctgaaaa tggatagcct gcaggatatt    2040
aaagcgctgc tgaccggcct gtttgtgcag dataacgtga acaaagatgc ggtgaccgat    2100
cgcctggcga gcgtggaaac cgatatgccg ctgaccctgc gccagcatcg cattagcgcg    2160
accagcagca gcgaagaaag cagcaacaaa ggccagcgcc agctgaccgt gagcgcggcg    2220
gcgggcggca gcggcggcag cggcggcagc gatgcgctgg atgattttga tctggatatg    2280
ctgggcagcg atgcgctgga tgattttgat ctggatatgc tgggcagcga tgcgctggat    2340
gattttgatc tggatatgct gggcagcgat gcgctggatg attttgatct ggatatgctg    2400
```

<210> SEQ ID NO 95
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ser Met Ser Trp Val Arg Gln Ala Pro Gly Lys Gly Leu Glu Trp Val
            35                  40                  45

Ser Ser Ile Ser Gly Ser Ser Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
            115                 120                 125

Glu Ile Val Leu Thr Gln Ser Pro Gly Thr Leu Ser Leu Ser Pro Gly
        130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
            195                 200                 205

Pro Glu Asp Phe Ala Val Tyr Tyr Cys Gln Gln Thr Gly Arg Ile Pro
        210                 215                 220

Pro Thr Phe Gly Gln Gly Thr Lys Val Glu Ile Lys Asp Leu Glu Pro
225                 230                 235                 240

Lys Ser Cys Asp Lys Thr His Thr Cys Pro Pro Cys Pro Asp Pro Lys
                245                 250                 255
```

-continued

```
Phe Trp Val Leu Val Val Val Gly Gly Val Leu Ala Cys Tyr Ser Leu
            260             265             270

Leu Val Thr Val Ala Phe Ile Ile Phe Trp Val Arg Ser Lys Arg Ser
            275             280             285

Arg Leu Leu His Ser Asp Tyr Met Asn Met Thr Pro Arg Arg Pro Gly
            290             295             300

Pro Thr Arg Lys His Tyr Gln Pro Tyr Ala Pro Pro Arg Asp Phe Ala
305             310             315             320

Ala Tyr Arg Ser Arg Val Lys Phe Ser Arg Ser Ala Asp Ala Pro Ala
                325             330             335

Tyr Gln Gln Gly Gln Asn Gln Leu Tyr Asn Glu Leu Asn Leu Gly Arg
            340             345             350

Arg Glu Glu Tyr Asp Val Leu Asp Lys Arg Arg Gly Arg Asp Pro Glu
            355             360             365

Met Gly Gly Lys Pro Arg Arg Lys Asn Pro Gln Glu Gly Leu Tyr Asn
            370             375             380

Glu Leu Gln Lys Asp Lys Met Ala Glu Ala Tyr Ser Glu Ile Gly Met
385             390             395             400

Lys Gly Glu Arg Arg Arg Gly Lys Gly His Asp Gly Leu Tyr Gln Gly
                405             410             415

Leu Ser Thr Ala Thr Lys Asp Thr Tyr Asp Ala Leu His Met Gln Ala
            420             425             430

Leu Pro Pro Arg
            435
```

<210> SEQ ID NO 96
<211> LENGTH: 1308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
gaggttcagc ttcttgagtc tggggggggc ctggtgcaac ctggtggcag tcttaggctg      60
agttgcgccg cgtcagggtt tacttttct tccttcagca tgtcatgggt ccgccaggct     120
ccaggtaagg gcctggaatg ggttagtagc atcagtggca gtagtggtac aacatactac     180
gctgatagtg ttaaagggag attcactata agtaggata attctaaaaa tacccttat     240 ctgcaaatga attctttgag ggccgaagat actgcggtct attactgtgc caaacctttt     300
ccatactttg attactgggg ccagggacg cttgtcactg tctcctctgg cgacggctcc     360
tccggcggaa gtggaggcgc gtcagaaatt gtactgactc agtccccggg cacgctctca     420
ctcagtccag gcgaaagagc tacgttgtct tgtcgcgcaa gccagtccgt aagctctagc     480
ttcctcgcat ggtatcaaca aaagcccggg caggctccgc ggctgctcat ttactatgct     540
agttcaaggg ctacgggaat tccagaccga tttagtggat ctgggagtgg aactgacttc     600
acacttacga tcagcaggct tgagccggaa gattttgccg tgtactactg ccagcaaact     660
ggaagaatcc ccccaacatt cggacaaggc acgaaggtgg aaatcaagga tctcgagccc     720
aaatcttgtg acaaaactca cacatgccca ccgtgcccgg atcccaagtt ctgggtgctg     780
gtggtcgtgg gcggagtgct ggcctgttac agcctgctcg tgaccgtggc cttcatcatc     840
ttttgggtgc gcagcaagcg gagccggctg ctgcacagcg actacatgaa catgaccccc     900
agacggcctg gccccaccag aaagcactac cagccttacg ccctcccag agacttcgcc     960
```

```
gcctaccggt ccagagtgaa gttcagcaga agcgccgacg cccctgccta tcagcagggc    1020
cagaaccagc tgtacaacga gctgaacctg ggcagacggg aagagtacga cgtgctggac    1080
aagcggagag gcagggaccc tgagatgggc ggcaagccca gaagaaagaa cccccaggaa    1140
ggcctgtata cgaactgca gaaagacaag atggccgagg cctacagcga gatcggcatg    1200
aagggcgagc ggagaagagg caagggccac gatggcctgt accagggact gagcaccgcc    1260
accaaggaca cctacgacgc cctgcacatg caggccctgc tccaaga                  1308
```

```
<210> SEQ ID NO 97
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
            115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
                180                 185                 190

Gly Ser Gly Ser Gly Thr Asp Phe Thr Leu Thr Ile Ser Arg Leu Glu
            195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Pro Ala Lys Pro
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Ile Tyr Ile
            275                 280                 285

Trp Ala Pro Leu Ala Gly Thr Cys Gly Val Leu Leu Leu Ser Leu Val
    290                 295                 300
```

```
Ile Thr Leu Tyr Cys Asn His Arg Asn Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465
```

```
<210> SEQ ID NO 98
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gaggttcagc ttcttgagtc tggggggcggc ctggtgcaac ctggtggcag tcttaggctg      60
agttgcgccg cgtcagggtt tacttttttct tccttcagca tgtcatgggt ccgccaggct     120
ccaggtaagg gcctggaatg ggttagtagc atcagtggca gtagtggtac aacatactac     180
gctgatagtg ttaaagggag attcactata agtagggata attctaaaaa taccctttat     240
ctgcaaatga attctttgag ggccgaagat actgcggtct attactgtgc caaacctttt     300
ccatactttg attactgggg ccaggggacg cttgtcactg tctcctctgg cgacggctcc     360
tccggcggaa gtgaggcgc gtcagaaatt gtactgactc agtccccggg cacgctctca     420
ctcagtccag gcgaaagagc tacgttgtct tgtcgcgcaa gccagtccgt aagctctagc     480
ttcctcgcat ggtatcaaca aaagcccggg caggctccgc ggctgctcat ttactatgct     540
agttcaaggg ctacgggaat tccagaccga tttagtggat ctgggagtgg aactgacttc     600
acacttacga tcagcaggct tgagccggaa gattttgccg tgtactactg ccagcaaact     660
ggaagaatcc ccccaacatt cggacaaggc acgaaggtgg aaatcaagcc agccaagccc     720
accacaaccc ctgctcctag acctcctacc ccagccccta ccattgcctc ccagccactg     780
tctctgaggc ccgaggcttg tagacctgct gcaggcggag ccgtgcacac cagaggactg     840
gatttcgcct gcgacatcta tatctgggcc cctctggccg cacctgtgg cgtgctgctg     900 ctgtcactcg tgatcaccct gtactgcaac accggaacc gcagcaagcg gagccggctg     960
ctgcacagcg actacatgaa catgaccccc agacggcctg gccccaccag aaagcactac    1020
```

-continued

```
cagccttacg cccctcccag agacttcgcc gcctaccggt ccagagtgaa gttcagcaga    1080
agcgccgacg cccctgccta tcagcagggc cagaaccagc tgtacaacga gctgaacctg    1140
ggcagacggg aagagtacga cgtgctggac aagcggagag gcagggaccc tgagatgggc    1200
ggcaagccca gaagaaagaa ccccaggaa ggcctgtata cgaactgca gaaagacaag    1260 atggccgagg cctacagcga gatcggcatg aagggcgagc ggagaagagg caagggccac    1320
gatggcctgt accagggact gagcaccgcc accaaggaca cctacgacgc cctgcacatg    1380
caggccctgc tccaaga                                                   1398
```

```
<210> SEQ ID NO 99
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Pro Ala Lys Pro
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Ile Tyr Ile
        275                 280                 285
```

```
Trp Ala Pro Leu Ala Gly Thr Cys Gly Val Leu Leu Leu Ser Leu Val
    290                 295                 300

Ile Thr Leu Tyr Cys Asn His Arg Asn Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Arg Val Lys Phe Ser Arg Ser Ala Asp Ala Pro Ala Tyr
            355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
            435                 440                 445

Ser Thr Ala Thr Lys Asp Thr Tyr Asp Ala Leu His Met Gln Ala Leu
    450                 455                 460

Pro Pro Arg
465
```

```
<210> SEQ ID NO 100
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gaggttcagc ttcttgagtc tggggggcggc ctggtgcaac ctggtggcag tcttaggctg      60
agttgcgccg cgtcagggtt tactttttct tccttcagca tgtcatgggt ccgccaggct     120
ccaggtaagg gcctggaatg ggttagtagc atcagtggca gtagtggtac aacatactac     180
gctgatagtg ttaaagggag attcactata agtagggata attctaaaaa tacccttat      240 ctgcaaatga attctttgag gccgaagat actgcggtct attactgtgc caaacctttt      300
ccatactttg attactgggg ccagggacg cttgtcactg tctcctctgg cgacggctcc     360
tccggcggaa gtggaggcgc gtcagaaatt gtactgactc agtccccggg cacgctctca     420
ctcagtccag gcgaaagagc tacgttgtct tgtcgcgcaa gccagtccgt aagctctagc     480
ttcctcgcat ggtatcaaca aaagcccggg caggctccgc ggctgctcat ttactatgct     540
agttcaaggg ctacgggaat tccagaccga tttagtggat ctgggagtgg aactgacttc     600
acacttacga tcagcaggct tgagccggaa gattttgccg tgtactactg ccagcaaact     660
ggaagaatcc ccccaacatt cggacaaggc acgaaggtgg aaatcaagcc agccaagccc     720
accacaaccc ctgctcctag acctcctacc ccagcccta ccattgcctc ccagccactg      780
tctctgaggc ccgaggcttg tagacctgct gcaggcggag ccgtgcacac cagaggactg     840
gatttcgcct gcgacatcta tatctgggcc cctctggccg gcacctgtgg cgtgctgctg     900
ctgtcactcg tgatcaccct gtactgcaac caccggaaca aacgcggccg caaaaaactg     960
```

-continued

```
ctgtatattt ttaaacagcc gtttatgcgc ccggtgcaga ccacccagga agaagatggc    1020
tgcagctgcc gctttccgga agaagaagaa ggcggctgcg aactgcgcgt gaaatttagc    1080
cgcagcgcgg atgcgccggc gtatcagcag ggccagaacc agctgtataa cgaactgaac    1140
ctgggccgcc gcaagaaata tgatgtgctg gataaacgcc gcggccgcga tccggaaatg    1200
ggcggcaaac cgcgccgcaa aaacccgcag gaaggcctgt ataacgaact gcagaaagat    1260
aaaatggcgg aagcgtatag cgaaattggc atgaaaggcg aacgccgccg cggcaaaggc    1320
catgatggcc tgtatcaggg cctgagcacc gcgaccaaag atacctatga tgcgctgcat    1380
atgcaggcgc tgccgccgcg c                                              1401
```

```
<210> SEQ ID NO 101
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ser Met Ser Trp Val Arg Gln Ala Pro Gly Lys Gly Leu Glu Trp Val
            35                  40                  45

Ser Ser Ile Ser Gly Ser Ser Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Pro Ala Lys Pro
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Ile Tyr Ile
```

-continued

```
            275                 280                 285

Trp Ala Pro Leu Ala Gly Thr Cys Gly Val Leu Leu Leu Ser Leu Val
    290                 295                 300

Ile Thr Leu Tyr Cys Asn His Arg Asn Arg Asp Gln Arg Leu Pro Pro
305                 310                 315                 320

Asp Ala His Lys Pro Pro Gly Gly Gly Ser Phe Arg Thr Pro Ile Gln
                325                 330                 335

Glu Glu Gln Ala Asp Ala His Ser Thr Leu Ala Lys Ile Arg Val Lys
                340                 345                 350

Phe Ser Arg Ser Ala Asp Ala Pro Ala Tyr Gln Gln Gly Gln Asn Gln
                355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
                420                 425                 430

Lys Gly His Asp Gly Leu Tyr Gln Gly Leu Ser Thr Ala Thr Lys Asp
                435                 440                 445

Thr Tyr Asp Ala Leu His Met Gln Ala Leu Pro Pro Arg
    450                 455                 460
```

<210> SEQ ID NO 102
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
gaggttcagc ttcttgagtc tggggcggc ctggtgcaac ctggtggcag tcttaggctg     60
agttgcgccg cgtcagggtt tacttttct tccttcagca tgtcatgggt ccgccaggct    120
ccaggtaagg gcctggaatg ggttagtagc atcagtggca gtagtggtac aacatactac    180
gctgatagtg ttaaagggag attcactata agtaggggata attctaaaaa tacccttat    240 ctgcaaatga attctttgag ggccgaagat actgcggtct attactgtgc caaacctttt    300
ccatactttg attactgggg ccagggggacg cttgtcactg tctcctctgg cgacggctcc    360
tccggcggaa gtggaggcgc gtcagaaatt gtactgactc agtccccggg cacgctctca    420
ctcagtccag gcgaaagagc tacgttgtct tgtcgcgcaa gccagtccgt aagctctagc    480
ttcctcgcat ggtatcaaca aaagcccggg caggctccgc ggctgctcat ttactatgct    540
agttcaaggg ctacgggaat ccagaccga tttagtggat ctgggagtgg aactgacttc    600
acacttacga tcagcaggct tgagccggaa gattttgccg tgtactactg ccagcaaact    660
ggaagaatcc ccccaacatt cggacaaggc acgaaggtgg aaatcaagcc agccaagccc    720
accacaaccc ctgctcctag acctcctacc ccagcccta ccattgcctc ccagccactg    780
tctctgaggc ccgaggcttg tagacctgct gcaggcggag ccgtgcacac cagaggactg    840
gatttcgcct gcgacatcta tatctgggcc cctctggccg gcacctgtgg cgtgctgctg    900
ctgtcactcg tgatcaccct gtactgcaac caccggaacc gcgatcagcg cctgccgccg    960
gatgcgcata aaccgccggg cggcggcagc tttcgcaccc cgattcagga agaacaggcg   1020
```

```
gatgcgcata gcaccctggc gaaaattcgc gtgaaattta gccgcagcgc ggatgcgccg      1080
gcgtatcagc agggccagaa ccagctgtat aacgaactga acctgggccg ccgcgaagaa      1140
tatgatgtgc tggataaacg ccgcggccgc gatccggaaa tgggcggcaa accgcgccgc      1200
aaaaacccgc aggaaggcct gtataacgaa ctgcagaaag ataaaatggc ggaagcgtat      1260
agcgaaattg gcatgaaagg cgaacgccgc cgcggcaaag ccatgatggc cctgtatcag      1320
ggcctgagca ccgcgaccaa agatacctat gatgcgctgc atatgcaggc gctgccgccg      1380
cgc                                                                   1383
```

<210> SEQ ID NO 103
<211> LENGTH: 661
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 103

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
            195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Pro Ala Lys Pro
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Ile Tyr Ile
            275                 280                 285
```

-continued

```
Trp Ala Pro Leu Ala Gly Thr Cys Gly Val Leu Leu Leu Ser Leu Val
    290                 295                 300

Ile Thr Leu Tyr Cys Asn His Arg Asn Val Ala Ala Gly Gly Pro Gly
305                 310                 315                 320

Ala Gly Ser Ala Ala Pro Val Ser Ser Thr Ser Ser Leu Pro Leu Ala
            325                 330                 335

Ala Leu Asn Met Arg Val Arg Arg Arg Leu Ser Leu Phe Leu Asn Val
            340                 345                 350

Arg Thr Gln Val Ala Ala Asp Trp Thr Ala Leu Ala Glu Glu Met Asp
            355                 360                 365

Phe Glu Tyr Leu Glu Ile Arg Gln Leu Glu Thr Gln Ala Asp Pro Thr
    370                 375                 380

Gly Arg Leu Leu Asp Ala Trp Gln Gly Arg Pro Gly Ala Ser Val Gly
385                 390                 395                 400

Arg Leu Leu Glu Leu Leu Thr Lys Leu Gly Arg Asp Asp Val Leu Leu
            405                 410                 415

Glu Leu Gly Pro Ser Ile Glu Glu Asp Cys Gln Lys Tyr Ile Leu Lys
            420                 425                 430

Gln Gln Gln Glu Glu Ala Glu Lys Pro Leu Gln Val Ala Ala Val Asp
            435                 440                 445

Ser Ser Val Pro Arg Thr Ala Glu Leu Ala Gly Ile Thr Thr Leu Asp
    450                 455                 460

Asp Pro Leu Gly His Met Pro Glu Arg Phe Asp Ala Phe Ile Cys Tyr
465                 470                 475                 480

Cys Pro Ser Asp Ile Val Glu Lys Lys Val Ala Lys Lys Pro Thr Asn
            485                 490                 495

Lys Ala Pro His Pro Lys Gln Glu Pro Gln Glu Ile Asn Phe Pro Asp
            500                 505                 510

Asp Leu Pro Gly Ser Asn Thr Ala Ala Pro Val Gln Glu Thr Leu His
            515                 520                 525

Gly Cys Gln Pro Val Thr Gln Glu Asp Gly Lys Glu Ser Arg Ile Ser
    530                 535                 540

Val Gln Glu Arg Gln Arg Val Lys Phe Ser Arg Ser Ala Asp Ala Pro
545                 550                 555                 560

Ala Tyr Gln Gln Gly Gln Asn Gln Leu Tyr Asn Glu Leu Asn Leu Gly
            565                 570                 575

Arg Arg Glu Glu Tyr Asp Val Leu Asp Lys Arg Arg Gly Arg Asp Pro
            580                 585                 590

Glu Met Gly Gly Lys Pro Arg Arg Lys Asn Pro Gln Glu Gly Leu Tyr
            595                 600                 605

Asn Glu Leu Gln Lys Asp Lys Met Ala Glu Ala Tyr Ser Glu Ile Gly
    610                 615                 620

Met Lys Gly Glu Arg Arg Arg Gly Lys Gly His Asp Gly Leu Tyr Gln
625                 630                 635                 640

Gly Leu Ser Thr Ala Thr Lys Asp Thr Tyr Asp Ala Leu His Met Gln
            645                 650                 655

Ala Leu Pro Pro Arg
            660
```

<210> SEQ ID NO 104
<211> LENGTH: 1980
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 104

```
gaggttcagc ttcttgagtc tgggggcggc ctggtgcaac ctggtggcag tcttaggctg        60
agttgcgccg cgtcagggtt tacttttct tccttcagca tgtcatgggt ccgccaggct       120
ccaggtaagg gcctggaatg ggttagtagc atcagtggca gtagtggtac aacatactac       180
gctgatagtg ttaaagggag attcactata agtagggata attctaaaaa tacccttttat      240 ctgcaaatga attctttgag ggccgaagat actgcggtct attactgtgc caaacctttt       300
ccatactttg attactgggg ccaggggacg cttgtcactg tctcctctgg cgacggctcc       360
tccggcggaa gtggaggcgc gtcagaaatt gtactgactc agtccccggg cacgctctca       420
ctcagtccag gcgaaagagc tacgttgtct tgtcgcgcaa gccagtccgt aagctctagc       480
ttcctcgcat ggtatcaaca aaagcccggg caggctccgc ggctgctcat ttactatgct       540
agttcaaggg ctacgggaat tccagaccga tttagtggat ctgggagtgg aactgacttc       600
acacttacga tcagcaggct tgagccggaa gattttgccg tgtactactg ccagcaaact       660
ggaagaatcc ccccaacatt cggacaaggc acgaaggtgg aaatcaagcc agccaagccc       720
accacaaccc ctgctcctag acctcctacc ccagcccta ccattgcctc ccagccactg        780
tctctgaggc ccgaggcttg tagacctgct gcaggcggag ccgtgcacac cagaggactg       840
gatttcgcct gcgacatcta tatctgggcc cctctggccg gcacctgtgg cgtgctgctg       900
ctgtcactcg tgatcaccct gtactgcaac caccggaacg ctgctggcgg acctggcgcc       960
ggatctgctg ctcctgtgtc tagcacaagc agcctgcctc tggccgccct gaacatgaga      1020
gtgcggagaa ggctgagcct gttcctgaac gtgcggacac aggtggccgc cgattggaca      1080
gccctggccg aggaaatgga cttcgagtac ctggaaatcc ggcagctgga aacccaggcc      1140
gaccctacag gcagactgct ggatgcttgg caggcagac caggcgcttc tgtgggaagg       1200
ctgctggaac tgctgaccaa gctgggcagg gacgacgtgc tgctggaact gggccctagc      1260
atcgaagagg actgccagaa gtacatcctg aagcagcagc aggaagaggc cgagaagcct      1320
ctgcaggtgg cagccgtgga tagcagcgtg ccaagaacag ccgagctggc cggcatcacc      1380
accctggatg atcctctggg ccacatgccc gagagattcg acgccttcat ctgctactgc      1440
cccagcgaca tcgtggaaaa gaaggtggcc aagaagccca ccaacaaggc cccccacccc      1500
aagcaggaac cccaggaaat caacttcccc gacgacctgc ccggcagcaa tactgctgca      1560
cccgtgcagg aaaccctgca cggctgtcag cctgtgaccc aggaagatgg caaagaaagc      1620
cggatctctg tgcaggaacg ccagagagtg aagttcagca ggagcgcaga cgccccccgcg      1680 taccagcagg gccagaacca gctctataac gagctcaatc taggacgaag agaggagtac      1740 gatgtttttgg acaagagacg tggccgggac cctgagatgg gcggcaagcc cagaagaaag      1800 aaccccagg aaggcctgta taacgaactg cagaaagaca agatggccga ggcctacagc       1860
gagatcggca tgaagggcga gcggagaaga ggcaagggcc acgatggcct gtaccaggga      1920
ctgagcaccg ccaccaagga cacctacgac gccctgcaca tgcaggccct gcctccaaga      1980
```

<210> SEQ ID NO 105
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
            115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
            165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
            195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Asp Leu Glu Pro
225                 230                 235                 240

Lys Ser Cys Asp Lys Thr His Thr Cys Pro Pro Cys Pro Asp Pro Lys
            245                 250                 255

Phe Trp Val Leu Val Val Val Gly Gly Val Leu Ala Cys Tyr Ser Leu
            260                 265                 270

Leu Val Thr Val Ala Phe Ile Ile Phe Trp Val Lys Arg Gly Arg Lys
            275                 280                 285

Lys Leu Leu Tyr Ile Phe Lys Gln Pro Phe Met Arg Pro Val Gln Thr
    290                 295                 300

Thr Gln Glu Glu Asp Gly Cys Ser Cys Arg Phe Pro Glu Glu Glu Glu
305                 310                 315                 320

Gly Gly Cys Glu Leu Arg Val Lys Phe Ser Arg Ser Ala Asp Ala Pro
            325                 330                 335

Ala Tyr Gln Gln Gly Gln Asn Gln Leu Tyr Asn Glu Leu Asn Leu Gly
            340                 345                 350

Arg Arg Glu Glu Tyr Asp Val Leu Asp Lys Arg Arg Gly Arg Asp Pro
            355                 360                 365

Glu Met Gly Gly Lys Pro Arg Arg Lys Asn Pro Gln Glu Gly Leu Tyr
    370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
```

-continued

```
                405             410             415
Gly Leu Ser Thr Ala Thr Lys Asp Thr Tyr Asp Ala Leu His Met Gln
            420             425             430

Ala Leu Pro Pro Arg
        435
```

```
<210> SEQ ID NO 106
<211> LENGTH: 1311
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
gaggttcagc ttcttgagtc tgggggcggc ctggtgcaac ctggtggcag tcttaggctg      60
agttgcgccg cgtcagggtt tacttttttct tccttcagca tgtcatgggt ccgccaggct     120
ccaggtaagg gcctggaatg ggttagtagc atcagtggca gtagtggtac aacatactac     180
gctgatagtg ttaaagggag attcactata agtagggata attctaaaaa tacccttttat    240 ctgcaaatga attctttgag ggccgaagat actgcggtct attactgtgc caaacctttt     300
ccatactttg attactgggg ccaggggacg cttgtcactg tctcctctgg cgacggctcc     360
tccggcggaa gtggaggcgc gtcagaaatt gtactgactc agtccccggg cacgctctca     420
ctcagtccag gcgaaagagc tacgttgtct tgtcgcgcaa gccagtccgt aagctctagc     480
ttcctcgcat ggtatcaaca aaagcccggg caggctccgc ggctgctcat ttactatgct     540
agttcaaggg ctacgggaat ccagaccgga tttagtggat ctgggagtgg aactgacttc     600
acacttacga tcagcaggct tgagccggaa gattttgccg tgtactactg ccagcaaact     660
ggaagaatcc ccccaacatt cggacaaggc acgaaggtgg aaatcaagga tctcgagccc     720
aaatcttgtg acaaaactca cacatgccca ccgtgcccgg atcccaagtt ctgggtgctg     780
gtggtcgtgg cggagtgct ggcctgttac agcctgctcg tgaccgtggc cttcatcatc     840 tttttgggtga aacgcggccg caaaaaactg ctgtatattt ttaaacagcc gtttatgcgc     900
ccggtgcaga ccacccagga agaagatggc tgcagctgcc gctttccgga agaagaagaa     960
ggcggctgcg aactgcgcgt gaaatttagc cgcagcgcgg atgcgccggc gtatcagcag    1020
ggccagaacc agctgtataa cgaactgaac ctgggccgcc gcgaagaata tgatgtgctg    1080
gataaacgcc gcggccgcga tccggaaatg ggcggcaaac cgcgccgcaa aaacccgcag    1140
gaaggcctgt ataacgaact gcagaaagat aaaatggcgg aagcgtatag cgaaattggc    1200
atgaaaggcg aacgccgccg cggcaaaggc catgatggcc tgtatcaggg cctgagcacc    1260
gcgaccaaag atacctatga tgcgctgcat atgcaggcgc tgccgccgcg c            1311
```

```
<210> SEQ ID NO 107
<211> LENGTH: 431
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30
```

-continued

```
Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Asp Leu Glu Pro
225                 230                 235                 240

Lys Ser Cys Asp Lys Thr His Thr Cys Pro Pro Cys Pro Asp Pro Lys
            245                 250                 255

Phe Trp Val Leu Val Val Val Gly Gly Val Leu Ala Cys Tyr Ser Leu
            260                 265                 270

Leu Val Thr Val Ala Phe Ile Ile Phe Trp Val Arg Asp Gln Arg Leu
        275                 280                 285

Pro Pro Asp Ala His Lys Pro Pro Gly Gly Gly Ser Phe Arg Thr Pro
    290                 295                 300

Ile Gln Glu Glu Gln Ala Asp Ala His Ser Thr Leu Ala Lys Ile Arg
305                 310                 315                 320

Val Lys Phe Ser Arg Ser Ala Asp Ala Pro Ala Tyr Gln Gln Gly Gln
            325                 330                 335

Asn Gln Leu Tyr Asn Glu Leu Asn Leu Gly Arg Arg Glu Glu Tyr Asp
            340                 345                 350

Val Leu Asp Lys Arg Arg Gly Arg Asp Pro Glu Met Gly Gly Lys Pro
        355                 360                 365

Arg Arg Lys Asn Pro Gln Glu Gly Leu Tyr Asn Glu Leu Gln Lys Asp
    370                 375                 380

Lys Met Ala Glu Ala Tyr Ser Glu Ile Gly Met Lys Gly Glu Arg Arg
385                 390                 395                 400

Arg Gly Lys Gly His Asp Gly Leu Tyr Gln Gly Leu Ser Thr Ala Thr
            405                 410                 415

Lys Asp Thr Tyr Asp Ala Leu His Met Gln Ala Leu Pro Pro Arg
            420                 425                 430
```

```
<210> SEQ ID NO 108
<211> LENGTH: 1293
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
gaggttcagc ttcttgagtc tggggggcggc ctggtgcaac ctggtggcag tcttaggctg       60
agttgcgccg cgtcagggtt tacttttttct tccttcagca tgtcatgggt ccgccaggct      120
ccaggtaagg gcctggaatg ggttagtagc atcagtggca gtagtggtac aacatactac      180
gctgatagtg ttaaagggag attcactata agtagggata attctaaaaa tacccttttat     240 ctgcaaatga attctttgag ggccgaagat actgcggtct attactgtgc caaacctttt      300
ccatactttg attactgggg ccaggggacg cttgtcactg tctcctctgg cgacggctcc      360
tccggcggaa gtggaggcgc gtcagaaatt gtactgactc agtccccggg cacgctctca      420
ctcagtccag gcgaaagagc tacgttgtct tgtcgcgcaa gccagtccgt aagctctagc      480
ttcctcgcat ggtatcaaca aaagcccggg caggctccgc ggctgctcat ttactatgct      540
agttcaaggg ctacgggaat tccagaccga tttagtggat ctgggagtgg aactgacttc      600
acacttacga tcagcaggct tgagccggaa gattttgccg tgtactactg ccagcaaact      660
ggaagaatcc ccccaacatt cggacaaggc acgaaggtgg aaatcaagga tctcgagccc      720
aaatcttgtg acaaaactca cacatgccca ccgtgcccgg atcccaagtt ctgggtgctg      780
gtggtcgtgg gcggagtgct ggcctgttac agcctgctcg tgaccgtggc cttcatcatc      840 tttttgggtgc gcgatcagcg cctgccgccg gatgcgcata aaccgccggg cggcggcagc      900
tttcgcaccc cgattcagga agaacaggcg gatgcgcata gcaccctggc gaaaattcgc      960
gtgaaattta gccgcagcgc ggatgcgccg gcgtatcagc agggccagaa ccagctgtat     1020
aacgaactga acctgggccg ccgcgaagaa tatgatgtgc tggataaacg ccgcggccgc     1080
gatccggaaa tgggcggcaa accgcgccgc aaaaacccgc aggaaggcct gtataacgaa     1140
ctgcagaaag ataaaatggc ggaagcgtat agcgaaattg gcatgaaagg cgaacgccgc     1200
cgcggcaaag gccatgatgg cctgtatcag ggcctgagca ccgcgaccaa agatacctat     1260
gatgcgctgc atatgcaggc gctgccgccg cgc                                   1293

<210> SEQ ID NO 109
<211> LENGTH: 630
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

-continued

```
                    85                   90                   95

Ala Lys Pro Phe Pro Tyr Phe Asp Tyr Trp Gly Gln Gly Thr Leu Val
                100                 105                 110

Thr Val Ser Ser Gly Asp Gly Ser Ser Gly Gly Ser Gly Gly Ala Ser
            115                 120                 125

Glu Ile Val Leu Thr Gln Ser Pro Gly Thr Leu Ser Leu Ser Pro Gly
        130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
                180                 185                 190

Gly Ser Gly Ser Gly Thr Asp Phe Thr Leu Thr Ile Ser Arg Leu Glu
                195                 200                 205

Pro Glu Asp Phe Ala Val Tyr Tyr Cys Gln Gln Thr Gly Arg Ile Pro
        210                 215                 220

Pro Thr Phe Gly Gln Gly Thr Lys Val Glu Ile Lys Asp Leu Glu Pro
225                 230                 235                 240

Lys Ser Cys Asp Lys Thr His Thr Cys Pro Pro Cys Pro Asp Pro Lys
                245                 250                 255

Phe Trp Val Leu Val Val Val Gly Gly Val Leu Ala Cys Tyr Ser Leu
                260                 265                 270

Leu Val Thr Val Ala Phe Ile Ile Phe Trp Val Ala Ala Gly Gly Pro
                275                 280                 285

Gly Ala Gly Ser Ala Ala Pro Val Ser Ser Thr Ser Ser Leu Pro Leu
        290                 295                 300

Ala Ala Leu Asn Met Arg Val Arg Arg Leu Ser Leu Phe Leu Asn
305                 310                 315                 320

Val Arg Thr Gln Val Ala Ala Asp Trp Thr Ala Leu Ala Glu Glu Met
                325                 330                 335

Asp Phe Glu Tyr Leu Glu Ile Arg Gln Leu Glu Thr Gln Ala Asp Pro
                340                 345                 350

Thr Gly Arg Leu Leu Asp Ala Trp Gln Gly Arg Pro Gly Ala Ser Val
            355                 360                 365

Gly Arg Leu Leu Glu Leu Leu Thr Lys Leu Gly Arg Asp Asp Val Leu
        370                 375                 380

Leu Glu Leu Gly Pro Ser Ile Glu Glu Asp Cys Gln Lys Tyr Ile Leu
385                 390                 395                 400

Lys Gln Gln Gln Glu Glu Ala Glu Lys Pro Leu Gln Val Ala Ala Val
                405                 410                 415

Asp Ser Ser Val Pro Arg Thr Ala Glu Leu Ala Gly Ile Thr Thr Leu
            420                 425                 430

Asp Asp Pro Leu Gly His Met Pro Glu Arg Phe Asp Ala Phe Ile Cys
        435                 440                 445

Tyr Cys Pro Ser Asp Ile Val Glu Lys Lys Val Ala Lys Lys Pro Thr
    450                 455                 460

Asn Lys Ala Pro His Pro Lys Gln Glu Pro Gln Glu Ile Asn Phe Pro
465                 470                 475                 480

Asp Asp Leu Pro Gly Ser Asn Thr Ala Ala Pro Val Gln Glu Thr Leu
                485                 490                 495

His Gly Cys Gln Pro Val Thr Gln Glu Asp Gly Lys Glu Ser Arg Ile
            500                 505                 510
```

```
Ser Val Gln Glu Arg Gln Arg Val Lys Phe Ser Arg Ser Ala Asp Ala
        515                 520                 525

Pro Ala Tyr Gln Gln Gly Gln Asn Gln Leu Tyr Asn Glu Leu Asn Leu
        530                 535                 540

Gly Arg Arg Glu Glu Tyr Asp Val Leu Asp Lys Arg Arg Gly Arg Asp
545                 550                 555                 560

Pro Glu Met Gly Gly Lys Pro Arg Arg Lys Asn Pro Gln Glu Gly Leu
                565                 570                 575

Tyr Asn Glu Leu Gln Lys Asp Lys Met Ala Glu Ala Tyr Ser Glu Ile
                580                 585                 590

Gly Met Lys Gly Glu Arg Arg Arg Gly Lys Gly His Asp Gly Leu Tyr
        595                 600                 605

Gln Gly Leu Ser Thr Ala Thr Lys Asp Thr Tyr Asp Ala Leu His Met
        610                 615                 620

Gln Ala Leu Pro Pro Arg
625                 630
```

```
<210> SEQ ID NO 110
<211> LENGTH: 1890
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
gaggttcagc ttcttgagtc tggggcggc ctggtgcaac ctggtggcag tcttaggctg      60
agttgcgccg cgtcagggtt actttttct tccttcagca tgtcatgggt ccgccaggct     120
ccaggtaagg gcctggaatg ggttagtagc atcagtggca gtagtggtac aacatactac     180
gctgatagtg ttaaagggag attcactata agtagggata attctaaaaa tacccttat     240 ctgcaaatga attctttgag ggccgaagat actgcggtct attactgtgc caaacctttt     300
ccatactttg attactgggg ccaggggacg cttgtcactg tctcctctgg cgacggctcc     360
tccggcggaa gtggaggcgc gtcagaaatt gtactgactc agtccccggg cacgctctca     420
ctcagtccag gcgaaagagc tacgttgtct tgtcgcgcaa gccagtccgt aagctctagc     480
ttcctcgcat ggtatcaaca aaagcccggg caggctccgc ggctgctcat ttactatgct     540
agttcaaggg ctacgggaat ccagaccga tttagtggat ctgggagtgg aactgacttc     600
acacttacga tcagcaggct tgagccggaa gattttgccg tgtactactg ccagcaaact     660
ggaagaatcc ccccaacatt cggacaaggc acgaaggtgg aaatcaagga tctcgagccc     720
aaatcttgtg acaaaactca cacatgccca ccgtgcccgg atcccaagtt ctgggtgctg     780
gtggtcgtgg cggagtgct ggcctgttac agcctgctcg tgaccgtggc cttcatcatc     840
ttttgggtgg ctgctggcgg acctggcgcc ggatctgctg ctcctgtgtc tagcacaagc     900
agcctgcctc tggccgccct gaacatgaga gtgcggagaa ggctgagcct gttcctgaac     960
gtgcggacac aggtggccgc cgattggaca gccctggccg aggaaatgga cttcgagtac    1020
ctggaaatcc ggcagctgga aacccaggcc gaccctacag cagactgct ggatgcttgg    1080 cagggcagac caggcgcttc tgtgggaagg ctgctggaac tgctgaccaa gctgggcagg    1140
gacgacgtgc tgctggaact gggccctagc atcgaagagg actgccagaa gtacatcctg    1200 aagcagcag aggaagaggc cgagaagcct ctgcaggtgg cagccgtgga tagcagcgtg    1260
ccaagaacag ccgagctggc cggcatcacc accctggatg atcctctggg ccacatgccc    1320
```

-continued

```
gagagattcg acgccttcat ctgctactgc cccagcgaca tcgtggaaaa gaaggtggcc   1380
aagaagccca ccaacaaggc cccccacccc aagcaggaac cccaggaaat caacttcccc   1440
gacgacctgc ccggcagcaa tactgctgca cccgtgcagg aaaccctgca cggctgtcag   1500
cctgtgaccc aggaagatgg caaagaaagc cggatctctg tgcaggaacg ccagagagtg   1560
aagttcagca ggagcgcaga cgcccccgcg taccagcagg gccagaacca gctctataac   1620
gagctcaatc taggacgaag agaggagtac gatgttttgg acaagagacg tggccgggac   1680
cctgagatgg gcggcaagcc cagaagaaag aacccccagg aaggcctgta taacgaactg   1740
cagaaagaca gatgggccga ggcctacagc gagatcggca tgaagggcga gcggagaaga   1800
ggcaagggcc acgatggcct gtaccaggga ctgagcaccg ccaccaagga cacctacgac   1860
gccctgcaca tgcaggccct gcctccaaga                                    1890
```

<210> SEQ ID NO 111
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
            115                 120                 125

Glu Ile Val Leu Thr Gln Ser Pro Gly Thr Leu Ser Leu Ser Pro Gly
        130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
            195                 200                 205

Pro Glu Asp Phe Ala Val Tyr Tyr Cys Gln Gln Thr Gly Arg Ile Pro
        210                 215                 220

Pro Thr Phe Gly Gln Gly Thr Lys Val Glu Ile Lys Ile Glu Val Met
225                 230                 235                 240

Tyr Pro Pro Pro Tyr Leu Asp Asn Glu Lys Ser Asn Gly Thr Ile Ile
                245                 250                 255
```

```
His Val Lys Gly Lys His Leu Cys Pro Ser Pro Leu Phe Pro Gly Pro
            260                 265                 270

Ser Lys Pro Phe Trp Val Leu Val Val Val Gly Gly Val Leu Ala Cys
            275                 280                 285

Tyr Ser Leu Leu Val Thr Val Ala Phe Ile Ile Phe Trp Val Arg Ser
    290                 295                 300

Lys Arg Ser Arg Leu Leu His Ser Asp Tyr Met Asn Met Thr Pro Arg
305                 310                 315                 320

Arg Pro Gly Pro Thr Arg Lys His Tyr Gln Pro Tyr Ala Pro Pro Arg
                325                 330                 335

Asp Phe Ala Ala Tyr Arg Ser Arg Val Lys Phe Ser Arg Ser Ala Asp
                340                 345                 350

Ala Pro Ala Tyr Gln Gln Gly Gln Asn Gln Leu Tyr Asn Glu Leu Asn
            355                 360                 365

Leu Gly Arg Arg Glu Glu Tyr Asp Val Leu Asp Lys Arg Arg Gly Arg
    370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
            435                 440                 445

Met Gln Ala Leu Pro Pro Arg
    450                 455
```

<210> SEQ ID NO 112
<211> LENGTH: 1364
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 112

```
gaggttcagc ttcttgagtc tggggggcggc ctggtgcaac ctggtggcag tcttaggctg      60
agttgcgccg cgtcagggtt tacttttct tccttcagca tgtcatgggt ccgccaggct     120
ccaggtaagg gcctggaatg ggttagtagc atcagtggca gtagtggtac aacatactac     180
gctgatagtg ttaaagggag attcactata agtaggdata attctaaaaa tacccttat      240 ctgcaaatga attctttgag ggccgaagat actgcggtct attactgtgc caaacctttt     300
ccatactttg attactgggg ccagggggacg cttgtcactg tctcctctgg cgacggctcc     360
tccggcggaa gtggaggcgc gtcagaaatt gtactgactc agtccccggg cacgctctca     420
ctcagtccag gcgaaagagc tacgttgtct tgtcgcgcaa gccagtccgt aagctctagc     480
ttcctcgcat ggtatcaaca aaagcccggg caggctccgc ggctgctcat ttactatgct     540
agttcaaggg ctacgggaat tccagaccga tttagtggat ctgggagtgg aactgacttc     600
acacttacga tcagcaggct tgagccggaa gattttgccg tgtactactg ccagcaaact     660
ggaagaatcc ccccaacatt cggacaaggc acgaaggtgg aaatcaagat cgaagtgatg     720
tacccgcctc cttacctgga caacgagaag tccaacggca ccatcatcca cgtgaaggga     780
aagcacctgt gtccttctcc actgttcccc ggacctagca agccttctgg gtgctggtgg     840
```

-continued

```
tcgtgggcgg agtgctggcc tgttacagcc tgctcgtgac cgtggccttc atcatctttt    900
gggtgcgcag caagcggagc cggctgctgc acagcgacta catgaacatg accccccagac   960 ggcctggccc caccagaaag cactaccagc cttacgcccc tcccagagac ttcgccgcct    1020
accggtccag agtgaagttc agcagaagcg ccgacgcccc tgcctatcag cagggccaga    1080
accagctgta caacgagctg aacctgggca gacgggaaga gtacgacgtg ctggacaagc    1140
ggagaggcag ggaccctgag atgggcggca gcccagaag aaagaacccc caggaaggcc     1200
tgtataacga actgcagaaa gacaagatgg ccgaggccta cagcgagatc ggcatgaagg    1260
gcgagcggag aagaggcaag ggccacgatg gcctgtacca gggactgagc accgccacca    1320
aggacaccta cgacgccctg cacatgcagg ccctgcctcc aaga                     1364
```

```
<210> SEQ ID NO 113
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Ile Glu Val Met
225                 230                 235                 240

Tyr Pro Pro Pro Tyr Leu Asp Asn Glu Lys Ser Asn Gly Thr Ile Ile
                245                 250                 255

His Val Lys Gly Lys His Leu Cys Pro Ser Pro Leu Phe Pro Gly Pro
            260                 265                 270
```

-continued

```
Ser Lys Pro Phe Trp Val Leu Val Val Val Gly Gly Val Leu Ala Cys
    275                 280                 285

Tyr Ser Leu Leu Val Thr Val Ala Phe Ile Ile Phe Trp Val Lys Arg
    290                 295                 300

Gly Arg Lys Lys Leu Leu Tyr Ile Phe Lys Gln Pro Phe Met Arg Pro
305                 310                 315                 320

Val Gln Thr Thr Gln Glu Glu Asp Gly Cys Ser Cys Arg Phe Pro Glu
                325                 330                 335

Glu Glu Glu Gly Gly Cys Glu Leu Arg Val Lys Phe Ser Arg Ser Ala
                340                 345                 350

Asp Ala Pro Ala Tyr Gln Gln Gly Gln Asn Gln Leu Tyr Asn Glu Leu
    355                 360                 365

Asn Leu Gly Arg Arg Glu Glu Tyr Asp Val Leu Asp Lys Arg Arg Gly
    370                 375                 380

Arg Asp Pro Glu Met Gly Gly Lys Pro Arg Arg Lys Asn Pro Gln Glu
385                 390                 395                 400

Gly Leu Tyr Asn Glu Leu Gln Lys Asp Lys Met Ala Glu Ala Tyr Ser
                405                 410                 415

Glu Ile Gly Met Lys Gly Glu Arg Arg Arg Gly Lys Gly His Asp Gly
                420                 425                 430

Leu Tyr Gln Gly Leu Ser Thr Ala Thr Lys Asp Thr Tyr Asp Ala Leu
    435                 440                 445

His Met Gln Ala Leu Pro Pro Arg
    450                 455
```

```
<210> SEQ ID NO 114
<211> LENGTH: 1367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
gaggttcagc ttcttgagtc tggggggcggc ctggtgcaac ctggtggcag tcttaggctg      60
agttgcgccg cgtcagggtt tactttttct tccttcagca tgtcatgggt ccgccaggct     120
ccaggtaagg gcctggaatg ggttagtagc atcagtggca gtagtggtac aacatactac     180
gctgatagtg ttaaagggag attcactata agtagggata attctaaaaa tacccttat     240 ctgcaaatga attctttgag ggccgaagat actgcggtct attactgtgc caaacctttt     300
ccatactttg attactgggg ccagggggacg cttgtcactg tctcctctgg cgacggctcc     360
tccggcggaa gtggaggcgc gtcagaaatt gtactgactc agtccccggg cacgctctca     420
ctcagtccag gcgaaagagc tacgttgtct gtcgcgcaa gccagtccgt aagctctagc     480
ttcctcgcat ggtatcaaca aaagcccggg caggctccgc ggctgctcat ttactatgct     540
agttcaaggg ctacgggaat ccagaccga tttagtggat ctgggagtgg aactgacttc     600
acacttacga tcagcaggct tgagccggaa gattttgccg tgtactactg ccagcaaact     660
ggaagaatcc ccccaacatt cggacaaggc acgaaggtgg aaatcaagat cgaagtgatg     720
tacccgcctc cttacctgga caacgagaag tccaacggca ccatcatcca cgtgaaggga     780
aagcacctgt gtccttctcc actgttcccc ggacctagca gccttctgg gtgctggtgg     840 tcgtgggcgc agtgctggcc tgttacagcc tgctcgtgac cgtggccttc atcatctttt     900
gggtgaaacg cggccgcaaa aaactgctgt atattttaa acagccgttt atgcgcccgg     960
```

-continued

```
tgcagaccac ccaggaagaa gatggctgca gctgccgctt tccggaagaa gaagaaggcg    1020
gctgcgaact gcgcgtgaaa tttagccgca gcgcggatgc gccggcgtat cagcagggcc    1080
agaaccagct gtataacgaa ctgaacctgg gccgccgcga agaatatgat gtgctggata    1140
aacgccgcgg ccgcgatccg gaaatgggcg gcaaaccgcg ccgcaaaaac ccgcaggaag    1200
gcctgtataa cgaactgcag aaagataaaa tggcggaagc gtatagcgaa attggcatga    1260
aaggcgaacg ccgccgcggc aaaggccatg atggcctgta tcagggcctg agcaccgcga    1320
ccaaagatac ctatgatgcg ctgcatatgc aggcgctgcc gccgcgc    1367
```

<210> SEQ ID NO 115
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
            115                 120                 125

Glu Ile Val Leu Thr Gln Ser Pro Gly Thr Leu Ser Leu Ser Pro Gly
        130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
            195                 200                 205

Pro Glu Asp Phe Ala Val Tyr Tyr Cys Gln Gln Thr Gly Arg Ile Pro
        210                 215                 220

Pro Thr Phe Gly Gln Gly Thr Lys Val Glu Ile Lys Ile Glu Val Met
225                 230                 235                 240

Tyr Pro Pro Pro Tyr Leu Asp Asn Glu Lys Ser Asn Gly Thr Ile Ile
                245                 250                 255

His Val Lys Gly Lys His Leu Cys Pro Ser Pro Leu Phe Pro Gly Pro
            260                 265                 270

Ser Lys Pro Phe Trp Val Leu Val Val Val Gly Gly Val Leu Ala Cys
            275                 280                 285
```

```
Tyr Ser Leu Leu Val Thr Val Ala Phe Ile Ile Phe Trp Val Arg Asp
    290                 295                 300

Gln Arg Leu Pro Pro Asp Ala His Lys Pro Pro Gly Gly Gly Ser Phe
305                 310                 315                 320

Arg Thr Pro Ile Gln Glu Glu Gln Ala Asp Ala His Ser Thr Leu Ala
                325                 330                 335

Lys Ile Arg Val Lys Phe Ser Arg Ser Ala Asp Ala Pro Ala Tyr Gln
                340                 345                 350

Gln Gly Gln Asn Gln Leu Tyr Asn Glu Leu Asn Leu Gly Arg Arg Glu
                355                 360                 365

Glu Tyr Asp Val Leu Asp Lys Arg Arg Gly Arg Asp Pro Glu Met Gly
    370                 375                 380

Gly Lys Pro Arg Arg Lys Asn Pro Gln Glu Gly Leu Tyr Asn Glu Leu
385                 390                 395                 400

Gln Lys Asp Lys Met Ala Glu Ala Tyr Ser Glu Ile Gly Met Lys Gly
                405                 410                 415

Glu Arg Arg Arg Gly Lys Gly His Asp Gly Leu Tyr Gln Gly Leu Ser
                420                 425                 430

Thr Ala Thr Lys Asp Thr Tyr Asp Ala Leu His Met Gln Ala Leu Pro
                435                 440                 445

Pro Arg
    450
```

```
<210> SEQ ID NO 116
<211> LENGTH: 1349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
gaggttcagc ttcttgagtc tggggggcggc ctggtgcaac ctggtggcag tcttaggctg      60
agttgcgccg cgtcaggggtt tactttttct tccttcagca tgtcatgggt ccgccaggct     120
ccaggtaagg gcctggaatg ggttagtagc atcagtggca gtagtggtac aacatactac     180
gctgatagtg ttaaagggag attcactata agtagggata attctaaaaa tacccttat     240 ctgcaaatga attctttgag ggccgaagat actgcggtct attactgtgc caaacctttt     300
ccatactttg attactgggg ccaggggacg cttgtcactg tctcctctgg cgacggctcc     360
tccggcggaa gtggaggcgc gtcagaaatt gtactgactc agtccccggg cacgctctca     420
ctcagtccag gcgaaagagc tacgttgtct tgtcgcgcaa gccagtccgt aagctctagc     480
ttcctcgcat ggtatcaaca aaagcccggg caggctccgc ggctgctcat ttactatgct     540
agttcaaggg ctacgggaat tccagaccga tttagtggat ctgggagtgg aactgacttc     600
acacttacga tcagcaggct tgagccggaa gattttgccg tgtactactg ccagcaaact     660
ggaagaatcc ccccaacatt cggacaaggc acgaaggtgg aaatcaagat cgaagtgatg     720
tacccgcctc cttacctgga caacgagaag tccaacggca ccatcatcca cgtgaaggga     780
aagcacctgt gtccttctcc actgttcccc ggacctagca agccttctgg gtgctggtgg     840
tcgtgggcgg agtgctggcc tgttacagcc tgctcgtgac cgtggccttc atcatctttt     900
gggtgcgcga tcagcgcctg ccgccggatg cgcataaacc gccgggcggc ggcagctttc     960
gcaccccgat tcaggaagaa caggcggatg cgcatagcac cctggcgaaa attcgcgtga    1020
```

-continued

```
aatttagccg cagcgcggat gcgccggcgt atcagcaggg ccagaaccag ctgtataacg    1080
aactgaacct gggccgccgc gaagaatatg atgtgctgga taaacgccgc ggccgcgatc    1140
cggaaatggg cggcaaaccg cgccgcaaaa acccgcagga aggcctgtat aacgaactgc    1200
agaaagataa aatggcggaa gcgtatagcg aaattggcat gaaaggcgaa cgccgccgcg    1260
gcaaaggcca tgatggcctg tatcagggcc tgagcaccgc gaccaaagat acctatgatg    1320
cgctgcatat gcaggcgctg ccgccgcgc                                      1349
```

```
<210> SEQ ID NO 117
<211> LENGTH: 649
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Ile Glu Val Met
225                 230                 235                 240

Tyr Pro Pro Pro Tyr Leu Asp Asn Glu Lys Ser Asn Gly Thr Ile Ile
                245                 250                 255

His Val Lys Gly Lys His Leu Cys Pro Ser Pro Leu Phe Pro Gly Pro
            260                 265                 270

Ser Lys Pro Phe Trp Val Leu Val Val Val Gly Gly Val Leu Ala Cys
        275                 280                 285

Tyr Ser Leu Leu Val Thr Val Ala Phe Ile Ile Phe Trp Val Ala Ala
    290                 295                 300
```

-continued

```
Gly Gly Pro Gly Ala Gly Ser Ala Ala Pro Val Ser Ser Thr Ser Ser
305             310             315             320

Leu Pro Leu Ala Ala Leu Asn Met Arg Val Arg Arg Arg Leu Ser Leu
                325             330             335

Phe Leu Asn Val Arg Thr Gln Val Ala Ala Asp Trp Thr Ala Leu Ala
                340             345             350

Glu Glu Met Asp Phe Glu Tyr Leu Glu Ile Arg Gln Leu Glu Thr Gln
            355             360             365

Ala Asp Pro Thr Gly Arg Leu Leu Asp Ala Trp Gln Gly Arg Pro Gly
        370             375             380

Ala Ser Val Gly Arg Leu Leu Glu Leu Leu Thr Lys Leu Gly Arg Asp
385             390             395             400

Asp Val Leu Leu Glu Leu Gly Pro Ser Ile Glu Glu Asp Cys Gln Lys
                405             410             415

Tyr Ile Leu Lys Gln Gln Gln Glu Glu Ala Glu Lys Pro Leu Gln Val
                420             425             430

Ala Ala Val Asp Ser Ser Val Pro Arg Thr Ala Glu Leu Ala Gly Ile
            435             440             445

Thr Thr Leu Asp Asp Pro Leu Gly His Met Pro Glu Arg Phe Asp Ala
        450             455             460

Phe Ile Cys Tyr Cys Pro Ser Asp Ile Val Glu Lys Lys Val Ala Lys
465             470             475             480

Lys Pro Thr Asn Lys Ala Pro His Pro Lys Gln Glu Pro Gln Glu Ile
                485             490             495

Asn Phe Pro Asp Asp Leu Pro Gly Ser Asn Thr Ala Ala Pro Val Gln
            500             505             510

Glu Thr Leu His Gly Cys Gln Pro Val Thr Gln Glu Asp Gly Lys Glu
        515             520             525

Ser Arg Ile Ser Val Gln Glu Arg Gln Arg Val Lys Phe Ser Arg Ser
        530             535             540

Ala Asp Ala Pro Ala Tyr Gln Gln Gly Gln Asn Gln Leu Tyr Asn Glu
545             550             555             560

Leu Asn Leu Gly Arg Arg Glu Glu Tyr Asp Val Leu Asp Lys Arg Arg
                565             570             575

Gly Arg Asp Pro Glu Met Gly Gly Lys Pro Arg Arg Lys Asn Pro Gln
            580             585             590

Glu Gly Leu Tyr Asn Glu Leu Gln Lys Asp Lys Met Ala Glu Ala Tyr
        595             600             605

Ser Glu Ile Gly Met Lys Gly Glu Arg Arg Arg Gly Lys Gly His Asp
        610             615             620

Gly Leu Tyr Gln Gly Leu Ser Thr Ala Thr Lys Asp Thr Tyr Asp Ala
625             630             635             640

Leu His Met Gln Ala Leu Pro Pro Arg
                645
```

<210> SEQ ID NO 118
<211> LENGTH: 1946
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
gaggttcagc ttcttgagtc tggggggcggc ctggtgcaac ctggtggcag tcttaggctg      60

```
agttgcgccg cgtcaggggtt tactttttct tccttcagca tgtcatgggt ccgccaggct    120
ccaggtaagg gcctggaatg ggttagtagc atcagtggca gtagtggtac aacatactac    180
gctgatagtg ttaaagggag attcactata agtagggata attctaaaaa taccctttat    240
ctgcaaatga attctttgag ggccgaagat actgcggtct attactgtgc caaacctttt    300
ccatactttg attactgggg ccaggggacg cttgtcactg tctcctctgg cgacggctcc    360
tccggcggaa gtggaggcgc gtcagaaatt gtactgactc agtccccggg cacgctctca    420
ctcagtccag gcgaaagagc tacgttgtct tgtcgcgcaa gccagtccgt aagctctagc    480
ttcctcgcat ggtatcaaca aaagcccggg caggctccgc ggctgctcat ttactatgct    540
agttcaaggg ctacgggaat tccagaccga tttagtggat ctgggagtgg aactgacttc    600
acacttacga tcagcaggct tgagccggaa gattttgccg tgtactactg ccagcaaact    660
ggaagaatcc ccccaacatt cggacaaggc acgaaggtgg aaatcaagat cgaagtgatg    720
tacccgcctc cttacctgga caacgagaag tccaacggca ccatcatcca cgtgaaggga    780
aagcacctgt gtccttctcc actgttcccc ggacctagca agccttctgg gtgctggtgg    840 tcgtgggcg agtgctggcc tgttacagcc tgctcgtgac cgtggccttc atcatctttt    900
gggtggctgc tggcggacct ggcgccggat ctgctgctcc tgtgtctagc acaagcagcc    960
tgcctctggc cgccctgaac atgagagtgc ggagaaggct gagcctgttc ctgaacgtgc   1020
ggacacaggt ggccgccgat tggacagccc tggccgagga aatggacttc gagtacctgg   1080
aaatccggca gctggaaacc caggccgacc ctacaggcag actgctggat gcttggcagg   1140
gcagaccagg cgcttctgtg ggaaggctgc tggaactgct gaccaagctg ggcagggacg   1200
acgtgctgct ggaactgggc cctagcatcg aagaggactg ccagaagtac atcctgaagc   1260
agcagcagga agaggccgag aagcctctgc aggtggcagc cgtggatagc agcgtgccaa   1320
gaacagccga gctggccggc atcaccaccc tggatgatcc tctgggccac atgcccgaga   1380
gattcgacgc cttcatctgc tactgcccca gcgacatcgt ggaaaagaag gtggccaaga   1440
agcccaccaa caaggccccc cacccccaagc aggaacccca ggaaatcaac ttccccgacg   1500
acctgcccgg cagcaatact gctgcacccg tgcaggaaac cctgcacggc tgtcagcctg   1560
tgacccagga agatggcaaa gaaagccgga tctctgtgca ggaacgccag agagtgaagt   1620
tcagcaggag cgcagacgcc cccgcgtacc agcagggcca gaaccagctc tataacgagc   1680
tcaatctagg acgaagagag gagtacgatg ttttggacaa gagacgtggc cgggaccctg   1740
agatgggcgg caagcccaga agaaagaacc cccaggaagg cctgtataac gaactgcaga   1800
aagacaagat ggccgaggcc tacagcgaga tcggcatgaa gggcgagcgg agaagaggca   1860
agggccacga tggcctgtac caggggactga gcaccgccac caaggacacc tacgacgccc   1920
tgcacatgca ggccctgcct ccaaga                                        1946
```

<210> SEQ ID NO 119
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Met Asp Trp Ile Trp Arg Ile Leu Phe Leu Val Gly Ala Ala Thr Gly
1               5                   10                  15
```

Ala His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Ser Phe Ser Met Ser Trp Val Arg Gln Ala Pro Gly Lys Gly Leu
        50                  55                  60

Glu Trp Val Ser Ser Ile Ser Gly Ser Ser Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Pro Phe Pro Tyr Phe Asp Tyr Trp Gly Gln Gly
            115                 120                 125

Thr Leu Val Thr Val Ser Ser Gly Asp Gly Ser Ser Gly Gly Ser Gly
        130                 135                 140

Gly Ala Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
            180                 185                 190

Arg Leu Leu Ile Tyr Tyr Ala Ser Ser Arg Ala Thr Gly Ile Pro Asp
            195                 200                 205

Arg Phe Ser Gly Ser Gly Ser Gly Thr Asp Phe Thr Leu Thr Ile Ser
        210                 215                 220

Arg Leu Glu Pro Glu Asp Phe Ala Val Tyr Tyr Cys Gln Gln Thr Gly
225                 230                 235                 240

Arg Ile Pro Pro Thr Phe Gly Gln Gly Thr Lys Val Glu Ile Lys Asp
                245                 250                 255

Leu Glu Pro Lys Ser Cys Asp Lys Thr His Thr Cys Pro Pro Cys Pro
                260                 265                 270

Asp Pro Lys Phe Trp Val Leu Val Val Val Gly Gly Val Leu Ala Cys
            275                 280                 285

Tyr Ser Leu Leu Val Thr Val Ala Phe Ile Ile Phe Trp Val Arg Ser
        290                 295                 300

Lys Arg Ser Arg Leu Leu His Ser Asp Tyr Met Asn Met Thr Pro Arg
305                 310                 315                 320

Arg Pro Gly Pro Thr Arg Lys His Tyr Gln Pro Tyr Ala Pro Pro Arg
                325                 330                 335

Asp Phe Ala Ala Tyr Arg Ser Arg Val Lys Phe Ser Arg Ser Ala Asp
            340                 345                 350

Ala Pro Ala Tyr Gln Gln Gly Gln Asn Gln Leu Tyr Asn Glu Leu Asn
            355                 360                 365

Leu Gly Arg Arg Glu Glu Tyr Asp Val Leu Asp Lys Arg Arg Gly Arg
        370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His

-continued

```
            435              440              445
Met Gln Ala Leu Pro Pro Arg
    450              455
```

<210> SEQ ID NO 120
<211> LENGTH: 1365
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 120

```
atggactgga tctggcgcat cctcttcctc gtcggcgctg ctaccggcgc tcattctgag       60
gttcagcttc ttgagtctgg gggcggcctg gtgcaacctg gtggcagtct taggctgagt      120
tgcgccgcgt cagggtttac tttttcttcc ttcagcatgt catgggtccg ccaggctcca      180
ggtaagggcc tggaatgggt tagtagcatc agtggcagta gtggtacaac atactacgct      240
gatagtgtta aagggagatt cactataagt agggataatt ctaaaaatac cctttatctg      300
caaatgaatt ctttgagggc cgaagatact gcggtctatt actgtgccaa accttttcca      360
tactttgatt actggggcca ggggacgctt gtcactgtct cctctggcga cggctcctcc      420
ggcggaagtg gaggcgcgtc agaaattgta ctgactcagt ccccgggcac gctctcactc      480
agtccaggcg aaagagctac gttgtcttgt cgcgcaagcc agtccgtaag ctctagcttc      540
ctcgcatggt atcaacaaaa gcccgggcag gctccgcggc tgctcattta ctatgctagt      600
tcaagggcta cgggaattcc agaccgattt agtggatctg ggagtggaac tgacttcaca      660
cttacgatca gcaggcttga gccggaagat tttgccgtgt actactgcca gcaaactgga      720
agaatccccc caacattcgg acaaggcacg aaggtggaaa tcaaggatct cgagcccaaa      780
tcttgtgaca aaactcacac atgcccaccg tgcccggatc ccaagttctg ggtgctggtg      840
gtcgtgggcg gagtgctggc ctgttacagc ctgctcgtga ccgtggcctt catcatcttt      900
tgggtgcgca gcaagcggag ccggctgctg cacagcgact acatgaacat gacccccaga      960
cggcctggcc ccaccagaaa gcactaccag ccttacgccc tcccagaga cttcgccgcc     1020 taccggtcca gagtgaagtt cagcagaagc gccgacgccc tgcctatca gcagggccag     1080 aaccagctgt acaacgagct gaacctgggc agacgggaag agtacgacgt gctggacaag     1140
cggagaggca gggaccctga gatgggcggc aagcccagaa gaaagaaccc ccaggaaggc     1200
ctgtataacg aactgcagaa agacaagatg gccgaggcct acagcgagat cggcatgaag     1260
ggcgagcgga agaggcaa gggccacgat ggcctgtacc agggactgag caccgccacc     1320
aaggacacct acgacgccct gcacatgcag gccctgcctc caaga                    1365
```

<210> SEQ ID NO 121
<211> LENGTH: 781
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 121

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30
```

-continued

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
            115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
            195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Ile Leu Asp Tyr
225                 230                 235                 240

Ser Phe Gly Gly Gly Ala Gly Arg Asp Ile Pro Pro Leu Ile Glu
                245                 250                 255

Glu Ala Cys Glu Leu Pro Glu Cys Gln Glu Asp Ala Gly Asn Lys Val
            260                 265                 270

Cys Ser Leu Gln Cys Asn Asn His Ala Cys Gly Trp Asp Gly Gly Asp
            275                 280                 285

Cys Ser Leu Asn Phe Asn Asp Pro Trp Lys Asn Cys Thr Gln Ser Leu
    290                 295                 300

Gln Cys Trp Lys Tyr Phe Ser Asp Gly His Cys Asp Ser Gln Cys Asn
305                 310                 315                 320

Ser Ala Gly Cys Leu Phe Asp Gly Phe Asp Cys Gln Arg Ala Glu Gly
            325                 330                 335

Gln Cys Asn Pro Leu Tyr Asp Gln Tyr Cys Lys Asp His Phe Ser Asp
            340                 345                 350

Gly His Cys Asp Gln Gly Cys Asn Ser Ala Glu Cys Glu Trp Asp Gly
            355                 360                 365

Leu Asp Cys Ala Glu His Val Pro Glu Arg Leu Ala Ala Gly Thr Leu
    370                 375                 380

Val Val Val Val Leu Met Pro Pro Glu Gln Leu Arg Asn Ser Ser Phe
385                 390                 395                 400

His Phe Leu Arg Glu Leu Ser Arg Val Leu His Thr Asn Val Val Phe
                405                 410                 415

Lys Arg Asp Ala His Gly Gln Gln Met Ile Phe Pro Tyr Tyr Gly Arg
            420                 425                 430

Glu Glu Glu Leu Arg Lys His Pro Ile Lys Arg Ala Ala Glu Gly Trp
            435                 440                 445

Ala Ala Pro Asp Ala Leu Leu Gly Gln Val Lys Ala Ser Leu Leu Pro

-continued

```
         450                455                460
Gly Gly Ser Glu Gly Gly Arg Arg Arg Arg Glu Leu Asp Pro Met Asp
465                 470                475                480

Val Arg Gly Ser Ile Val Tyr Leu Glu Ile Asp Asn Arg Gln Cys Val
                485                490                495

Gln Ala Ser Ser Gln Cys Phe Gln Ser Ala Thr Asp Val Ala Ala Phe
            500                505                510

Leu Gly Ala Leu Ala Ser Leu Gly Ser Leu Asn Ile Pro Tyr Lys Ile
            515                520                525

Glu Ala Val Gln Ser Glu Thr Val Glu Pro Pro Pro Ala Gln Leu
            530                535                540

His Phe Met Tyr Val Ala Ala Ala Phe Val Leu Leu Phe Phe Val
545                 550                555                560

Gly Cys Gly Val Leu Leu Ser Arg Lys Arg Arg Met Lys Leu Leu
                565                570                575

Ser Ser Ile Glu Gln Ala Cys Asp Ile Cys Arg Leu Lys Lys Leu Lys
            580                585                590

Cys Ser Lys Glu Lys Pro Lys Cys Ala Lys Cys Leu Lys Asn Asn Trp
            595                600                605

Glu Cys Arg Tyr Ser Pro Lys Thr Lys Arg Ser Pro Leu Thr Arg Ala
            610                615                620

His Leu Thr Glu Val Glu Ser Arg Leu Glu Arg Leu Glu Gln Leu Phe
625                 630                635                640

Leu Leu Ile Phe Pro Arg Glu Asp Leu Asp Met Ile Leu Lys Met Asp
                645                650                655

Ser Leu Gln Asp Ile Lys Ala Leu Leu Thr Gly Leu Phe Val Gln Asp
                660                665                670

Asn Val Asn Lys Asp Ala Val Thr Asp Arg Leu Ala Ser Val Glu Thr
            675                680                685

Asp Met Pro Leu Thr Leu Arg Gln His Arg Ile Ser Ala Thr Ser Ser
            690                695                700

Ser Glu Glu Ser Ser Asn Lys Gly Gln Arg Gln Leu Thr Val Ser Ala
705                 710                715                720

Ala Ala Gly Gly Ser Gly Gly Ser Gly Gly Ser Asp Ala Leu Asp Asp
                725                730                735

Phe Asp Leu Asp Met Leu Gly Ser Asp Ala Leu Asp Asp Phe Asp Leu
            740                745                750

Asp Met Leu Gly Ser Asp Ala Leu Asp Asp Phe Asp Leu Asp Met Leu
            755                760                765

Gly Ser Asp Ala Leu Asp Asp Phe Asp Leu Asp Met Leu
            770                775                780
```

<210> SEQ ID NO 122
<211> LENGTH: 2343
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 122

```
gaggttcagc ttcttgagtc tgggggcggc ctggtgcaac ctggtggcag tcttaggctg      60
agttgcgccg cgtcaggggtt tacttttttct tccttcagca tgtcatgggt ccgccaggct     120
ccaggtaagg gcctggaatg ggttagtagc atcagtggca gtagtggtac aacatactac     180
```

```
gctgatagtg ttaaagggag attcactata agtagggata attctaaaaa tacccttttat    240 ctgcaaatga attctttgag ggccgaagat actgcggtct attactgtgc caaacctttt    300
ccatactttg attactgggg ccaggggacg cttgtcactg tctcctctgg cgacggctcc    360
tccggcggaa gtggaggcgc gtcagaaatt gtactgactc agtccccggg cacgctctca    420
ctcagtccag gcgaaagagc tacgttgtct tgtcgcgcaa gccagtccgt aagctctagc    480
ttcctcgcat ggtatcaaca aaagcccggg caggctccgc ggctgctcat ttactatgct    540
agttcaaggg ctacgggaat tccagaccga tttagtggat ctgggagtgg aactgacttc    600
acacttacga tcagcaggct tgagccggaa gattttgccg tgtactactg ccagcaaact    660
ggaagaatcc ccccaacatt cggacaaggc acgaaggtgg aaatcaagat tctggattat    720
agctttggcg gcggcgcggg ccgcgatatt ccgccgccgc tgattgaaga agcgtgcgaa    780
ctgccggaat gccaggaaga tgcgggcaac aaagtgtgca gcctgcagtg caacaaccat    840
gcgtgcggct gggatggcgg cgattgcagc ctgaacttta cgatccgtg gaaaaactgc    900 acccagagcc tgcagtgctg gaaatatttt agcgatggcc attgcgatag ccagtgcaac    960
agcgcgggct gcctgtttga tggctttgat tgccagcgcg cggaaggcca gtgcaacccg    1020
ctgtatgatc agtattgcaa agatcatttt agcgatggcc attgcgatca gggctgcaac    1080
agcgcggaat gcgaatggga tggcctggat tgcgcggaac atgtgccgga acgcctggcg    1140
gcgggcaccc tggtggtggt ggtgctgatg ccgccgaac agctgcgcaa cagcagcttt    1200
cattttctgc gcgaactgag ccgcgtgctg cataccaacg tggtgtttaa acgcgatgcg    1260
catggccagc agatgatttt tccgtattat ggccgcgaag aagaactgcg caaacatccg    1320
attaaacgcg cggcggaagg ctgggcggcg ccggatgcgc tgctgggcca ggtgaaagcg    1380
agcctgctgc cggcggcag cgaaggcggc cgccgccgcc gcgaactgga tccgatggat    1440
gtgcgcggca gcattgtgta tctggaaatt gataaccgcc agtgcgtgca ggcgagcagc    1500
cagtgctttc agagcgcgac cgatgtggcg cgtttctgg cgcgctggc gagcctgggc    1560 agcctgaaca ttccgtataa aattgaagcg gtgcagagcg aaaccgtgga accgccgccg    1620
ccggcgcagc tgcattttat gtatgtggcg cggcggcgcg ttgtgctgct gttttttgtg    1680
ggctgcggcg tgctgctgag ccgcaaacgc cgccgcatga aactgctgag cagcattgaa    1740
caggcgtgcg atatttgccg cctgaaaaaa ctgaaatgca gcaaagaaaa accgaaatgc    1800
gcgaaatgcc tgaaaaacaa ctgggaatgc cgctatagcc cgaaaaccaa acgcagcccg    1860
ctgacccgcg cgcatctgac cgaagtggaa agccgcctgg aacgcctgga acagctgttt    1920
ctgctgattt ttccgcgcga agatctggat atgattctga aaatggatag cctgcaggat    1980
attaaagcgc tgctgaccgg cctgtttgtg caggataacg tgaacaaaga tgcggtgacc    2040
gatcgcctgg cgagcgtgga aaccgatatg ccgctgaccc tgcgccagca tcgcattagc    2100
gcgaccagca gcagcgaaga aagcagcaac aaaggccagc gccagctgac cgtgagcgcg    2160
gcggcgggcg gcagcggcgg cagcggcggc agcgatgcgc tggatgattt tgatctggat    2220
atgctgggca gcgatgcgct ggatgatttt gatctggata tgctgggcag cgatgcgctg    2280
gatgattttg atctggatat gctgggcagc gatgcgctgg atgattttga tctggatatg    2340
ctg                                                                    2343
```

<210> SEQ ID NO 123
<211> LENGTH: 339
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 123
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgctaa                             339

<210> SEQ ID NO 124
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggcgg caagcccaga agaaagaacc cccaggaagg cctgtataac     180
gaactgcaga aagacaagat ggccgaggcc tacagcgaga tcggcatgaa gggcgagcgg     240
agaagaggca agggccacga tggcctgtac cagggactga gcaccgccac caaggacacc     300
tacgacgccc tgcacatgca ggccctgcct ccaaga                               336

<210> SEQ ID NO 125
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggcgg caagcccaga agaaagaacc cccaggaagg cctgtataac     180
gaactgcaga aagacaagat ggccgaggcc tacagcgaga tcggcatgaa gggcgagcgg     240
agaagaggca agggccacga tggcctgtac cagggactga gcaccgccac caaggacacc     300
tacgacgccc tgcacatgca ggccctgcct ccaaga                               336

<210> SEQ ID NO 126
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
cgcgtgaaat ttagccgcag cgcggatgcg ccggcgtatc agcagggcca gaaccagctg      60
tataacgaac tgaacctggg ccgccgcgaa gaatatgatg tgctggataa acgccgcggc     120
```

-continued

```
cgcgatccgg aaatgggcgg caaaccgcgc cgcaaaaacc cgcaggaagg cctgtataac    180
gaactgcaga aagataaaat ggcggaagcg tatagcgaaa ttggcatgaa aggcgaacgc    240
cgccgcggca aaggccatga tggcctgtat cagggcctga gcaccgcgac caaagatacc    300
tatgatgcgc tgcatatgca ggcgctgccg ccgcgc                              336
```

<210> SEQ ID NO 127
<211> LENGTH: 108
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 127

```
cgcgatcagc gcctgccgcc ggatgcgcat aaaccgccgg gcggcggcag ctttcgcacc    60
ccgattcagg aagaacaggc ggatgcgcat agcaccctgg cgaaaatt                 108
```

<210> SEQ ID NO 128
<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 128

```
atggactgga tctggcgcat cctcttcctc gtcggcgctg ctaccggcgc tcattct       57
```

<210> SEQ ID NO 129
<211> LENGTH: 708
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 129

```
gaagtgcagc tgctggaaag cggcggcggc ctggtgcagc cgggcggcag cctgcgcctg    60
agctgcgcgg cgagcggctt tacctttagc agctttagca tgagctgggt gcgccaggcg    120
ccgggcaaag cctggaatg  ggtgagcagc attagcggca gcagcggcac cacctattat    180
gcggatagcg tgaaaggccg ctttaccatt agccgcgata acagcaaaaa caccctgtat    240
ctgcagatga acagcctgcg cgcggaagat accgcggtgt attattgcgc gaaaccgttt    300
ccgtattttg attattgggg ccagggcacc ctggtgaccg tgagcagcgg cgatggcagc    360
agcggcggca gcggcggcgc gagcgaaatt gtgctgaccc agagcccggg caccctgagc    420
ctgagcccgg gcgaacgcgc gaccctgagc tgccgcgcga gccagagcgt gagcagcagc    480
tttctggcgt ggtatcagca gaaaccgggc caggcgccgc gcctgctgat ttattatgcg    540
agcagccgcg cgaccggcat tccggatcgc tttagcggca gcggcagcgg caccgatttt    600
accctgacca ttagccgcct ggaaccggaa gattttgcgg tgtattattg ccagcagacc    660
ggccgcattc gccgaccttt tggccagggc accaaagtgg aaattaaa               708
```